(12) United States Patent  
Chen et al.

(10) Patent No.: US 8,889,714 B2  
(45) Date of Patent: Nov. 18, 2014

(54) 3,4-SUBSTITUTED PIPERIDINE DERIVATIVES AS RENIN INHIBITORS

(75) Inventors: Austin Chih-Yu Chen, Pierrefonds (CA); Daniel Dube, St. Lazare (CA); Pierre-Andre Fournier, Laval (CA); Erich L. Grimm, Baie d'Urfe (CA); Patrick Lacombe, Montreal (CA); Sebastien Laliberte, St. Lazare (CA); Dwight Macdonald, L'lle Bizard (CA); D. Bruce MacKay, Dollard-des-Ormeaux (CA); Daniel James McKay, Chute a Blondeau (CA); Tom Yao-Hsiang Wu, San Diego, CA (US); Louis-Charles Campeau, Vaudreuil-Dorion (CA); Jeremy Peter Scott, Herford (GB); Nadine Bremeyer, Cambridge (GB)

(73) Assignee: Actelion Pharmaceuticals Ltd., Allschwil (CH)

( * ) Notice: Subject to any disclaimer, the term of this patent is extended or adjusted under 35 U.S.C. 154(b) by 382 days.

(21) Appl. No.: 12/990,927

(22) PCT Filed: May 4, 2009

(86) PCT No.: PCT/CA2009/000611  
§ 371 (c)(1),  
(2), (4) Date: Nov. 3, 2010

(87) PCT Pub. No.: WO2009/135299  
PCT Pub. Date: Nov. 12, 2009

(65) Prior Publication Data  
US 2011/0053940 A1    Mar. 3, 2011

Related U.S. Application Data

(60) Provisional application No. 61/188,303, filed on Aug. 7, 2008, provisional application No. 61/126,529, filed on May 5, 2008.

(51) Int. Cl.  
*A61K 31/4545* (2006.01)  
*C07D 401/14* (2006.01)  
*C07D 417/14* (2006.01)  
*C07D 401/04* (2006.01)

(52) U.S. Cl.  
CPC ............ *C07D 401/14* (2013.01); *C07D 417/14* (2013.01); *C07D 401/04* (2013.01)

USPC ............................ 514/318; 546/193; 546/194

(58) Field of Classification Search  
USPC ..................................... 514/318; 546/193, 194  
See application file for complete search history.

(56) References Cited

U.S. PATENT DOCUMENTS

| 5,380,758 A | 1/1995 | Stamler et al. |
|---|---|---|
| 5,703,073 A | 12/1997 | Garvey et al. |

(Continued)

FOREIGN PATENT DOCUMENTS

| CA | 2230931 | 3/1997 |
|---|---|---|
| CA | 2426461 | 4/2002 |

(Continued)

OTHER PUBLICATIONS

Bohlender, J. et al., "Rats Transgenic for Human Renin and Human Angiotensinogen as a Model for Gestational Hypertension", J. Am. Soc. Nephrol., vol. 11, pp. 2056-2061, (2000).

(Continued)

*Primary Examiner* — Celia Chang  
(74) *Attorney, Agent, or Firm* — Hoxie & Associates LLC

(57) ABSTRACT

The present invention relates to 3,4-substituted piperidinyl-based renin inhibitor compounds bearing at 4-position oxopyridine and having the formula (I). The invention further relates to pharmaceutical compositions containing said compounds, as well as their use in treating cardiovascular events and renal insufficiency.

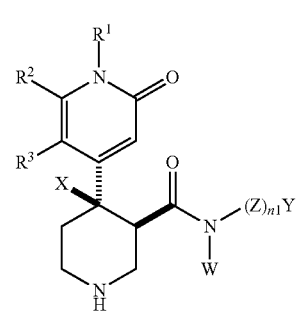

15 Claims, 5 Drawing Sheets

(56) References Cited

U.S. PATENT DOCUMENTS

| | | | |
|---|---|---|---|
| 5,994,294 A | 11/1999 | Garvey et al. | |
| 6,218,417 B1 | 4/2001 | Soldato | |
| 6,242,432 B1 | 6/2001 | Soldato | |
| 8,084,450 B2 * | 12/2011 | Breitenstein et al. | 514/230.5 |
| 8,178,559 B2 * | 5/2012 | Breitenstein et al. | 514/330 |
| 2007/0167433 A1 | 7/2007 | Herold et al. | |
| 2010/0249163 A1 * | 9/2010 | Dube et al. | 514/274 |

FOREIGN PATENT DOCUMENTS

| | | |
|---|---|---|
| WO | WO 98/19672 | 5/1998 |
| WO | 2004096116 | 11/2002 |
| WO | 2003093267 | 11/2003 |
| WO | 2004002957 | 1/2004 |
| WO | 2004089903 | 10/2004 |
| WO | 2004096366 | 11/2004 |
| WO | 2004096769 | 11/2004 |
| WO | 2004096799 | 11/2004 |
| WO | 2004096803 | 11/2004 |
| WO | 2004096804 | 11/2004 |
| WO | 2005040120 | 5/2005 |
| WO | 2005040165 | 5/2005 |
| WO | 2005040173 | 5/2005 |
| WO | 2005054243 | 6/2005 |
| WO | 2005054244 | 6/2005 |
| WO | 2005061457 | 7/2005 |
| WO | 2006005741 | 1/2006 |
| WO | 2006021399 | 3/2006 |
| WO | 2006021401 | 3/2006 |
| WO | 2006021402 | 3/2006 |
| WO | 2006021403 | 3/2006 |
| WO | 2006059304 | 6/2006 |
| WO | 2006061791 | 6/2006 |
| WO | 2006064484 | 6/2006 |
| WO | 2006069788 | 7/2006 |
| WO | 2006074924 | 7/2006 |
| WO | 2006079988 | 8/2006 |
| WO | 2006092268 | 9/2006 |
| WO | 2006094763 | 9/2006 |
| WO | 2006103275 | 10/2006 |
| WO | 2006103277 | 10/2006 |
| WO | 2006125621 | 11/2006 |
| WO | 2006128659 | 12/2006 |
| WO | 2006129237 | 12/2006 |
| WO | 2006131884 | 12/2006 |
| WO | WO 2007/009250 | 1/2007 |
| WO | 2007034406 | 3/2007 |
| WO | 2007034445 | 3/2007 |
| WO | 2007049224 | 5/2007 |
| WO | 2007077005 | 7/2007 |
| WO | 2007088514 | 8/2007 |
| WO | 2007099509 | 9/2007 |
| WO | 2007102127 | 9/2007 |
| WO | 2008036216 | 3/2008 |
| WO | 2009018662 | 2/2009 |
| WO | 2009070869 | 6/2009 |
| WO | 2009140769 | 11/2009 |
| WO | 2011020193 | 2/2011 |

OTHER PUBLICATIONS

Breyer, J.A. et al., "Angiotensin Converting Enzyme Inhibition in Diabetic Nephropathy", Kidney International, vol. 45, Suppl. 45, pp. S-156-S-160, (1994).

Fouad-Tarazi, F. M., et al. "The Renin-Angiotensin System and Treatment of Heart Failure", The American Journal of Medicine, vol. 84, Suppl. 3A, pp. 83-86, (Mar. 11, 1988).

Fraley, M. E., et al., "Optimization of a Pyrazolo[1,5-a]pyrimidine Class of KDR Kinase Inhibitors: Improvements in Physical Properties Enhance Cellular Activity and Pharmacokinetics", Bioorganic & Medicinal Chemistry Letters, vol. 12, pp. 3537-3541, (2002).

Gould, P. L., "Salt Selection for Basic Drugs", International Journal of Pharmaceutics, vol. 33, pp. 201-217, (1986).

Husain, A., "The Chymase-Angiotensin System in Humans," Journal of Hypertension, vol. 11, pp. 1155-1159, (1993).

Israili, Z. H., et al., "Cough and Angioneurotic Edema Associated with Angiotensin-Converting Enzyme Inhibitor Therapy", Annals of Internal Medicine, vol. 117, pp. 234-242, (1992).

Kleinert, H. D., et al., "Renin Inhibition", Cardiovascular Drugs and Therapy, vol. 9, pp. 645-655, (1995).

Larock, R.C., "Comprehensive Organic Transformations", $2^{nd}$ Edition, Wiley-VCH, New York, (1999).

McElroy, W. T., et al., "Siloxane-Based Cross-Coupling of Bromopyridine Derivatives: Studies for the Synthesis of Streptonigrin and Lavendamycin", Organic Letters, vol. 5, No. 25, pp. 4779-4782, (2003).

Oae, S. et al., "Organic Thionitrites and Related Substances. A Review", Organic Preparations and Procedures Int., vol. 15, No. 3, pp. 165-198, (1983).

Paschalidou, K., et al., "Highly Sensitive Intramolecularly Quenched Fluorogenic Substrates for Renin Based on the Combination of L-2-Amino-3-(7-Methoxy-4-Coumaryl)Propionic Acid with 2,4-Dinitrophenyl Groups at Various Positions", Biochem. J., vol. 382, pp. 1031-1038, (2004).

Pfeffer, M.A. et al., "Effect of Captopril on Mortality and Morbidity in Patients with Left Ventricular Dysfunction After Myocardial Infarction", The New England Journal of Medicine, vol. 327, No. 10, pp. 669-677, (Sep. 3, 1992).

Rosenberg, M. E., et al., "The Paradox of the Renin-Angiotensin System in Chronic Renal Disease", Kidney International, vol. 45, pp. 403-410, (1994).

Ujjainwalla, F. et al., "Design and Syntheses of Melanocortin Subtype-4 Receptor Agonists. Part 2: Discovery of the Dihydropyridazinone Motif", Bioorganic and Medicinal Chemistry Letters, vol. 15, pp. 4023-4028, (2005).

Vaughan, D. E., et al. "Angiotensin Converting Enzyme Inhibitors and Cardiovascular Remodelling", Cardiovascular Research, vol. 28, pp. 159-165, (1994).

Waeber, B. et al., "The Renin-Angiotensin System: Role in Experimental and Human Hypertension", Handbook of Hypertension, vol. 8, pp. 489-519, (1986).

Weber, M. A. "Clinical Experience with the Angiotensin II Receptor Antagonist Losartan", The American Journal of Hypertension, vol. 5, pp. 247S-251S, (1992).

* cited by examiner

# 3,4-SUBSTITUTED PIPERIDINE DERIVATIVES AS RENIN INHIBITORS

CROSS-REFERENCE TO RELATED APPLICATIONS

This application claims the benefit of U.S. Provisional Application Nos. 61/188,303 and 61/126,529, filed Aug. 7, 2008 and May 5, 2008, respectively.

JOINT RESEARCH AGREEMENT

The claimed invention was made as a result of activities undertaken within the scope of a joint research agreement between Merck & Co., Inc. and Actelion Pharmaceuticals Ltd. The agreement was executed on Dec. 4, 2003. The field of the invention is described below.

FIELD OF THE INVENTION

The invention relates to novel renin inhibitors of the general formula (I). The invention also concerns related aspects including processes for the preparation of the compounds, pharmaceutical compositions containing one or more compounds of formula (I) and especially their use as renin inhibitors in cardiovascular events and renal insufficiency.

BACKGROUND OF THE INVENTION

In the renin-angiotensin system (RAS) the biologically active angiotensin II (Ang II) is generated by a two-step mechanism. The highly specific enzyme renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAS represents a major advance in the treatment of cardiovascular diseases. ACE inhibitors and $AT_1$ blockers have been accepted to treat hypertension (Waeber B. et al., "The renin-angiotensin system: role in experimental and human hypertension", in Birkenhager W. H., Reid J. L. (eds): *Hypertension*, Amsterdam, Elsevier Science Publishing Co, 1986, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (Suppl. 3A), 83) and myocardial infarction (Pfeffer M. A. et al., *N. Engl. J. Med.*, 1992, 327, 669).

The rationale to develop renin inhibitors is the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be by-passed by chymase, a serine protease (Husain A., *J. Hypertens.*, 1993, 11, 1155). In patients, inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the $AT_1$ receptor (e.g. by losartan) on the other hand overexposes other AT-receptor subtypes (e.g. $AT_2$) to Ang II, whose concentration is significantly increased by the blockade of $AT_1$ receptors. In summary, renin inhibitors are expected to demonstrate a different pharmaceutical profile than ACE inhibitors and $AT_1$ blockers with regard to efficacy in blocking the RAS and in safety aspects.

The present invention relates to the identification of renin inhibitors of a non-peptidic nature and of low molecular weight. Specifically, orally active renin inhibitors are described which are of long duration of action and active in indications beyond blood pressure regulation where the tissular renin-chymase system may be activated leading to pathophysiologically altered local functions such as renal, cardiac and vascular remodeling, atherosclerosis, and possibly restenosis.

The compounds described in this invention represent a novel structural class of renin inhibitors.

SUMMARY OF THE INVENTION

The present invention is directed to certain compounds and their use in the inhibition of the renin enzyme, including treatment of conditions known to be associated with the renin system.

The invention in particular is directed to compounds of Formula I:

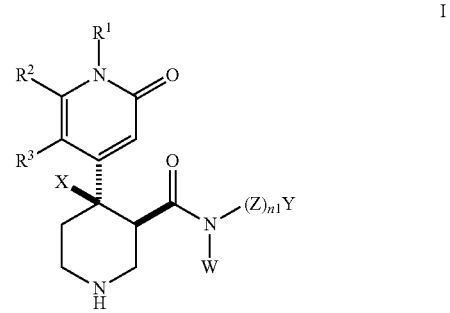

and optically pure enantiomers, mixtures of enantiomers such as racemates, diastereomers, mixtures of diastereomers, diastereomeric racemates, mixtures of diastereomeric racemates, meso-forms, salts, solvates, and morphological forms thereof, wherein constituent members are provided herein.

DETAILED DESCRIPTION OF THE DISCLOSURE

Figure 1A:
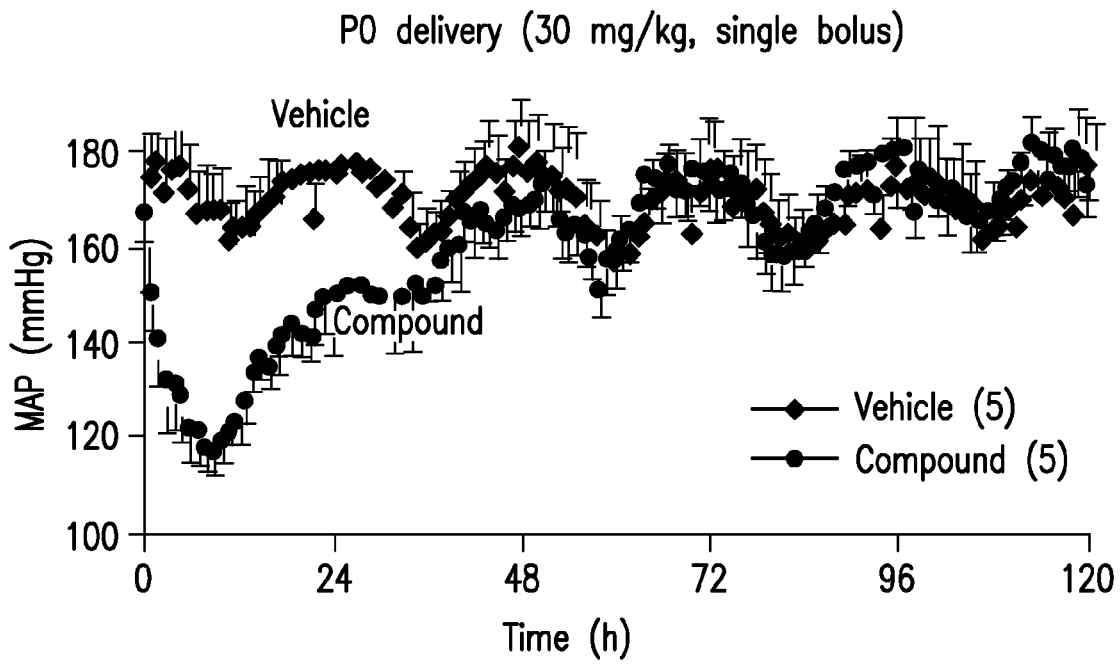
FIGS. 1A-B illustrate a comparison of TD vs. PO delivery of the test compound on mean arterial blood pressure in dTG rats.

The present invention provides compounds having Formula I:

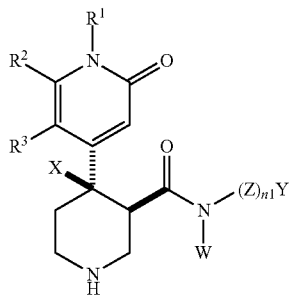

or a pharmaceutically acceptable salt thereof, wherein:
$R^1$ is selected from the group consisting of: $C_1$-$C_6$-alkyl, $C_3$-$C_6$ cycloalkyl, $C_2$-$C_6$ alkenyl, $C_3$-$C_6$ cycloalkenyl and $C_2$-$C_6$ alkynyl, wherein each of the foregoing is optionally substituted with 1-3 halogens and/or $C_1$-$C_5$ alkoxy;

$R^2$ and $R^3$ are independently selected from the group consisting of: hydrogen, halogen, $C_1$-$C_5$ alkyl, $C_3$-$C_8$ cycloalkyl, $C_2$-$C_5$ alkenyl, $C_3$-$C_8$ cycloalkenyl, $C_2$-$C_5$ alkynyl, cyano, $C_1$-$C_5$ alkoxy, aryl and heteroaryl,
wherein said heteroaryl contains from 1 to 3 heteroatoms, independently selected from the group consisting of N, O and S, wherein each N is optionally in the form of an oxide and each S is optionally in the form of an oxide selected from the group consisting of: $S(=O)$ and $S(=O)_2$,
wherein said aryl and heteroaryl are optionally substituted with 1-4 halogens,
wherein said alkyl, cycloalkyl, alkenyl, cycloalkenyl, alkynyl and alkoxy are optionally substituted with 1-3 substituents, each of which is independently selected from the group consisting of: halogen, $C_1$-$C_5$ alkyl, $C_2$-$C_5$ alkenyl, cyano and $C_1$-$C_5$ alkoxy, wherein each of the foregoing alkyl, alkenyl and alkoxy substituents is optionally substituted with 1-3 halogens;

W is cyclopropyl, unsubstituted or mono-, di-, tri-, tetra- or penta-substituted with fluorine;

X is selected from the group consisting of: $OR^4$, $R^4$, $-(C_1$-$C_5$ alkylene)-$(O)_{0-1}$-aryl and $-(C_1$-$C_5$ alkylene)-$(O)_{0-1}$-heteroaryl,
wherein $R^4$ is selected from the group consisting of: hydrogen, $C_1$-$C_5$ alkyl, $C_3$-$C_8$ cycloalkyl, $C_2$-$C_5$ alkenyl, $C_3$-$C_8$ cycloalkenyl, $C_2$-$C_5$ alkynyl, $C_1$-$C_5$-cyano, $-(C_1$-$C_5$ alkylene)-O-$R^5$, $-(C_1$-$C_5$ alkylene)-N($-R^5$)-C(=O)-$(C_1$-$C_5$ alkyl), $-(C_1$-$C_5$ alkylene)-C(=O)-N($-R^5$)-$(C_1$-$C_5$ alkyl), $-(C_1$-$C_5$ alkylene)-N($-R^5$)-C(=O)-O-$(C_1$-$C_5$ alkyl), $-(C_1$-$C_5$ alkylene)-O-C(=O)-N($-R^5$)-$(C_1$-$C_5$ alkyl); $-(C_1$-$C_5$ alkylene)-N($-R^5$)-$(C_1$-$C_5$ alkyl), $-(C_1$-$C_5$ alkylene)-S-$(C_1$-$C_5$ alkyl), $-(C_1$-$C_5$ alkylene)-S(=O)-$(C_1$-$C_5$ alkyl) and $-(C_1$-$C_5$ alkylene)-S(=O)$_2$-$(C_1$-$C_5$ alkyl),
wherein $R^4$, except hydrogen, is optionally substituted with 1-3 substituents, independently selected from the group consisting of: halogen, C(=O)OH, $C_1$-$C_5$ alkyl, $C_2$-$C_5$ alkenyl, and $C_1$-$C_5$ alkoxy, wherein each of the alkyl, alkenyl, and alkoxy substituents is optionally substituted with 1-3 halogens,
wherein the heteroaryl of the $-(C_1$-$C_5$ alkylene)-$(O)_{0-1}$-heteroaryl contains 1-3 heteroatoms, independently selected from the group consisting of: N, O and S, wherein each N is optionally in the form of an oxide and each S is optionally in the form of an oxide selected from the group consisting of: $S(=O)$ and $S(=O)_2$,
wherein the aryl and heteroaryl of $-(C_1$-$C_5$ alkylene)-$(O)_{0-1}$-aryl and $-(C_1$-$C_5$ alkylene)-$(O)_{0-1}$-heteroaryl, respectively, are optionally substituted with 1-4 halogens, and
wherein $R^5$ is selected from the group consisting of: hydrogen, $C_1$-$C_6$ alkyl, $C_3$-$C_6$ cycloalkyl, $C_2$-$C_6$ alkenyl, $C_3$-$C_6$ cycloalkenyl, and $C_2$-$C_6$ alkynyl, wherein each of the foregoing alkyl, cycloalkyl, alkenyl, cycloalkenyl and alkynyl substituents is optionally substituted with 1-3 halogens;

Z is $C_1$-$C_2$ alkylene optionally substituted with 1-2 substituents, independently selected from the group consisting of: halogen, $C_1$-$C_3$ alkyl and $C_3$ cycloalkyl, wherein the foregoing alkyl and cycloalkyl substituents are optionally substituted with 1-3 halogens;

n1 is 0 or 1;

Y is (i) a five- or six-membered saturated or unsaturated heterocyclic or carbocyclic monocyclic ring ("monocyclic ring") or (ii) a five- or six-membered saturated or unsaturated heterocyclic or carbocyclic ring which is fused to a five- or six-membered saturated or unsaturated heterocyclic or carbocyclic ring ("fused ring"),
wherein the heterocyclic ring(s) of (i) or (ii) contain from 1-3 heteroatoms, independently selected from N, O and S, wherein each N is optionally in the form of an oxide and each S is optionally in the form of an oxide selected from the group consisting of: $S(=O)$ and $S(=O)_2$,
wherein the heterocyclic or carbocyclic ring(s) of (i) or (ii) is optionally mono-, di-, tri-, tetra-, penta- or hexa-substituted, each substituent of which is independently selected from the group consisting of:
(1) halogen,
(2) —OH,
(3) —NH($R^6$),
(4) oxo,
(5) —C(=O)—$R^6$,
(6) —O—C(=O)—$R^6$,
(7) $C_1$-$C_5$ alkyl optionally substituted with 1-3 halogens,
(8) $C_3$-$C_8$ cycloalkyl optionally substituted with 1-3 halogens,
(9) $C_2$-$C_5$ alkenyl optionally substituted with 1-3 halogens,
(10) $C_3$-$C_8$ cycloalkenyl optionally substituted with 1-3 halogens,
(11) $C_2$-$C_5$ alkynyl optionally substituted with 1-3 halogens,
(12) $C_1$-$C_5$ alkoxy optionally substituted with 1-3 halogens,
(13) cyano,
(14) $C_1$-$C_5$-cyano optionally substituted with 1-3 halogens,
(15) —$OCF_3$,
(16) —C($R^7$)$_3$,
(17) —$(C_1$-$C_5$ alkylene)-$OR^8$ optionally substituted with 1-3 halogens,
(18) —N($R^6$)—$(C_1$-$C_5$ alkylene)-$OR^8$ optionally substituted with 1-3 halogens,
(19) —O—$(C_1$-$C_5$ alkylene)-$OR^8$ optionally substituted with 1-3 halogens,
(20) —S—$(C_1$-$C_5$ alkylene)-$OR^8$ optionally substituted with 1-3 halogens,
(21) —S(=O)—$(C_1$-$C_5$ alkylene)-$OR^8$ optionally substituted with 1-3 halogens,

(22) —S(=O)₂—(C₁-C₅ alkylene)-OR⁸ optionally substituted with 1-3 halogens,
(23) —(C₁-C₅ alkylene)-N(R⁶)—C(=O)—(C₁-C₅ alkylene)-R⁸ optionally substituted with 1-3 halogens,
(24) —(C₁-C₅ alkylene)-N(R⁶)—C(=O)—OR⁸ optionally substituted with 1-3 halogens,
(25) —(C₁-C₅ alkylene)-N(R⁶)(R⁸) optionally substituted with 1-3 halogens,
(26) —O—(C₁-C₅ alkylene)-C(R⁶)₂—C(=O)OR⁸ optionally substituted with 1-3 halogens,
(27) —(C₁-C₅ alkylene)-C(R⁶)₂—C(=O)—OR⁸ optionally substituted with 1-3 halogens,
(28) —O—(C₁-C₅ alkylene)-morpholine optionally substituted with 1-3 halogens,
(29) —OC(=O)-morpholine,
(30) —SR⁸,
(31) —S(=O)—R⁸,
(32) —S(=O)₂—R⁸
(33) —N(R⁶)(R⁸),
(34) —(C₁-C₅ alkylene)-C(R⁶)₂—(R⁸) optionally substituted with 1-3 halogens,
(35) —(R⁹)₀₋₁R¹⁰,
(36) C₂-C₅ alkenyl-OR⁸ optionally substituted with 1-3 halogens,
(37) C₂-C₅ alkynyl-OR⁸ optionally substituted with 1-3 halogens,
(38) —(C₁-C₅ alkylene)-C(=O)—(C₁-C₅ alkylene)-R⁸ optionally substituted with 1-3 halogens,
(39) —(C₁-C₅ alkylene)-O—C(=O)—(C₁-C₅ alkylene)-R⁸ optionally substituted with 1-3 halogens,
(40) —(C₁-C₅ alkylene)-C(=O)—N(R⁶)(R⁸) optionally substituted with 1-3 halogens,
(41) —(C₁-C₅ alkylene)-O—C(=O)—N(R⁶)(R⁸) optionally substituted with 1-3 halogens,
(42) —(C₁-C₅ alkylene)-SR⁸ optionally substituted with 1-3 halogens,
(43) —(C₁-C₅ alkylene)-S(=O)—R⁸ optionally substituted with 1-3 halogens, and
(44) —(C₁-C₅ alkylene)-S(=O)₂—R⁸ optionally substituted with 1-3 halogens, wherein R⁶ is selected from the group consisting of: hydrogen, C₁-C₆ alkyl, C₃-C₈ cycloalkyl, C₂-C₆ alkenyl, C₃-C₈ cycloakenyl and C₂-C₆ alkynyl, wherein each of the foregoing alkyl, cycloalkyl, alkenyl, cycloalkenyl and alkynyl substituents is optionally substituted with 1-3 halogens, wherein R⁷ is halogen, wherein R⁸ is selected from the group consisting of: hydrogen, C₁-C₆ alkyl, C₃-C₈ cycloalkyl, C₂-C₆ alkenyl, C₃-C₈ cycloalkenyl and C₂-C₆ alkynyl, wherein each of the foregoing alkyl, cycloalkyl, alkenyl, cycloalkenyl and alkynyl substituents is optionally substituted with 1-3 halogens, wherein R⁹ is selected from the group consisting of:
—C(H)(OH)—, —C(=O)—, —OC(=O)—, —C(=O)O—, —O—, —OC(=O)O—, C₁-C₅ alkylene, C₂-C₅ alkenylene, —N(R⁶)—, —S—, —S(=O)—, —S(=O)₂—, —N(R⁶)—C(=O)—, —C(=O)—N(R⁶)—, —OC(=O)—N(R⁶)—, —N(R⁶)—C(=O)O—, —N(R⁶)—S(=O)₂—, —S(=O)₂—N(R⁶)—, wherein each of the foregoing alkylene and alkenylene substituents is optionally substituted with 1-3 halogens, and wherein R⁶ is defined above, and wherein R¹⁰ is a five- or six-membered saturated or unsaturated heterocyclic or carbocyclic ring which is optionally mono-, di-, tri-, tetra- or penta-substituted, wherein each substituent is independently selected from the group consisting of: halogen, —OH, —SR⁶, —N(R⁶)(R⁸), C₁-C₅ alkyl, C₃-C₈ cycloalkyl, C₂-C₅ alkenyl, C₃-C₆ cycloalkenyl, C₂-C₅ alkynyl, C₁-C₅ alkoxy, cyano and C₁-C₅-cyano, wherein said heterocyclic ring contains from 1 to 3 heteroatoms, independently selected from N, O and S, wherein each N is optionally in the form of an oxide and each S is optionally is in the form of an oxide selected from the group consisting of: S(=O) or S(=O)₂, and wherein R6 and R8 are defined above.

In one embodiment, the invention provides compounds of Formula I, or a pharmaceutically acceptable salt thereof, or an optical isomer thereof, wherein the monocyclic or fused ring(s) of Y (i) or (ii), respectively, is selected from the following:

TABLE 3

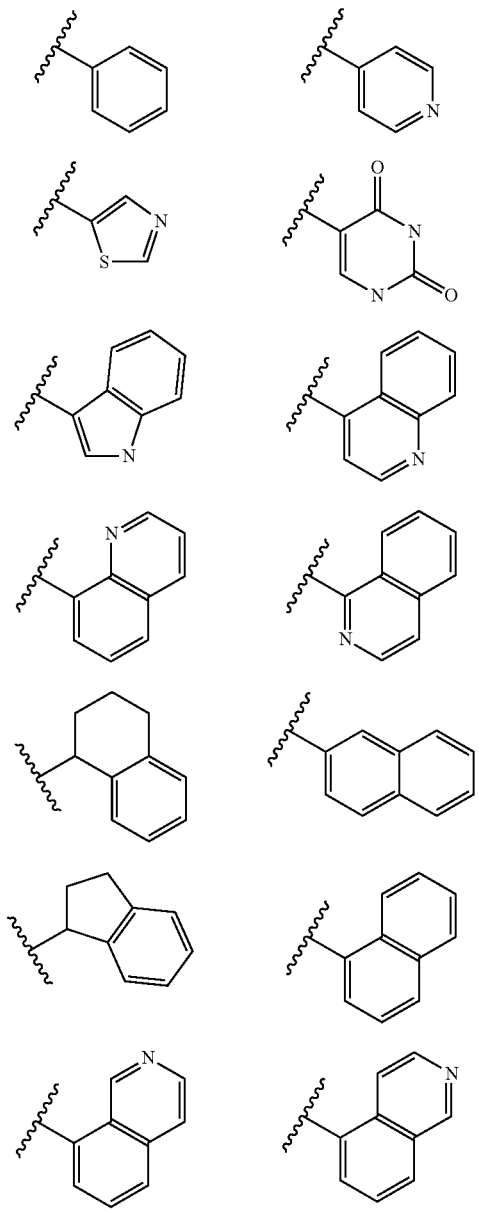

TABLE 3-continued

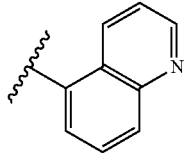 [SMILES: *c1cccc2ncccc12]

optionally mono-, di-, tri-, tetra- or penta-substituted as described in Formula I.

In another embodiment, the invention provides compounds of Formula I, or a pharmaceutically acceptable salt thereof, or an optical isomer thereof, wherein $R^1$ is —$CH_3$ or —$CH_2CH_3$.

In another embodiment, the invention provides compounds of Formula I, or a pharmaceutically acceptable salt thereof, or an optical isomer thereof, wherein $R^2$ and $R^3$ are independently selected from the group consisting of: H, —$OCH_2OCH_3$ and —$CH_3$.

In another embodiment, the invention provides compounds of Formula I, or a pharmaceutically acceptable salt thereof, or an optical isomer thereof, wherein X is H, —OH or —$OCH_3$.

In another embodiment, the invention provides compounds of Formula I, or a pharmaceutically acceptable salt thereof, or an optical isomer thereof, wherein W is cyclopropyl.

In another embodiment, the invention provides compounds of Formula I, or a pharmaceutically acceptable salt thereof, or an optical isomer thereof, wherein $(Z)_{n1}$ is —$CH_2$— or a bond.

In another embodiment, the invention provides compounds of Formula I, or a pharmaceutically acceptable salt thereof, or an optical isomer thereof, wherein:
  $R^1$ is $C_1$-$C_2$ alkyl optionally substituted with 1-3 halogens,
  $R^2$ and $R^3$ are independently selected from the group consisting of: hydrogen, halogen, $C_1$-$C_5$ alkyl, $C_1$-$C_5$ alkoxy and —O—($C_1$-$C_5$ alkylene)-O—$(CH_2)_{0-3}$—$CH_3$, wherein the alkyl, alkoxy and —O—($C_1$-$C_5$ alkylene)-O—$(CH_2)_{0-3}$—$CH_3$ are optionally substituted with 1-3 substituents independently selected from the group consisting of: halogen, $C_1$-$C_5$ alkyl optionally substituted with 1-3 halogens and $C_1$-$C_5$ alkoxy optionally substituted with 1-3 halogens,
  X is selected from the group consisting of hydrogen, —OH and $C_1$-$C_5$ alkoxy, and
  Z is $C_1$-$C_2$ alkylene.

In another embodiment, the invention provides compounds of Formula I, or a pharmaceutically acceptable salt thereof, or an optical isomer thereof, wherein Y is

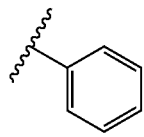 [SMILES: *c1ccccc1]

optionally mono-, di-, tri-, tetra- or penta-substituted as described in Formula I.

In another embodiment, the invention provides compounds of Formula II, or a pharmaceutically acceptable salt thereof, or an optical isomer thereof,

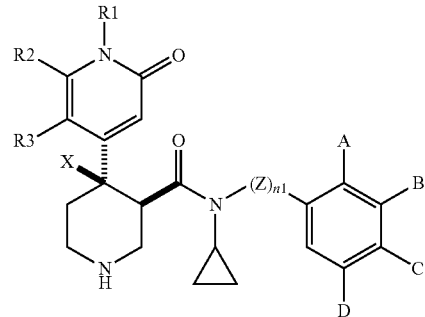

II wherein:
  A is selected from the group consisting of:
    (1) hydrogen,
    (2) halogen,
    (3) $C_1$-$C_5$ alkyl,
    (4) $C_1$-$C_5$ alkoxy, and
    (5) —S—$(CH_2)_{0-3}$—$CH_3$,
    wherein (3) and (4) are optionally substituted with 1-3 halogens,
  B is selected from the group consisting of:
    (1) hydrogen,
    (2) halogen,
    (3) $C_1$-$C_5$ alkyl,
    (4) $C_1$-$C_5$ alkoxy,
    (5) —OH,
    (6) —$CF_3$,
    (7) —C(=O)—$CH_3$,
    (8) —O—($C_1$-$C_5$ alkylene)-O-cyclopropyl,
    (9) —O—($C_1$-$C_5$ alkylene)-O—$(CH_2)_{0-2}$—$CH_3$,
    (10) —($C_1$-$C_5$ alkylene)-O—$(CH_2)_{0-2}$—$CH_3$,
    (11) —OC(=O)-morpholine,
    (12) —O—($C_1$-$C_5$ alkylene)-morpholine,
    (13) —O—($C_1$-$C_5$ alkylene)-C$(CH_3)_2$—C(=O)OH,
    (14) —O—($C_1$-$C_5$ alkylene)-C$(CH_3)_2$—C(=O)O$CH_3$,
    (15)

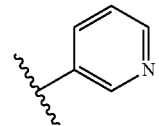 [SMILES: *c1cccnc1]

and
    (16)

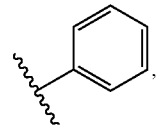

wherein (3), (4), (8), (9), (10), (12), (13), (14), (15) and (16) are optionally substituted with 1-3 halogens,
  C is selected from the group consisting of:
    (1) hydrogen,
    (2) $C_1$-$C_5$ alkyl optionally substituted with 1-3 halogens, and
    (3) $C_1$-$C_5$ alkoxy optionally substituted with 1-3 halogens, and D is selected from the group consisting of:
(1) hydrogen,
(2) halogen,
(3) $C_1$-$C_5$ alkyl,
(4) $C_1$-$C_5$ alkoxy,
(5) $C_1$-$C_5$-cyano,
(6) $C_2$-$C_5$ alkenylene-O—$(CH_2)_{0-2}$—$CH_3$,
(7) —($C_1$-$C_5$ alkylene)-N(H)—C(=O)—O—$(CH_2)_{0-2}$—$CH_3$,
(8) —($C_1$-$C_5$ alkylene)-N(H)—C(=O)—$(CH_2)_{0-2}$—$CH_3$,
(9) —($C_1$-$C_5$ alkylene)-O—$CHF_2$,
(10) —($C_1$-$C_5$ alkylene)-O—$(CH_2)_{0-2}$—$CH_3$,
(11) —O—($C_1$-$C_5$ alkylene)-O—$(CH_2)_{0-2}$—$CH_3$,
(12) —($C_1$-$C_5$ alkylene)-OH,
(13) —S—($C_1$-$C_5$ alkylene)-OH,
(14) —$SCF_3$
(15) —N(H)—($C_1$-$C_5$ alkylene)-O—$(CH_2)_{0-2}$—$CH_3$, and
(16)

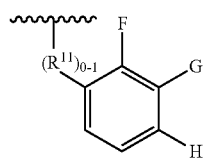

wherein F, G and H are independently selected from the group consisting of: hydrogen, halogen and $C_1$-$C_3$ alkyl optionally substituted with 1-3 halogens, and
wherein $R^{11}$ is selected from the group consisting of: —$CH_2$—, —C(H)(OH)— and —C(=O)—,
wherein (3), (4), (5), (6), (7), (8), (9), (10), (11), (12), (13) and (15) are optionally substituted with 1-3 halogens, and
wherein $R^1$, $R^2$, $R^3$, X and $(Z)_{n1}$ are as described in Formula I.

In another embodiment, the invention provides compounds of Formula I, or a pharmaceutically acceptable salt thereof, or an optical isomer thereof, wherein Y is

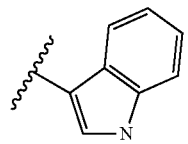 [SMILES: *c1c[nH]c2ccccc12]

optionally mono-, di-, tri-, tetra-, penta- or hexa-substituted as described above in Formula I.

In another embodiment, the invention provides compounds of Formula III, or a pharmaceutically acceptable salt thereof, or an optical isomer thereof,

III

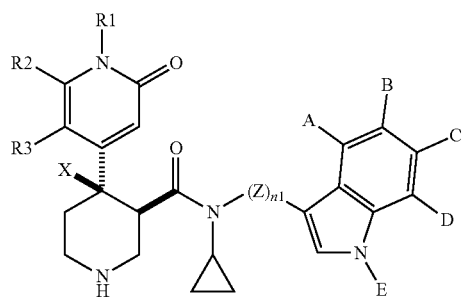

wherein:
A is selected from the group consisting of:
(1) hydrogen,
(2) halogen,
(3) $C_1$-$C_5$ alkyl optionally substituted with 1-3 halogens,
(4) $C_1$-$C_5$ alkoxy optionally substituted with 1-3 halogens, and
(5) cyano, and
B is selected from the group consisting of: hydrogen and halogen,
C is selected from the group consisting of:
(1) hydrogen,
(2) halogen,
(3) $C_1$-$C_5$ alkyl optionally substituted with 1-3 halogens,
(4) $C_1$-$C_5$ alkoxy optionally substituted with 1-3 halogens, and
(5) cyano,
D is selected from the group consisting of:
(1) hydrogen,
(2) halogen,
(3) $C_1$-$C_5$ alkyl optionally substituted with 1-3 halogens,
(4) $C_1$-$C_5$ alkoxy optionally substituted with 1-3 halogens,
(5) —($C_1$-$C_5$ alkylene)-O—$(CH_2)_{0-2}$—$CH_3$ optionally substituted with 1-3 halogens, and
(5) cyano, and
E is selected from the group consisting of:
(1) hydrogen,
(2) halogen,
(3) $C_1$-$C_5$ alkyl,
(4) $C_1$-$C_5$ alkenyl,
(5) $C_1$-$C_5$ alkoxy,
(6) cyano,
(7) —($C_1$-$C_5$ alkylene)-C(CF$_3$)$_2$(H),
(8) —($C_1$-$C_5$ alkylene)-N(H)—C(=O)—$(CH_2)_{0-2}$—$CH_3$,
(9) —($C_1$-$C_5$ alkylene)-O—$(CH_2)_{0-2}$—$CH_3$, (10)

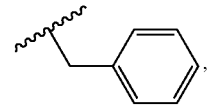

(11)

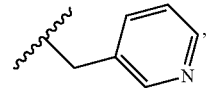

(12)

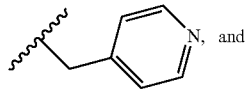

, and (13)

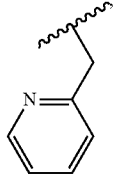

wherein (3), (4), (5), (7), (8) and (9) are optionally substituted with 1-3 halogens, and
wherein (10), (11), (12) and (13) are optionally substituted with 1-3 substituents independently selected from the group consisting of: halogen, $C_1$-$C_5$ alkyl, $C_1$-$C_5$ alkoxy and cyano,
wherein $R^1$, $R^2$, $R^3$, X and $(Z)_{n1}$ are as described in Formula I.

In another embodiment, the invention provides compounds of Formula I, or a pharmaceutically acceptable salt thereof, or an optical isomer thereof, wherein Y is selected from the group consisting of:

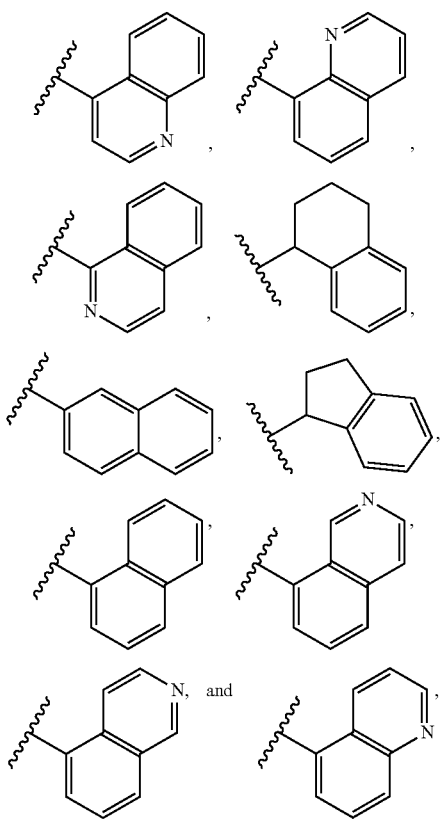
optionally mono-, di-, tri-, tetra- or penta-substituted as described above in Formula I.
In another embodiment, the invention provides the following compounds of Formula I, or a pharmaceutically acceptable salt thereof, or an optical isomer thereof, having the following formulas:
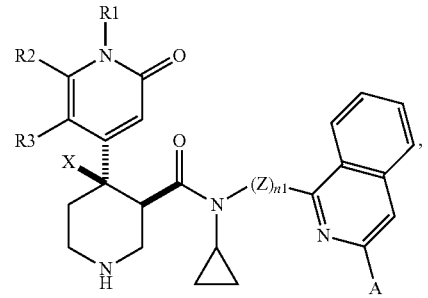
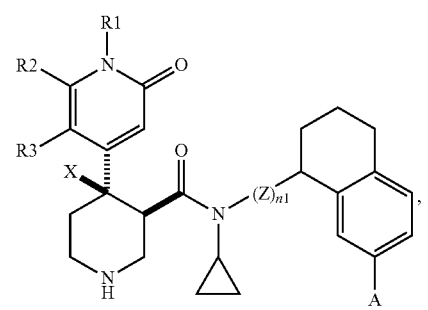
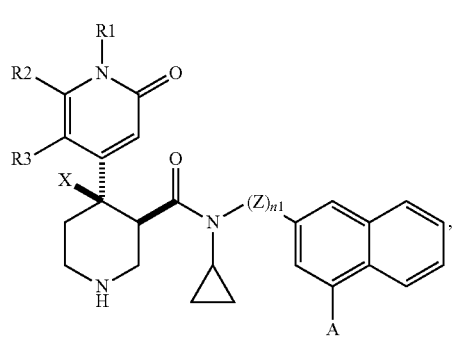
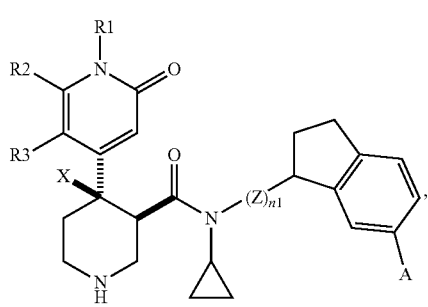
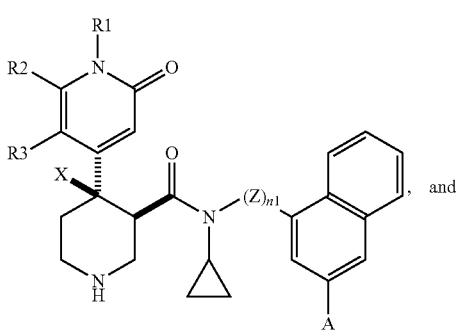

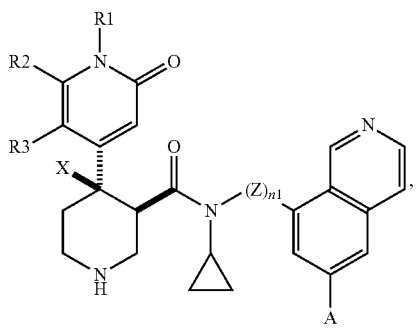

wherein A is selected from the group consisting of:
(1) hydrogen,
(2) halogen,
(3) $C_1$-$C_5$ alkyl,
(4) $C_1$-$C_5$ alkoxy,
(5) cyano,
(6) $C_1$-$C_5$-cyano,
(7) —($C_1$-$C_5$ alkylene)-N(H)—C(=O)—$(CH_2)_{0-2}$—$CH_3$,
(8) —($C_1$-$C_5$ alkylene)-O—$(CH_2)_{0-2}$—$CH_3$, and
(9) —N(H)—($C_1$-$C_5$ alkylene)-O—$(CH_2)_{0-2}$—$CH_3$,
wherein (3), (4), (6), (7), (8) and (9) are optionally substituted with 1-3 halogens, and
wherein $R^1$, $R^2$, $R^3$, X and $(Z)_{n1}$ are as described above in Formula I.

In another embodiment, the invention provides compounds of Formula I, or a pharmaceutically acceptable salt thereof, or an optical isomer thereof, wherein Y is

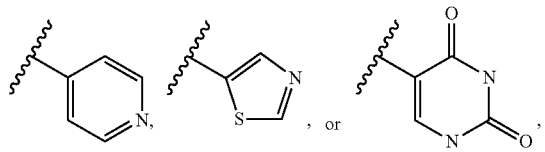

optionally mono- or di-substituted as described above for Formula I.

In another embodiment, the invention provides the following compounds of Formula I, or a pharmaceutically acceptable salt thereof, or an optical isomer thereof, which is

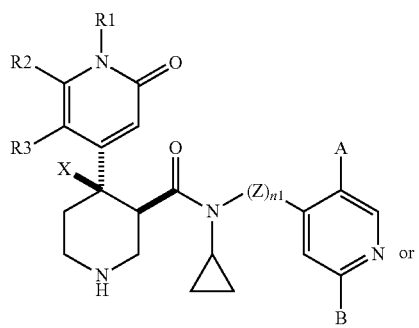

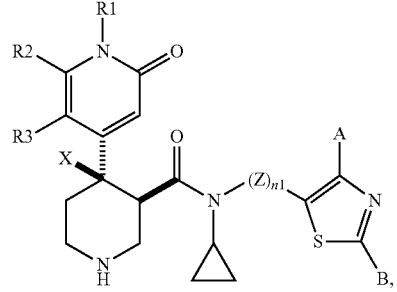

wherein:
A is selected from the group consisting of:
(1) hydrogen,
(2) halogen,
(3) $C_1$-$C_5$ alkyl,
(4) $C_1$-$C_5$ alkoxy, and
(5) —($C_1$-$C_5$ alkylene)-O—$(CH_2)_{0-2}$—$CH_3$,
wherein (3), (4) and (5) are optionally substituted with 1-3 halogens, and
B is selected from the group consisting of:
(1) hydrogen,
(2) halogen,
(3) $C_1$-$C_5$ alkyl,
(4) $C_1$-$C_5$ alkoxy,
(5) —($C_1$-$C_5$ alkylene)-O—$(CH_2)_{0-2}$—$CH_3$, and
(6) —N(H)—($C_1$-$C_5$ alkylene)-O—$(CH_2)$—O—$(CH_2)_{0-2}$—$CH_3$,
wherein (3), (4), (5) and (6) are optionally substituted with 1-3 halogens, and
wherein $R^1$, $R^2$, $R^3$, X and $(Z)_{n1}$ are as described above in Formula I.

The present invention also relates to crystalline forms of Formula I. In particular embodiments, the present invention relates to crystalline Form I defined as (3S,4R)-N-({3-Bromo-4-methyl-5-[3-(methyloxy)propyl]phenyl}methyl)-N-cyclopropyl-4-(1-methyl-2-oxo-1,2-dihydro-4-pyridinyl)-3-piperidinecarboxamide hydrochloride or a pharmaceutically acceptable hydrate thereof. In other embodiments, the present invention relates to crystalline forms of Formula I (e.g., Form I as described above) characterized by $^{13}$C-SSNMR as having chemical shift peaks having at least one or more of the following chemical shifts expressed in parts per million: 120.1, 31.2, 17.1, 43.5, 41.6, 29.4, 58.5, 71.4, 28.7, 42.5, 138.3, and 143.6. Specific embodiments have at least two, three, four, five, six seven, eight, nine, ten or eleven of the above chemical shifts. Other embodiments have all 12 chemical shifts. In other embodiments, the present invention relates to crystalline forms of Formula I (e.g., Form I as described above) characterized by the solid-state $^{13}$C-SSNMR CPMAS nuclear magnetic resonance spectrum of FIG. 2. In other embodiments, the present invention relates to crystalline forms of Formula I (e.g., Form I as described above) characterized by the thermogravimetric analysis curve of FIG. 3. In other embodiments, the present invention relates to crystalline forms of Formula I (e.g., Form I as described above) characterized by the differential scanning calorimetry curve of FIG. 4. In other embodiments, the present invention relates to crystalline forms of Formula I (e.g., Form I as described above) characterized by X-ray powder diffraction as having one or more of the following reflections corresponding to d-spacings: 10.59, 7.04, 4.24, 4.22, 3.88, 3.58, 3.51, 3.31 and 3.08. Specific embodiments have at least two, three, four, five, six seven or eight of the above reflections. Other embodiments have all nine reflections. In other embodiments, the present invention relates to crystalline forms of Formula I (e.g., Form I as described above) characterized by the X-ray diffraction pattern of FIG. 5.

The compounds of Formula I above, and pharmaceutically acceptable salts thereof, are renin inhibitors. The compounds are useful for inhibiting renin and treating conditions such as hypertension.

Any reference to a compound of formula (I) is to be understood as referring also to optically pure enantiomers, mixtures of enantiomers such as racemates, diastereomers, mixtures of diastereomers, diastereomeric racemates, mixtures of diastereomeric racemates, meso-forms, as well as salts (especially pharmaceutically acceptable salts) and solvates (including hydrates) of such compounds, and morphological forms, as appropriate and expedient. The present invention encompasses all these forms. Mixtures are separated in a manner known per se, e.g. by column chromatography, thin layer chromatography (TLC), high performance liquid chromatography (HPLC), or crystallization. The compounds of the present invention may have chiral centers, e.g. one chiral center (providing for two stereoisomers, (R) and (S)), or two chiral centers (providing for up to four stereoisomers, (R,R), (S,S), (R,S), and (S,R)). This invention includes all of these optical isomers and mixtures thereof. Unless specifically mentioned otherwise, reference to one isomer applies to any of the possible isomers. Whenever the isomeric composition is unspecified, e.g., when bonds to a chiral carbon are depicted as straight lines, it is understood that both (R) and (S) configurations of that chiral carbon, and hence both enantiomers and mixtures thereof, are represented.

In addition, compounds with carbon-carbon double bonds may occur in Z- and E-forms with all isomeric forms of the compounds being included in the present invention.

Compounds of the invention also include nitrosated compounds of formula (I) that have been nitrosated through one or more sites such as oxygen (hydroxyl condensation), sulfur (sulfydryl condensation) and/or nitrogen. The nitrosated compounds of the present invention can be prepared using conventional methods known to one skilled in the art. For example, known methods for nitrosating compounds are described in U.S. Pat. Nos. 5,380,758, 5,703,073, 5,994,294, 6,242,432 and 6,218,417; WO 98/19672; and Oae et al., Org. Prep. Proc. Int., 15(3): 165-198 (1983).

Salts are, in specific embodiments, the pharmaceutically acceptable salts of the compounds of Formula (I). The expression "pharmaceutically acceptable salts" encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, palmoic acid, stearic acid, glutamic acid, aspartic acid, methanesulfonic acid, ethanesulfonic acid, ethanedisulfonic acid, p-toluenesulfonic acid, salicylic acid, succinic acid, trifluoroacetic acid, and the like that are non toxic to living organisms or, in case the compound of formula (I) is acidic in nature, with an inorganic base like an alkali or earth alkali base, e.g. sodium hydroxide, potassium hydroxide, calcium hydroxide and the like. For other examples of pharmaceutically acceptable salts, reference can be made notably to "Salt selection for basic drugs", *Int. J. Pharm.* (1986), 33, 201-217.

The invention also includes derivatives of the compound of Formula I, acting as prodrugs. These prodrugs, following administration to the patient, are converted in the body by normal metabolic processes to the compound of Formula I. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The general terms used hereinbefore in Formula I and hereinafter have, within this disclosure, the following meanings, unless otherwise indicated. Where the plural form is used for compounds, salts, pharmaceutical compositions, diseases and the like, this is intended to mean also a single compound, salt, or the like.

The term "alkyl", alone or in combination with other groups, unless indicated otherwise, means saturated, straight and branched chain groups with one to six carbon atoms (which may be represented by "$C_{1-6}$ alkyl" or "$C_1$-$C_6$ alkyl"). When the intended meaning is other than this, for example, when the number of carbon atoms is in the range of one to four carbon atoms, this meaning is represented in like fashion as "$C_{1-4}$ alkyl" or "$C_1$-$C_4$ alkyl". Examples of alkyl groups are methyl, ethyl, n-propyl, iso-propyl, n-butyl, iso-butyl, sec-butyl, tert-butyl, pentyl, hexyl and heptyl. The methyl, ethyl and isopropyl groups are used in specific embodiments herein.

Structural depictions of compounds may show a terminal methyl group as "—CH$_3$", "CH$_3$", "-Me", "Me" or

(i.e., these have equivalent meanings). A terminal ethyl group may be depicted as "—CH$_2$CH$_3$", "CH$_2$CH$_3$", "-Et", "Et" or

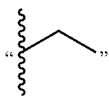

(i.e. these have equivalent meanings).

The term "alkylene" refers to any divalent linear or branched chain aliphatic hydrocarbon radical having a number of carbon atoms in the specified range. Thus, for example, "—$C_1$-$C_6$ alkylene-" refers to any of the $C_1$ to $C_6$ linear or branched alkylenes, and "—$C_1$-$C_4$ alkylene-" refers to any of the $C_1$ to $C_4$ linear or branched alkylenes. A class of alkylenes of particular interest with respect to the invention is —(CH$_2$)$_{1-6}$—, and sub-classes of particular interest include —(CH$_2$)$_{1-4}$—, —(CH$_2$)$_{1-3}$—, —(CH$_2$)$_{1-2}$—, and —CH$_2$—. Another sub-class of interest is an alkylene selected from the group consisting of —CH$_2$—, —CH(CH$_3$)—, and —C(CH$_3$)$_2$—. Expressions such as "$C_1$-$C_4$ alkylene-phenyl" and "$C_1$-$C_4$ alkyl substituted with phenyl" have the same meaning and are used interchangeably.

The term "alkenyl", alone or in combination with other groups, unless indicated otherwise, means unsaturated (i.e., having at least one double bond) straight and branched chain groups with two to six carbon atoms (which may be represented by "$C_{2-6}$ alkenyl" or "$C_2$-$C_6$ alkenyl"). When the intended meaning is other than this, for example, when the number of carbon atoms is in the range of two to four carbon atoms, this meaning is represented in like fashion as "$C_{2-4}$ alkenyl" or "$C_2$-$C_4$ alkenyl".

The term "alkenylene" refers to any divalent linear or branched chain aliphatic mono-unsaturated hydrocarbon radical having a number of carbon atoms in the specified range.

The term "alkynyl", alone or in combination with other groups, unless indicated otherwise, means unsaturated (i.e., having at least one triple bond) straight and branched chain groups with two to six carbon atoms (which may be represented by "$C_{2-6}$ alkynyl" or "$C_2$-$C_6$ alkynyl"). When the intended meaning is other than this, for example, when the number of carbon atoms is in the range of two to four carbon atoms, this meaning is represented in like fashion as "$C_{2-4}$ alkynyl" or "$C_2$-$C_4$ alkynyl".

The term "alkoxy", alone or in combination with other groups, refers to an R—O— group, wherein R is an alkyl group. Examples of alkoxy groups are methoxy, ethoxy, propoxy, iso-propoxy, iso-butoxy, sec-butoxy and tert-butoxy.

The term "hydroxy-alkyl", alone or in combination with other groups, refers to an HO—R— group, wherein R is an alkyl group. Examples of hydroxy-alkyl groups are HO—CH$_2$—, HO—CH$_2$CH$_2$—, HO—CH$_2$CH$_2$CH$_2$— and CH$_3$CH(OH)—.

The term "halogen" means fluorine, chlorine, bromine or iodine. In specific embodiments, halogen is fluorine, chlorine or bromine. In particular embodiments, halogen is fluorine or chlorine.

The term "cycloalkyl", alone or in combination with other groups, unless indicated otherwise, means a saturated cyclic hydrocarbon ring system with 3 to 8 carbon atoms, e.g., cyclopropyl, cyclobutyl, cyclopentyl, cyclohexyl, cycloheptyl and cyclooctyl. This may be represented by "$C_{3-8}$ cycloalkyl" or "$C_3$-$C_8$ cycloalkyl"). When the intended meaning is other than this, for example, when the number of carbon atoms is in the range of three to six carbon atoms, this meaning is represented in like fashion as "$C_{3-6}$ cycloalkyl" or "$C_3$-$C_6$ cycloalkyl".

The term "carbocycle" (and variations thereof such as "carbocyclic" or "carbocyclyl") as used herein, unless otherwise indicated, refers to a $C_3$ to $C_8$ monocyclic saturated or unsaturated ring. The carbocycle may be attached to the rest of the molecule at any carbon atom which results in a stable compound. Saturated carbocyclic rings are also referred to as cycloalkyl rings, e.g., cyclopropyl, cyclobutyl, etc.

The term "monocycle" (and variations thereof such as "monocyclic") as used herein refers to a single ring which may be substituted or unsubstituted with one or more substituents as described herein.

The term "heterocycle" (and variations thereof such as "heterocyclic" or "heterocyclyl") broadly refers to a stable 4- to 8-membered, saturated or unsaturated monocyclic ring which contains one or more heteroatoms (e.g., from 1 to 6 heteroatoms, or from 1 to 4 heteroatoms) selected from N, O and S and a balance of carbon atoms (typically at least one carbon atom); wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

The term "aryl", alone or in combination, relates to a phenyl, naphthyl or indanyl group. In specific embodiments, the "aryl" is phenyl. The abbreviation "Ph" represents phenyl.

The term "heteroaryl", alone or in combination, means six-membered aromatic rings containing one to four nitrogen atoms; benzofused six-membered aromatic rings containing one to three nitrogen atoms; five-membered aromatic rings containing one oxygen, one nitrogen or one sulfur atom; benzofused five-membered aromatic rings containing one oxygen, one nitrogen or one sulfur atom; five-membered aromatic rings containing two heteroatoms independently selected from oxygen, nitrogen and sulfur and benzofused derivatives of such rings; five-membered aromatic rings containing three nitrogen atoms and benzofused derivatives thereof; a tetrazolyl ring; a thiazinyl ring; or coumarinyl. Examples of such ring systems are furanyl, thienyl, pyrrolyl, pyridinyl, pyrimidinyl, indolyl, quinolinyl, isoquinolinyl, imidazolyl, triazinyl, thiazolyl, isothiazolyl, pyridazinyl, pyrazolyl, oxazolyl, isoxazolyl, benzothienyl, quinazolinyl and quinoxalinyl.

Specific examples of compounds of formula I, and pharmaceutically acceptable salts thereof; include those listed below:

trans-N-Cyclopropyl-N-[(2,3-dichlorophenyl)methyl]-4-(1-methyl-2-oxo-1,2-dihydro-4-pyridinyl)-3-piperidinecarboxamide (Ex. 1)

trans-N-[{5-Chloro-2-[3-(methyloxy)propyl]-4-pyridinyl}methyl]-N-cyclopropyl-4-(1-methyl-2-oxo-1,2-dihydro-4-pyridinyl)-3-piperidinecarboxamide (Ex. 2)

trans-N-({2-Chloro-5-[3-(methyloxy)propyl]phenyl}methyl)-N-cyclopropyl-4-(1-methyl-2-oxo-1,2-dihydro-4-pyridinyl)-3-piperidinecarboxamide (Ex. 3)

trans-N-({2-Chloro-5-[2-(methyloxy)ethyl]phenyl}methyl)-N-cyclopropyl-4-(1-methyl-2-oxo-1,2-dihydro-4-pyridinyl)-3-piperidinecarboxamide (Ex. 4)

trans-N-Cyclopropyl-N-({2,3-dichloro-5-[3-(methyloxy)propyl]phenyl}methyl)-4-(1-methyl-2-oxo-1,2-dihydro-4-pyridinyl)-3-piperidinecarboxamide (Ex. 5)

trans-N-Cyclopropyl-N-({2,3-dichloro-5-[2-(methyloxy)ethyl]phenyl}methyl)-4-(1-methyl-2-oxo-1,2-dihydro-4-pyridinyl)-3-piperidinecarboxamide (Ex. 6)

trans-N-Cyclopropyl-N-({2-methyl-5-[3-(methyloxy)propyl]phenyl}methyl)-4-(1-methyl-2-oxo-1,2-dihydro-4-pyridinyl)-3-piperidinecarboxamide (Ex. 7)

trans-N-Cyclopropyl-N-({2-methyl-5-[2-(methyloxy)ethyl]phenyl}methyl)-4-(1-methyl-2-oxo-1,2-dihydro-4-pyridinyl)-3-piperidinecarboxamide (Ex. 8)

trans-N-Cyclopropyl-N-({2,3-difluoro-5-[3-(methyloxy)propyl]phenyl}methyl)-4-(1-methyl-2-oxo-1,2-dihydro-4-pyridinyl)-3-piperidinecarboxamide (Ex. 9)

trans-N-Cyclopropyl-4-(1-methyl-2-oxo-1,2-dihydro-4-pyridinyl)-N-({3-(methyloxy)-5-[3-(methyloxy)propyl]phenyl}methyl)-3-piperidinecarboxamide (Ex. 10)

trans-N-Cyclopropyl-4-(1-methyl-2-oxo-1,2-dihydro-4-pyridinyl)-N-({3-{[2-(methyloxy)-ethyl]oxy}-5-[3-(methyloxy)propyl]phenyl}methyl)-3-piperidinecarboxamide (Ex. 11)

trans-N-Cyclopropyl-4-(1-ethyl-2-oxo-1,2-dihydro-4-pyridinyl)-N-({3-{[2-(methyloxy)-ethyl]oxy}-5-[3-(methyloxy)propyl]phenyl}methyl)-3-piperidinecarboxamide (Ex. 12)

trans-N-Cyclopropyl-N-({3-{[2-(methyloxy)ethyl]oxy}-5-[3-(methyloxy)propyl]phenyl}methyl)-4-(1,5,6-trimethyl-2-oxo-1,2-dihydro-4-pyridinyl)-3-piperidinecarboxamide (Ex. 13)

trans-N-Cyclopropyl-4-(1-methyl-5-{[(methyloxy)methyl]oxy}-2-oxo-1,2-dihydro-4-pyridinyl)-N-({3-{[2-(methyloxy)ethyl]oxy}-5-[3-(methyloxy)propyl]
phenyl}methyl)-3-piperidinecarboxamide (Ex. 14)

trans-N-Cyclopropyl-N-{[2,3-dichloro-5-(3-cyanopropyl)
phenyl]methyl}-4-(1-methyl-2-oxo-1,2-dihydro-4-pyridinyl)-3-piperidinecarboxamide (Ex. 15)

trans-N-{[5-(3-Cyanopropyl)-2,3-difluorophenyl]methyl}-N-cyclopropyl-4-(1-methyl-2-oxo-1,2-dihydro-4-pyridinyl)-3-piperidinecarboxamide (Ex. 16)

trans-N-Cyclopropyl-N-{[2,3-dichloro-5-(4-hydroxybutyl)
phenyl]methyl}-4-(1-methyl-2-oxo-1,2-dihydro-4-pyridinyl)-3-piperidinecarboxamide (Ex. 17)

trans-N-Cyclopropyl-4-(1-methyl-2-oxo-1,2-dihydro-4-pyridinyl)-N-({3-[3-(methyloxy)propyl]-1-naphthalenyl}methyl)-3-piperidinecarboxamide (Ex. 18)

trans-Methyl (2-{3,4-dichloro-5-[(cyclopropyl{[4-(1-methyl-2-oxo-1,2-dihydro-4-pyridinyl)-3-piperidinyl]
carbonyl}amino)methyl]phenyl}ethyl)carbamate (Ex. 19)

trans-N-Cyclopropyl-4-(1-methyl-2-oxo-1,2-dihydro-4-pyridinyl)-N-(8-quinolinylmethyl)-3-piperidinecarboxamide (Ex. 20)

trans-N-Cyclopropyl-N-(8-isoquinolinylmethyl)-4-(1-methyl-2-oxo-1,2-dihydro-4-pyridinyl)-3-piperidinecarboxamide (Ex. 21)

trans-N-Cyclopropyl-N-(5-isoquinolinylmethyl)-4-(1-methyl-2-oxo-1,2-dihydro-4-pyridinyl)-3-piperidinecarboxamide (Ex. 22)

trans-N-Cyclopropyl-4-(1-methyl-2-oxo-1,2-dihydro-4-pyridinyl)-N-(5-quinolinylmethyl)-3-piperidinecarboxamide (Ex. 23)

trans-N-Cyclopropyl-N-(1-isoquinolinylmethyl)-4-(1-methyl-2-oxo-1,2-dihydro-4-pyridinyl)-3-piperidinecarboxamide (Ex. 24)

trans-N-Cyclopropyl-4-(1-methyl-2-oxo-1,2-dihydro-4-pyridinyl)-N-({2-[3-(methyloxy)propyl]-4-quinolinyl}methyl)-3-piperidinecarboxamide (Ex. 25)

trans-N-Cyclopropyl-4-(1-methyl-2-oxo-1,2-dihydro-4-pyridinyl)-N-({6-[3-(methyloxy)propyl]-8-quinolinyl}methyl)-3-piperidinecarboxamide (Ex. 26)

trans-N-[(5-Bromo-2,3-dichlorophenyl)methyl]-N-cyclopropyl-4-(1-methyl-2-oxo-1,2-dihydro-4-pyridinyl)-3-piperidinecarboxamide (Ex. 27)

trans-N-({3-Chloro-5-[3-(methyloxy)propyl]phenyl)methyl}-N-cyclopropyl-4-(1-methyl-2-oxo-1,2-dihydro-4-pyridinyl)-3-piperidinecarboxamide (Ex. 28)

trans-N-Cyclopropyl-4-(1-methyl-2-oxo-1,2-dihydro-4-pyridinyl)-N-({1-[3-(methyloxy)propyl]-1H-indol-3-yl}methyl)-3-piperidinecarboxamide (Ex. 29)

trans-N-Cyclopropyl-N-{[2,3-dichloro-5-(2-cyanoethyl)
phenyl]methyl}-4-(1-methyl-2-oxo-1,2-dihydro-4-pyridinyl)-3-piperidinecarboxamide (Ex. 30)

trans-Ethyl (2-{3,4-dichloro-5-[(cyclopropyl{[4-(1-methyl-2-oxo-1,2-dihydro-4-pyridinyl)-3-piperidinyl]
carbonyl}amino)methyl]phenyl}ethyl)carbamate (Ex. 31)

trans-N-({3-Bromo-5-[3-(methyloxy)propyl]
phenyl}methyl)-N-cyclopropyl-4-(1-methyl-2-oxo-1,2-dihydro-4-pyridinyl)-3-piperidinecarboxamide (Ex. 32)

trans-N-Cyclopropyl-4-(1-methyl-2-oxo-1,2-dihydro-4-pyridinyl)-N-({5-[3-(methyloxy)propyl]-3-biphenylyl}methyl)-3-piperidinecarboxamide (Ex. 33)

trans-N-Cyclopropyl-4-(1-methyl-2-oxo-1,2-dihydro-4-pyridinyl)-N-{[[3-(methyloxy)propyl]-5-(3-pyridinyl)phenyl]methyl}-3-piperidinecarboxamide (Ex. 34)

trans-N-Cyclopropyl-N-[(2,3-dichloro-5-{[2-(methyloxy)
ethyl]amino}phenyl)methyl]-4-(1-methyl-2-oxo-1,2-dihydro-4-pyridinyl)-3-piperidinecarboxamide (Ex. 35)

trans-N-Cyclopropyl-4-(1-methyl-2-oxo-1,2-dihydro-4-pyridinyl)-N-[(3-{[2-(methyloxy)ethyl]amino}-1-naphthalenyl)methyl]-3-piperidinecarboxamide (Ex. 36)

trans-N-{[6-(2-cyanoethyl)-8-quinolinyl]methyl}-N-cyclopropyl-4-(1-methyl-2-oxo-1,2-dihydro-4-pyridinyl)-3-piperidinecarboxamide (Ex. 37)

trans-N-Cyclopropyl-4-(1-methyl-2-oxo-1,2-dihydro-4-pyridinyl)-N-({3-[2-(methyloxy)ethyl]-1-naphthalenyl}methyl)-3-piperidinecarboxamide (Ex. 38)

trans-N-({3-[2-(Acetylamino)ethyl]-1-naphthalenyl}methyl)-N-cyclopropyl-4-(1-methyl-2-oxo-1,2-dihydro-4-pyridinyl)-3-piperidinecarboxamide (Ex. 39)

trans-N-[(2-Bromophenyl)methyl]-N-cyclopropyl-4-(1-methyl-2-oxo-1,2-dihydro-4-pyridinyl)-3-piperidinecarboxamide (Ex. 40)

trans-N-Cyclopropyl-4-(1-methyl-2-oxo-1,2-dihydro-4-pyridinyl)-N-({1-[2-(methyloxy)ethyl]-1H-indol-3-yl}methyl)-3-piperidinecarboxamide (Ex. 41)

trans-N-Cyclopropyl-4-(1-methyl-2-oxo-1,2-dihydro-4-pyridinyl)-N-{[1-(2,2,2-trifluoroethyl)-1H-indol-3-yl]methyl}-3-piperidinecarboxamide (Ex. 42)

trans-N-Cyclopropyl-4-(1-methyl-2-oxo-1,2-dihydro-4-pyridinyl)-N-{[1-(4,4,4-trifluorobutyl)-1H-indol-3-yl]methyl}-3-piperidinecarboxamide (Ex. 43)

trans-N-[(1-Butyl-1H-indol-3-yl)methyl]-N-cyclopropyl-4-(1-methyl-2-oxo-1,2-dihydro-4-pyridinyl)-3-piperidinecarboxamide (Ex. 44)

trans-N-Cyclopropyl-N-({1-[3-(ethyloxy)propyl]-1H-indol-3-yl}methyl)-4-(1-methyl-2-oxo-1,2-dihydro-4-pyridinyl)-3-piperidinecarboxamide (Ex. 45)

trans-N-Cyclopropyl-4-(1-methyl-2-oxo-1,2-dihydro-4-pyridinyl)-N-({1-[3,3,3-trifluoro-2-(trifluoromethyl)propyl]-1H-indol-3-yl}methyl)-3-piperidinecarboxamide (Ex. 46)

trans-N-({1-[3-(Acetylamino)propyl]-1H-indol-3-yl}methyl)-N-cyclopropyl-4-(1-methyl-2-oxo-1,2-dihydro-4-pyridinyl)-3-piperidinecarboxamide (Ex. 47)

trans-N-Cyclopropyl-4-(1-methyl-2-oxo-1,2-dihydro-4-pyridinyl)-N-({1-[3-(propanoylamino)propyl]-1H-indol-3-yl}methyl)-3-piperidinecarboxamide (Ex. 48)

trans-N-({1-[2-(Acetylamino)ethyl]-1H-indol-3-yl}methyl)-N-cyclopropyl-4-(1-methyl-2-oxo-1,2-dihydro-4-pyridinyl)-3-piperidinecarboxamide (Ex. 49)

trans-N-Cyclopropyl-4-(1-methyl-2-oxo-1,2-dihydro-4-pyridinyl)-N-({1-[2-(propanoylamino)ethyl]-1H-indol-3-yl}methyl)-3-piperidinecarboxamide (Ex. 50)

trans-N-Cyclopropyl-4-(1-methyl-2-oxo-1,2-dihydro-4-pyridinyl)-N-{[1-(2-propen-1-yl)-1H-indol-3-yl]methyl}-3-piperidinecarboxamide (Ex. 51)

trans-N-Cyclopropyl-4-(1-methyl-2-oxo-1,2-dihydro-4-pyridinyl)-N-{[1-(phenylmethyl)-1H-indol-3-yl]methyl}-3-piperidinecarboxamide (Ex. 52)

trans-N-Cyclopropyl-4-(1-methyl-2-oxo-1,2-dihydro-4-pyridinyl)-N-{[1-(2-pyridinylmethyl)-1H-indol-3-yl]methyl}-3-piperidinecarboxamide (Ex. 53)

trans-N-Cyclopropyl-4-(1-methyl-2-oxo-1,2-dihydro-4-pyridinyl)-N-{[1-(3-pyridinylmethyl)-1H-indol-3-yl]methyl}-3-piperidinecarboxamide (Ex. 54)

trans-N-Cyclopropyl-4-(1-methyl-2-oxo-1,2-dihydro-4-pyridinyl)-N-{[1-(4-pyridinylmethyl)-1H-indol-3-yl]methyl}-3-piperidinecarboxamide (Ex. 55)

trans-N-Cyclopropyl-N-({1-[(4-fluorophenyl)methyl]-1H-indol-3-yl}methyl)-4-(1-methyl-2-oxo-1,2-dihydro-4-pyridinyl)-3-piperidinecarboxamide (Ex. 56)

trans-N-({1-[(4-Chlorophenyl)methyl]-1H-indol-3-yl}methyl)-N-cyclopropyl-4-(1-methyl-2-oxo-1,2-dihydro-4-pyridinyl)-3-piperidinecarboxamide (Ex. 57)

trans-N-Cyclopropyl-N-({1-[(3-fluorophenyl)methyl]-1H-indol-3-yl}methyl)-4-(1-methyl-2-oxo-1,2-dihydro-4-pyridinyl)-3-piperidinecarboxamide (Ex. 58)

trans-N-({1-[(3-Chlorophenyl)methyl]-1H-indol-3-yl}methyl)-N-cyclopropyl-4-(1-methyl-2-oxo-1,2-dihydro-4-pyridinyl)-3-piperidinecarboxamide (Ex. 59)

trans-N-({1-[(3-Cyanophenyl)methyl]-1H-indol-3-yl}methyl)-N-cyclopropyl-4-(1-methyl-2-oxo-1,2-dihydro-4-pyridinyl)-3-piperidinecarboxamide (Ex. 60)

trans-N-Cyclopropyl-4-(1-methyl-2-oxo-1,2-dihydro-4-pyridinyl)-N-({1-[(3-methylphenyl)methyl]-1H-indol-3-yl}methyl)-3-piperidinecarboxamide (Ex. 61)

trans-N-Cyclopropyl-N-({5-fluoro-1-[3-(methyloxy)propyl]-1H-indol-3-yl}methyl)-4-(1-methyl-2-oxo-1,2-dihydro-4-pyridinyl)-3-piperidinecarboxamide (Ex. 62)

trans-N-{[6-Bromo-1-(phenylmethyl)-1H-indol-3-yl]methyl}-N-cyclopropyl-4-(1-methyl-2-oxo-1,2-dihydro-4-pyridinyl)-3-piperidinecarboxamide (Ex. 63)

trans-N-Cyclopropyl-N-{[1-[(3-fluorophenyl)methyl]-6-(methyloxy)-1H-indol-3-yl]methyl}-4-(1-methyl-2-oxo-1,2-dihydro-4-pyridinyl)-3-piperidinecarboxamide (Ex. 64)

trans-N-Cyclopropyl-4-(1-methyl-2-oxo-1,2-dihydro-4-pyridinyl)-N-{[4-methyl-1-(phenylmethyl)-1H-indol-3-yl]methyl}-3-piperidinecarboxamide (Ex. 65)

trans-N-{[4-Cyano-1-(phenylmethyl)-1H-indol-3-yl]methyl}-N-cyclopropyl-4-(1-methyl-2-oxo-1,2-dihydro-4-pyridinyl)-3-piperidinecarboxamide (Ex. 66)

trans-N-Cyclopropyl-N-{[4-fluoro-1-(phenylmethyl)-1H-indol-3-yl]methyl}-4-(1-methyl-2-oxo-1,2-dihydro-4-pyridinyl)-3-piperidinecarboxamide (Ex. 67)

trans-N-Cyclopropyl-N-({4-fluoro-1-[(3-fluorophenyl)methyl]-1H-indol-3-yl}methyl)-4-(1-methyl-2-oxo-1,2-dihydro-4-pyridinyl)-3-piperidinecarboxamide (Ex. 68)

trans-N-Cyclopropyl-N-({4-fluoro-1-[3-(methyloxy)propyl]-1H-indol-3-yl}methyl)-4-(1-methyl-2-oxo-1,2-dihydro-4-pyridinyl)-3-piperidinecarboxamide (Ex. 69)

trans-N-({4-Chloro-1-[3-(methyloxy)propyl]-1H-indol-3-yl}methyl)-N-cyclopropyl-4-(1-methyl-2-oxo-1,2-dihydro-4-pyridinyl)-3-piperidinecarboxamide (Ex. 70)

trans-N-{[4-Chloro-1-(phenylmethyl)-1H-indol-3-yl]methyl}-N-cyclopropyl-4-(1-methyl-2-oxo-1,2-dihydro-4-pyridinyl)-3-piperidinecarboxamide (Ex. 71)

trans-N-{[4-Bromo-1-(phenylmethyl)-1H-indol-3-yl]methyl}-N-cyclopropyl-4-(1-methyl-2-oxo-1,2-dihydro-4-pyridinyl)-3-piperidinecarboxamide (Ex. 72)

trans-N-({4-Bromo-1-[(3-fluorophenyl)methyl]-1H-indol-3-yl}methyl)-N-cyclopropyl-4-(1-methyl-2-oxo-1,2-dihydro-4-pyridinyl)-3-piperidinecarboxamide (Ex. 73)

trans-N-({Bromo-1-[3-(methyloxy)propyl]-1H-indol-3-yl}methyl)-N-cyclopropyl-4-(1-methyl-2-oxo-1,2-dihydro-4-pyridinyl)-3-piperidinecarboxamide (Ex. 74)

trans-N-Cyclopropyl-N-[(4-fluoro-1H-indol-3-yl)methyl]-4-(1-methyl-2-oxo-1,2-dihydro-4-pyridinyl)-3-piperidinecarboxamide (Ex. 75)

trans-N-Cyclopropyl-N-{[4-fluoro-1-(3-pyridinylmethyl)-1H-indol-3-yl]methyl}-4-(1-methyl-2-oxo-1,2-dihydro-4-pyridinyl)-3-piperidinecarboxamide (Ex. 76)

trans-N-Cyclopropyl-N-{[4-fluoro-1-(4-pyridinylmethyl)-1H-indol-3-yl]methyl}-4-(1-methyl-2-oxo-1,2-dihydro-4-pyridinyl)-3-piperidinecarboxamide (Ex. 77)

trans-N-({3-Acetyl-5-[3-(methyloxy)propyl]phenyl}methyl)-N-cyclopropyl-4-(1-methyl-2-oxo-1,2-dihydro-4-pyridinyl)-3-piperidinecarboxamide (Ex. 78)

trans-N-({1,3-Bis[3-(methyloxy)propyl]-2,4-dioxo-1,2,3,4-tetrahydro-5-pyrimidinyl}methyl)-N-cyclopropyl-4-(1-methyl-2-oxo-1,2-dihydro-4-pyridinyl)-3-piperidinecarboxamide (Ex. 79)

trans-N-Cyclopropyl-N-({2,3-dimethyl-5-[3-(methyloxy)propyl]phenyl}methyl)-4-(1-methyl-2-oxo-1,2-dihydro-4-pyridinyl)-3-piperidinecarboxamide (Ex. 80)

trans-N-[(2-Chloro-5-{[2-(methyloxy)ethyl]oxy}phenyl)methyl]-N-cyclopropyl-4-(1-methyl-2-oxo-1,2-dihydro-4-pyridinyl)-3-piperidinecarboxamide (Ex. 81)

trans-N-Cyclopropyl-4-(1-methyl-2-oxo-1,2-dihydro-4-pyridinyl)-N-(2-naphthalenylmethyl)-3-piperidinecarboxamide (Ex. 82)

trans-N-Cyclopropyl-4-(1-methyl-2-oxo-1,2-dihydro-4-pyridinyl)-N-({3-[(trifluoromethyl)thio]phenyl}methyl)-3-piperidinecarboxamide (Ex. 83)

trans-N-Cyclopropyl-4-(1-methyl-2-oxo-1,2-dihydro-4-pyridinyl)-N-{[5-[3-(methyloxy)propyl]-2-(methylthio)phenyl]methyl}-3-piperidinecarboxamide (Ex. 84)

trans-N-({3-Bromo-4-methyl-5-[3-(methyloxy)propyl]phenyl}methyl)-N-cyclopropyl-4-(1-methyl-2-oxo-1,2-dihydro-4-pyridinyl)-3-piperidinecarboxamide (Ex. 85)

trans-N-[3,5-Bis(3-methoxypropyl)benzyl]-N-cyclopropyl-4-(1-methyl-2-oxo-1,2-dihydro-4-pyridinyl)-3-piperidinecarboxamide (Ex. 86)

trans-N-Cyclopropyl-N-[3-(3-methoxypropyl)-5-methylbenzyl]-4-(1-methyl-2-oxo-1,2-dihydro-4-pyridinyl)-3-piperidinecarboxamide (Ex. 87)

trans-N-[2-Bromo-3,5-bis(3-methoxypropyl)benzyl]-N-cyclopropyl-4-(1-methyl-2-oxo-1,2-dihydro-4-pyridinyl)-3-piperidinecarboxamide (Ex. 88)

trans-N-[2-Chloro-3,5-bis(3-methoxypropyl)benzyl]-N-cyclopropyl-4-(1-methyl-2-oxo-1,2-dihydro-4-pyridinyl)-3-piperidinecarboxamide (Ex. 89)

trans-N-Cyclopropyl-N-[2-methoxy-3,5-bis(3-methoxypropyl)benzyl]-4-(1-methyl-2-oxo-1,2-dihydro-4-pyridinyl)-3-piperidinecarboxamide (Ex. 90)

trans-N-Cyclopropyl-N-[3-(3-methoxypropyl)-5-(trifluoromethyl)benzyl]-4-(1-methyl-2-oxo-1,2-dihydro-4-pyridinyl)-3-piperidinecarboxamide (Ex. 91)

trans-N-Cyclopropyl-N-[3-hydroxy-5-(3-methoxypropyl)benzyl]-4-(1-methyl-2-oxo-1,2-dihydro-4-pyridinyl)-3-piperidinecarboxamide (Ex. 92)

trans-N-(3-Benzoyl-5-bromobenzyl)-N-cyclopropyl-4-(1-methyl-2-oxo-1,2-dihydro-4-pyridinyl)-3-piperidinecarboxamide (Ex. 93)

trans-N-{3-Bromo-5-[(1E)-3-methoxy-1-propen-1yl]benzyl}-N-cyclopropyl-4-(1-methyl-2-oxo-1,2-dihydro-4-pyridinyl)-3-piperidinecarboxamide (Ex. 94)

trans-N-{3-Bromo-5-[(2-hydroxyethyl)thio]benzyl}-N-cyclopropyl-4-(1-methyl-2-oxo-1,2-dihydro-4-pyridinyl)-3-piperidinecarboxamide (Ex. 95)

trans-N-Cyclopropyl-N-[3-[2-(cyclopropyloxy)ethoxy]-5-(3-methoxypropyl)benzyl]-4-(1-methyl-2-oxo-1,2-dihydro-4-pyridinyl)-3-piperidinecarboxamide (Ex. 96)

trans-N-Cyclopropyl-N-{3-(3-methoxypropyl)-5-[2-(4-morpholinyl)ethoxy]benzyl}-4-(1-methyl-2-oxo-1,2-dihydro-4-pyridinyl)-3-piperidinecarboxamide (Ex. 97)

Trans-3-[((Cyclopropyl{[4-(1-methyl-2-oxo-1,2-dihydro-4-pyridinyl)-3-piperidinyl]carbonyl}amino)methyl]-5-(3-methoxypropyl)phenyl 4-morpholinecarboxylate (Ex. 98)

trans-N-Cyclopropyl-N-[6-(3-methoxypropyl)-2,3-dihydro-1H-inden-1-yl]-4-(1-methyl-2-oxo-1,2-dihydro-4-pyridinyl)-3-piperidinecarboxamide (Ex. 99)

trans-N-Cyclopropyl-N-[7-(3-methoxypropyl)-1,2,3,4-tetrahydro-1-naphthalenyl]-4-(1-methyl-2-oxo-1,2-dihydro-4-pyridinyl)-3-piperidinecarboxamide (Ex. 100)

trans-N-[3-Bromo-5-(3-hydroxypropyl)-4-methylbenzyl]-N-cyclopropyl-4-(1-methyl-2-oxo-1,2-dihydro-4-pyridinyl)-3-piperidinecarboxamide (Ex. 101)
trans-N-[3-Bromo-5-(3-ethoxypropyl)-4-methylbenzyl]-N-cyclopropyl-4-(1-methyl-2-oxo-1,2-dihydro-4-pyridinyl)-3-piperidinecarboxamide (Ex. 102)
trans-N-{3-Bromo-5-[3-(difluoromethoxy)propyl]-4-methylbenzyl}-N-cyclopropyl-4-(1-methyl-2-oxo-1,2-dihydro-4-pyridinyl)-3-piperidinecarboxamide (Ex. 103)
trans-N-(3-Benzyl-5-methylbenzyl)-N-cyclopropyl-4-(1-methyl-2-oxo-1,2-dihydro-4-pyridinyl)-3-piperidinecarboxamide (Ex. 104)
trans-N-[3-Bromo-5-(3-fluorobenzyl)-4-methylbenzyl]-N-cyclopropyl-4-(1-methyl-2-oxo-1,2-dihydro-4-pyridinyl)-3-piperidinecarboxamide (Ex. 105)
trans-N-[3-Bromo-5-(3-fluorobenzoyl)-4-methylbenzyl]-N-cyclopropyl-4-(1-methyl-2-oxo-1,2-dihydro-4-pyridinyl)-3-piperidinecarboxamide (Ex. 106)
trans-N-{3-Bromo-5-[(3-fluorophenyl)(hydroxyl)methyl]-4-methylbenzyl}-N-cyclopropyl-4-(1-methyl-2-oxo-1,2-dihydro-4-pyridinyl)-3-piperidinecarboxamide (Ex. 107)
trans-N-[2-Chloro-5-(2-methoxyethyl)benzyl]-N-cyclopropyl-4-hydroxy-4-(1-methyl-2-oxo-1,2-dihydro-4-pyridinyl)-3-piperidinecarboxamide (Ex. 108)
trans-N-[2-Chloro-5-(2-methoxyethyl)benzyl]-N-cyclopropyl-4-methoxy-4-(1-methyl-2-oxo-1,2-dihydro-4-pyridinyl)-3-piperidinecarboxamide (Ex. 109)
trans-N-Cyclopropyl-4-hydroxy-N-[3-(2-methoxyethoxy)-5-(3-methoxypropyl)benzyl]-4-(1-methyl-2-oxo-1,2-dihydro-4-pyridinyl)-3-piperidinecarboxamide (Ex. 110)
trans-N-Cyclopropyl-4-methoxy-N-[3-(2-methoxyethoxy)-5-(3-methoxypropyl)benzyl]-4-(1-methyl-2-oxo-1,2-dihydro-4-pyridinyl)-3-piperidinecarboxamide (Ex. 111)

The present invention also encompasses a pharmaceutical formulation comprising a pharmaceutically acceptable carrier and the compound of Formula I or a pharmaceutically acceptable crystal form or hydrate thereof. A particular embodiment is a pharmaceutical composition of the compound of Formula I, comprising, in addition, a second agent.

List of Abbreviations:
BINAP 2,2'-bis(diphenylphosphino)-1,1'-binaphthyl
BOC t-butyloxycarbonyl
BSA bovine serum albumin
COD 1,5-cyclooctadiene
DBU 1,8-diazabicyclo[5.4.0]undec-7-ene
DCM dichloromethane
DIBAl-H diisobutylaluminum hydride
DMAP 4-dimethylamino pyridine
DME 1,2-dimethoxyethane
DMF N,N-dimethylformamide
DMP Dess-Martin periodinane
DMSO dimethylsulfoxide
DPPB 1,4-bis(diphenylphosphino)butane
DPPF 1,1'-bis(diphenylphosphino)ferrocene
EDTA ethylenediaminetetraacetic acid
EIA enzyme immunoassay
Et$_2$O diethylether
EtOAc ethyl acetate
HATU O-(7-azabenzotriazol-1-yl)-N,N,N',N'-tetramethyluronium hexafluorophosphate
Hex hexanes
IPA Isopropyl alcohol
KHMDS potassium hexamethyldisilazide
mCPBA meta-chloroperbenzoic acid
MeOH methanol
NBS N-bromo succinimide
NMO N-methylmorpholine-N-oxide
n-PrOH n-propanol
PBS phosphate-buffered saline
PG protecting group
PPh3 triphenylphosphine
RT room temperature
TBAF tetrabutylammonium fluoride
TFA trifluoroacetic acid
THF tetrahydrofuran
TMEDA N,N,N',N'-tetramethylethylenediamine
Tol toluene
MTBE methyl tert-butyl ether
COD cyclooctadiene
c.HCL concentrated HCL Unless expressly stated to the contrary, all ranges cited herein are inclusive. For example, an alkyl group described as $C_1$-$C_6$ alkyl means the alkyl group can contain 1, 2, 3, 4, 5 or 6 carbon atoms.

When a given range includes 0 (e.g., $(CH_2)_{0-3}$), 0 implies a direct covalent bond.

When any variable occurs more than one time in any constituent or in any formula depicting and describing compounds of the invention, its definition on each occurrence is independent of its definition at every other occurrence.

Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed and results in a stable compound.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

In compounds of the invention having pyridyl N-oxide moieties, the pyridyl-N-oxide portion is structurally depicted using conventional representations such as

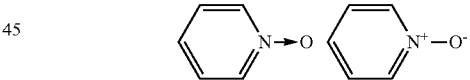

which have equivalent meanings.

The invention relates to a method for the treatment and/or prophylaxis of diseases which are related to hypertension, congestive heart failure, pulmonary hypertension, systolic hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system, which method comprises administrating a compound as defined above to a human being or animal.

In another embodiment, the invention relates to a method for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy. In another embodiment, the invention relates to a method for the treatment and/or prophylaxis of diseases, which are associated with a dysregulation of the renin-angiotensin system as well as for the treatment of the above-mentioned diseases.

The invention also relates to the use of compounds of formula (I) for the preparation of a medicament for the treatment and/or prophylaxis of the above-mentioned diseases.

Compounds of formula (I) or the above-mentioned pharmaceutical compositions are also of use in combination with other pharmacologically active compounds comprising ACE-inhibitors, neutral endopeptidase inhibitors, angiotensin H receptor antagonists, endothelin receptors antagonists, vasodilators, calcium antagonists, potassium activators, diuretics, sympatholitics, beta-adrenergic antagonists, alpha-adrenergic antagonists or with other drugs beneficial for the prevention or the treatment of the above-mentioned diseases.

The term "administration" and variants thereof (e.g., "administering" a compound) in reference to a compound of Formula I mean providing the compound or a prodrug of the compound to the individual in need of treatment or prophylaxis. When a compound of the invention or a prodrug thereof is provided in combination with one or more other active agents (e.g., an agent such as anangiotensin H receptor antagonist, ACE inhibitor, or other active agent which is known to reduce blood pressure), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" as used herein refers to an animal, in particular embodiments, a mammal, and in specific embodiments, a human, who has been the object of treatment, observation or experiment.

The term "effective amount" or "pharmaceutically active amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit renin and thereby elicit the response being sought (i.e., an "inhibition effective amount"). When the active compound (i.e., active ingredient) is administered as the salt, references to the amount of active ingredient are to the free form (i.e., the non-salt form) of the compound. In specific embodiments, this amount is comprised between 1 mg and 1000 mg per day. In other embodiments, this amount is comprised between 1 mg and 500 mg per day. In other embodiments, this amount is comprised between 1 mg and 200 mg per day.

In the method of the present invention (i.e., inhibiting renin), the compounds of Formula I, optionally in the form of a salt, can be administered by any means that produces contact of the active agent with the agent's site of action. Such administration methods as described form particular embodiments of the present invention. The compounds can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, mucosally (including sublingual, buccal, rectal, nasal or vaginal administrations), parenterally (including subcutaneous injection, bolus injection, intraarterial, intravenous, intramuscular, intrasternal injection or infusion administration techniques), by inhalation spray, transdermal, such as passive or iontophoretic delivery, or topical administration, in the form of a unit dosage of a pharmaceutical composition containing an effective amount of the compound and conventional non-toxic pharmaceutically-acceptable carriers, adjuvants and vehicles. The above-described administration techniques using the compounds as described herein form important embodiments of the present invention. Examples of dosage forms contemplated as part of the present invention include, but are not limited to: tablets, caplets, capsules, such as soft elastic gelatin capsules, cachets, troches, lozenges, dispersions, suppositories, ointments, cataplasms (poultices), pastes, powders, dressings, creams, plasters, solutions, patches, aerosols (e.g., nasal sprays or inhalers), gels, liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs, liquid dosage forms suitable for parenteral administration to a patient, and sterile solids (e.g., crystalline or amorphous solids) that can be reconstituted to provide liquid dosage forms suitable for parenteral administration to a patient. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990.

The present invention also relates to process for preparing compounds described herein. In particular embodiments, the present invention relates to a process for preparing compounds of the following formula:

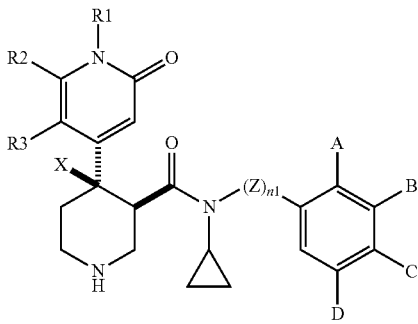

wherein:
R$^1$ is C$_1$-C$_2$ alkyl optionally substituted with 1-3 halogens,
R$^2$ and R$^3$ are independently selected from the group consisting of: hydrogen, halogen, C$_1$-C$_5$ alkyl, C$_1$-C$_5$ alkoxy and —O—(C$_1$-C$_5$ alkylene)-O—(CH$_2$)$_{0-3}$—CH$_3$, wherein the alkyl, alkoxy and —O—(C$_1$-C$_5$ alkylene)-O—(CH$_2$)$_{0-3}$—CH$_3$ are optionally substituted with 1-3 substituents independently selected from the group consisting of: halogen, C$_1$-C$_5$ alkyl optionally substituted with 1-3 halogens and C$_1$-C$_5$ alkoxy optionally substituted with 1-3 halogens,
X is selected from the group consisting of hydrogen, —OH and C$_1$-C$_5$ alkoxy,
(Z)$_{n1}$ is C$_1$-C$_2$ alkylene,
A is selected from the group consisting of:
(1) hydrogen,
(2) halogen,
(3) C$_1$-C$_5$ alkyl,
(4) C$_1$-C$_5$ alkoxy, and
(5) —S—(CH$_2$)$_{0-3}$—CH$_3$,
wherein (3) and (4) are optionally substituted with 1-3 halogens,
B is selected from the group consisting of:
(1) hydrogen,
(2) halogen,
(3) C$_1$-C$_5$ alkyl,
(4) C$_1$-C$_5$ alkoxy,
(5) —OH,
(6) —CF$_3$,
(7) —C(=O)—CH$_3$,
(8) —O—(C$_1$-C$_5$ alkylene)-O—(CH$_2$)$_{0-2}$—CH$_3$,
(9) —(C$_1$-C$_5$ alkylene)-O—(CH$_2$)$_{0-2}$—CH$_3$,
(10) —O—(C$_1$-C$_5$ alkylene)-C(CH$_3$)$_2$—C(=O)OH, and
(11) —O—(C$_1$-C$_5$ alkylene)-C(CH$_3$)$_2$—C(=O)OCH$_3$,
wherein (3), (4), (8), (9), (10) and (11) are optionally substituted with 1-3 halogens,
C is selected from the group consisting of:
(1) hydrogen,
(2) C$_1$-C$_5$ alkyl optionally substituted with 1-3 halogens, and
(3) C$_1$-C$_5$ alkoxy optionally substituted with 1-3 halogens, and
D is selected from the group consisting of:
(1) hydrogen,
(2) halogen,
(3) C$_1$-C$_5$ alkyl,
(4) C$_1$-C$_5$ alkoxy,
(5) C$_1$-C$_5$-cyano,
(6) C$_2$-C$_5$ alkenylene-O—(CH$_2$)$_{0-2}$—CH$_3$,
(7) —(C$_1$-C$_5$ alkylene)-N(H)—C(=O)—O—(CH$_2$)$_{0-2}$—CH$_3$,
(8) —(C$_1$-C$_5$ alkylene)-N(H)—C(=O)—(CH$_2$)$_{0-2}$—CH$_3$,
(9) —(C$_1$-C$_5$ alkylene)-O—CHF$_2$,
(10) —(C$_1$-C$_5$ alkylene)-O—(CH$_2$)$_{0-2}$—CH$_3$,
(11) —O—(C$_1$-C$_5$ alkylene)-O—(CH$_2$)$_{0-2}$—CH$_3$,
(12) —(C$_1$-C$_5$ alkylene)-OH,
(13) —S—(C$_1$-C$_5$ alkylene)-OH,
(14) —SCF$_3$, and
(15) —N(H)—(C$_1$-C$_5$ alkylene)-O—(CH$_2$)$_{0-2}$—CH$_3$,
wherein (3), (4), (5), (6), (7), (8), (9), (10), (11), (12), (13) and (15) are optionally substituted with 1-3 halogens,
which comprises the following steps:
(1) coupling a compound of formula (a), or a salt thereof, to a compound of formula (b), or a salt thereof:

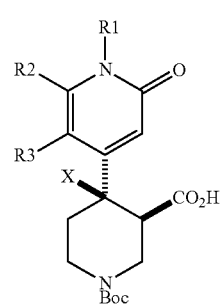

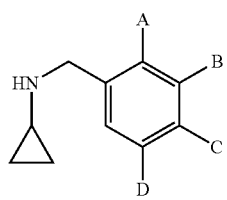

in the presence of a solvent, to form a compound of formula (c), or a salt thereof

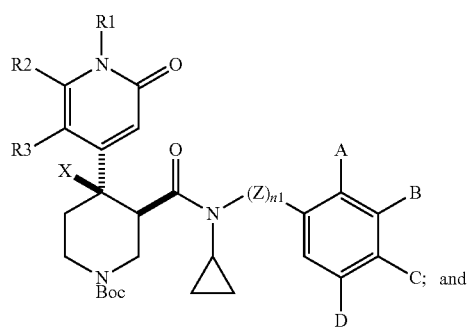

(2) deprotecting compound (c) by removing Boc.

In specific embodiments, the solvent is/comprises one or more compounds selected from the group consisting of: DMF, oxalyl chloride and iPr$_2$Net. In specific embodiments, the deprotecting step is conducted with one or more compounds selected from the group consisting of: HCl, IPA and MTBE.

In particular embodiments, the present invention relates to a process for preparing compounds of the following formula:

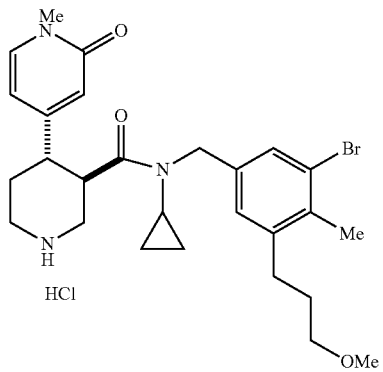

HCl which comprises the following steps:

(1) coupling compounds of formula (a) having a Boc group and formula (b) below in the presence of DMF, oxalyl chloride and iPr₂NEt:

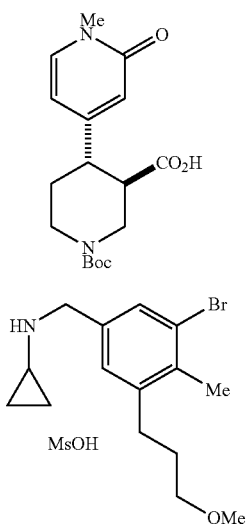

to form a compound of formula (c)

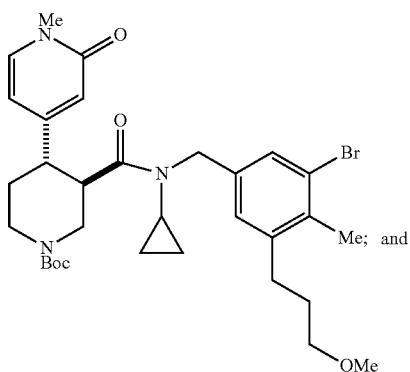

(2) deprotecting compound formed through removal of Boc group in the presence of HCL, IPA and MTBE.

Methods of Synthesis

Compounds of the present invention can be made by a variety of methods depicted in the illustrative synthetic reaction schemes shown and described below which form particular embodiments of the present invention. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2.sup.nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes and examples are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specifically stated otherwise, the experimental procedures were performed under the following conditions. Evaporation of solvent was carried out using a rotary evaporator under reduced pressure (600-4000 pascals: 4.5-30 mm Hg) with a bath temperature of up to 60° C. Reactions are typically run under nitrogen atmosphere at ambient temperature if not otherwise mentioned. Anhydrous solvent such as THF, DMF, Et₂O, DME and Toluene are commercial grade. Reagents are commercial grade and were used without further purification. Flash chromatography is run on silica gel (230-400 mesh). The course of the reaction was followed by either thin layer chromatography (TLC) or nuclear magnetic resonance (NMR) spectrometry and reaction times given are for illustration only. The structure and purity of all final products were ascertained by TLC, mass spectrometry, ¹H NMR and high-pressure liquid chromatography (HPLC). Chemical symbols have their usual meanings. The following abbreviations have also been used: v (volume), w (weight), b.p. (boiling point), m.p. (melting point), L (liter(s)), mL (milliliter(s)), g (gram(s)), mg (milligram(s)), mol (mole(s)), mmol (millimole(s)), eq. (equivalent(s)). Unless otherwise specified, all variables mentioned below have the meanings as provided above.

Generally, compounds of the present invention can be prepared via the coupling of an appropriately substituted pyridone I with an appropriately functionalized amine II, followed by the removal of the BOC-protecting group from amide III (Scheme 1).

Scheme 1

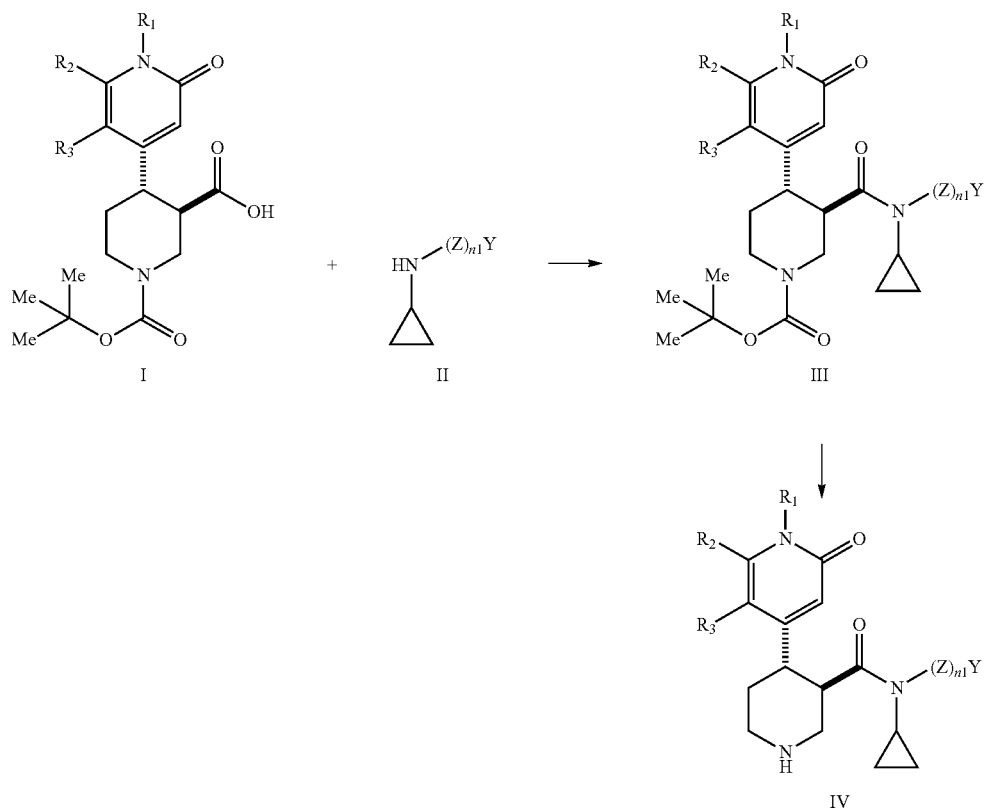

Synthesis of the requisite pyridone I can, for example, be performed as exemplified in Scheme 2. Typically, metal-catalyzed Suzuki coupling of boronate VI, prepared from known triflate V (e.g., Ujjarnwalla et al., Bioorg. Med. Chem. Lett.; 15 (18), 2005, p. 4023-4028), with halide VII, can provide α,β-unsaturated ester VIII. Reduction of the double bond; most conveniently accomplished using either magnesium or samarium iodide, and subsequent base-mediated equilibration, would then afford saturated ester IX as a single diastereomer. Its conversion to the corresponding pyridone X can be realized in two steps via the initial treatment of ester IX with mCPBA; or an equivalent oxidant, followed by the reaction of the resulting pyridine N-oxide with TFAA in triethylamine; or an equivalent rearrangement promoter. Alternatively, for cases where the V group of ester IX is OBn, a simple hydrogenation under typical conditions would directly furnish pyridone X. Also, for cases where the V group of ester IX is OMe, reaction with an alkyl halide in the presence of sodium iodide would afford pyridone XI. Indeed, one can also access XI via N-alkylation of pyridone X with an appropriate reagent. Finally, saponification of pyridone XI would furnish pyridone I.

Scheme 2

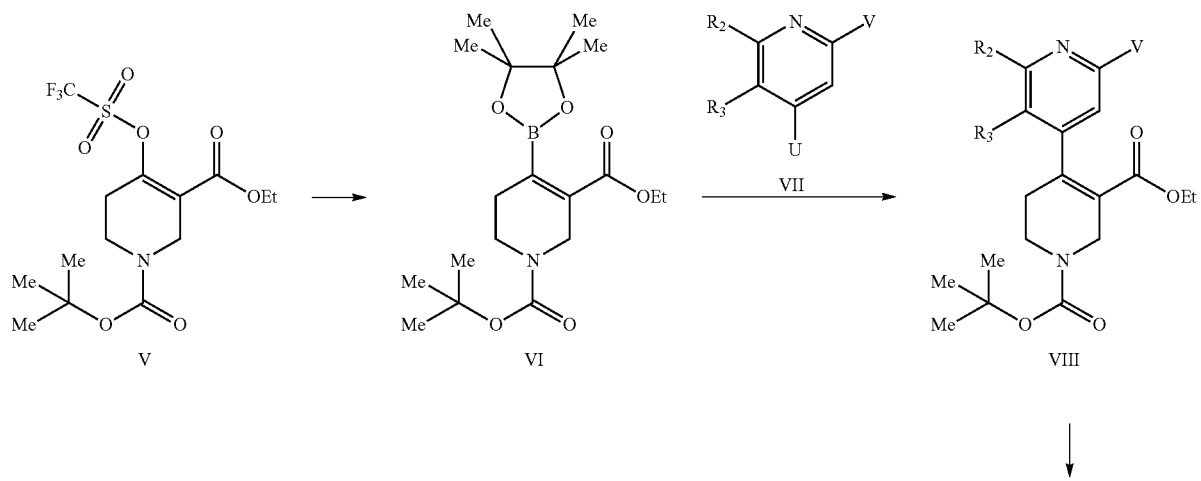

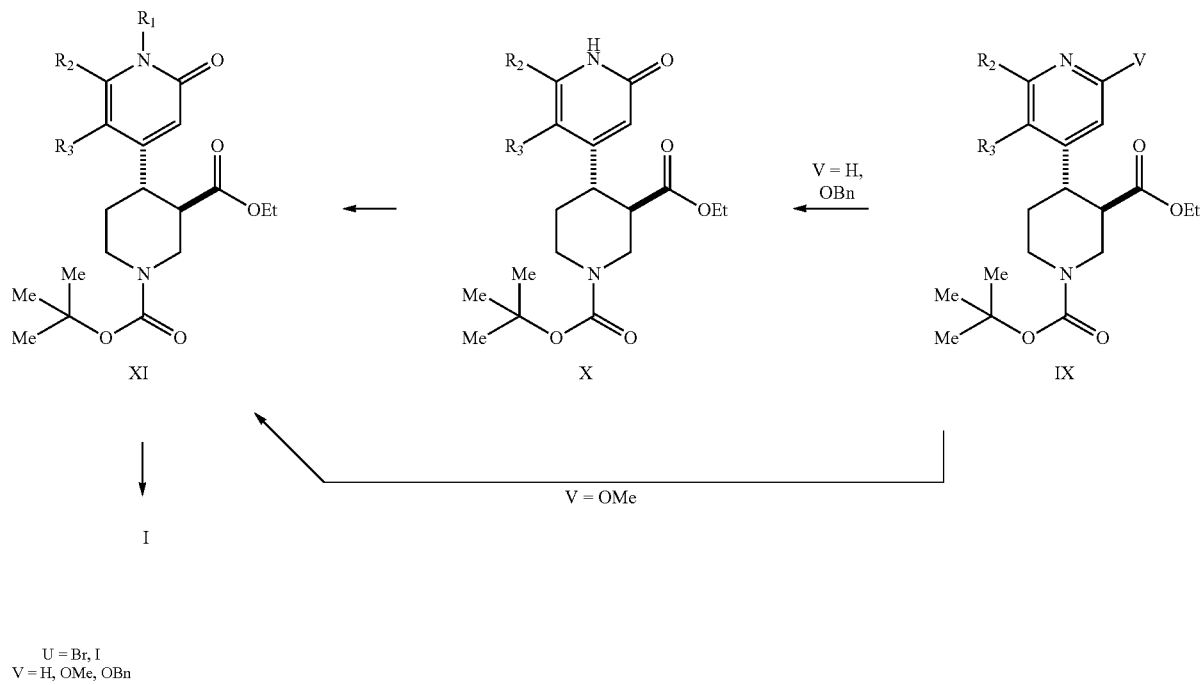

U = Br, I
V = H, OMe, OBn

For halides VII used in the preparation of I where V is either OMe or OBn, their synthesis can most readily be accomplished from the corresponding pyridone XIV. For example, this transformation can be effected by reacting pyridone XIV with either methyl or benzyl halide in the presence of silver carbonate (Scheme 3). For cases where pyridone XIV was neither commercially available nor known in the literature, the requisite compound could be prepared from its corresponding pyridine XII via the intermediacy of pyridine N-oxide XIII.

Scheme 3

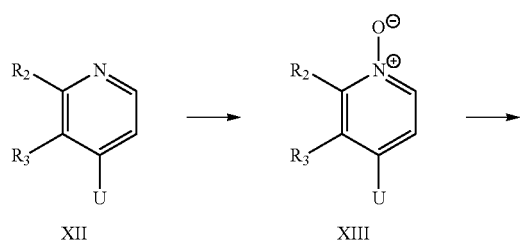

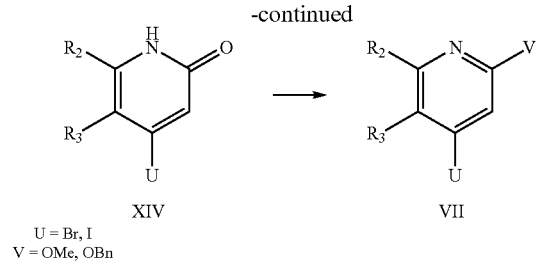

U = Br, I
V = OMe, OBn

In most cases, approaches to the preparation of amine II used in Scheme 1 have already been disclosed in published patent application WO 2007/009250 A1. Those not already known can be synthesized according to, for example, methods exemplified in Scheme 4. Where appropriate, aldehyde XV is first regio selectively brominated. The resulting bromide XVI is then subjected to the usual reductive amination conditions to afford amine XVII. If necessary, amine XVII could subsequently be protected as its corresponding N-BOC derivative XVIII. Using typical metal-mediated couplings such as the Suzuki or Buchwald-Hartwig variants, the R chain in amine II can be appended onto either amine XVII or amine XVIII. Simple chemical modifications such as hydrogenation, Wittig olefination, reduction, acylation, ozonolysis, oxidation and others, where necessary, may be carried out to arrive at the desired R group in amine II. Finally, for amine XIX, a simple deprotection step is required.

Scheme 4

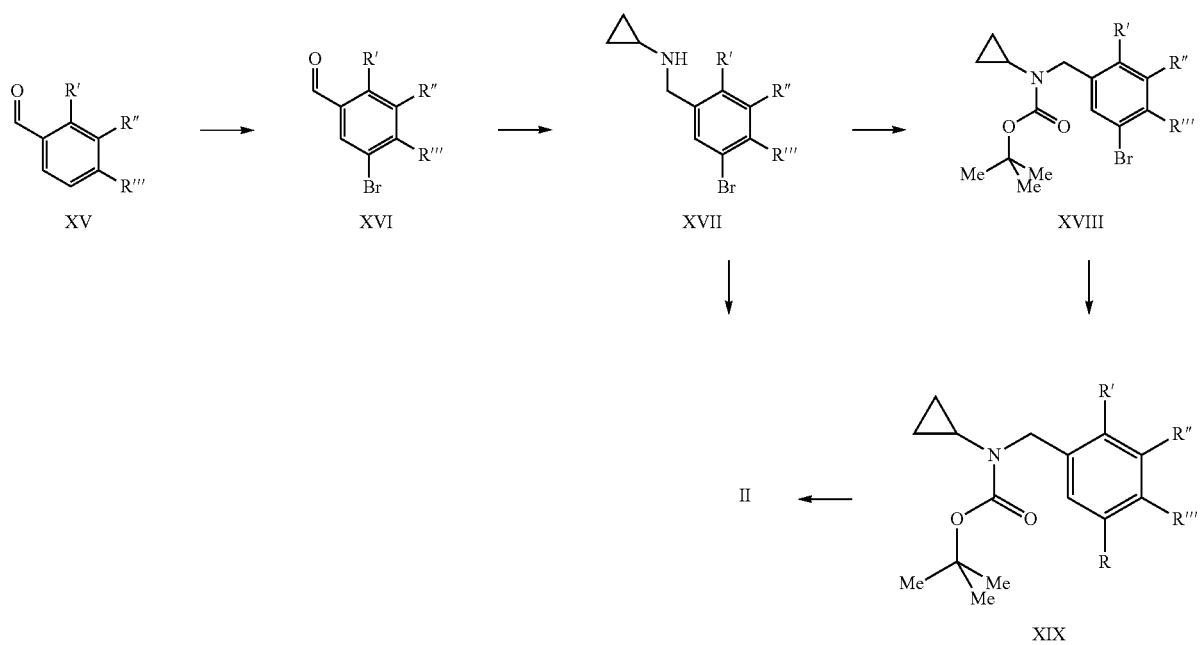

Indole is another common scaffold seen in amine II. These amines can be prepared, for example, from alkylation of indole XXI under typical reaction conditions. Again, simple chemical modifications such as hydrogenation, Wittig olefination, reduction, acylation, ozonolysis, oxidation and others, where necessary, may be carried out to arrive at the desired R group in amine II. Finally, reductive amination of XXII would furnish the desired amine II. Should indole XXI not be commercially available, it can be accessed via, for example, a simple formylation of indole XX, which is most conveniently accomplished with $POCl_3$ in DMF.

Scheme 5

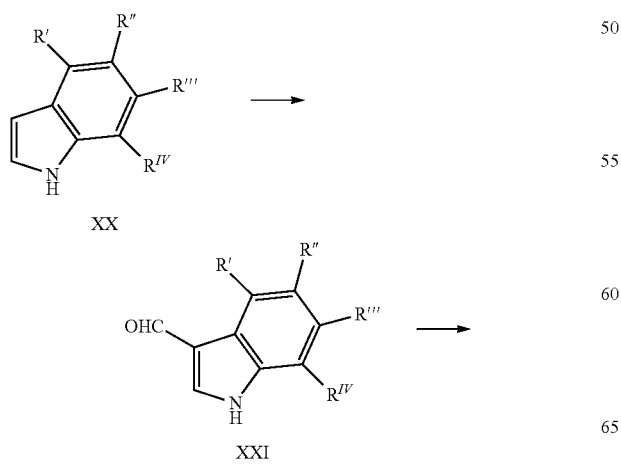

-continued

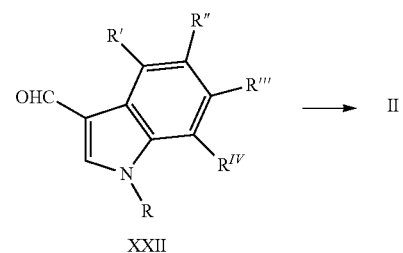

For compounds of the present invention bearing an alkoxy group at position 4 of the piperidine ring, they are most conveniently accessed via an initial amide formation between amine II and β-ketoester XXIII, followed by the addition of Grignard reagent derived from a suitably-protected and appropriately substituted hydroxypyridine. Functionalization of the resulting alcohol XXV, if necessary, would precede the conversion of the protected hydroxypyridine XXVI into the desired pyridone XXVII using chemistry described earlier. Finally, BOC removal can be accomplished under typical conditions (Scheme 6).

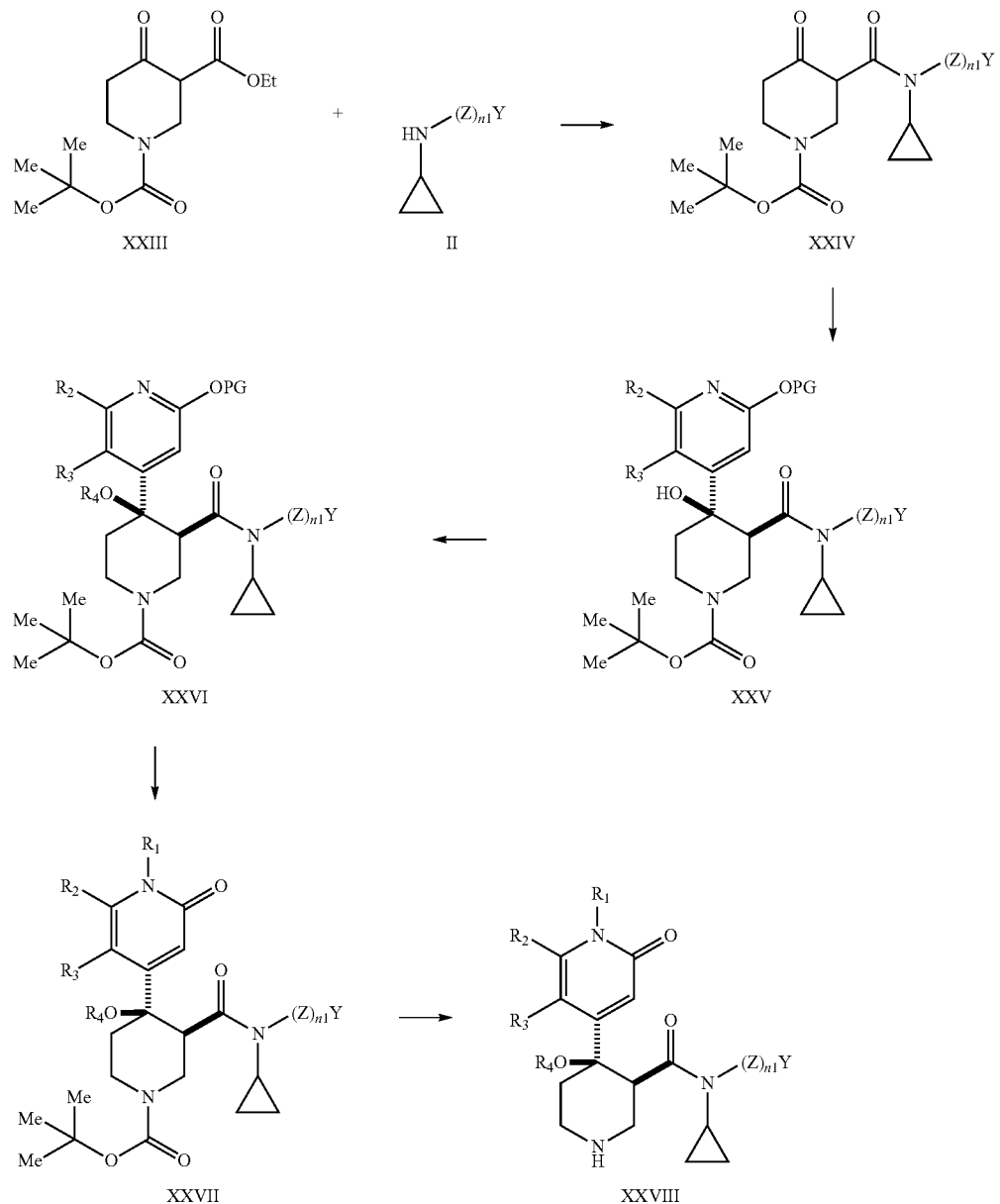
Scheme 6
Representative cyclopropylamine building blocks are shown in Table 1.
TABLE 1
| Compound | Structure |
| --- | --- |
| Amine 1 | (cyclopropyl-NH-CH2-2,3-dichlorophenyl) |
TABLE 1-continued
| Compound | Structure |
| --- | --- |
| Amine 2 | (cyclopropyl-NH-CH2-(5-chloro-2-(3-methoxypropyl)pyridin-4-yl)) |

TABLE 1-continued

| Compound | Structure |
|---|---|
| Amine 3 | N-cyclopropyl-1-(4-chloro-3-(3-methoxypropyl)phenyl)methanamine |
| Amine 4 | N-cyclopropyl-1-(4-chloro-3-(2-methoxyethyl)phenyl)methanamine |
| Amine 5 | N-cyclopropyl-1-(3,4-dichloro-5-(3-methoxypropyl)phenyl)methanamine |
| Amine 6 | N-cyclopropyl-1-(3,4-dichloro-5-(2-methoxyethyl)phenyl)methanamine |
| Amine 7 | N-cyclopropyl-1-(4-methyl-3-(3-methoxypropyl)phenyl)methanamine |
| Amine 8 | N-cyclopropyl-1-(4-methyl-3-(2-methoxyethyl)phenyl)methanamine |
| Amine 9 | N-cyclopropyl-1-(2,3-difluoro-5-(3-methoxypropyl)phenyl)methanamine |
| Amine 10 | N-cyclopropyl-1-(3-methoxy-5-(3-methoxypropyl)phenyl)methanamine |
| Amine 11 | N-cyclopropyl-1-(3-(2-methoxyethoxy)-5-(3-methoxypropyl)phenyl)methanamine |
| Amine 12 | N-cyclopropyl-1-(3,4-dichloro-5-(2-cyanoethyl)phenyl)methanamine |
| Amine 13 | N-cyclopropyl-1-(2,3-difluoro-5-(2-cyanoethyl)phenyl)methanamine |

TABLE 1-continued
| Compound | Structure |
|---|---|
| Amine 14 | 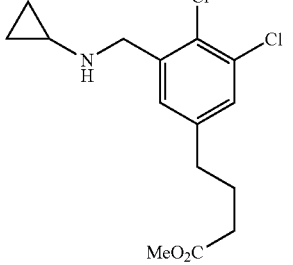 |
| Amine 15 | 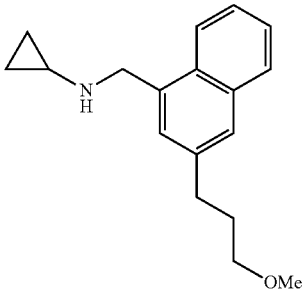 [SMILES: COCCCc1cc(CNC2CC2)c2ccccc2c1] |
| Amine 16 | 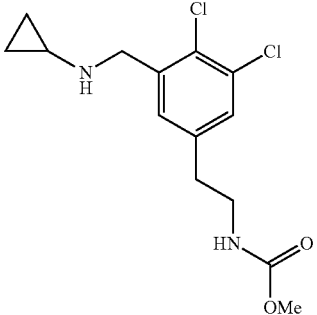 [SMILES: COC(=O)NCCc1cc(Cl)c(Cl)c(CNC2CC2)c1] |
| Amine 17 | 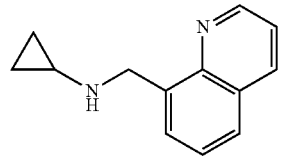 [SMILES: c1cnc2c(CNC3CC3)cccc2c1] |
| Amine 18 | 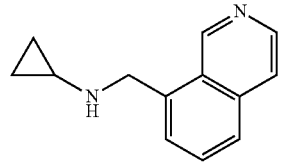 [SMILES: c1cc(CNC2CC2)c2cnccc2c1] |
| Amine 19 | 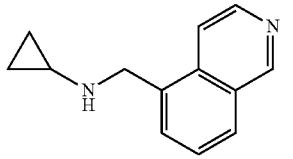 [SMILES: c1cc(CNC2CC2)c2ccncc2c1] |
| Amine 20 | 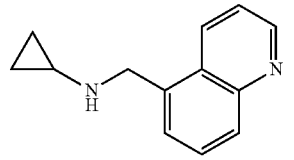 [SMILES: c1cc(CNC2CC2)c2cccnc2c1] |
| Amine 21 | 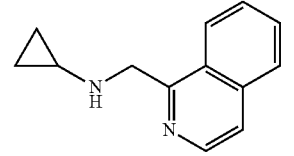 [SMILES: c1ccc2c(CNC3CC3)nccc2c1] |
| Amine 22 | 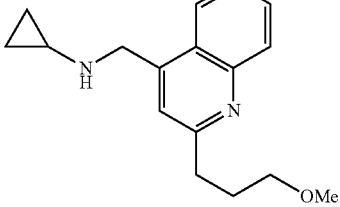 |
| Amine 23 | 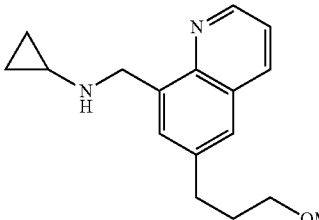 |
| Amine 24 | 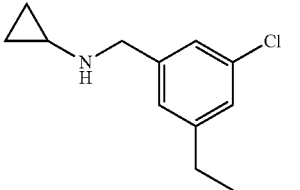 |
| Amine 25 | 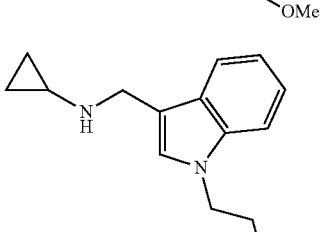 |
| Amine 26 | 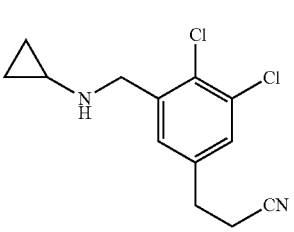 [SMILES: N#CCCc1cc(Cl)c(Cl)c(CNC2CC2)c1] |

TABLE 1-continued

| Compound | Structure |
|---|---|
| Amine 27 | cyclopropyl-NH-CH2-(3,4-dichlorophenyl with CH2CH2-NHC(O)Et at 5-position) |
| Amine 28 | cyclopropyl-NH-CH2-(3-bromo-5-(CH2CH2CH2OMe)phenyl) |
| Amine 29 | cyclopropyl-NH-CH2-(naphthyl with NH-CH2CH2-OMe) |
| Amine 30 | cyclopropyl-NH-CH2-(quinolin-8-yl with CH2CH2CN) |
| Amine 31 | cyclopropyl-NH-CH2-(naphthyl with CH2CH2-OMe) |
| Amine 32 | cyclopropyl-NH-CH2-(naphthyl with CH2CH2-NHC(O)Me) |
| Amine 33 | cyclopropyl-NH-CH2-(2-bromophenyl) |
| Amine 34 | cyclopropyl-NH-CH2-(indol-3-yl, N-CH2CH2OMe) |
| Amine 35 | cyclopropyl-NH-CH2-(indol-3-yl, N-CH2CF3) |
| Amine 36 | cyclopropyl-NH-CH2-(indol-3-yl, N-(CH2)3CF3) |
| Amine 37 | cyclopropyl-NH-CH2-(indol-3-yl, N-(CH2)3Me) |
| Amine 38 | cyclopropyl-NH-CH2-(indol-3-yl, N-CH2CH2CH2OEt) |
| Amine 39 | cyclopropyl-NH-CH2-(indol-3-yl, N-CH2CH(CF3)2) |

TABLE 1-continued
| Compound | Structure |
|---|---|
| Amine 40 | 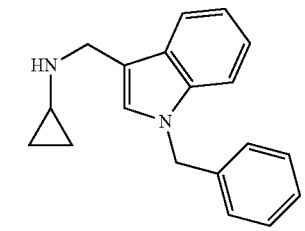 [SMILES: c1ccc(Cn2cc(CNC3CC3)c3ccccc32)cc1] |
| Amine 41 | 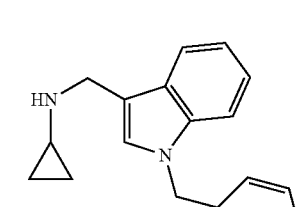 |
| Amine 42 | 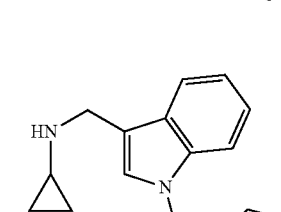 |
| Amine 43 | 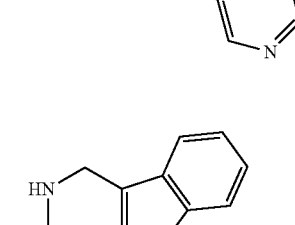 |
| Amine 44 | 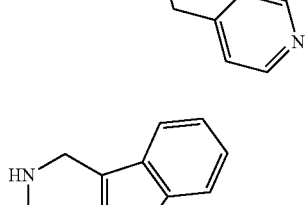 |
| Amine 45 | 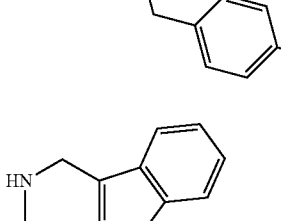 |
| Amine 46 | 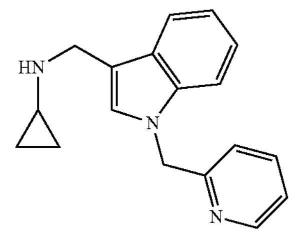 [SMILES: c1ccc(Cn2cc(CNC3CC3)c3ccccc32)nc1] |
| Amine 47 | 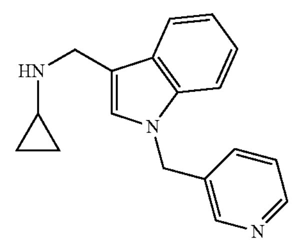 [SMILES: c1cncc(Cn2cc(CNC3CC3)c3ccccc32)c1] |
| Amine 48 | 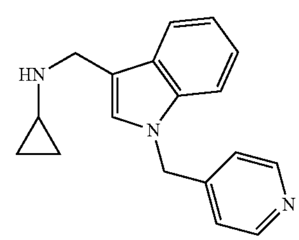 [SMILES: c1ccc2c(c1)c(CNC1CC1)cn2Cc1ccncc1] |
| Amine 49 | 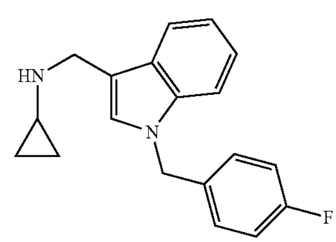 [SMILES: Fc1ccc(Cn2cc(CNC3CC3)c3ccccc32)cc1] |
| Amine 50 | 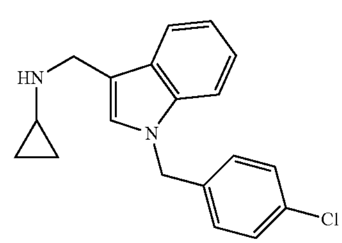 [SMILES: Clc1ccc(Cn2cc(CNC3CC3)c3ccccc32)cc1] |

TABLE 1-continued

| Compound | Structure |
|---|---|
| Amine 51 | 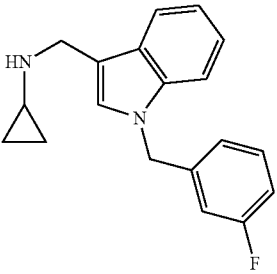 N-cyclopropyl-1-(3-fluorobenzyl)-1H-indol-3-ylmethylamine |
| Amine 52 | 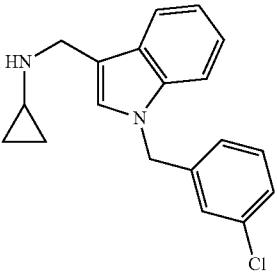 [SMILES: Clc1cccc(Cn2cc(CNC3CC3)c3ccccc32)c1] N-cyclopropyl-1-(3-chlorobenzyl)-1H-indol-3-ylmethylamine |
| Amine 53 | 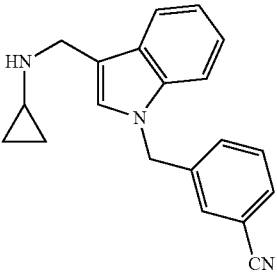 [SMILES: N#Cc1cccc(Cn2cc(CNC3CC3)c3ccccc32)c1] N-cyclopropyl-1-(3-cyanobenzyl)-1H-indol-3-ylmethylamine |
| Amine 54 | 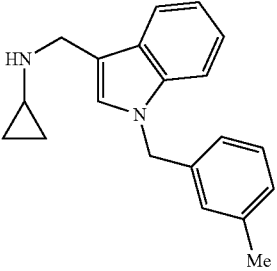 N-cyclopropyl-1-(3-methylbenzyl)-1H-indol-3-ylmethylamine |
| Amine 55 | 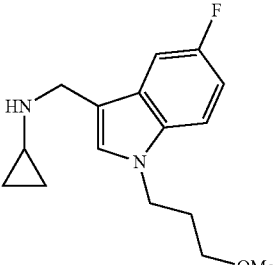 N-cyclopropyl-5-fluoro-1-(3-methoxypropyl)-1H-indol-3-ylmethylamine |
| Amine 56 | 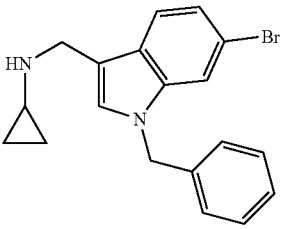 [SMILES: Brc1ccc2c(CNC3CC3)cn(Cc3ccccc3)c2c1] N-cyclopropyl-1-benzyl-6-bromo-1H-indol-3-ylmethylamine |
| Amine 57 | 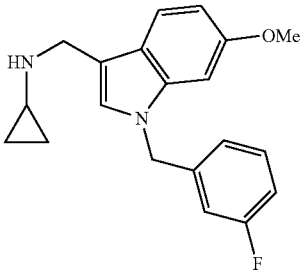 [SMILES: COc1ccc2c(CNC3CC3)cn(Cc3cccc(F)c3)c2c1] N-cyclopropyl-1-(3-fluorobenzyl)-6-methoxy-1H-indol-3-ylmethylamine |
| Amine 58 | 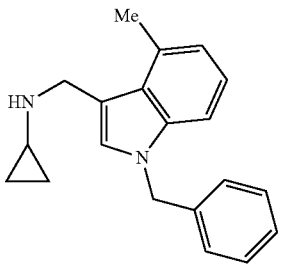 [SMILES: Cc1cccc2c1c(CNC1CC1)cn2Cc1ccccc1] N-cyclopropyl-1-benzyl-4-methyl-1H-indol-3-ylmethylamine |
| Amine 59 | 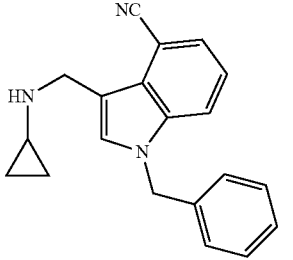 [SMILES: N#Cc1cccc2c1c(CNC1CC1)cn2Cc1ccccc1] N-cyclopropyl-1-benzyl-4-cyano-1H-indol-3-ylmethylamine |
| Amine 60 | 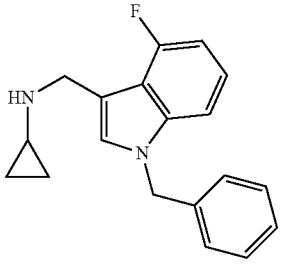 [SMILES: Fc1cccc2c1c(CNC1CC1)cn2Cc1ccccc1] N-cyclopropyl-1-benzyl-4-fluoro-1H-indol-3-ylmethylamine |

TABLE 1-continued
| Compound | Structure |
|---|---|
| Amine 61 | 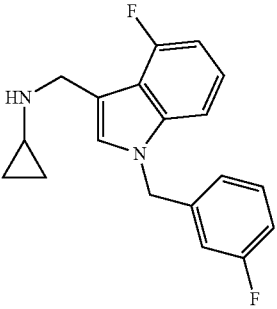 [SMILES: Fc1cccc(Cn2cc(CNC3CC3)c3c(F)cccc32)c1] |
| Amine 62 | 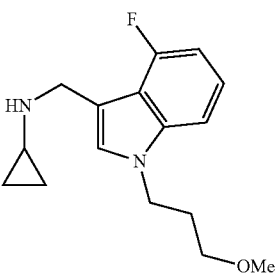 |
| Amine 63 | 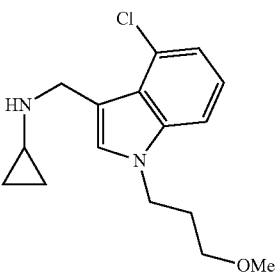 [SMILES: COCCCn1cc(CNC2CC2)c2c(F)cccc21] |
| Amine 64 | 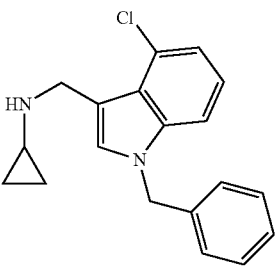 [SMILES: Clc1cccc2c1c(CNC1CC1)cn2Cc1ccccc1] |
| Amine 65 | 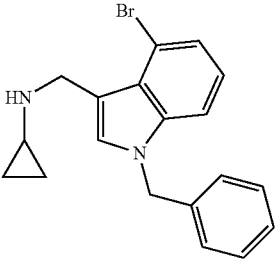 [SMILES: Brc1cccc2c1c(CNC1CC1)cn2Cc1ccccc1] |
| Amine 66 | 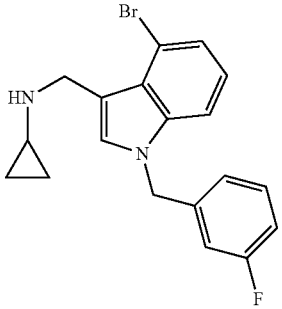 [SMILES: Fc1cccc(Cn2cc(CNC3CC3)c3c(Br)cccc32)c1] |
| Amine 67 | 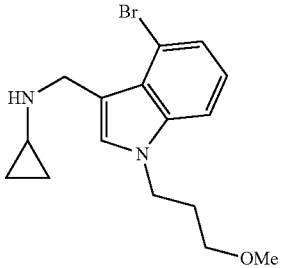 [SMILES: COCCCn1cc(CNC2CC2)c2c(Br)cccc21] |
| Amine 68 | 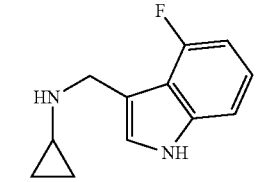 [SMILES: Fc1cccc2[nH]cc(CNC3CC3)c12] |
| Amine 69 | 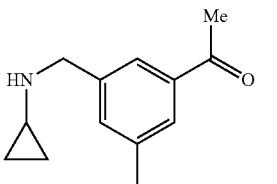 |
| Amine 70 | 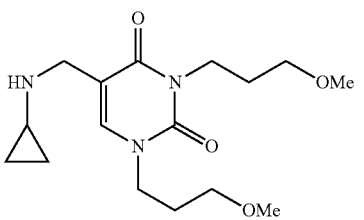 [SMILES: COCCCn1cc(CNC2CC2)c(=O)n(CCCOC)c1=O] |
| Amine 71 | 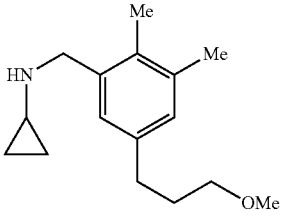 [SMILES: COCCCc1cc(C)c(C)c(CNC2CC2)c1] |

TABLE 1-continued

| Compound | Structure |
|---|---|
| Amine 72 | 2-chloro-5-(2-methoxyethoxy)benzyl cyclopropylamine |
| Amine 73 | N-(naphthalen-2-ylmethyl)cyclopropanamine |
| Amine 74 | N-(3-(trifluoromethylthio)benzyl)cyclopropanamine |
| Amine 75 | N-(5-(3-methoxypropyl)-2-(methylthio)benzyl)cyclopropanamine |
| Amine 76 | N-(3-bromo-5-(3-methoxypropyl)-4-methylbenzyl)cyclopropanamine |
| Amine 77 | N-(3-(3-methoxypropyl)-5-(4-methoxybutyl)benzyl)cyclopropanamine |
| Amine 78 | N-(3-(3-methoxypropyl)-5-methylbenzyl)cyclopropanamine |
| Amine 79 | N-(2-bromo-3-(3-methoxypropyl)-5-(3-methoxypropyl)benzyl)cyclopropanamine |
| Amine 80 | N-(2-chloro-3-(3-methoxypropyl)-5-(3-methoxypropyl)benzyl)cyclopropanamine |
| Amine 81 | N-(2-methoxy-3-(3-methoxypropyl)-5-(3-methoxypropyl)benzyl)cyclopropanamine |
| Amine 82 | N-(3-(3-methoxypropyl)-5-(trifluoromethyl)benzyl)cyclopropanamine |
| Amine 83 | 3-(cyclopropylaminomethyl)-5-(3-methoxypropyl)phenol |
| Amine 84 | N-(3-bromo-5-iodobenzyl)cyclopropanamine |

TABLE 1-continued

| Compound | Structure |
|---|---|
| Amine 85 | 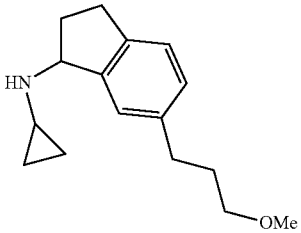 [SMILES: COCCCc1ccc2c(c1)C(NC1CC1)CC2] |
| Amine 86 | 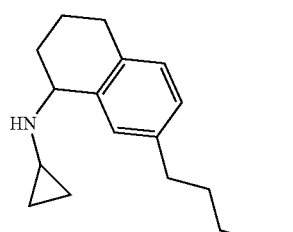 |
| Amine 87 | 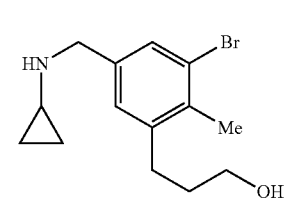 [SMILES: Cc1c(Br)cc(CNC2CC2)cc1CCCO] |
| Amine 88 | 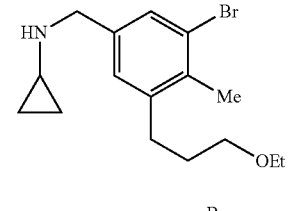 |
| Amine 89 | 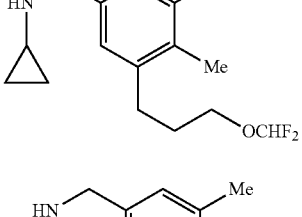 |
| Amine 90 | 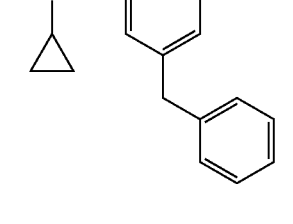 |
| Amine 91 | 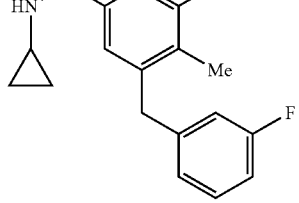 |
| Amine 92 | 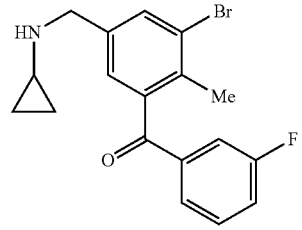 [SMILES: Cc1c(Br)cc(CNC2CC2)cc1C(=O)c1cccc(F)c1] |

Amine 1

N-(2,3-Dichlorobenzyl)cyclopropanamine

Amine 1 was prepared according to the procedure described in published patent application WO 2007/009250 A1.

Amine 2

N-{[5-Chloro-2-(3-methoxypropyl)-4-pyridinyl]methyl}cyclopropanamine

Amine 2 was prepared according to the procedure described in published patent application WO 2007/009250 A1.

Amine 3

N-({2-Chloro-5-[3-(methyloxy)propyl]phenyl}methyl)cyclopropanamine

Amine 3 was prepared according to the procedure described in published patent application WO 2007/009250 A1.

Amine 4

N-({2-Chloro-5-[2-(methyloxy)ethyl]phenyl}methyl)cyclopropanamine

Amine 4 was prepared according to the procedure described in published patent application WO 2007/009250 A1.

Amine 5

N-({2,3-Dichloro-5-[3-(methoxypropyl)propyl]phenyl}methyl)cyclopropanamine

Step 1: 5-Bromo-2,3-dichlorobenzaldehyde

To a TFA solution (0.38 M) of 2,3-dichlorobenzaldehyde (1 eq.) was added sulfuric acid (5 eq.). Over a period of 3 h, N-bromosuccinimide (1.5 eq.) was added portionwise at RT to afford, in the end, a yellow-orange solution. After 72 h, the crude reaction mixture was diluted with 9:1 (v/v) hexanes: ether and then washed sequentially with water, 1 N aq. NaOH, water and brine. The organic extract was dried over Na$_2$SO$_4$, filtered and the filtrate concentrated in vacuo to afford the title compound as a white solid.

Step 2: N-[(5-Bromo-2,3-dichlorophenyl)methyl]cyclopropanamine

5-Bromo-2,3-dichlorobenzaldehyde (1 eq.) from the previous step and cyclopropylamine (2 eq.) were combined in $CH_2Cl_2$ (0.1 M). To this was then added $MgSO_4$ (1 eq.) and the resulting suspension was stirred at RT for 18 h. The insolubles were then removed via filtration through a pad of celite and the filtrate was concentrated in vacuo. The crude imine thus obtained was then re-taken up in a 2:1 (v/v) mixture of THF:MeOH (0.17 M). To this solution was added sodium borohydride (10 eq.) portionwise and the resulting mixture was stirred at RT for 48 h. The reaction was quenched with 1 N aq. HCl, neutralized with 1 N aq. NaOH and extracted with ether. The combined organic extracts were then washed with water and brine, dried over $Na_2SO_4$, filtered and the filtrate concentrated in vacuo. Purification of the crude product thus obtained by way of flash chromatography ($SiO_2$, Hex→1:1 (v/v) Hex:EtOAc) afforded the title compound as a colorless oil.

Step 3: N-({2,3-Dichloro-5-[(1E)-3-(methyloxy)-1-propen-1-1]phenyl}methyl)cyclopropanamine N-[(5-Bromo-2,3-dichlorophenyl)methyl]cyclopropanamine (1 eq.) from the previous step and 4,4,5,5-tetramethyl-2-[(1E)-3-(methyloxy)-1-propen-1-yl]-1,3,2-dioxaborolane (1.5 eq.) were combined in a 5:1 (v/v) mixture of DMF:n-PrOH (0.17 M). To this solution was then added trans-bis(triphenylphosphine) palladium(II) bromide (0.05 eq.) and the vessel was repeatedly evacuated and back-filled with nitrogen. Finally, 2 N aq. $Na_2CO_3$ (2 eq.) was added and the resulting biphasic suspension was heated at 90° C. for 8 h. The now black suspension was cooled to RT, diluted with water and extracted with ether. The combined organic extracts were then washed further with 1 N aq. NaOH, water and brine. This was then dried over $Na_2SO_4$, filtered and the filtrate concentrated in vacuo to afford a viscous red oil. Purification of the crude product thus obtained by way of flash chromatography ($SiO_2$, Hex→3:7 (v/v) Hex:EtOAc) afforded the title compound as a yellow oil.

Step 4: Amine 5

N-({2,3-Dichloro-5-[(1E)-3-(methyloxy)-1-propen-1-yl]phenyl}methyl)-cyclopropanamine (1 eq.) from the previous step and 10% w/w palladium over charcoal (0.1 eq.) were suspended in EtOAc (0.03 M). The vessel was then evacuated and purged with $H_2$. Under a balloon-filled $H_2$ atmosphere, the reaction suspension was stirred at RT for 2 h. The reaction was then quenched with $CH_2Cl_2$, filtered through a bed of celite and the filtrate concentrated in vacuo. Purification of the crude product thus obtained by way of flash chromatography ($SiO_2$, Hex→1:1 (v/v) Hex:EtOAc) afforded the title compound as a colorless oil.

Amine 6

N-({2,3-Dichloro-5-[2-(methyloxy)ethyl]phenyl}methyl)cyclopropanamine

Step 1: 1,1-Dimethylethyl[(5-bromo-2,3-dichlorophenyl)methyl]cyclopropylcarbamate N-[(5-Bromo-2,3-dichlorophenyl)methyl]cyclopropanamine (1 eq.) from Step 2, Amine 5 and di-tert-butyl dicarbonate (1.1 eq.) were combined in $CH_2Cl_2$ (0.17 M). To this solution was then added Hunig's base (1.2 eq.) and the resulting yellow solution was stirred at RT for 3 h. The reaction mixture was then diluted with ether and washed sequentially with water and brine. The organic layer was then dried over $Na_2SO_4$, filtered and the filtrate concentrated in vacuo to afford a yellow oil. Purification of the crude product thus obtained by way of flash chromatography ($SiO_2$, Hex→3:7 (v/v) Hex:EtOAc) afforded the title compound as a colorless oil.

Step 2: 1,1-Dimethylethyl cyclopropyl[(2,3-dichloro-5-ethenylphenyl)methyl]carbamate 1,1-Dimethylethyl[(5-bromo-2,3-dichlorophenyl)methyl]cyclopropylcarbamate (1 eq.) from the previous step and 2-ethenyl-4,4,5,5-tetramethyl-1,3,2-dioxaborolane (1 eq.) were combined in a 2:1 (v/v) mixture of DMF:n-PrOH (0.1 M). To this solution was then added palladium(II) acetate (0.05 eq.) and triphenylphosphine (0.15 eq.) before the vessel was repeatedly evacuated and back-filled with nitrogen. Finally, 2 N aq. $Na_2CO_3$ (2 eq.) was added and the resulting biphasic suspension was heated at 90° C. for 18 h. The now black suspension was cooled to RT, diluted with water and extracted with 1:1 (v/v) hexanes:ether. The combined organic extracts were then washed further with 1 N aq. NaOH, water and brine. This was then dried over $Na_2SO_4$, filtered and the filtrate concentrated in vacuo to afford a pale yellow oil. Purification of the crude product thus obtained by way of flash chromatography ($SiO_2$, Hex→9:1 (v/v) Hex:EtOAc) afforded the title compound as a colorless oil.

Step 3: 1,1-Dimethylethyl cyclopropyl{[2,3-dichloro-5-(2-hydroxyethyl)phenyl]methyl}carbamate 1,1-Dimethylethyl cyclopropyl[(2,3-dichloro-5-ethenylphenyl)methyl]carbamate (1 eq.) from the previous step, $[Ir(COD)Cl]_2$ (0.025 eq.) and DPPB (0.05 eq.) were combined in THF (0.11 M). To this solution was then added 4,4,5,5-tetramethyl-1,3,2-dioxaborolane (1.3 eq.) and the resulting red solution was stirred at RT for 12 h. Finally, sodium perborate (0.1 M aqueous solution, 1 eq.) was added and the now black biphasic solution was vigorously stirred at RT for another 12 h. The aqueous layer was separated and back-extracted with ether. The combined organic extracts were then washed further with 1 N aq. NaOH, water and brine. This was then dried over $Na_2SO_4$, filtered and the filtrate concentrated in vacuo to afford a pale yellow oil. Purification of the crude product thus obtained by way of flash chromatography ($SiO_2$, 9:1 (v/v) Hex:EtOAc→3:7 (v/v) EtOAc:Hex) afforded the title compound as a colorless oil.

Step 4: 1,1-Dimethylethyl cyclopropyl({2,3-dichloro-5-[2-(methyloxy)ethyl]phenyl}methyl)carbamate 1,1-Dimethylethyl cyclopropyl{[2,3-dichloro-5-(2-hydroxyethyl)phenyl]-methyl}carbamate (1 eq.) was taken up in THF (0.3 M). To this solution was then added sodium hydride (60% w/w dispersion in oil, 1 eq.) and the resulting suspension was stirred at RT for 5 min. Finally, iodomethane (10 eq.) was added and the now pale yellow solution was stirred in darkness at RT for another 10 h. The volatiles were then removed in vacuo and the resulting residue partitioned between ether and 1 N aq. HCl. The aqueous layer was separated and back-extracted with ether. The combined organic extracts were then washed further with 1 N aq. NaOH, water and brine. This was then dried over Na$_2$SO$_4$, filtered and the filtrate concentrated in vacuo to give the title compound (contaminated with oil) as a pale yellow oil.

Step 5: Amine 6

1,1-Dimethylethyl cyclopropyl({2,3-dichloro-5-[2-(methyloxy)ethyl]-phenyl}methyl)carbamate (1 eq.) from the previous step was taken up in CH$_2$Cl$_2$ (0.1 M). To this solution was then added HCl (4.0 M in dioxane, 30 eq.) and the resulting solution was stirred at RT for 2 h. The reaction was then quenched with 1 N aq. NaOH and extracted with ether. The combined organic extracts were then washed further with water and brine, dried over Na$_2$SO$_4$, filtered and the filtrate concentrated in vacuo. Purification of the crude product thus obtained by way of flash chromatography (SiO$_2$, 9:1 (v/v) Hex:EtOAc→EtOAc) afforded the title compound as a colorless oil.

Amine 7

N-(2-Methyl-5-[3-(methyloxy)propyl] phenyl}methyl)cyclopropanamine

Step 1: 5-Chloro-N-cyclopropyl-2-methylbenzamide

To a toluene solution (1 M) of 5-chloro-2-methylbenzoic acid (1 eq.) and DMF (1.2 eq.) was added at 0° C. oxalyl chloride (1.2 eq.) dropwise over 1 h. The resulting solution was stirred at 0° C. for 2 h before the volatiles were removed in vacuo. The resulting residue was taken up in dichloromethane (1 M), cooled to 0° C. and added sequentially cyclopropylamine (1.5 eq.) and Hunig's base (2 eq.) dropwise. The resulting suspension was stirred at RT for 18 h. The reaction was quenched with 1 N aq. HCl and extracted with dichloromethane. The combined organic extracts were dried over MgSO$_4$, filtered and the filtrate concentrated in vacuo to ~1/3 in volume. The resulting white suspension was added an equivalent volume of hexanes and the title compound was isolated via vacuum filtration.

Step 2: N-[(5-Chloro-2-methylphenyl)methyl]cyclopropanamine

At 0° C., a suspension of 5-chloro-N-cyclopropyl-2-methylbenzamide (1 eq.) from the previous step in THF (0.4 M) was added borane (1.0 M in THF, 3 eq.). The resulting suspension was warmed to RT over 1 h and then heated at reflux for 1 h. The now pale yellow solution was re-cooled to 0° C. and carefully quenched with 1 N aq. HCl. The resulting mixture was heated at reflux for 1 h to ensure complete breakdown of the amine-borane complex. Following careful neutralization with 1 N aq. NaOH, the aqueous layer was separated and back extracted with EtOAc. The combined organic extracts were washed with brine, dried over MgSO$_4$ and filtered. The filtrate was concentrated in vacuo and the crude product thus obtained was purified further by way of flash chromatography (SiO$_2$, Hex→4:1 (v/v) Hex:Et$_2$O) to reveal the title compound as a colorless oil.

Step 3: 1,1-Dimethylethyl[(5-chloro-2-methylphenyl)methyl]cyclopropylcarbamate

A THF solution (0.3 M) of N-[(5-Chloro-2-methylphenyl) methyl]cyclopropanamine from the previous step (1 eq.) was added at −78° C. potassium hexamethyldisilazide (0.5 M in toluene, 1.2 eq.). After 1 h of stirring at −78° C., di-tert-butyl dicarbonate (1.1 eq.) was added and the resulting mixture was slowly warmed to RT over 2 h. The reaction was quenched with sat. aq. NH$_4$Cl and then extracted with ether. The combined organic extracts were washed with brine, dried over MgSO$_4$, filtered and the filtrate concentrated in vacuo. Further purification by way of flash chromatography (SiO$_2$, Hex→4:1 (v/v) Hex:Et$_2$O) afforded the title compound as a pale yellow oil.

Step 4: 1,1-Dimethylethyl cyclopropyl({2-methyl-5-[(1E)-3-(methyloxy)-1-propen-1-yl]phenyl}methyl) carbamate 1,1-Dimethylethyl[(5-chloro-2-methylphenyl)methyl]cyclopropylcarbamate (1 eq.) from the previous step and 4,4,5,5-tetramethyl-2-[(1E)-3-(methyloxy)-1-propen-1-yl]-1,3,2-dioxaborolane (1 eq.) were combined in n-BuOH (0.48 M). To this solution was then added tris(dibenzylideneacetone) dipalladium(0) chloroform adduct (0.02 eq.), [2',6'-bis(methyloxy)-2-biphenylyl](dicyclohexyl)phosphane (0.08 eq.) and powdered potassium phosphate (2 eq.). The vessel was repeatedly evacuated and back-filled with nitrogen before the resulting suspension was heated at 100° C. for 16 h. The now black suspension was cooled to RT, diluted with EtOAc and filtered through a pad of SiO$_2$. The filtrate was then concentrated in vacuo and the crude product thus obtained was directly subjected to purification by way of flash chromatography (SiO$_2$, Hex→3:7 (v/v) Hex:EtOAc). The title compound was isolated as a pale yellow oil.

Step 5: 1,1-Dimethylethyl cyclopropyl({2-methyl-5-[3-(methyloxy)propyl]phenyl}methyl)-carbamate 1,1-Dimethylethyl cyclopropyl({2-methyl-5-[(1E)-3-(methyloxy)-1-propen-1-yl]phenyl}methyl)carbamate (1 eq.) from the previous step and 10% w/w palladium over charcoal (0.1 eq.) were suspended in EtOAc (0.08 M). The vessel was then evacuated and purged with H$_2$. Under a balloon-filled H$_2$ atmosphere, the reaction suspension was stirred at RT for 2 h. The reaction was then quenched with CH$_2$Cl$_2$, filtered through a bed of celite and the filtrate concentrated in vacuo. Purification of the crude product thus obtained by way of flash chromatography (SiO$_2$, Hex→1:1 (v/v) Hex:EtOAc) afforded the title compound as a colorless oil.

Step 6: Amine 7

1,1-Dimethylethyl cyclopropyl({2-methyl-5-[3-(methyloxy)propyl]phenyl}methyl)carbamate (1 eq.) from the previous step was taken up in CH$_2$Cl$_2$ (0.1 M). To this solution was then added HCl (4.0 M in dioxane, 30 eq.) and the resulting solution was stirred at RT for 2 h. The reaction was then quenched with 1 N aq. NaOH and extracted with ether. The combined organic extracts were then washed further with water and brine, dried over Na$_2$SO$_4$, filtered and the filtrate concentrated in vacuo. Purification of the crude product thus obtained by way of flash chromatography (SiO$_2$, 9:1 (v/v) Hex:EtOAc→EtOAc) afforded the title compound as a colorless oil.

Amine 8

N-({2-Methyl-5-[2-(methyloxy)ethyl] phenyl}methyl)cyclopropanamine

Amine 8 was prepared according to the procedure described in Amine 6 but using instead 1,1-dimethylethyl[(5- chloro-2-methylphenyl)methyl]cyclopropylcarbamate from Step 3, Amine 7 as the substrate, n-BuOH as the solvent, tris(dibenzylideneacetone)dipalladium(0) chloroform adduct as the palladium source, [2',6'-bis(methyloxy)-2-biphenylyl](dicyclohexyl)phosphane as the ligand and powdered potassium phosphate as the base for the Suzuki coupling (step 2).

Amine 9

N-({2,3-Difluoro-5-[3-(methyloxy)propyl] phenyl}methyl)cyclopropanamine

Amine 9 was prepared according to the procedure described in Amine 5 but using instead 2,3-difluorobenzaldehyde as starting material.

Amine 10

N-({3-(Methyloxy)-5-[3-(methyloxy)propyl] phenyl}methyl)cyclopropanamine

Step 1: 3-Bomo-5-hydroxybenzaldehyde

To a toluene solution (1.6 M) of n-butyl lithium (2.5 M in hexane, 2.1 eq.) was added at −10° C. n-butyl magnesium chloride (2.0 M in THF, 0.6 eq.). The reaction mixture was stirred at −10° C. for 30 min before a toluene solution (0.7 M) of 3,5-dibromophenol (1 eq.) was added dropwise at −10° C. over a period of 35 min. After stirring at −10° C. for a further 30 min, the reaction mixture was cooled to −40° C. before DMF (20 eq.) was added dropwise over 20 min. The reaction mixture was then slowly warmed to RT and allowed to stir at RT for 1 h. The reaction was carefully quenched at 0° C. with 1 N aq. HCl and extracted with ether. The combined organic extracts were washed with water and brine, dried over MgSO$_4$ and filtered. Concentration of the filtrate in vacuo afforded a yellow solid. Recystallization of the crude product thus obtained from ether-hexane afforded the title compound as a beige powder.

Step 2: 3-Hydroxy-5-[(1E)-3-(methyloxy)-1-propen-1-yl]benzaldehyde

3-Bomo-5-hydroxybenzaldehyde (1 eq.) from the previous step and 2-[(1E)-3-methoxyprop-1-en-1-yl]-4,4,5,5-tetramethyl-1,3,2-dioxaborolane (1 eq.) were combined in DMF (0.05 M). To this solution was then added palladium acetate (0.1 eq.), triphenylphosphine (0.2 eq.) and 2 M aq. sodium carbonate (4 eq.). The resulting suspension was heated at 80° C. for 16 h. The reaction mixture was quenched with 1 N aq. HCl and extracted with ether. The combined organic extracts were washed with water, sat. aq. NaHCO$_3$ and brine. Drying over MgSO$_4$, filtration and concentration of the filtrate in vacuo afforded the crude product as a brown tar. Further purification by way of flash chromatography (SiO$_2$, 4:1 (v/v) Hex:EtOAc→2:1 (v/v) Hex:EtOAc) afforded the title compound as a yellow oil.

Step 3: 3-(Methyloxy)-5-[(1E)-3-(methyloxy)-1-prop-1-en-1-yl]benzaldehyde

3-Hydroxy-5-[(1E)-3-(methyloxy)-1-propen-1-yl]benzaldehyde (1 eq.) from the previous step and iodomethane (2.2 eq.) were combined in acetone (0.07 M). To this solution was then added potassium carbonate (2 eq.) and the reaction suspension was heated at reflux for 16 h. The resulting reaction mixture was concentrated in vacuo and the residue partitioned between water and ether. The aqueous wash was separated and back-extracted with ether. The combined organic extracts were washed further with brine, dried over MgSO$_4$, filtered and the filtrate concentrated in vacuo. Further purification of the crude product thus obtained by way of flash chromatography (SiO$_2$, 19:1 (v/v) Hex:EtOAc→1:1 (v/v) Hex:EtOAc) afforded the title compound as a yellow oil.

Step 4: N-({3-(Methyloxy)-5-[(1E)-3-(methyloxy)-1-propen-1-yl]phenyl}methyl)-cyclopropanamine To a solution of 3-(methyloxy)-5-[(1E)-3-(methyloxy)-1-prop-1-en-1-yl]benzaldehyde (1 eq.) from the previous step (1 eq.) in dichloromethane (0.5 M) was added cyclopropylamine (2 eq.) and magnesium sulfate (1.5 eq.). The resulting suspension was stirred at RT for 12 h. The insolubles were removed via filtration. Concentration of the filtrate in vacuo afforded the crude imine as a yellow oil. This was then taken up in methanol (0.3 M) and then added at 0° C. sodium borohydride (1.5 eq.) portionwise over 5 min. The reaction mixture was slowly warmed to RT over 1 h and then stirred at RT for 2 h. After carefully quenching with sat. aq. NaHCO$_3$, the resulting mixture was extracted with ether. The combined organic extracts were washed with water and brine, dried over MgSO$_4$ and filtered. Concentration of the filtrate in vacuo afforded the title compound as a golden, yellow oil.

Step 5: Amine 10

To a solution of N-({3-(methyloxy)-5-[(1E)-3-(methyloxy)-1-propen-1-yl]phenyl}methyl)cyclopropanamine (1 eq.) from the previous step in EtOAc (0.04 M) was added palladium (10% w/w over activated carbon, 0.1 eq). The vessel was evacuated and back filled with hydrogen. The reaction suspension was then stirred under a balloon atmosphere of hydrogen for 1.5 h. The reaction was quenched with dichloromethane and filtered through a bed of celite. The insolubles were washed further with EtOAc and methanol. Concentration of the filtrate in vacuo afforded the title compound as a colorless oil.

Amine 11

N-({3-{[2-(Methyloxy)ethyl]oxy}-5-[3-(methyloxy) propyl]phenyl}methyl)cyclopropanamine Amine 11 was prepared according to the procedure described in Amine 10 but using instead 2-bromoethyl methyl ether as the alkylating reagent, cesium carbonate as the base and DMF as the solvent in step 3.

Amine 12

4-{3,4-Dichloro-5-[(cyclopropylamino)methyl] phenyl}butanenitrile

Step 1: 1,1-Dimethylethyl cyclopropyl{[2,3-dichloro-5-(2-oxoethyl)phenyl]methyl}carbamate 1,1-Dimethylethyl cyclopropyl{[2,3-dichloro-5-(2-hydroxyethyl)phenyl]methyl}carbamate (1 eq.) from Step 3, Amine 6 and sodium bicarbonate (1 eq.) were suspended in CH$_2$Cl$_2$ (0.1 M). At 0° C., DMP (1 eq.) was added and the resulting mixture was stirred at 0° C. for 15 min and then at RT for 45 min. The reaction was quenched with 1 N aq. NaOH and extracted with ether. The combined organic extracts were then washed further with water and brine, dried over Na$_2$SO$_4$, filtered and the filtrate concentrated in vacuo to afford the title compound as an unstable, colorless oil.

Step 2: 1,1-Dimethylethyl cyclopropyl({2,3-dichloro-5-[(2E)-3-cyano-2-propen-1-yl]phenyl}methyl)carbamate To a THF (0.1 M) suspension of anhydrous lithium chloride (1.2 eq.) was added sequentially diethyl(cyanomethyl)phosphonate (1.2 eq.) and DBU (1 eq.). The resulting suspension was stirred at RT for 15 min before 1,1-dimethylethyl cyclopropyl{[2,3-dichloro-5-(2-oxoethyl)phenyl]methyl}carbamate (1 eq.) from the previous step was added dropwise as a THF (0.1 M) solution. The resulting pink suspension was allowed to stir at RT for 12 h before it was carefully quenched with 1 N aq. HCl and then extracted with ether. The combined organic extracts were washed further with water and brine, dried over Na$_2$SO$_4$, filtered and the filtrate concentrated in vacuo. Purification of the crude product thus obtained by way of flash chromatography (SiO$_2$, Hex→3:7 (v/v) Hex:EtOAc) afforded the title compound as a colorless oil.

Step 3: 1,1-Dimethylethyl cyclopropyl{[2,3-dichloro-5-(3-cyanopropyl)phenyl]methyl}carbamate To a solution of 1,1-dimethylethyl cyclopropyl({2,3-dichloro-5-[(2E)-3-cyano-2-propen-1-yl]phenyl}methyl)carbamate (1 eq.) from the previous step in EtOAc (0.04 M) was added palladium (10% w/w over activated carbon, 0.1 eq). The vessel was evacuated and back filled with hydrogen. The reaction suspension was then stirred under a balloon atmosphere of hydrogen for 1.5 h. The reaction was quenched with dichloromethane and filtered through a bed of celite. The insolubles were washed further with EtOAc. Concentration of the filtrate in vacuo afforded the title compound as a colorless oil.

Step 4: Amine 12

To a solution of 1,1-dimethylethyl cyclopropyl{[2,3-dichloro-5-(3-cyanopropyl)phenyl]methyl}carbamate (1 eq.) from the previous step in CH$_2$Cl$_2$ (0.06 M) was added zinc(II) bromide (10 eq.). The resulting suspension was sonicated for 15 min and then allowed to stir at RT for 18 h. The reaction was quenched with 1 N aq. NaOH and then extracted with EtOAc. The combined organic extracts were washed further with water and brine, dried over Na$_2$SO$_4$, filtered and the filtrate concentrated in vacuo. Purification of the crude product thus obtained by way of flash chromatography (SiO$_2$, 9:1 (v/v) Hex:EtOAc→3:7 (v/v) Hex:EtOAc) afforded the title compound as a colorless oil.

Amine 13

4-{3-[(Cyclopropylamino)methyl]-4,5-difluorophenyl}butanenitrile

Amine 13 was synthesized according to the procedure described in Amine 12 but using instead 1,1-dimethylethyl cyclopropyl{[2,3-difluoro-5-(2-hydroxyethyl)phenyl]methyl}carbamate prepared analogously from 2,3-difluorobenzaldehyde.

Amine 14

Methyl 4-{3,4-dichloro-5-[(cyclopropylamino)methyl]phenyl}butanoate

Amine 14 was prepared according to the procedure described in Amine 12 but replacing anhydrous lithium chloride, diethyl(cyanomethyl)phosphonate and DBU with methyl (triphenyl-λ$^5$-phosphanylidene)acetate in the Wittig-olefination step (step 2).

Amine 15

N-({3-[3-(Methyloxy)propyl]-1-naphthalenyl}methyl)cyclopropanamine

Step 1: Methyl 3-[(1E)-3-(methyloxy)-1-propen-1-yl]-1-naphthalenecarboxylate Methyl 3-bromo-1-naphthalenecarboxylate (1 eq.) and 4,4,5,5-tetramethyl-2-[(1E)-3-(methyloxy)-1-propen-1-yl]-1,3,2-dioxaborolane (1.5 eq.) were combined in a 5:1 (v/v) mixture of DMF:n-PrOH (0.2 M). To this solution was then added trans-bis(triphenylphosphine) palladium(II) bromide (0.05 eq.) and the vessel was repeatedly evacuated and back-filled with nitrogen. Finally, 2 N aq. Na$_2$CO$_3$ (2 eq.) was added and the resulting biphasic suspension was heated at 90° C. for 8 h. The now black suspension was cooled to RT, diluted with water and extracted with 1:1 (v/v) hexanes:ether. The combined organic extracts were then washed further with 1 N aq. NaOH, 1 N aq. HCl, water and brine. This was then dried over Na$_2$SO$_4$, filtered and the filtrate concentrated in vacuo to afford the title compound as a red oil.

Step 2: Methyl 3-[3-(methyloxy)propyl]-1-naphthalenecarboxylate

Methyl 3-[(1E)-3-(methyloxy)-1-propen-1-yl]-1-naphthalenecarboxylate (1 eq.) from the previous step and 10% w/w palladium over charcoal (0.1 eq.) were suspended in MeOH (0.08 M). The vessel was then evacuated and purged with H$_2$. Under a balloon-filled H$_2$ atmosphere, the reaction suspension was stirred at RT for 2 h. The reaction was then quenched with CH$_2$Cl$_2$, filtered through a bed of celite and the filtrate concentrated in vacuo. Purification of the crude product thus obtained by way of flash chromatography (SiO$_2$, Hex→1:1 (v/v) Hex:EtOAc) afforded the title compound as a colorless oil.

Step 3: 3-[3-(Methyloxy)propyl]-1-naphthalenecarboxylic acid

Methyl 3-[3-(methyloxy)propyl]-1-naphthalenecarboxylate (1 eq.) from the previous step was taken up in a 2:1 (v/v) mixture of MeOH:THF (0.08 M). To this solution was then added LiOH (2.0 M aq. solution, 3 eq.) and the resulting cloudy solution was vigorously stirred at RT for 24 h. The volatiles were then removed in vacuo and the pH of the residue was carefully adjusted to ~2 with 1 N aq. HCl before it was extracted with EtOAc. The combined organic extracts were washed further with water and brine, dried over Na$_2$SO$_4$ and filtered. Concentration of the filtrate in vacuo afforded the title compound as a white solid.

Step 4: N-Cyclopropyl-3-[3-(methyloxy)propyl]-1-naphthalenecarboxamide

To a CH$_2$Cl$_2$ solution (0.1 M) of 3-[3-(methyloxy)propyl]-1-naphthalenecarboxylic acid (1 eq.) from the previous step was added at 0° C. oxalyl chloride (1.2 eq.) followed by a few drops of DMF. The resulting solution was stirred at RT for 2 h before the volatiles were removed in vacuo. The resulting residue was taken up in dichloromethane (0.1 M), cooled to 0° C. and added sequentially Hunig's base (1.2 eq.) an cyclopropylamine (1.1 eq.) dropwise. The resulting suspension was stirred at RT for 18 h. The reaction was quenched with 1 N aq. HCl and extracted with ether. The combined organic extracts were washed further with 1 N aq. NaOH, water and brine, dried over $Na_2SO_4$ and filtered. Concentration of the filtrate in vacuo afforded the title compound as a white solid.

Step 5: Amine 15

To a THF solution (0.1 M) of N-cyclopropyl-3-[3-(methyloxy)propyl]-1-naphthalenecarboxamide (1 eq.) from the previous step was added, at reflux, borane-methyl sulfide complex (6.6 eq.). To the reaction vessel was the attached a short path distillation apparatus and most of the volatiles were slowly distilled off over a period of 1.5 h. The now yellow solution was re-cooled to 0° C. and carefully quenched with 1 N aq. HCl. The resulting mixture was heated at reflux for 1 h to ensure complete breakdown of the amine-borane complex. Following careful neutralization with 1 N aq. NaOH, the aqueous layer was separated and back extracted with EtOAc. The combined organic extracts were washed with brine, dried over $Na_2SO_4$ and filtered. The filtrate was concentrated in vacuo and the crude product thus obtained was purified further by way of flash chromatography ($SiO_2$, 9:1 (v/v) Hex:EtOAc→3:7 (v/v) Hex:EtOAc) to reveal the title compound as a colorless oil.

Amine 16

Methyl (2-{3,4-Dichloro-5-[(cyclopropylamino)methyl]phenyl}ethyl)carbamate

Step 1: 1,1-Dimethylethyl cyclopropyl[(2,3-dichloro-5-formylphenyl)methyl]carbamate To a dichloromethane (0.03 M) solution of 1,1-dimethylethyl cyclopropyl[(2,3-dichloro-5-ethenylphenyl)methyl] carbamate (1 eq.) from Step 2, Amine 6 was bubbled at −78° C. freshly generated ozone until a persistent blue color was obtained. To this was then added triphenylphosphine (1.2 eq.) in one rapid portion and the resulting mixture was slowly warmed to RT over 3 h. The volatiles were removed in vacuo and the remaining residue was triturated with 2:1 (v/v) Hex:$Et_2O$. The insolubles were removed via filtration and the filtrate was concentrated in vacuo. Purification of the crude product thus obtained by way of flash chromatography ($SiO_2$, Hex→1:1 (v/v) Hex:EtOAc) afforded the title compound as a colorless oil.

Step 2: 1,1-Dimethylethyl cyclopropyl{[2,3-dichloro-5-(hydroxymethyl)phenyl]methyl}carbamate To a methanol (0.16 M) solution of 1,1-dimethylethyl cyclopropyl[(2,3-dichloro-5-formylphenyl)methyl]carbamate from the previous step was added at 0° C. sodium borohydride (1.3 eq.). The resulting solution was stirred at 0° C. for 2 h before the volatiles were then removed in vacuo. The resulting residue was then partitioned between ether and 1 N aq. HCl. The aqueous layer was separated and back-extracted with ether. The combined organic extracts were washed further with water and brine, dried over $Na_2SO_4$, filtered and the filtrate concentrated in vacuo. Purification of the crude product thus obtained by way of flash chromatography ($SiO_2$, Hex→3:7 (v/v) Hex:EtOAc) afforded the title compound as a colorless oil.

Step 3: {3,4-Dichloro-5-[(cyclopropyl{[(1,1-dimethylethyl)oxy]carbonyl}amino)methyl]phenyl}methyl methanesulfonate To a solution of 1,1-dimethylethyl cyclopropyl{[2,3-dichloro-5-(hydroxymethyl)phenyl]methyl}carbamate (1 eq.) from the previous step in dichloromethane (0.1 M) was added sequentially at 0 Hunig's base (3 eq.) and methanesulfonyl chloride (1.1 eq.). The resulting solution was stirred at 0° C. for 30 min and then at RT for 15 min. The reaction mixture was then diluted with ether and carefully quenched with 1 N aq. HCl. The aqueous layer was separated and back-extracted with ether. The combined organic extracts were washed further with water and brine, dried over $Na_2SO_4$, filtered and the filtrate concentrated in vacuo to afford the crude title compound as a colorless oil.

Step 4: 1,1-Dimethylethyl cyclopropyl{[2,3-dichloro-5-(cyanomethyl)phenyl]methyl}carbamate To a solution of {3,4-dichloro-5-[(cyclopropyl{[(1,1-dimethylethyl)oxy]carbonyl}amino)methyl]phenyl}methyl methanesulfonate (1 eq.) from the previous step in DMSO (0.48 M) was added potassium cyanide (1.3 eq.) and sodium iodide (0.1 eq.). The resulting solution was stirred at RT for 3 h before it was diluted with ether and quenched with 1 N aq. NaOH. The aqueous layer was separated and back-extracted with ether. The combined organic extracts were washed further with water and brine, dried over $Na_2SO_4$, filtered and the filtrate concentrated in vacuo. Purification of the crude product thus obtained by way of flash chromatography ($SiO_2$, 19:1 (v/v) Hex:EtOAc→3:7 (v/v) Hex:EtOAc) afforded the title compound as a colorless oil.

Step 5: 1,1-Dimethylethyl{[5-(2-aminoethyl)-2,3-dichlorophenyl]methyl}cyclopropylcarbamate To a solution of 1,1-dimethylethyl cyclopropyl{[2,3-dichloro-5-(cyanomethyl)phenyl]methyl}carbamate (1 eq.) from the previous step and cobalt(II) chloride hexahydrate (2 eq.) in methanol (0.07 M) was added sodium borohydride (10 eq.) portionwise at 0° C. The resulting mixture was stirred at 0° C. for 10 min and then at RT for 2 h. The now brown suspension was quenched with 1 N aq. NaOH and then extracted with EtOAc. The combined organic extracts were washed further with water and brine, dried over $Na_2SO_4$ and filtered through a bed of celite. Concentration of the filtrate in vacuo afforded the crude title compound as a pale brown, amorphous solid.

Step 6: 1,1-Dimethylethyl cyclopropyl{[2,3-dichloro-5-(2-{[(methyloxy)carbonyl]amino}ethyl)phenyl]methyl}carbamate To a solution of 1,1-dimethylethyl{[5-(2-aminoethyl)-2,3-dichlorophenyl]methyl}cyclopropylcarbamate (1 eq.) from the previous step in dichloromethane (0.07 M) was added sequentially at 0 Hunig's base (1.2 eq.) and methyl chloroformate. The resulting solution was then allowed to warm slowly to RT over 3 h. The crude reaction mixture was subsequently diluted with ether and washed sequentially with 1 N aq. NaOH, 1 N aq. HCl, water and brine. The ether extract was then dried over Na₂SO₄, filtered and the filtrate concentrated in vacuo. Purification of the crude product thus obtained by way of flash chromatography (SiO₂, 19:1 (v/v) Hex:EtOAc→EtOAc) afforded the title compound as a pale yellow oil.

Step 7: Amine 16

To a solution of 1,1-dimethylethyl cyclopropyl{[2,3-dichloro-5-(2-{[(methyloxy)carbonyl]amino}ethyl)phenyl] methyl}carbamate (1 eq.) from the previous step in CH₂Cl₂ (0.06 M) was added HCl (4.0 M in dioxane, 30 eq.). The resulting solution was stirred at RT for 3 h. The reaction was then quenched with 1 N aq. NaOH and extracted with ether. The combined organic extracts were then washed further with water and brine, dried over Na₂SO₄, filtered and the filtrate concentrated in vacuo. Purification of the crude product thus obtained by way of flash chromatography (SiO₂, 24:1 (v/v) CH₂Cl₂:MeOH) afforded the title compound as a colorless oil.

Amine 17

N-(8-Quinolinylmethyl)cyclopropanamine

To a dichloromethane (0.13 M) solution of 8-quinolinecarbaldehyde (1 eq.) was added magnesium sulphate (1 eq.) and cyclopropyl amine (2 eq.). The resulting suspension was stirred at RT for 16 h. The insolubles were removed via filtration and rinsed with dichloromethane before the combined filtrate was concentrated in vacuo. The crude imine thus obtained was taken up in methanol (0.13 M) and then added sodium borohydride (1.5 eq.) portionwise. The reaction mixture was stirred at RT for 2 h before it was quenched with 1 N aq. HCl. The pH of the solution was then adjusted to ~10 with 1 N aq. NaOH before it was extracted with ether. The combined organic extracts were washed further with water and brine, dried over Na₂SO₄, filtered and the filtrate concentrated in vacuo to afford the crude title compound as a yellow oil.

Amine 18

N-(8-Isoquinolinylmethyl)cyclopropanamine

Amine 18 was prepared according to the procedure described in Amine 17 but using instead 8-isoquinolinecarbaldehyde as starting material.

Amine 19

N-(5-Isoquinolinylmethyl)cyclopropanamine

Amine 19 was prepared according to the procedure described in Amine 17 but using instead 5-isoquinolinecarbaldehyde as starting material.

Amine 20

N-(5-Quinolinylmethyl)cyclopropanamine

Amine 20 was prepared according to the procedure described in Amine 17 but using instead 5-quinolinecarbaldehyde as starting material.

Amine 21

N-(1-Isoquinolinylmethyl)cyclopropanamine

Amine 21 was prepared according to the procedure described in Amine 17 but using instead 1-isoquinolinecarbaldehyde as starting material.

Amine 22

N-({2-[3-(Methyloxy)propyl]-4-quinolinyl}methyl) cyclopropanamine

Amine 22 was prepared according to the procedure described in published patent application WO 2007/009250 A1.

Amine 23

N-({6-[3-(Methyloxy)propyl]-8-quinolinyl}methyl) cyclopropanamine

Step 1: 6-({[(1,1-Dimethylethyl)(dimethyl)silyl] oxy}methyl)-8-quinolinecarbaldehyde To a THF (0.06 M) solution of 8-bromo-6-({[(1,1-dimethylethyl)(dimethyl)silyl]oxy}methyl)quinoline (1 eq.) was added at −78° C. n-butyl lithium (2.5 M in hexane, 2.1 eq.) dropwise over a period of 10 min. The resulting yellow solution was stirred at −78° C. for 15 min before DMF (2 eq.) was added dropwise over a period of 10 min. The now red solution was stirred at −78° C. for another 2 h before the reaction mixture was quenched with the addition of sat. aq. NH₄Cl. The aqueous layer was separated and back-extracted with ether. The combined organic extracts were then washed with brine, dried over Na₂SO₄, filtered and the filtrate concentrated in vacuo. Purification of the crude product thus obtained by way of flash chromatography (SiO₂, Hex→3:7 (v/v) Hex:EtOAc) afforded the title compound as a yellow oil that solidified upon standing.

Step 2: N-{[6-({[(1,1-Dimethylethyl)(dimethyl)silyl] oxy}methyl)-8-quinolinyl]methyl}cyclopropanamine To a dichloromethane (0.12 M) solution of 6-({[(1,1-dimethylethyl)(dimethyl)silyl]oxy}methyl)-8-quinolinecarbaldehyde (1 eq.) from the previous step was added magnesium sulphate (1 eq.) and cyclopropyl amine (2 eq.). The resulting suspension was stirred at RT for 16 h. The insolubles were removed via filtration and rinsed with dichloromethane before the combined filtrate was concentrated in vacuo. The crude imine thus obtained was taken up in methanol (0.12 M) and then added sodium borohydride (1.5 eq.) portionwise. The reaction mixture was stirred at RT for 2 h. The volatiles were then removed in vacuo and the resulting residue was partitioned between ether and 1 N aq. NaOH. The aqueous layer was separated and back-extracted with ether. The combined organic extracts were washed further with water and brine, dried over Na₂SO₄, filtered and the filtrate concentrated in vacuo to afford the crude title compound as a yellow oil.

Step 3: 1,1-Dimethylethyl cyclopropyl{[6-({[(1,1-dimethylethyl)(dimethyl)silyl]oxy}methyl)-8-quinolinyl]methyl}carbamate To a solution of N-{[6-({[(1,1-dimethylethyl)(dimethyl) silyl]oxy}methyl)-8-quinolinyl]methyl}cyclopropanamine (1 eq.) from the previous step in dichloromethane (0.12 M) was added sequentially Hunig's base (1.2 eq.) and bis(1,1-dimethylethyl)dicarbonate (1.1 eq.). The resulting solution was stirred at RT for 8 h. The volatiles were then removed in vacuo. Purification of the crude product thus obtained by way of flash chromatography (SiO$_2$, Hex→3:7 (v/v) Hex:EtOAc) afforded the title compound as a colorless oil.

Step 4: 1,1-Dimethylethyl cyclopropyl{[6-(hydroxymethyl)-8-quinolinyl]methyl}carbamate To a solution of 1,1-dimethylethyl cyclopropyl{[6-({[(1,1-dimethylethyl)(dimethyl)silyl]oxy}methyl)-8-quinolinyl]methyl}carbamate (1 eq.) from the previous step in THF (0.12 M) was added TBAF (1.0 M in hexane, 1.6 eq.). The resulting solution was stirred at RT for 2 h before the volatiles were removed in vacuo. The resulting residue was partitioned between ether and water. The aqueous layer was separated and back-extracted with ether. The combined organic extracts were washed further with water and brine, dried over Na$_2$SO$_4$, filtered and the filtrate concentrated in vacuo. Purification of the crude product thus obtained by way of flash chromatography (SiO$_2$, 9:1 (v/v) Hex:EtOAc→3:7 (v/v) Hex:EtOAc) afforded the title compound as a colorless oil.

Step 5: 1,1-Dimethylethyl cyclopropyl[(6-formyl-8-quinolinyl)methyl]carbamate

To a suspension of 1,1-dimethylethyl cyclopropyl{[6-(hydroxymethyl)-8-quinolinyl]methyl}carbamate (1 eq.) from the previous step and sodium bicarbonate (1.1 eq.) in dichloromethane (0.1 M) was added DMP (1.1 eq.) at 0° C. The resulting mixture was stirred at RT for 2 h before it was quenched with sat. aq. NaHSO$_3$ and then extracted with Et$_2$O. The combined organic extracts were washed further with 1 N aq. NaOH, water and brine, dried over Na$_2$SO$_4$, and filtered. Concentration of the filtrate in vacuo afforded the crude title compound as a white solid.

Step 6: Methyl 3-{8-[(cyclopropyl{[(1,1-dimethylethyl)oxy]carbonyl}amino)methyl]-6-quinolinyl}-2-propenoate To a solution of 1,1-dimethylethyl cyclopropyl[(6-formyl-8-quinolinyl)methyl]carbamate (1 eq.) from the previous step in dichloromethane (0.06 M) was added methyl(triphenylphosphoranylidene)acetate (1.1 eq.) at 0° C. The resulting solution was then allowed to warm slowly to RT over 4 h. The volatiles were then removed in vacuo. Purification of the crude product thus obtained by way of flash chromatography (SiO$_2$, 9:1 (v/v) Hex:EtOAc→3:7 (v/v) Hex:EtOAc) afforded the title compound as a white solid.

Step 7: Methyl 3-{8-[(cyclopropyl{[(1,1-dimethylethyl)oxy]carbonyl}amino)methyl]-6-quinolinyl}propanoate To a solution of methyl 3-{8-[(cyclopropyl{[(1,1-dimethylethyl)oxy]carbonyl}amino)methyl]-6-quinolinyl}-2-propenoate (1 eq.) from the previous step in EtOAc (0.1 M) was added palladium (10% (w/w) over carbon, 0.1 eq.). The resulting suspension was evacuated and back-filled repeatedly with hydrogen. Finally, the reaction suspension was allowed to stir under a hydrogen-filled balloon atmosphere for 3 h. The reaction was quenched with the addition of dichloromethane and filtered through a bed of celite. The filtrate was then concentrated in vacuo. Purification of the crude product thus obtained by way of flash chromatography (SiO$_2$, 9:1 (v/v) Hex:EtOAc→EtOAc) afforded the title compound as a yellow oil.

Step 8: 1,1-Dimethylethyl cyclopropyl{[6-(3-hydroxypropyl)-8-quinolinyl]methyl}carbamate To a solution of methyl 3-{8-[(cyclopropyl{[(1,1-dimethylethyl)oxy]carbonyl}amino)methyl]-6-quinolinyl}propanoate (1 eq.) from the previous step in THF (0.08 M) was added lithium borohydride (5 eq.). The resulting mixture was stirred at RT for 14 h before it was diluted with ether and quenched with 1 N aq. NaOH. The aqueous layer was separated and back-extracted with ether. The combined organic extracts were washed further with water and brine, dried over Na$_2$SO$_4$, and filtered. Concentration of the filtrate in vacuo afforded the crude title compound as a colorless oil.

Step 9: 1,1-Dimethylethyl cyclopropyl({6-[3-(methyloxy)propyl]-8-quinolinyl}methyl)carbamate To a solution of 1,1-dimethylethyl cyclopropyl{[6-(3-hydroxypropyl)-8-quinolinyl]methyl}carbamate (1 eq.) from the previous step in THF (0.3 M) was added sodium hydride (60% (w/w) dispersion in paraffin oil, 1.2 eq.). The resulting suspension was stirred at RT for 15 min before iodomethane (1.4 eq.) was added. The now yellow solution was stirred at RT for 12 h before the reaction was quenched with the addition of 1 N aq. NaOH. The aqueous layer was separated and back-extracted with ether. The combined organic extracts were washed further with water and brine, dried over Na$_2$SO$_4$, filtered and the filtrate concentrated in vacuo. Purification of the crude product thus obtained by way of flash chromatography (SiO$_2$, 9:1 (v/v) Hex:EtOAc→EtOAc) afforded the title compound as a colorless oil.

Step 10: Amine 23

To a solution of 1,1-dimethylethyl cyclopropyl({6-[3-(methyloxy)propyl]-8-quinolinyl}methyl)carbamate (1 eq.) from the previous step in CH$_2$Cl$_2$ (0.06 M) was added HCl (4.0 M in dioxane, 30 eq.). The resulting solution was stirred at RT for 6 h. The reaction was then quenched with 1 N aq. NaOH and extracted with EtOAc. The combined organic extracts were then washed further with water and brine, dried over Na$_2$SO$_4$ and filtered. Concentration of the filtrate in vacuo afforded the title compound as a yellow oil.

Amine 24

N-({3-Chloro-5-[3-(methyloxy)propyl]phenyl}methyl)cyclopropanamine

Step 1:
N-[(3-Bromo-5-chlorophenyl)methyl]cyclopropanamine

To a 4:1 (v/v) MeOH:THF solution (0.06 M) of 3-bromo-5-chlorobenzaldehyde (1 eq.) and cyclopropylamine (1.1 eq.) was added sodium cyanoborohydride (1.5 eq.) portionwise followed by neat acetic acid (3 eq.). The resulting mixture was stirred at RT for 20 h. The volatiles were then removed in vacuo. The resulting residue was taken up in ether and sat. aq. NH$_4$Cl. The aqueous layer was separated and back-extracted with ether. The combined organic extracts were then washed with brine, dried over MgSO$_4$ and filtered. Concentration of the filtrate in vacuo afforded the crude title compound as a yellow oil.

Step 2: N-({3-Chloro-5-[(1E)-3-(methyloxy)-1-propen-1-yl]phenyl}methyl)cyclopropanamine To a 4:1 (v/v) DMF:n-propanol solution (0.15 M) of N-[(3-bromo-5-chlorophenyl)methyl]cyclopropanamine (1 eq.) from the previous step and 4,4,5,5-tetramethyl-2-[(1E)-3-(methyloxy)-1-propen-1-yl]-1,3,2-dioxaborolane (2 eq.) was added trans-dibromobis(triphenylphosphine) palladium(II) (0.05 eq.) followed by sodium carbonate (2 M aqueous solution, 3 eq.). The reaction vessel was evacuated and purged with nitrogen five times and then heated at 100° C. for 2 h. The cooled reaction mixture was poured into aq. sat. NH$_4$Cl and then extracted with EtOAc. The combined organic extracts were washed further with water and brine, dried over MgSO$_4$, filtered and the filtrate concentrated in vacuo. Purification of the crude product thus obtained by way of flash chromatography (SiO$_2$, 3:7 (v/v) Hex:EtOAc→EtOAc) afforded the title compound as an oil.

Step 3: Amine 24

To a solution of N-({3-chloro-5-[(1E)-3-(methyloxy)-1-propen-1-yl]phenyl}methyl)cyclopropanamine (1 eq.) from the previous step in EtOAc (0.2 M) was added palladium (10% (w/w) on carbon, 0.4 eq.). The reaction vessel was evacuated and purged with hydrogen two times and then stirred at RT for 14 h. The reaction suspension was then filtered through a pad of silica gel and the insolubles rinsed with EtOAc. Concentration of the filtrate in vacuo afforded the title compound as a pale green oil.

Amine 25

N-{[1-(3-Methoxypropyl)-1H-indol-3-yl]methyl}cyclopropanamine

Step 1: 1-(3-Methoxypropyl)-1H-indole-3-carbaldehyde

To a DMF (0.1 M) solution of indole-3-carbaldehyde (1 eq) was added sodium hydride (60% (w/w) dispersion in oil, 1.1 eq.) at 0° C. followed by 1-bromo-3-methoxypropane (1.5 eq.). The reaction mixture was stirred at 50° C. for 4 h. The mixture was then diluted with ether, washed with water and brine, dried over MgSO$_4$, filtered and the filtrate concentrated in vacuo. Purification of the crude product thus obtained by way of flash chromatography (SiO$_2$, 1:1 (v/v) Hex:EtOAc→EtOAc) afforded the title compound as a colorless oil.

Step 2: Amine 25

To a 3:1 (v/v) CH$_2$Cl$_2$:MeOH solution (0.1 M) of 1-(3-methoxypropyl)-1H-indole-3-carbaldehyde (1 eq) was added cyclopropyl amine (2 eq), acetic acid (2.5 eq) and then sodium triacetoxyborohydride (1.5 eq) at 0° C. The reaction was slowly warmed to RT and stirred at RT for 3 h. The reaction was then quenched with saturated aq. NaHCO$_3$, extracted with dichloromethane, dried over MgSO$_4$, filtered and the filtrate concentrated in vacuo. Purification of the crude product thus obtained by way of flash chromatography (SiO$_2$, 96:4 (v/v) CH$_2$Cl$_2$:2.0 M NH$_3$ in MeOH) afforded the title compound as a colorless oil.

Amine 26

3-{3,4-Dichloro-5-[(cyclopropylamino)methyl]phenyl}propanenitrile

Step 1: (5-Bromo-2,3-dichlorophenyl)methanol

To a 5:1 (v/v) MeOH:THF solution (0.38 M) of 5-bromo-2,3-dichlorobenzaldehyde (1 eq.) from Step 1, Amine 5 was added at 0° C. sodium borohydride (1.1 eq.) portionwise over 45 min. The reaction solution was stirred at 0° C. for 2 h before the volatiles were removed in vacuo. The resulting residue was then partitioned between ether and 10% aq. HCl. The aqueous layer was separated and back-extracted with ether. The combined organic extracts were washed further with 1 N aq. NaOH, water and brine, dried Na$_2$SO$_4$, filtered and the filtrate concentrated in vacuo. Purification of the crude product thus obtained by way of flash chromatography (SiO$_2$, 9:1 (v/v) Hex:EtOAc→3:7 (v/v) Hex:EtOAc) afforded the title compound as a white solid.

Step 2: {[(5-Bromo-2,3-dichlorophenyl)methyl]oxy}(1,1-dimethylethyl)dimethylsilane To a DMF (0.34 M) solution of (5-bromo-2,3-dichlorophenyl)methanol (1 eq.) from the previous step was added chloro(1,1-dimethylethyl)dimethylsilane (1.1 eq.) and imidazole (1.5 eq.). The resulting yellow solution was stirred at RT for 16 h. The reaction mixture was then diluted with ether and washed sequentially with 10% aq. HCl, water and brine. The ether extract was dried Na$_2$SO$_4$, filtered and the filtrate concentrated in vacuo to afford the crude title compound as a colorless oil.

Step 3: {[(2,3-Dichloro-5-ethenylphenyl)methyl]oxy}(1,1-dimethylethyl)dimethylsilane {[(5-Bromo-2,3-dichlorophenyl)methyl]oxy}(1,1-dimethylethyl)dimethylsilane (1 eq.) from the previous step and 2-ethenyl-4,4,5,5-tetramethyl-1,3,2-dioxaborolane (1 eq.) were combined in a 2:1 (v/v) mixture of DMF:n-PrOH (0.11 M). To this solution was then added palladium(II) acetate (0.05 eq.) and triphenylphosphine (0.15 eq.) before the vessel was repeatedly evacuated and back-filled with nitrogen. Finally, 2 N aq. Na$_2$CO$_3$ (2 eq.) was added and the resulting biphasic suspension was heated at 90° C. for 8 h. The now black suspension was cooled to RT, diluted with water and extracted with 1:1 (v/v) hexanes:ether. The combined organic extracts were then washed further with 1 N aq. NaOH, water and brine. This was then dried over Na$_2$SO$_4$, filtered and the filtrate concentrated in vacuo to afford the crude title compound as a black oil.

Step 4: 2-[3,4-Dichloro-5-({[(1,1-dimethylethyl)(dimethyl)silyl]oxy}methyl)phenyl]ethanol {[(2,3-Dichloro-5-ethenylphenyl)methyl]oxy}(1,1-dimethylethyl)dimethylsilane (1 eq.) from the previous step, [Ir(COD)Cl]$_2$ (0.025 eq.) and DPPB (0.05 eq.) were combined in THF (0.11 M). To this solution was then added 4,4,5,5-tetramethyl-1,3,2-dioxaborolane (1.3 eq.) and the resulting red solution was stirred at RT for 16 h. Finally, sodium perborate (0.1 M aqueous solution, 1 eq.) was added and the now black biphasic solution was vigorously stirred at RT for another 8 h. The aqueous layer was separated and back-extracted with ether. The combined organic extracts were then washed further with 1 N aq. NaOH, water and brine. This was then dried over $Na_2SO_4$, filtered and the filtrate concentrated in vacuo to afford a black oil. Purification of the crude product thus obtained by way of flash chromatography ($SiO_2$, 9:1 (v/v) Hex:EtOAc→1:1 (v/v) EtOAc:Hex) afforded the title compound as a pale yellow oil.

Step 5: 2-[3,4-Dichloro-5-({[(1,1-dimethylethyl)(dimethyl)silyl]oxy}methyl)phenyl]ethyl methanesulfonate To a dichloromethane (0.11 M) solution of 2-[3,4-dichloro-5-({[(1,1-dimethylethyl)(dimethyl)silyl]oxy}methyl)phenyl]ethanol (1 eq.) from the previous step was added at 0° C. Hunig's base (1.5 eq.) and methanesulfonyl chloride (1.1 eq.). The resulting suspension was stirred at 0° C. for 30 min and at RT for 15 min. The reaction was then diluted with ether and quenched with 1N aq. HCl. The aqueous layer was separated and back-extracted with ether. The combined organic extracts were washed further with 1 N aq. NaOH, water and brine, dried over $Na_2SO_4$, filtered and the filtrate concentrated in vacuo to give the title compound as a brown oil.

Step 6: 3-[3,4-Dichloro-5-({[(1,1-dimethylethyl)(dimethyl)silyl]oxy}methyl)phenyl]propanenitrile To a DMSO (0.4 M) solution of 2-[3,4-dichloro-5-({[(1,1-dimethylethyl)(dimethyl)silyl]oxy}methyl)phenyl]ethyl methanesulfonate (1 eq.) from the previous step was added potassium cyanide (1.3 eq.). The resulting solution was stirred at 80° C. for 4 h. The reaction was then diluted with ether and quenched with water. The aqueous layer was separated and back-extracted with ether. The combined organic extracts were washed further with water and brine, dried over $Na_2SO_4$, filtered and the filtrate concentrated in vacuo to give the title compound as a pink oil.

Step 7: 3-[3,4-Dichloro-5-(hydroxymethyl)phenyl]propanenitrile

To a THF (0.1 M) solution of 3-[3,4-dichloro-5-({[(1,1-dimethylethyl)(dimethyl)silyl]oxy}methyl)phenyl]propanenitrile (1 eq.) from the previous step was added TBAF (1.0 M THF solution, 1.2 eq.). The resulting solution was stirred at RT for 3 h. The reaction was then diluted with ether and quenched with water. The aqueous layer was separated and back-extracted with ether. The combined organic extracts were washed further with water and brine, dried over $Na_2SO_4$, filtered and the filtrate concentrated in vacuo. Purification of the crude product thus obtained by way of flash chromatography ($SiO_2$, 9:1 (v/v) Hex:EtOAc→3:7 (v/v) Hex:EtOAc) afforded the title compound as a colorless oil.

Step 8: 3-(3,4-Dichloro-5-formylphenyl)propanenitrile

To a suspension of 3-([3,4-dichloro-5-(hydroxymethyl)phenyl]propanenitrile (1 eq.) from the previous step and sodium bicarbonate (1.1 eq.) in dichloromethane (0.1 M) was added DMP (1.1 eq.) at 0° C. The resulting mixture was stirred at RT for 2 h before it was quenched with sat. aq. $NaHSO_3$ and then extracted with $Et_2O$. The combined organic extracts were washed further with 1 N aq. NaOH, water and brine, dried over $Na_2SO_4$, and filtered. Concentration of the filtrate in vacuo afforded the crude title compound as a white solid.

Step 9: Amine 26

To a dichloromethane (0.11 M) solution of 3-(3,4-dichloro-5-formylphenyl)propanenitrile (1 eq.) from the previous step was added magnesium sulphate (1 eq.) and cyclopropyl amine (1.2 eq.). The resulting suspension was stirred at RT for 16 h. The insolubles were removed via filtration and rinsed with dichloromethane before the combined filtrate was concentrated in vacuo. The crude imine thus obtained was taken up in methanol (0.11 M) and then added sodium borohydride (3 eq.) portionwise. The reaction mixture was stirred at RT for 16 h. The volatiles were then removed in vacuo and the resulting residue was partitioned between ether and 1 N aq. NaOH. The aqueous layer was separated and back-extracted with ether. The combined organic extracts were washed further with water and brine, dried over $Na_2SO_4$, filtered and the filtrate concentrated in vacuo. Purification of the crude product thus obtained by way of flash chromatography ($SiO_2$, 9:1 (v/v) Hex:EtOAc→EtOAc) afforded the title compound as a colorless oil.

Amine 27

N-(2-{3,4-Dichloro-5-[(cyclopropylamino)methyl]phenyl}ethyl)propanamide

Step 1: ({[5-(2-Azidoethyl)-2,3-dichlorophenyl]methyl}oxy)(1,1-dimethylethyl)dimethylsilane To a DMF (0.4 M) solution of 2-[3,4-dichloro-5-({[(1,1-dimethylethyl)(dimethyl)silyl]oxy}methyl)phenyl]ethyl methanesulfonate (1 eq.) from Step 5, Amine 26 was added at RT sodium azide (5 eq.). The resulting solution was stirred at RT for 12 h and then at 80° C. for 3 h. The reaction mixture was then diluted with ether and washed with water. The aqueous layer was separated and back-extracted with ether. The combined organic extracts were washed further with water and brine, dried over $Na_2SO_4$, filtered and the filtrate concentrated in vacuo to afford the crude title compound as a pink oil.

Step 2: 2-[3,4-Dichloro-5-({[(1,1-dimethylethyl)(dimethyl)silyl]oxy}methyl)phenyl]ethanamine To a THF (0.1 M) solution of ({[5-(2-azidoethyl)-2,3-dichlorophenyl]methyl}oxy)(1,1-dimethylethyl)dimethylsilane (1 eq.) from the previous step and triphenylphosphine (1.2 eq.) was added water (3 eq.). The resulting solution was stirred at 50° C. for 18 h. The volatiles were then removed in vacuo and purification of the crude product thus obtained by way of flash chromatography ($SiO_2$, 96:4 (v/v) $CH_2Cl_2$:2.0 M $NH_3$ in MeOH) afforded the title compound as a colorless oil.

Step 3: N-{2-[3,4-Dichloro-5-({[(1,1-dimethylethyl)(dimethyl)-silyl]oxy}methyl)phenyl]-ethyl}propanamide To a DMF (0.2 M) solution of 2-[3,4-dichloro-5-({[(1,1-dimethylethyl)(dimethyl)-silyl]oxy}methyl)phenyl]ethanamine (1 eq.) from the previous step, Hunig's base (3 eq.) and propionic acid (1.1 eq.) was added portionwise O-(7-azabenzotriazol-1-yl)-N,N,N',N'-tetramethyluronium hexafluorophosphate (1.2 eq.). The resulting reaction solution was stirred at RT for 48 h. The now reddish solution was diluted with ether and washed sequentially with 1 N aq. NaOH, water and brine. The organic extract was then dried over $Na_2SO_4$, filtered and the filtrate concentrated in vacuo to afford a brown oil. Purification of the crude product thus obtained by way of flash chromatography ($SiO_2$, 7:3 (v/v) Hex:EtOAc→EtOAc) afforded the title compound as a colorless oil.

Step 4: N-{2-[3,4-Dichloro-5-(hydroxymethyl)phenyl]ethyl}propanamide

To a THF (0.12 M) solution of N-{2-[3,4-dichloro-5-({[(1,1-dimethylethyl)(dimethyl)silyl]oxy}methyl)phenyl]ethyl}propanamide (1 eq.) from the previous step was added TBAF (1.0 M THF solution, 1.1 eq.). The resulting solution was stirred at RT for 2 h. The now orange solution was diluted with ether and quenched with 1 N aq. NaOH. The aqueous layer was separated and back-extracted with ether. The combined organic extracts were washed further with water and brine, dried over $Na_2SO_4$ and filtered. Concentration of the filtrate in vacuo afforded the crude title compound as a pale yellow oil.

Step 5: N-[2-(3,4-Dichloro-5-formylphenyl)ethyl]propanamide

To a suspension of N-{2-[3,4-dichloro-5-(hydroxymethyl)phenyl]ethyl}propanamide (1 eq.) from the previous step and sodium bicarbonate (1.1 eq.) in dichloromethane (0.1 M) was added DMP (1.1 eq.) at 0° C. The resulting mixture was stirred at RT for 2 h before it was quenched with sat. aq. $NaHSO_3$ and then extracted with $Et_2O$. The combined organic extracts were washed further with 1 N aq. NaOH, water and brine, dried over $Na_2SO_4$, filtered and the filtrate concentrated in vacuo. Purification of the crude product thus obtained by way of flash chromatography ($SiO_2$, 19:1 (v/v) Hex:EtOAc→3:7 (v/v) Hex:EtOAc) afforded the title compound as a white solid.

Step 6: Amine 27

To a dichloromethane (0.11 M) solution of N-[2-(3,4-dichloro-5-formylphenyl)-ethyl]propanamide (1 eq.) from the previous step was added magnesium sulphate (1 eq.) and cyclopropyl amine (1.2 eq.). The resulting suspension was stirred at RT for 16 h. The insolubles were removed via filtration and rinsed with dichloromethane before the combined filtrate was concentrated in vacuo. The crude imine thus obtained was taken up in methanol (0.11 M) and then added sodium borohydride (1.5 eq.) portionwise. The reaction mixture was stirred at RT for 8 h. The volatiles were then removed in vacuo and the resulting residue was partitioned between EtOAc and 1 N aq. NaOH. The aqueous layer was separated and back-extracted with EtOAc. The combined organic extracts were washed further with water and brine, dried over $Na_2SO_4$, filtered and the filtrate concentrated in vacuo. Purification of the crude product thus obtained by way of flash chromatography ($SiO_2$, 95:5 $CH_2Cl_2$:2.0 M $NH_3$ in MeOH) afforded the title compound as a colorless oil.

Amine 28

N-[3-Bromo-5-(3-methoxypropyl)benzyl]cyclopropanamine

Step 1: 3-Bromo-5-(3-methoxypropyl)benzaldehyde

To a THF solution (0.3 M) of allyl methyl ether (3.1 eq.) at RT was added borane-methyl sulfide complex (1.0 eq.). The solution was stirred at RT for 30 min. To this solution was then added sequentially 3,5-dibromobenzaldehyde (1.0 eq.), Pd(dppf)$Cl_2$ (0.025 eq.) and solid sodium methoxide (1.5 eq.). The resulting mixture was heated to reflux for 15 h. The cooled reaction mixture was diluted with water and extracted with ether. The combined organic extracts were dried over $MgSO_4$, filtered and the filtrate concentrated in vacuo. Purification of the crude product thus obtained by way of flash chromatography ($SiO_2$, 5:95 (v/v) EtOAc:Hex→7:3 (v/v) EtOAc:Hex) afforded the title compound as a colorless oil.

Step 2: Amine 28

3-Bromo-5-(3-methoxypropyl)benzaldehyde (1 eq.) from the previous step and cyclopropylamine (2 eq.) were combined in $CH_2Cl_2$ (0.19 M). To this was then added $MgSO_4$ (1 eq.) and the resulting suspension was stirred at RT for 23 h. The insolubles were then removed via filtration through a pad of celite and the filtrate was concentrated in vacuo. The crude imine thus obtained was then re-taken up in MeOH (0.19 M). To this solution was added sodium borohydride (1.5 eq.) portionwise and the resulting mixture was stirred at 0° C. for 30 min, then at RT for 16 h. The reaction was quenched by stirring with 2 N aq. HCl for 30 min. The resulting mixture was subsequently basified with 1 N aq. NaOH and the volatiles were removed in vacuo. The residue was extracted with $Et_2O$ from water, dried over $Na_2SO_4$, filtered and the filtrate concentrated in vacuo to afford the title compound as a colorless oil.

Amine 29

4-[(Cyclopropylamino)methyl]-N-[2-(methyloxy)ethyl]-2-naphthalenamine

Step 1: Methyl 3-{[2-(methyloxy)ethyl]amino}-1-naphthalenecarboxylate

Freshly purified cesium carbonate (1.4 eq.), palladium(II) acetate (0.02 eq.) and rac-BINAP (0.03 eq.) were combined in anhydrous toluene (0.25 M). The vessel was repeatedly evacuated and back-filled with nitrogen. Finally, methyl 3-bromo-1-naphthalenecarboxylate (1 eq.) and 2-methoxyethylamine (1.2 eq.) were added and the resulting mixture was heated at 100° C. for 20 h. The now black suspension was cooled to RT, diluted with ether and filtered through a pad of celite. Concentration of the filtrate in vacuo afforded a brown oil that can be purified further by way of column chromatography ($SiO_2$, 19:1 (v/v) Hex:EtOAc→1:1 (v/v) Hex:EtOAc) to afford the title compound as a yellow oil.

Step 2: 3-{[2-(Methyloxy)ethyl]amino}-1-naphthalenecarboxylic acid

Methyl 3-{[2-(methyloxy)ethyl]amino}-1-naphthalenecarboxylate (1 eq.) from the previous step was taken up in a 2:1 (v/v) mixture of MeOH:THF (0.08 M). To this solution was then added LiOH (1.0 M aq. solution, 3.4 eq.) and the resulting cloudy solution was vigorously stirred at RT for 16 h. The volatiles were then removed in vacuo and the pH of the residue was carefully adjusted to ~2 with 1 N aq. HCl before it was extracted with EtOAc. The combined organic extracts were washed further with water and brine, dried over $Na_2SO_4$ and filtered. Concentration of the filtrate in vacuo afforded the title compound as a yellow solid.

Step 3: N-Cyclopropyl-3-{[2-(methyloxy)ethyl] amino}-1-naphthalenecarboxamide To a DMF (0.1 M) solution of 3-{[2-(methyloxy)ethyl] amino}-1-naphthalenecarboxylic acid (1 eq.) from the previous step, Hunig's base (3 eq.) and cyclopropylamine (1.5 eq.) was added portionwise O-(7-azabenzotriazol-1-yl)-N,N,N', N'-tetramethyluronium hexafluorophosphate (1.2 eq.). The resulting reaction solution was stirred at RT for 48 h. The now reddish solution was diluted with EtOAc and washed sequentially with 1 N aq. NaOH, water and brine. The organic extract was then dried over $Na_2SO_4$, filtered and the filtrate concentrated in vacuo to afford a brown oil. Purification of the crude product thus obtained by way of flash chromatography ($SiO_2$, 4:1 (v/v) Hex:EtOAc→EtOAc) afforded the title compound as a white solid.

Step 4: Amine 29

To a THF solution (0.09 M) of N-cyclopropyl-3-{[2-(methyloxy)ethyl]amino}-1-naphthalenecarboxamide (1 eq.) from the previous step was added, at reflux, borane-methyl sulfide complex (6.2 eq.). To the reaction vessel was then attached a short path distillation apparatus and most of the volatiles were slowly distilled off over a period of 1 h. The now brown solution was re-cooled to 0° C. and carefully quenched with 1 N aq. HCl. The resulting mixture was heated at reflux for 1 h to ensure complete breakdown of the amine-borane complex. Following careful neutralization with 1 N aq. NaOH, the aqueous layer was separated and back extracted with EtOAc. The combined organic extracts were washed with brine, dried over $Na_2SO_4$ and filtered. The filtrate was concentrated in vacuo and the crude product thus obtained was purified further by way of flash chromatography ($SiO_2$, 3:2 (v/v) Hex:EtOAc→EtOAc) to reveal the title compound as a yellow oil that rapidly darkened upon standing.

Amine 30

3-{8-[(Cyclopropylamino)methyl]-6-quinolinyl}propanenitrile

Step 1: 1,1-Dimethylethyl{[6-(2-cyanoethenyl)-8-quinolinyl]methyl}cyclopropylcarbamate To a THF (0.13 M) suspension of freshly dried lithium chloride (1.2 eq.) and diethyl(cyanomethyl)phosphonate (1.2 eq.) was added DBU (1.2 eq.). The reaction suspension was stirred at RT for 30 min before 1,1-dimethylethyl cyclopropyl [(6-formyl-8-quinolinyl)methyl]carbamate (1 eq., Amine 23, Step 5) was finally added. The resulting solution was then allowed to stir at RT for 16 h. The crude reaction mixture thus obtained was quenched with 10% aq. HCl and extracted with ether. The combined organic extracts were washed further with 1 N aq. NaOH, water and brine, dried over $Na_2SO_4$, filtered and the filtrate concentrated in vacuo. Purification of the crude product thus obtained by way of flash chromatography ($SiO_2$, 9:1 (v/v) Hex:EtOAc→3:7 (v/v) Hex:EtOAc) afforded the title compound as a white solid.

Step 2: 1,1-Dimethylethyl{[6-(2-cyanoethyl)-8-quinolinyl]methyl}cyclopropylcarbamate To a solution of 1,1-dimethylethyl{[6-(2-cyanoethenyl)-8-quinolinyl]methyl}cyclopropylcarbamate (1 eq.) from the previous step in EtOAc (0.1 M) was added palladium (10% (w/w) over carbon, 0.2 eq.). The resulting suspension was evacuated and back-filled repeatedly with hydrogen. Finally, the reaction suspension was allowed to stir under a hydrogen-filled balloon atmosphere for 4 h. The reaction was quenched with the addition of dichloromethane and filtered through a bed of celite. The filtrate was then concentrated in vacuo. Purification of the crude product thus obtained by way of flash chromatography ($SiO_2$, 9:1 (v/v) Hex:EtOAc→3:7 (v/v) Hex:EtOAc) afforded the title compound as a yellow oil.

Step 3: Amine 30

To a $CH_2Cl_2$ solution (0.05 M) of 1,1-dimethylethyl{[6-(2-cyanoethyl)-8-quinolinyl]methyl}cyclopropylcarbamate (1 eq.) from the previous step was added zinc(II) bromide (10 eq.). The resulting suspension was sonicated for 15 min and stirred at RT for 13 h. The reaction was quenched with the addition of EtOAc and 1 N aq. NaOH, and then sonicated for 15 min. The aqueous phase was separated and back-extracted with EtOAc. The combined organic extracts were washed further with water and brine, dried over $Na_2SO_4$ and filtered. Concentration of the filtrate in vacuo afforded the title compound as a yellow oil.

Amine 31

N-({3-[2-(Methyloxy)ethyl]-1-naphthalenyl}methyl) cyclopropanamine

Step 1: Methyl 3-ethenyl-1-naphthalenecarboxylate

Methyl 3-bromo-1-naphthalenecarboxylate (1 eq.) and 2-ethenyl-4,4,5,5-tetramethyl-1,3,2-dioxaborolane (1 eq.) were combined in a 2:1 (v/v) mixture of DMF:n-PrOH (0.1 M). To this solution was first added $Pd(PPh_3)_2Br_2$ (0.05 eq.) followed by 2 N aq. $Na_2CO_3$ (2 eq.). The biphasic suspension was evacuated and back-filled three times with nitrogen before it was heated at 90° C. for 8 h. The now black suspension was cooled to RT, diluted with water and extracted with 1:1 (v/v) hexanes:ether. The combined organic extracts were then washed further with 1 N aq. NaOH, 10% aq. HCl, water and brine. This was then dried over $Na_2SO_4$ and filtered through a pad of silica gel. Concentration of the filtrate in vacuo afforded the crude title compound as a golden yellow oil.

Step 2: Methyl 3-(2-hydroxyethyl)-1-naphthalenecarboxylate

Methyl 3-ethenyl-1-naphthalenecarboxylate (1 eq.) from the previous step, $[Ir(COD)Cl]_2$ (0.025 eq.) and DPPB (0.05 eq.) were combined in THF (0.12 M). To this solution was then added 4,4,5,5-tetramethyl-1,3,2-dioxaborolane (1.2 eq.) and the resulting red solution was stirred at RT for 16 h. Finally, sodium perborate (0.1 M aqueous solution, 2 eq.) was added and the now black biphasic solution was vigorously stirred at RT for another 12 h. The aqueous layer was separated and back-extracted with ether. The combined organic extracts were then washed further with 1 N aq. NaOH, water and brine. This was then dried over $Na_2SO_4$, filtered and the filtrate concentrated in vacuo to afford a pale yellow oil. Purification of the crude product thus obtained by way of flash chromatography ($SiO_2$, 9:1 (v/v) Hex:EtOAc→1:1 (v/v) EtOAc:Hex) afforded the title compound as a pale yellow oil.

Step 3: Methyl 3-[2-(methyloxy)ethyl]-1-naphthalenecarboxylate

Methyl 3-(2-hydroxyethyl)-1-naphthalenecarboxylate (1 eq.) from the previous step and iodomethane (19 eq.) were taken up in THF (0.3 M). To this solution was then added sodium hydride (60% w/w dispersion in oil, 1 eq.) and the resulting suspension was stirred at RT in darkness for 18 h. The volatiles were then removed in vacuo and the resulting residue partitioned between ether and 1 N aq. HCl. The aqueous layer was separated and back-extracted with ether. The combined organic extracts were then washed further with 1 N aq. NaOH, water and brine. This was then dried over $Na_2SO_4$, filtered and the filtrate concentrated in vacuo to afford a yellow oil. Purification of the crude product thus obtained by way of flash chromatography ($SiO_2$, 19:1 (v/v) Hex:EtOAc→1:1 (v/v) EtOAc:Hex) afforded the title compound as a pale yellow oil.

Step 4: {3-[2-(Methyloxy)ethyl]-1-naphthalenyl}methanol

Methyl 3-[2-(methyloxy)ethyl]-1-naphthalenecarboxylate (1 eq.) from the previous step was taken up in toluene (0.1 M). To this solution was then added DIBAl-H (1.5 M toluene solution, 2.4 eq.) and the resulting solution was vigorously stirred at RT for 4 h. The reaction mixture thus obtained was quenched with 1 N aq. HCl and extracted with ether. The combined organic extracts were washed further with water and brine, dried over $Na_2SO_4$ and filtered. Concentration of the filtrate in vacuo afforded the title compound as a colorless oil.

Step 5: 3-[2-(Methyloxy)ethyl]-1-naphthalenecarbaldehyde

To a suspension of {3-[2-(methyloxy)ethyl]-1-naphthalenyl}methanol (1 eq.) from the previous step and sodium bicarbonate (1.1 eq.) in dichloromethane (0.1 M) was added DMP (1.1 eq.) at 0° C. The resulting mixture was stirred at RT for 2 h before it was quenched with sat. aq. $NaHSO_3$ and then extracted with $Et_2O$. The combined organic extracts were washed further with 1 N aq. NaOH, water and brine, dried over $Na_2SO_4$, filtered and the filtrate concentrated in vacuo. Purification of the crude product thus obtained by way of flash chromatography ($SiO_2$, 19:1 (v/v) Hex:EtOAc 1:1 (v/v) Hex:EtOAc) afforded the title compound as a colorless oil.

Step 6: Amine 31

To a dichloromethane (0.15 M) solution of 3-[2-(methyloxy)ethyl]-1-naphthalenecarbaldehyde (1 eq.) from the previous step was added magnesium sulphate (1 eq.) and cyclopropyl amine (1.2 eq.). The resulting suspension was stirred at RT for 20 h. The insolubles were removed via filtration and rinsed with dichloromethane before the combined filtrate was concentrated in vacuo. The crude imine thus obtained was taken up in methanol (0.15 M) and then added sodium borohydride (1.5 eq.) portionwise. The reaction mixture was stirred at RT for 8 h. The volatiles were then removed in vacuo and the resulting residue was partitioned between EtOAc and 1 N aq. NaOH. The aqueous layer was separated and back-extracted with EtOAc. The combined organic extracts were washed further with water and brine, dried over $Na_2SO_4$ and filtered. Concentration of the filtrate in vacuo afforded the title compound as a colorless oil.

Amine 32

N-(2-{4-[(Cyclopropylamino)methyl]-2-naphthalenyl}ethyl)acetamide

Step 1: Methyl 3-{2-[(methylsulfonyl)oxy]ethyl}-1-naphthalenecarboxylate

To a dichloromethane (0.03 M) solution of methyl 3-(2-hydroxyethyl)-1-naphthalenecarboxylate (1 eq.) from Step 2, Amine 31 and Hunig's base (1.5 eq.) was added at 0 methanesulfonyl chloride (1.3 eq.). The resulting solution was stirred at 0° C. for 30 min and then at RT for 15 min. The reaction mixture was subsequently quenched with 10% aq. HCl. The aqueous wash was separated and back-extracted with ether. The combined organic extracts were washed further with water and brine, dried over $Na_2SO_4$, and filtered. Concentration of the filtrate in vacuo afforded the crude title compound as a colorless oil.

Step 2: 3-(2-Azidoethyl)-1-naphthalenecarboxylate

To a DMF (0.25 M) solution of methyl 3-{2-[(methylsulfonyl)oxy]ethyl}-1-naphthalenecarboxylate (1 eq.) from the previous step was added sodium azide (5 eq.). The resulting solution was stirred at 55° C. for 12 h and then at 80° C. another 3 h. The reaction mixture was then diluted with ether and washed with water. The aqueous layer was separated and back-extracted with ether. The combined organic extracts were washed further with water and brine, dried over $Na_2SO_4$, filtered and the filtrate concentrated in vacuo to afford the crude title compound as a pink oil.

Step 3: Methyl 3-(2-aminoethyl)-1-naphthalenecarboxylate

To a THF (0.1 M) solution of 3-(2-azidoethyl)-1-naphthalenecarboxylate (1 eq.) from the previous step and triphenylphosphine (1.2 eq.) was added water (3 eq.). The resulting solution was stirred at 50° C. for 5 h. The volatiles were then removed in vacuo and purification of the crude product thus obtained by way of flash chromatography ($SiO_2$, 96:4 (v/v) $CH_2Cl_2$:2.0 M $NH_3$ in MeOH) afforded the title compound as a colorless oil.

Step 4: Methyl 3-[2-(acetylamino)ethyl]-naphthalenecarboxylate

To a DMF (0.2 M) solution of methyl 3-(2-aminoethyl)-1-naphthalenecarboxylate (1 eq.) from the previous step, Hunig's base (3 eq.) and acetic acid (1.1 eq.) was added portionwise O-(7-azabenzotriazol-1-yl)-N,N,N',N'-tetramethyluronium hexafluorophosphate (1.1 eq.). The resulting reaction solution was stirred at RT for 48 h. The now reddish solution was diluted with ether and washed sequentially with 1 N aq. NaOH, water and brine. The organic extract was then dried over $Na_2SO_4$, filtered and the filtrate concentrated in vacuo to afford a pale yellow oil. Purification of the crude product thus obtained by way of flash chromatography ($SiO_2$, 7:3 (v/v) Hex:EtOAc EtOAc→95:5 (v/v) $CH_2Cl_2$:2.0 M $NH_3$ in MeOH) afforded the title compound as a colorless oil.

Step 5: N-{2-[4-(Hydroxymethyl)-2-naphthalenyl]ethyl}acetamide

Methyl 3-[2-(acetylamino)ethyl]-naphthalenecarboxylate (1 eq.) from the previous step was taken up in THF (0.18 M).

To this solution was then added lithium borohydride (12 eq.) and the resulting solution was vigorously stirred at 50° C. for 5 h. The reaction mixture thus obtained was diluted further with ether and carefully quenched with 1 N aq. HCl. The aqueous layer was separated and back-extracted with EtOAc. The combined organic extracts were washed further with 1 N aq. NaOH, water and brine, dried over $Na_2SO_4$ and filtered. Concentration of the filtrate in vacuo afforded the title compound as a white solid.

Step 6:
N-[2-(4-Formyl-2-naphthalenyl)ethyl]acetamide

To a suspension of N-{2-[4-(hydroxymethyl)-2-naphthalenyl]ethyl}acetamide (1 eq.) from the previous step and sodium bicarbonate (1.2 eq.) in dichloromethane (0.09 M) was added DMP (1.1 eq.) at 0° C. The resulting mixture was stirred at RT for 18 h before it was quenched with sat. aq. $NaHSO_3$ and then extracted with $Et_2O$. The combined organic extracts were washed further with 10% aq. HCl, water and brine, dried over $Na_2SO_4$, filtered and the filtrate concentrated in vacuo. Purification of the crude product thus obtained by way of flash chromatography ($SiO_2$, 19:1 (v/v) Hex:EtOAc→1:1 (v/v) Hex:EtOAc) afforded the title compound as a colorless oil.

Step 6: Amine 32

To a dichloromethane (0.12 M) solution of N-[2-(4-formyl-2-naphthalenyl)-ethyl]acetamide (1 eq.) from the previous step was added magnesium sulphate (1 eq.) and cyclopropyl amine (2 eq.). The resulting suspension was stirred at RT for 48 h. The insolubles were removed via filtration and rinsed with dichloromethane before the combined filtrate was concentrated in vacuo. The crude imine thus obtained was taken up in methanol (0.12 M) and then added sodium borohydride (1.5 eq.) portionwise. The reaction mixture was stirred at RT for 3 h. The volatiles were then removed in vacuo and the resulting residue was partitioned between EtOAc and 1 N aq. NaOH. The aqueous layer was separated and back-extracted with EtOAc. The combined organic extracts were washed further with water and brine, dried over $Na_2SO_4$ and filtered. Concentration of the filtrate in vacuo afforded the title compound as a colorless oil.

Amine 33

N-[(2-Bromophenyl)methyl]cyclopropanamine

To a THF solution (0.15 M) of 2-bromobenzyl alcohol (1 eq.) was added triethylamine (1.6 eq.). The reaction mixture was cooled to 0° C. before methanesulfonyl chloride (1.3 eq.) was added dropwise. The resulting solution was then allowed to warm slowly to RT. After 1.5 h, cyclopropylamine (5 eq.) was added to the now cloudy suspension. After another 18 h, the reaction mixture was diluted with ether and quenched with 1 N aq. NaOH. The organic extract was separated, washed with brine, dried over $Na_2SO_4$, filtered and the filtrate concentrated in vacuo. Purification of the crude product thus obtained by way of flash chromatography ($SiO_2$, 4:1 (v/v) Hex:EtOAc→1:4 (v/v) Hex:EtOAc) afforded the title compound as a light yellow oil.

Amine 34

N-{[1-(2-Methoxyethyl)-1H-indol-3-yl]methyl}cyclopropanamine

Step 1:
1-(2-Methoxyethyl)-1H-indole-3-carbaldehyde

Indole-3-carbaldehyde (1 eq.) was dissolved in DMF (0.46 M). Sodium hydride was added (1.3 eq.) and the resulting solution was stirred at RT for 20 min. Potassium iodide (1 eq.) and 1-bromo-2-methoxyethane (2 eq.) were then added and the reaction solution was allowed to stir at RT for 48 h. The reaction mixture was subsequently quenched with brine and extracted with EtOAc. The combined organic extracts were dried over $MgSO_4$. Filtration and concentration of the filtrate in vacuo afforded a yellow oil. Purification of the crude product thus obtained by way of flash chromatography ($SiO_2$, 9:1 (v/v) Hex:EtOAc→EtOAc) afforded the title compound as an orange oil.

Step 2: Amine 34

1-(2-Methoxyethyl)-1H-indole-3-carbaldehyde (1 eq.) from the previous step and cyclopropylamine (2 eq.) were dissolved in $CH_2Cl_2$ (0.15 M). Magnesium sulfate (1 eq.) and formic acid (0.1 eq.) were then added and the resulting suspension was stirred at RT for 8 h. The insolubles were removed via filtration and the filtrate was concentrated in vacuo. The residue was then taken up in MeOH (0.15 M) and sodium borohydride (1.5 eq) was added portionwise. The resulting suspension was stirred at RT for 16 h. The volatiles were removed in vacuo. The resulting residue was then taken up in ether, quenched carefully with 1 N aq. HCl. and then neutralized with 1 N aq. NaOH. The aqueous wash was separated and back-extracted with ether. The combined organic extracts were washed further with water and brine, dried over $Na_2SO_4$, filtered and the filtrate concentrated in vacuo. Purification of the crude product thus obtained by way of flash chromatography ($SiO_2$, EtOAc→7:3 (v/v) EtOAc:MeOH) afforded the title compound as an orange oil.

Amine 35

N-{[1-(2,2,2-Trifluoroethyl)-1H-indol-3-yl]methyl}cyclopropanamine

Amine 35 was prepared according to the procedure described in Amine 34 but using instead 1-iodo-2,2,2-trifluoroethane as the alkylation reagent in step 1.

Amine 36

N-{[1-(4,4,4-Trifluorobutyl)-1H-indol-3-yl]methyl}cyclopropanamine

Amine 36 was prepared according to the procedure described in Amine 34 but using instead 1-iodo-4,4,4-trifluorobutane as the alkylation reagent in step 1.

Amine 37

N-[(1-Butyl-1H-indol-3-yl)methyl]cyclopropanamine

Amine 37 was prepared according to the procedure described in Amine 34 but using instead 1-iodobutane as the alkylation reagent in step 1.

Amine 38

N-({1-[3-(Ethyloxy)propyl]-1H-indol-3-yl}methyl)cyclopropanamine

Amine 38 was prepared according to the procedure described in Amine 34 but using instead 1-bromo-3-ethoxypropane as the alkylation reagent in step 1.

Amine 39

N-({1-[3,3,3-Trifluoro-2-(trifluoromethyl)propyl]-1H-indol-3-yl}methyl)cyclopropanamine Amine 39 was prepared according to the procedure described in Amine 34 but using instead 1,1,1,3,3,3-hexafluoro-2-(iodomethyl)propane as the alkylation reagent in step 1.

Amine 40

N-(3-{3-[(Cyclopropylamino)methyl]-1H-indol-1-yl}propyl)acetamide

Step 1: tert-Butyl[3-(3-formyl-1H-indol-1-yl)propyl]carbamate

Indole-3-carbaldehyde (1 eq.) was dissolved in DMF (0.15 M). Sodium hydride was added (1.3 eq.) and the resulting solution was stirred at RT for 20 min. Tetrabutylammonium iodide (1 eq.) and tert-butyl 3-bromopropylcarbamate (2 eq.) were then added and the reaction solution was allowed to stir at RT for 18 h. The reaction mixture was subsequently quenched with sat. aq. $NH_4Cl$ and extracted with EtOAc. The combined organic extracts were dried over $MgSO_4$. Filtration and concentration of the filtrate in vacuo afforded a yellow oil. Purification of the crude product thus obtained by way of flash chromatography ($SiO_2$, 7:3 (v/v) Hex:EtOAc→EtOAc) afforded the title compound as a light pink solid.

Step 2: N-[3-(3-Formyl-1H-indol-1-yl)propyl]acetamide

To a stirred dichloromethane (0.09 M) solution of tert-butyl[3-(3-formyl-1H-indol-1-yl)propyl]carbamate from the previous step was added HCl (4 N solution in dioxane, 45 eq.). The resulting solution was stirred at RT for 1 h before the volatiles were removed in vacuo. Dichloromethane was then added to the red residue and the volatiles were again removed in vacuo to afford a red gum. To the crude amine thus obtained was then added dichloromethane (0.09 M) and triethylamine (2.2 eq.). When the reaction solution became homogeneous, acetyl chloride (1.05 eq.) was added and the resulting mixture was allowed to stir at RT for another 2 h. The reaction was finally quenched with 1 N aq. NaOH and extracted with dichloromethane. The combined organic extracts were dried over $MgSO_4$, filtered and concentration of the filtrate in vacuo afforded the crude title compound as a yellow solid.

Step 3: Amine 40

N-[3-(3-Formyl-1H-indol-1-yl)propyl]acetamide (1 eq.) from the previous step and cyclopropylamine (2 eq.) were dissolved in $CH_2Cl_2$ (0.1 M). Magnesium sulfate (2 eq.) and formic acid (0.2 eq.) were then added and the resulting suspension was stirred at RT for 20 h. The insolubles were removed via filtration and the filtrate was concentrated in vacuo. The residue was then taken up in MeOH (0.1 M) and sodium borohydride (1 eq) was added portionwise. The resulting suspension was stirred at RT for 16 h. The volatiles were removed in vacuo. The resulting residue was then taken up in ether, quenched carefully with 1 N aq. HCl. and then neutralized with 1 N aq. NaOH. The aqueous wash was separated and back-extracted with ether. The combined organic extracts were washed further with water and brine, dried over $Na_2SO_4$, filtered and the filtrate concentrated in vacuo. Purification of the crude product thus obtained by way of flash chromatography ($SiO_2$, 1:9 (v/v) MeOH:EtOAc→1:1 (v/v) EtOAc:MeOH) afforded the title compound as a white solid.

Amine 41

N-(3-{3-[(Cyclopropylamino)methyl]-1H-indol-1-yl}propyl)propanamide

Amine 41 was prepared according to the procedure described in Amine 40 but using instead propionyl chloride as the alkylation reagent in step 2.

Amine 42

N-(2-{3-[(Cyclopropylamino)methyl]-1H-indol-1-yl}ethyl)acetamide

Amine 42 was prepared according to the procedure described in Amine 40 but using instead tert-butyl 2-bromoethylcarbamate as the alkylation reagent in step 1.

Amine 43

N-(2-{3-[(Cyclopropylamino)methyl]-1H-indol-1-yl}ethyl)propanamide

Amine 42 was prepared according to the procedure described in Amine 40 but using instead tert-butyl 2-bromoethylcarbamate as the alkylation reagent in step 1 and propionyl chloride as the alkylation reagent in step 2

Amine 44

N-{[1-(2-Propen-1-yl)-1H-indol-3-yl]methyl}cyclopropanamine

Step 1: 1-Allyl-1H-indole-3-carbaldehyde

Indole-3-carbaldehyde (1 eq.) was dissolved in DMF (0.46 M). Sodium hydride was added (2.5 eq.) and the resulting solution was stirred at RT for 20 min. Allyl bromide (1 eq.) was then added and the reaction solution was allowed to stir at RT for 20 h. The reaction mixture was subsequently quenched with brine and extracted with EtOAc. The combined organic extracts were dried over $MgSO_4$. Filtration and concentration of the filtrate in vacuo afforded a yellow oil. Purification of the crude product thus obtained by way of flash chromatography ($SiO_2$, 4:1 (v/v) Hex:EtOAc→3:7 (v/v) Hex:EtOAc) afforded the title compound as a light yellow oil.

Step 2: Amine 44

1-Allyl-1H-indole-3-carbaldehyde (1 eq.) from the previous step and cyclopropylamine (2 eq.) were dissolved in MeOH (0.05 M). Sodium cyanoborohydride (2 eq.) and acetic acid (4 eq.) were then added and the resulting suspension was stirred at RT for 18 h. The volatiles were subsequently

Amine 45

N-{[1-(Phenylmethyl)-1H-indol-3-yl]methyl}cyclopropanamine

Amine 45 was prepared according to the procedure described in Amine 44 but using instead benzyl bromide as the alkylation reagent in step 1.

Amine 46

N-{[1-(2-Pyridinylmethyl)-1H-indol-3-yl]methyl}cyclopropanamine

Amine 46 was prepared according to the procedure described in Amine 44 but using instead tetrabutylammonium iodide (1 eq.) and 2-picolyl chloride hydrochloride (1.5 eq.) as the alkylation mixture in step 1.

Amine 47

N-{[1-(3-Pyridinylmethyl)-1H-indol-3-yl]methyl}cyclopropanamine

Amine 47 was prepared according to the procedure described in Amine 44 but using instead tetrabutylammonium iodide (1 eq.) and 3-picolyl chloride hydrochloride (1.5 eq.) as the alkylation mixture in step 1.

Amine 48

N-{[1-(4-Pyridinylmethyl)-1H-indol-3-yl]methyl}cyclopropanamine

Amine 48 was prepared according to the procedure described in Amine 44 but using instead 4-picolyl bromide hydrobromide (1 eq.) as the alkylation reagent in step 1.

Amine 49

N-({1-[(4-Fluorophenyl)methyl]-1H-indol-3-yl}methyl)cyclopropanamine

Amine 49 was prepared according to the procedure described in Amine 44 but using instead 1-(bromomethyl)-4-fluorobenzene (1.5 eq.) as the alkylation reagent in step 1.

Amine 50

N-({1-[(4-Chlorophenyl)methyl]-1H-indol-3-yl}methyl)cyclopropanamine

Amine 50 was prepared according to the procedure described in Amine 44 but using instead 1-(bromomethyl)-4-chlorobenzene (1.5 eq.) as the alkylation reagent in step 1.

Amine 51

N-({1-[(3-Fluorophenyl)methyl]-1H-indol-3-yl}methyl)cyclopropanamine

Amine 51 was prepared according to the procedure described in Amine 44 but using instead 1-(bromomethyl)-3-fluorobenzene (1.5 eq.) as the alkylation reagent in step 1.

Amine 52

N-({1-[(3-Chlorophenyl)methyl]-1H-indol-3-yl}methyl)cyclopropanamine

Amine 52 was prepared according to the procedure described in Amine 44 but using instead 1-(bromomethyl)-3-chlorobenzene (1.5 eq.) as the alkylation reagent in step 1.

Amine 53

3-({3-[(Cyclopropylamino)methyl]-1H-indol-1-yl}methyl)benzonitrile

Amine 53 was prepared according to the procedure described in Amine 44 but using instead 1-(bromomethyl)-3-cyanobenzene (1.5 eq.) as the alkylation reagent in step 1.

Amine 54

N-({1-[(3-Methylphenyl)methyl]-1H-indol-3-yl}methyl)cyclopropanamine

Amine 54 was prepared according to the procedure described in Amine 44 but using instead 1-(bromomethyl)-3-methylbenzene (1.5 eq.) as the alkylation reagent in step 1.

Amine 55

N-({5-Fluoro-1-[3-(methyloxy)propyl]-1H-indol-3-yl}methyl)cyclopropanamine

Amine 55 was prepared according to the procedure described in Amine 44 but using instead tetrabutylammonium iodide (1 eq.) and 1-bromo-3-methoxypropane (2.1 eq.) as the alkylation mixture and 5-fluoro-1H-indole-3-carbaldehyde (1 eq.) as the starting indole in step 1.

Amine 56

N-{[6-Bromo-1-(phenylmethyl)-1H-indol-3-yl]methyl}cyclopropanamine

Step 1: 6-Bromo-1H-indole-3-carbaldehyde

To a DMF (0.47 M) solution of 6-bromo-1H-indole (1 eq.) was added at 0° C. phosphorus oxychloride (1.2 eq.). The resulting solution was warmed to RT and stirred at RT for 16 h. The resulting solution was re-cooled to 0° C. and then carefully added NaOH (2 M aq. solution, 2.8 eq.). After stirring at RT for another 2 h, the crude reaction mixture was diluted with water and extracted with EtOAc. The combined organic extracts were dried over $MgSO_4$. Filtration and concentration of the filtrate in vacuo afforded a yellow oil. Purification of the crude product thus obtained by way of flash chromatography ($SiO_2$, Hex→EtOAc) afforded the title compound as a brown solid.

Step 2:
1-Benzyl-6-bromo-1H-indole-3-carbaldehyde

6-Bromo-1H-indole-3-carbaldehyde (1 eq.) from the previous step was dissolved in DMF (0.19 M). Sodium hydride was added (1.5 eq.) and the resulting solution was stirred at RT for 20 min. Benzyl bromide (1 eq.) was then added and the reaction solution was allowed to stir at RT for 24 h. The reaction mixture was subsequently quenched with water and extracted with EtOAc. The combined organic extracts were dried over $MgSO_4$. Filtration and concentration of the filtrate in vacuo afforded a yellow oil. Purification of the crude product thus obtained by way of flash chromatography ($SiO_2$, 4:1 (v/v) Hex:EtOAc 3:7 (v/v) Hex:EtOAc) afforded the title compound as a yellow solid.

Step 3: Amine 56

1-Benzyl-6-bromo-1H-indole-3-carbaldehyde (1 eq.) from the previous step and cyclopropylamine (2 eq.) were dissolved in MeOH (0.05 M). Sodium cyanoborohydride (2 eq.) and acetic acid (4 eq.) were then added and the resulting suspension was stirred at RT for 16 h. The volatiles were subsequently removed in vacuo. The resulting residue was then taken up in ether, quenched carefully with 1 N aq. NaOH. The aqueous wash was separated and back-extracted with ether. The combined organic extracts were washed further with water and brine, dried over $Na_2SO_4$, filtered and the filtrate concentrated in vacuo. Purification of the crude product thus obtained by way of flash chromatography ($SiO_2$, EtOAc→2:3 (v/v) EtOAc:MeOH) afforded the title compound as a yellow oil.

Amine 57

N-{[1-[(3-Fluorophenyl)methyl]-6-(methyloxy)-1H-indol-3-yl]methyl}cyclopropanamine Amine 57 was prepared according to the procedure described in Amine 44 but using instead 1-(bromomethyl)-3-fluorobenzene (1.5 eq.) as the alkylation reagent in step 2 and 6-methoxy-1H-indole-3-carbaldehyde (1 eq.) as the starting indole in step 1.

Amine 58

N-{[4-Methyl-1-(phenylmethyl)-1H-indol-3-yl]methyl}cyclopropanamine

Amine 58 was prepared according to the procedure described in Amine 56 but using instead 4-methyl-1H-indole (1 eq.) as the starting indole in step 1 and benzyl bromide (1 eq.) as the alkylation reagent in step 2.

Amine 59

3-[(Cyclopropylamino)methyl]-1-(phenylmethyl)-1H-indole-4-carbonitrile

Amine 59 was prepared according to the procedure described in Amine 56 but using instead 1H-indole-4-carbonitrile (1 eq.) as the starting indole in step 1 and benzyl bromide (1 eq.) as the alkylation reagent in step 2.

Amine 60

N-{[4-Fluoro-1-(phenylmethyl)-1H-indol-3-yl]methyl}cyclopropanamine

Amine 60 was prepared according to the procedure described in Amine 56 but using instead 4-fluoro-1H-indole (1 eq.) as the starting indole in step 1 and benzyl bromide (1.5 eq.) as the alkylation reagent in step 2.

Amine 61

N-({4-Fluoro-1-[(3-fluorophenyl)methyl]-1H-indol-3-yl}methyl)cyclopropanamine Amine 61 was prepared according to the procedure described in Amine 56 but using instead 4-fluoro-1H-indole (1 eq.) as the starting indole in step 1 and 1-(bromomethyl)-3-fluorobenzene (1.5 eq.) as the alkylation reagent in step 2.

Amine 62

N-({4-Fluoro-1-[3-(methyloxy)propyl]-1H-indol-3-yl}methyl)cyclopropanamine

Amine 62 was prepared according to the procedure described in Amine 56 but using instead 4-fluoro-1H-indole (1 eq.) as the starting indole in step 1. Furthermore, 1-bromo-3-methoxypropane (2 eq.) and tetrabutylammonium iodide (1 eq.) were used as the alkylation mixture in step 2.

Amine 63

N-({4-Chloro-1-[3-(methyloxy)propyl]-1H-indol-3-yl}methyl)cyclopropanamine

Amine 63 was prepared according to the procedure described in Amine 56 but using instead 4-chloro-1H-indole (1 eq.) as the starting indole in step 1. Furthermore, 1-bromo-3-methoxypropane (2 eq.) and tetrabutylammonium iodide (1 eq.) were used as the alkylation mixture in step 2.

Amine 64

N-{[4-Chloro-1-(phenylmethyl)-1H-indol-3-yl]methyl}cyclopropanamine

Amine 64 was prepared according to the procedure described in Amine 56 but using instead 4-chloro-1H-indole (1 eq.) as the starting indole in step 1 and benzyl bromide (1.5 eq.) as the alkylation reagent in step 2.

Amine 65

N-{[4-Bromo-1-(phenylmethyl)-1H-indol-3-yl]methyl}cyclopropanamine

Amine 65 was prepared according to the procedure described in Amine 56 but using instead 4-bromo-1H-indole (1 eq.) as the starting indole in step 1 and benzyl bromide (1.5 eq.) as the alkylation reagent in step 2.

Amine 66

N-[{4-Bromo-1-[(3-fluorophenyl)methyl]-1H-indol-3-yl}methyl]cyclopropanamine Amine 66 was prepared according to the procedure described in Amine 56 but using instead 4-bromo-1H-indole (1 eq.) as the starting indole in step 1 and 1-(bromomethyl)-3-fluorobenzene (1.5 eq.) as the alkylation reagent in step 2.

Amine 67

N-({4-Bromo-[3-(methyloxy)propyl]-1H-indol-3-yl}methyl)cyclopropanamine

Amine 67 was prepared according to the procedure described in Amine 56 but using instead 4-bromo-1H-indole (1 eq.) as the starting indole in step 1. Furthermore, 1-bromo-3-methoxypropane (2 eq.) and tetrabutylammonium iodide (1 eq.) were used as the alkylation mixture in step 2.

Amine 68

N-[(4-Fluoro-1H-indol-3-yl)methyl]cyclopropanamine

Amine 68 was prepared according to the procedure described in Amine 56 but using instead 4-fluoro-1H-indole (1 eq.) as the starting indole in step 1. Furthermore, step 2 was not necessary.

Amine 69

1-{3-[(Cyclopropylamino)methyl]-5-[3-(methyloxy)propyl]phenyl}ethanone

Amine 69 was prepared according to the procedure described in published patent application WO 2007/009250 A1.

Amine 70

5-[(Cyclopropylamino)methyl]-1,3-bis[3-(methyloxy)propyl]-2,4(1H,3H)-pyrimidinedione

Step 1: 1,3-Bis(3-methoxypropyl)-2,4-dioxo-1,2,3,4-tetrahydropyrimidine-5-carbaldehyde To a DMF (0.35 M) solution of 5-formyluracil (1 eq.) was added sequentially at 0° C. 1-bromo-3-methoxypropane (2.2 eq.) and DBU (2.2 eq.). The resulting solution was stirred at RT for 72 h. The volatiles were then removed in vacuo. The crude product mixture thus obtained was directly subjected to purification by way of column chromatography (SiO$_2$, EtOAc) to afford the title compound as a yellow oil.

Step 2: Amine 70

To a dichloromethane (0.1 M) solution of 1,3-bis(3-methoxypropyl)-2,4-dioxo-1,2,3,4-tetrahydropyrimidine-5-carbaldehyde (1 eq.) from the previous step was added magnesium sulphate (1 eq.) and cyclopropyl amine (2 eq.). The resulting suspension was stirred at RT for 16 h. The insolubles were removed via filtration and rinsed with dichloromethane before the combined filtrate was concentrated in vacuo. The crude imine thus obtained was taken up in methanol (0.1 M) and then added sodium borohydride (1.5 eq.) portionwise. The reaction mixture was stirred at RT for 16 h before it was quenched with sat. aq. NaHCO$_3$ and then extracted with EtOAc. The combined organic extracts were washed further with water and brine, dried over Na$_2$SO$_4$, filtered and the filtrate concentrated in vacuo. Purification of the crude product thus obtained by way of column chromatography (SiO$_2$, CH$_2$Cl$_2$→85:15 (v/v) CH$_2$Cl$_2$:2 M NH$_3$ in MeOH) afforded the title compound as a white solid.

Amine 71

N-[5-(3-Methoxypropyl)-2,3-dimethylbenzyl]cyclopropanamine

Step 1: 5-Bromo-2,3-dimethylbenzoic acid

To a stirred acetic acid solution (0.2 M) of 2,3-dimethylbenzoic acid (1 eq.) was added sequentially nitric acid (12 eq.), water (25 eq.) and bromine (1.1 eq.). Finally, silver nitrate (1 M aqueous solution, 1.3 eq.) was added dropwise over a period of 30 min. After another hour of stirring at RT, the crude reaction mixture was diluted with water and extracted with EtOAc. The combined organic extracts were then washed with brine, dried over Na$_2$SO$_4$, filtered and the filtrate concentrated in vacuo. Trituration of the crude product thus obtained in hexanes afforded the title compound as a yellow solid.

Step 2: 5-Bromo-N-cyclopropyl-2,3-dimethylbenzamide

To a stirred DMF (0.2 M) solution of 5-bromo-2,3-dimethylbenzoic acid (1 eq.) from the previous step was added HATU (1.3 eq.), cyclopropylamine (1.2 eq.) and Hunig's base (3 eq.). The resulting reaction mixture was stirred at RT for 18 h. The reaction was then quenched with saturated aqueous ammonium chloride and extracted with EtOAc. The combined organic extracts were washed further with water and brine, dried over Na$_2$SO$_4$, filtered and the filtrate concentrated in vacuo. Purification of the crude product thus obtained by way of flash chromatography (SiO$_2$, 7:3 (v/v) Hex:EtOAc→EtOAc) afforded the title compound as a white solid.

Step 3: N-Cyclopropyl-5-[(1E)-3-methoxy-1-propen-1-yl]-2,3-dimethylbenzamide 5-Bromo-N-cyclopropyl-2,3-dimethylbenzamide (1 eq.) from the previous step and 4,4,5,5-tetramethyl-2-[(1E)-3-(methyloxy)-1-propen-1-yl]-1,3,2-dioxaborolane (1.5 eq.) were combined in a 5:1 (v/v) mixture of DMF:n-PrOH (0.1 M). To this solution was then added trans-bis(triphenylphosphine) palladium(II) bromide (0.05 eq.) and the vessel was repeatedly evacuated and back-filled with nitrogen. Finally, 2 M aq. Na$_2$CO$_3$ (3 eq.) was added and the resulting biphasic suspension was heated at 100° C. for 18 h. The now black suspension was cooled to RT, diluted with water and extracted with ether. The combined organic extracts were then washed with water and brine, dried over Na$_2$SO$_4$, filtered and the filtrate concentrated in vacuo. Purification of the crude product by way of flash chromatography (SiO$_2$, 9:1 (v/v) Hex:EtOAc→EtOAc) afforded the title compound as a white solid.

Step 4: N-Cyclopropyl-5-(3-methoxypropyl)-2,3-dimethylbenzamide

N-Cyclopropyl-5-[(1E)-3-methoxy-1-propen-1-yl]-2,3-dimethylbenzamide (1 eq.) from the previous step and 10% w/w palladium over charcoal (0.05 eq.) were suspended in EtOAc (0.2 M). The vessel was then evacuated and purged with H$_2$. Under a balloon-filled H$_2$ atmosphere, the reaction suspension was stirred at RT for 6 h. The reaction suspension was then filtered through a bed of celite and the filtrate concentrated in vacuo to afford the title compound as a white solid.

Step 5: Amine 71

To a refluxing solution of N-cyclopropyl-5-(3-methoxypropyl)-2,3-dimethylbenzamide (1 eq.) from the previous step in THF (0.1 M) equipped with a short-path distillation apparatus was added dropwise borane-dimethyl sulfide complex (6 eq.). The solution was concentrated to 0.3 M over 30 min and HCl (2 N aq. solution, 6.5 eq.) was added. The mixture was stirred at 80° C. for 1 h, cooled to RT, rendered basic with 2 N aq. NaOH and extracted with EtOAc. The combined organic extracts were then washed with brine, dried over $Na_2SO_4$, filtered and the filtrate concentrated in vacuo. Purification of the crude product by way of flash chromatography ($SiO_2$, 9:1 (v/v) Hex:EtOAc→EtOAc) afforded the title compound as a pale yellow oil.

Amine 72

N-[2-Chloro-5-(2-methoxyethoxy)benzyl]cyclopropanamine

Step 1: 1-Chloro-4-(2-methoxyethoxy)-2-methylbenzene

To a stirred solution of 4-chloro-3-methylphenol (1 eq.) in DMF (0.7 M) was added $K_2CO_3$ (1.2 eq.). The mixture was stirred at 50° C. for 5 min before 1-bromo-2-methoxyethane (1.5 eq.) was added. After 2 h at 70° C., the reaction mixture was cooled down to RT and then diluted with water and ether. The organic phase was separated and washed sequentially with 2 N aq. NaOH, water and brine. The organic extract was dried over $Na_2SO_4$, filtered and the filtrate concentrated in vacuo to afford the title compound as a yellowish oil.

Step 2: 2-(Bromomethyl)-1-chloro-4-(2-methoxyethoxy)benzene

A mixture of 1-chloro-4-(2-methoxyethoxy)-2-methylbenzene (1 eq.) from the previous step, NBS (1.1 eq.) and benzoyl peroxide (0.05 eq.) in $CCl_4$ (0.2 M) was refluxed for 2 h. The volatiles were then removed in vacuo and the resulting residue was suspended in hexanes. The insolubles were removed via filtration and washed further with hexanes. The filtrate was concentrated in vacuo to afford the title compound as a colorless oil.

Step 3: 2-Chloro-5-(2-methoxyethoxy)benzaldehyde 2-(Bromomethyl)-1-chloro-4-(2-methoxyethoxy)benzene (1 eq.) from the previous step and NMO (3 eq.) were stirred in dioxane (0.3 M) at 90° C. for 6 h. The reaction mixture was then quenched with saturated aqueous sodium bicarbonate and extracted with ether. The combined organic extracts were washed further with water and brine, dried over $Na_2SO_4$, filtered and the filtrate concentrated in vacuo. Purification of the crude product thus obtained by way of flash chromatography ($SiO_2$, 9:1 (v/v) Hex:EtOAc→EtOAc) afforded the title compound.

Step 4: Amine 72

2-Chloro-5-(2-methoxyethoxy)benzaldehyde (1 eq.) from the previous step and cyclopropylamine (2 eq.) were combined in $CH_2Cl_2$ (0.2 M). To this was then added $MgSO_4$ (1.5 eq.) and the resulting suspension was stirred at RT for 18 h. The insolubles were then removed via filtration through a pad of celite and the filtrate was concentrated in vacuo. The crude imine thus obtained was then re-taken up in a 2:1 (v/v) mixture of THF:MeOH (0.2 M). To this solution was added sodium borohydride (5 eq.) portionwise and the resulting mixture was stirred at RT for 18 h. The reaction was quenched with saturated aqueous sodium bicarbonate and extracted with ethyl acetate. The combined organic extracts were then washed with brine, dried over $Na_2SO_4$, filtered and the filtrate concentrated in vacuo. Purification of the crude product by way of flash chromatography ($SiO_2$, 9:1 (v/v) Hex:EtOAc→EtOAc) afforded the title compound as a yellowish oil.

Amine 73

N-(2-Naphthylmethyl)cyclopropanamine

Amine 73 was prepared according to the procedure described in Amine 17 but using instead 2-naphthaldehyde as the starting material.

Amine 74

N-({3-[(Trifluoromethyl)thio]phenyl}methyl)cyclopropanamine

Amine 74 was prepared according to the procedure described in Amine 17 but using instead 3-[(trifluoromethyl)thio]benzaldehyde as the starting material.

Amine 75

N-{[5-[3-(Methyloxy)propyl]-2-(methylthio)phenyl]methyl}cyclopropanamine

Step 1: Methyl 5-bromo-2-(methylthio)benzoate

To a DMF (0.2 M) suspension of cesium carbonate (3 eq.) and 5-bromo-2-mercaptobenzoic acid (1 eq.) was added iodomethane (5 eq.). The resulting suspension was then stirred at RT for 1 h. The volatiles were removed before EtOAc and sat. aq. $NH_4Cl$ were added. The organic phase was separated, dried over $Na_2SO_4$, filtered and the filtrate concentrated in vacuo to a pale yellow oil. This was taken up again in DMF (0.2 M) and added sequentially sodium hydride (3 eq.) and iodomethane (5 eq.). The reaction vessel was then sealed and heated to 70° C. for 16 h. After cooling to RT, EtOAc and sat. aq. $NH_4Cl$ were added to the crude reaction mixture. The organic phase was separated, dried over $MgSO_4$, filtered and the filtrate concentrated in vacuo to a brown oil. Purification of the crude product thus obtained by way of flash chromatography ($SiO_2$, Hex→3:2 (v/v) Hex:EtOAc) afforded the title compound as a light yellow solid.

Step 2: Methyl 5-[3-(methyloxy)propyl]-2-(methylthio)benzoate

To a THF (0.29 M) solution of 9-BBN (2 eq.) was added allyl methyl ether (2.1 eq.) dropwise and the resulting solution was stirred at RT until no more gaseous evolution was observed. The reaction mixture was then heated to 50° C. for 1 h. To this solution was subsequently added a DMF (0.34 M) solution of methyl 5-bromo-2-(methylthio)benzoate (1 eq.) from the previous step, potassium phosphate (2.5 eq.) and

[1,1'-bis(diphenylphosphino)-ferrocene]dipalladium(II) dichloromethane complex (0.1 eq.). The resulting red suspension was heated at 80° C. for 16 h. After cooling to RT, the reaction was diluted with ether and water. The organic layer was separated and washed further with water and brine, dried over MgSO$_4$, filtered and the filtrate concentrated in vacuo. Purification of the crude product thus obtained by way of flash chromatography (SiO$_2$, 9:1 (v/v) Hex:EtOAc→7:3 (v/v) Hex:EtOAc) afforded the title compound as a colorless oil.

Step 3:
5-[3-(Methyloxy)propyl]-2-(methylthio)benzyl alcohol

Methyl 5-[3-(methyloxy)propyl]-2-(methylthio)benzoate (1 eq.) from the previous step was taken up in THF (0.1 M) and then added lithium aluminum hydride (1 eq.). The reaction mixture thus obtained was stirred at RT for 16 h. The reaction was then quenched with 1 N aq. HCl and extracted with ether. The combined organic extracts were washed further with water and brine, dried over Na$_2$SO$_4$ and filtered. Concentration of the filtrate in vacuo afforded the crude title compound as a white solid.

Step 4:
5-[3-(Methyloxy)propyl]-2-(methylthio)benzaldehyde

To a dichloromethane solution of 5-[3-(methyloxy)propyl]-2-(methylthio)benzyl alcohol (1 eq.) from the previous step was added sodium bicarbonate (5 eq.) and DMP (1.1 eq.). The resulting reaction suspension was stirred for 1.5 h at RT. The reaction was quenched with sat. aq. NaHSO$_3$ and then extracted with dichloromethane. The combined organic extracts were washed further with 1 N aq. NaOH, water and brine, dried over MgSO$_4$ and filtered. Concentration of the filtrate in vacuo afforded the crude title compound as a colorless oil.

Step 5: Amine 75

5-[3-(Methyloxy)propyl]-2-(methylthio)benzaldehyde (1 eq.) from the previous step and cyclopropylamine (2 eq.) were combined in CH$_2$Cl$_2$ (0.1 M). To this was then added MgSO$_4$ (2 eq.) and formic acid (0.1 eq.) before the resulting suspension was allowed to stir at RT for 20 h. The insolubles were then removed via filtration through a pad of celite and the filtrate was concentrated in vacuo. The crude imine thus obtained was then re-taken up in MeOH (0.1 M). To this solution was added sodium borohydride (5 eq.) portionwise and the resulting mixture was stirred at RT for 16 h. The reaction was quenched with 1 N aq. HCl, neutralized with 1 N aq. NaOH and extracted with ether. The combined organic extracts were then washed further with water and brine, dried over MgSO$_4$, filtered and the filtrate concentrated in vacuo. Purification of the crude product by way of flash chromatography (SiO$_2$, 3:2 (v/v) Hex:EtOAc→1:4 (v/v) Hex:EtOAc) afforded the title compound as a colorless oil.

Amine 76

N-[3-Bromo-5-(3-methoxypropyl)-4-methylbenzyl] cyclopropanamine

Step 1:
3,5-Dibromo-N-cyclopropyl-4-methylbenzamide

To a stirred solution of 3,5-dibromo-4-methylbenzoic acid (1 eq.) in DMF (0.4 M) was added HATU (1.3 eq.), cyclopropylamine (1.1 eq.) and Hunig's base (3 eq.). The resulting yellow mixture was stirred at RT for 18 h. The reaction was then quenched with saturated aqueous ammonium chloride and extracted with ethyl acetate. The combined organic extracts were washed further with water and brine, dried over Na$_2$SO$_4$, filtered and the filtrate concentrated in vacuo. Trituration of the crude product thus obtained in a mixture of ether and hexanes afforded the title compound as an off-white solid.

Step 2: 3-Bromo-N-cyclopropyl-5-[(1E)-3-methoxyprop-1-en-1-yl]-4-methylbenzamide To a solution of 3,5-dibromo-N-cyclopropyl-4-methylbenzamide (1 eq.) from the previous step and 4,4,5,5-tetramethyl-2-[(1E)-3-(methyloxy)-1-propen-1-yl]-1,3,2-dioxaborolane (1.1 eq.) in DMF (0.1 M) was added trans-bis(triphenylphosphine) palladium(II) bromide (0.05 eq.). The vessel was repeatedly evacuated and back-filled with nitrogen. Finally, 2 M aq. Na$_2$CO$_3$ (3 eq.) was added and the resulting mixture was heated at 100° C. for 1 h. The now black suspension was cooled to RT, diluted with water and extracted with ethyl acetate. The combined organic extracts were washed further with water and brine, dried over Na$_2$SO$_4$, filtered and the filtrate concentrated in vacuo. Purification of the crude product by way of flash chromatography (SiO$_2$, 9:1 (v/v) Hex:EtOAc→EtOAc) afforded the title compound as a yellow-orange oil.

Step 3: 3-Bromo-N-cyclopropyl-5-(3-methoxypropyl)-4-methylbenzamide

To a solution of 3-bromo-N-cyclopropyl-5-[(1E)-3-methoxyprop-1-en-1-yl]-4-methylbenzamide (1 eq.) from the previous step in refluxing toluene (0.1 M) was added portionwise benzenesulfonyl hydrazide (6 eq.) over 2 h. After heating at reflux for another hour, the now black reaction suspension was cooled to RT, quenched with saturated aqueous sodium bicarbonate and extracted with ethyl acetate. The combined organic extracts were then washed with brine, dried over Na$_2$SO$_4$, filtered and the filtrate concentrated in vacuo. Purification of the crude product by way of flash chromatography (SiO$_2$, 9:1 (v/v) Hex:EtOAc→EtOAc) afforded the title compound as a yellow oil.

Step 4: Amine 76

To a stirred solution of 3-bromo-N-cyclopropyl-5-(3-methoxypropyl)-4-methylbenzamide (1 eq.) from the previous step in THF (0.2 M) was added sequentially sodium borohydride (4 eq.) and BF$_3$-THF complex (4.5 eq.). The reaction solution thus obtained was heated at 40° C. for 5 h, cooled to 0° C. and then poured slowly into 6 N aq. HCl (4.5 eq.). The resulting mixture was re-heated at 50° C. for 1 h, cooled to RT, basified with 10 N aq. NaOH and finally extracted with ether. The combined organic extracts were then washed further with water and brine, dried over Na$_2$SO$_4$, filtered and the filtrate concentrated in vacuo to give the title compound as a colorless oil.

Amine 76 mesylate

N-[3-Bromo-5-(3-methoxypropyl)-4-methylbenzyl]cyclopropanamine mesylate

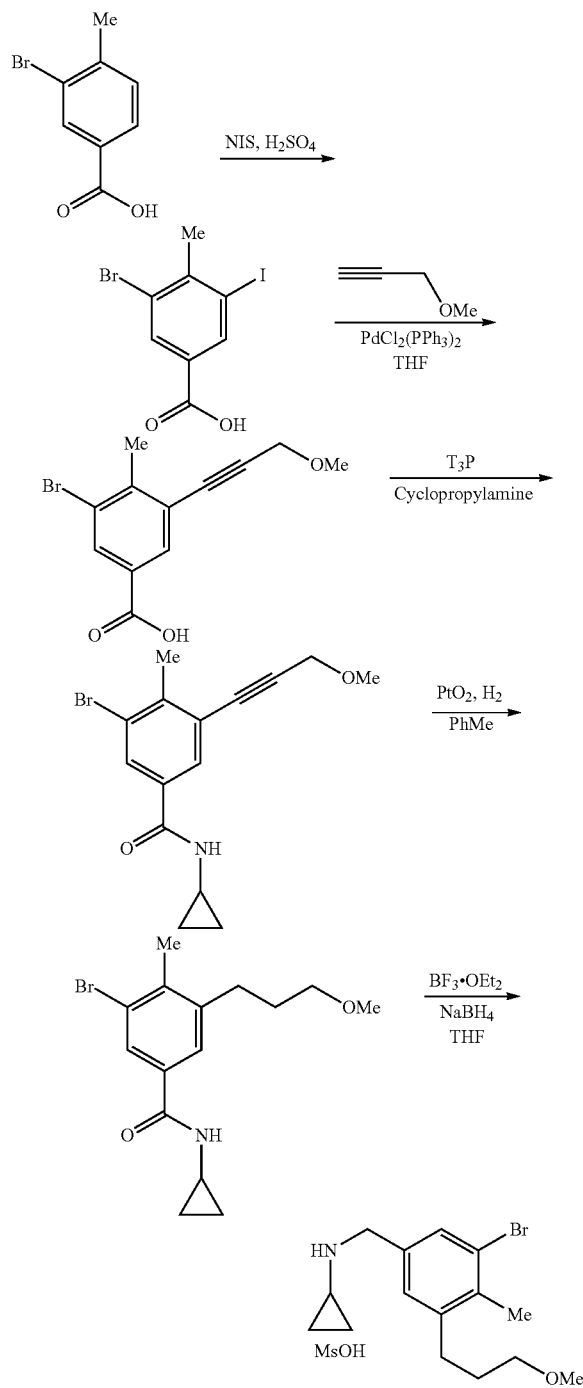

Step 1: 3-Bromo-5-iodo-4-methyl-benzoic acid

To a stirred solution of 3-bromo-4-methylbenzoic acid in 96% sulphuric acid (~0.58 M reaction concentration) was added N-iodosuccinimide (1.1 equiv.) over 1 h maintaining the temperature between 10 and 30° C. The reaction mixture was aged for 10 min then quenched into water. The slurry was filtered and washed with water, sodium bisulfite solution and then finally with water to give the title compound as an off-white solid. $^1$H NMR (400 MHz, dmso-$d_6$): δ 13.4 (br s, 1 H); 8.30 (s, 1 H); 8.00 (s, 1 H); 2.64 (s, 3 H). HRMS (ES, M–H) Calcd 338.8518. Found 338.8516.

Step 2: 3-Bromo-5-(3-methoxy-prop-1-ynyl)-4-methyl-benzoic acid

To a stirred solution of 3-bromo-5-iodo-4-methyl-benzoic acid in THF (0.98 M) was added triethylamine (7.5 equiv.) and copper iodide (0.01 equiv.) followed by PdCl$_2$(PPh$_3$)$_2$ (0.005 equiv). Propargyl methyl ether (1.5 equiv.) was then added and the mixture heated to ~65° C. for ~24 h. The mixture was cooled to 20° C. and then diluted with MTBE and water. The layers were cut and the organic washed with further water. The combined aqueous layers were mixed with further MTBE and 5 N HCl. The organic layer was washed with 1M HCl, twice with 3% w/v sodium bisulfite and finally with water. The resultant solution was concentrated to ~0.38 M and used in the next step as a solution in THF. $^1$H NMR (400 MHz, Acetone-$d_6$): δ 8.13 (s, 1 H); 8.00 (s, 1 H); 4.40 (s, 2 H); 3.41 (s, 3 H); 2.59 (s, 3 H). FIRMS (ES, M–H) Calcd 280.9813. Found 280.9820.

Step 3: 3-Bromo-N-cyclopropyl-5-(3-methoxy-prop-1-ynyl)-4-methyl-benzamide

To 3-bromo-5-(3-methoxy-prop-1-ynyl)-4-methyl-benzoic acid (0.38 M solution in THF) was added N,N-diisopropylethylamine (1.8 equiv.) and cyclopropylamine (1.35 equiv.) maintaining the internal temperature below 25° C. The mixture was cooled to 5° C. and 2-propanephosphoric acid anhydride (50 wt % in EtOAc, 1.5 equiv.) was added whilst maintaining the internal temperature below 25° C. The reaction mixture was aged for 1 h at ~20° C. then cooled to 2° C. and 10 wt % aq. NH$_4$Cl solution added, maintaining the internal temperature <30° C. Isopropyl acetate was added and the layers were allowed to settle. The lower aqueous layer removed. The organics were then washed with 1M HCl, followed by 10% NaHCO$_3$ solution and finally 10% NaCl solution. The organic layer was concentrated to ~1 M followed by the addition of toluene. The batch was then reconcentrated to ~2 M and the resultant slurry aged for 18 h. Heptane was then added and the solids were filtered, washed with a mixture of 1:1 toluene/heptane and dried to give the title compound as an off-white solid. $^1$H NMR (500 MHz, Acetone-$d_6$): δ 8.01 (s, 1 H), 7.92 (s, 1 H), 7.86 (s, 1 H), 4.37 (s, 2 H), 3.39 (s, 3 H), 2.95-2.89 (m, 1 H), 2.53 (s, 3 H), 0.76-0.67 (m, 2 H), 0.68-0.60 (m, 2 H). HRMS (ES, M+H) Calcd 322.0443. Found 322.0457.

Step 4: 3-Bromo-N-cyclopropyl-5-(3-methoxy-propyl)-4-methyl-benzamide

To a stirred solution of 3-bromo-N-cyclopropyl-5-(3-methoxy-prop-1-ynyl)-4-methyl-benzamide and platinum oxide (0.04 equiv.) in toluene (~0.12 M) was added triethylamine (0.2 equiv.). The resultant solution was hydrogenated at 1.8 Barg for 3 h and then filtered to remove the catalyst. The solution was concentrated to ~4 volumes and then heptane added (8 volumes). The resultant slurry was filtered to afford the product as an off-white solid. $^1$H NMR (500 MHz, Acetone-$d_6$): δ 7.87 (m, 2 H), 7.65 (s, 1 H), 3.35 (t, J=6.12 Hz, 2 H), 3.27 (s, 3 H), 2.93-2.86 (m, 1 H), 2.75 (t, J=7.91 Hz, 2

H); 2.39 (s, 3 H), 1.80-1.72 (m, 2 H), 0.75-0.67 (m, 2 H), 0.61-0.56 (m, 2 H). HRMS (ES, M+H) Calcd 326.0767. Found 326.0756.

Step 5: Amine 76

To a stirred solution of sodium borohydride (2.0 equiv.) in THF (8 volumes) was added boron trifluoride THF complex (2.5 equiv.) keeping the temperature <30° C. A solution of 3-bromo-N-cyclopropyl-5-(3-methoxy-propyl)-4-methyl-benzamide in THF (3 volumes) was then added and the solution aged at 35° C. for 18 h. The reaction mixture was quenched by addition to 5M hydrochloric acid solution and then the mixture was warmed to 50° C. and aged for 90 min. After cooling to 20° C., heptane (3 volumes) and methyl tert-butyl ether (3 volumes) were added. The layers were settled and the lower cut away. The upper organic was washed with 5M HCl and the lower aqueous combined with the first aqueous layer. The combined aqueous layers were cooled to 5° C. and then 48% NaOH was added to adjust the pH to 14. Methyl tert-butyl ether (6.8 volumes) was added and the layers separated. The aqueous layer was back-extracted with MTBE. The combined organics were concentrated to ~4 volumes and then THF (3 volumes) added. The solution was warmed to 40° C. and methanesulfonic acid (0.95 equiv.) added. The resultant slurry was cooled to ambient and then filtered and the solids washed with MTBE to give the title compound as off-white solid. $^1$H NMR (500 MHz, DMSO-d6) δ 8.87 (s, 2 H), 7.61 (s, 1 H), 7.30 (s, 1 H), 4.17 (s, 2 H), 3.35 (m, J=6.23 Hz, 2 H), 3.24 (s, 3 H), 2.71-2.64 (m, 3 H), 2.34 (s, 3 H), 2.30 (s, 3 H), 1.77-1.69 (m, 2 H), 0.82-0.77 (m, 2 H), 0.77-0.70 (m, 2 H). HRMS (ES, M+H) Calcd 312.0963. Found 312.0978.

Amine 77

N-({3,5-Bis[3-(methyloxy)propyl]phenyl}methyl)cyclopropanamine

Step 1: N-[(3,5-Dibromophenyl)methyl]cyclopropanamine 3,5-Dibromobenzaldehyde (1 eq.), cyclopropylamine (2 eq.) and magnesium sulfate (1 eq.) were stirred in dichloromethane (0.1 M) for 20 h. The insolubles were then removed via filtration through a pad of celite and washed further with dichloromethane. The filtrate was concentrated in vacuo to afford the crude imine which was then immediately re-taken up in MeOH (0.1 M). To this solution was added sodium borohydride (5 eq.) portionwise and the resulting mixture was stirred at RT for 4 h. The reaction was quenched with 1 N aq. HCl, neutralized with 1 N aq. NaOH and extracted with ether. The combined organic extracts were then washed further with water and brine, dried over MgSO$_4$, and filtered. Concentration of the filtrate in vacuo afforded the title compound as a pale yellow oil.

Step 2: tert-Butyl cyclopropyl(3,4-dibromobenzyl)carbamate

N-[(3,5-Dibromophenyl)methyl]cyclopropanamine (1 eq.) from the previous step and di-tert-butyl dicarbonate (1 eq.) were taken up in dichloromethane (0.12 M). To this was then added Hunig's base (1.3 eq.) and the resulting mixture was stirred at RT for 16 h. The volatiles were removed in vacuo and the resulting residue was taken up in a 1:1 (v/v) mixture of hexanes and ether. This suspension was subsequently washed with 10% aq. HCl, water and brine, dried over Na$_2$SO$_4$, filtered and the filtrate concentrated in vacuo. Purification of the crude product thus obtained by way of column chromatography (SiO$_2$, Hex→1:1 (v/v) Hex:EtOAc) afforded the title compound as a pale yellow oil.

Step 3: tert-Butyl{3,5-bis[(1E)-3-methoxy-1-propen-1-yl]benzyl}cyclopropylcarbamate To a solution of tert-butyl cyclopropyl(3,4-dibromobenzyl)carbamate (1 eq.) from the previous step and 4,4,5,5-tetramethyl-2-[(1E)-3-(methyloxy)-1-propen-1-yl]-1,3,2-dioxaborolane (2.2 eq.) in DMF (0.14 M) was added trans-bis(triphenylphosphine) palladium(II) bromide (0.1 eq.). The vessel was repeatedly evacuated and back-filled with nitrogen. Finally, 2 M aq. Na$_2$CO$_3$ (6 eq.) was added and the resulting mixture was heated at 90° C. for 6 h. The now black suspension was cooled to RT, diluted with water and extracted with ether. The combined organic extracts were washed further with 10% aq. HCl, 1 N aq. NaOH, water and brine, dried over Na$_2$SO$_4$, filtered and the filtrate concentrated in vacuo. Purification of the crude product by way of flash chromatography (SiO$_2$, Hex→1:1 (v/v) Hex:EtOAc) afforded the title compound as a pale yellow oil.

Step 4: tert-Butyl[3,5-bis(3-methoxypropyl)benzyl]cyclopropylcarbamate tert-Butyl{3,5-bis[(1E)-3-methoxy-1-propen-1-yl]benzyl}cyclopropylcarbamate (1 eq.) from the previous step and 10% w/w palladium over charcoal (0.1 eq.) were suspended in EtOAc (0.05 M). The vessel was then evacuated and purged with H$_2$. Under a balloon-filled H$_2$ atmosphere, the reaction suspension was stirred at RT for 3 h. The reaction suspension was then quenched with dichloromethane and filtered through a bed of celite. Concentration of the filtrate in vacuo to afford the title compound as a yellow oil.

Step 5: Amine 77

To a solution of tert-butyl[3,5-bis(3-methoxypropyl)benzyl]cyclopropyl-carbamate (1 eq.) from the previous step in CH$_2$Cl$_2$ (0.1 M) was added HCl (4.0 M in dioxane, 30 eq.). The resulting solution was stirred at RT for 2 h. The reaction was then quenched with 1 N aq. NaOH and extracted with ether. The combined organic extracts were then washed further with water and brine, dried over Na$_2$SO$_4$, filtered and the filtrate concentrated in vacuo. Purification of the crude product by way of flash chromatography (SiO$_2$, 4:1 (v/v) Hex:EtOAc→EtOAc) afforded the title compound as a colorless oil.

Amine 78

N-[3-(3-Methoxypropyl)-5-methylbenzyl]cyclopropanamine

Step 1: tert-Butyl (3-bromo-5-formylbenzyl)cyclopropylcarbamate

To a toluene (0.1 M) solution of n-butyl lithium (2.5 M in hexanes, 1.2 eq.) was added at −10° C. n-butyl magnesium bromide (2.0 M in THF, 0.4 eq.). The resulting suspension was stirred at −10° C. for 20 min before tert-butyl cyclopropyl (3,4-dibromobenzyl)carbamate (1 eq., Amine 77, Step 2) added. The now yellow-red suspension was stirred at 0° C. for 30 min before DMF (30 eq.) was added dropwise neat at −78°

C. The reaction mixture was allowed to warm slowly to RT over 3 h. The now black suspension was quenched with 10% aq. HCl and then extracted with ether. The combined organic extracts were washed further with water and brine, dried over Na$_2$SO$_4$, filtered and the filtrate concentrated in vacuo. Purification of the crude product by way of flash chromatography (SiO$_2$, Hex→1:1 (v/v) Hex:EtOAc) afforded the title compound as a golden yellow oil.

Step 2: tert-Butyl cyclopropyl{3-formyl-5-[(1E)-3-methoxy-1-propen-1-yl]benzyl}carbamate To a solution of tert-butyl (3-bromo-5-formylbenzyl)cyclopropylcarbamate (1 eq.) from the previous step and 4,4,5,5-tetramethyl-2-[(1E)-3-(methyloxy)-1-propen-1-yl]-1,3,2-dioxaborolane (1 eq.) in DMF (0.2 M) was added trans-bis(triphenylphosphine) palladium(II) bromide (0.05 eq.). The vessel was repeatedly evacuated and back-filled with nitrogen. Finally, 2 M aq. Na$_2$CO$_3$ (3 eq.) was added and the resulting mixture was heated at 90° C. for 6 h. The now black suspension was cooled to RT, diluted with water and extracted with ether. The combined organic extracts were washed further with 10% aq. HCl, 1 N aq. NaOH, water and brine, dried over Na$_2$SO$_4$, filtered and the filtrate concentrated in vacuo. Purification of the crude product by way of flash chromatography (SiO$_2$, Hex→3:7 (v/v) Hex:EtOAc) afforded the title compound as a pale yellow oil.

Step 3: tert-Butyl cyclopropyl[3-(3-methoxypropyl)-5-methylbenzyl]carbamate tert-Butyl cyclopropyl{3-formyl-5-[(1E)-3-methoxy-1-propen-1-yl]benzyl}carbamate (1 eq.) from the previous step and 10% w/w palladium over charcoal (0.1 eq.) were suspended in EtOAc (0.1 M). The vessel was then evacuated and purged with H$_2$. Under a balloon-filled H$_2$ atmosphere, the reaction suspension was stirred at RT for 3 h. The reaction suspension was then quenched with dichloromethane and filtered through a bed of celite. Concentration of the filtrate in vacuo to afford the title compound as a yellow oil.

Step 5: Amine 78 tert-Butyl cyclopropyl[3-(3-methoxypropyl)-5-methylbenzyl]carbamate (1 eq.) from the previous step in CH$_2$Cl$_2$ (0.1 M) was added HCl (4.0 M in dioxane, 30 eq.). The resulting solution was stirred at RT for 2 h. The reaction was then quenched with 1 N aq. NaOH and extracted with ether. The combined organic extracts were then washed further with water and brine, dried over Na$_2$SO$_4$ and filtered. Concentration of the filtrate in vacuo afforded the title compound as a colorless oil.

Amine 79

N-[2-Bromo-3,5-bis(3-methoxypropyl)benzyl]cyclopropanamine

Step 1: 3,5-Dibromo-N-cyclopropylbenzamide

To a stirred solution of 3,5-dibromobenzoic acid (1 eq.) in DMF (0.15 M) was added HATU (1.3 eq.), cyclopropylamine (1.1 eq.) and Hunig's base (3 eq.). The resulting yellow mixture was stirred at RT for 18 h. The reaction was then quenched with saturated aqueous ammonium chloride and extracted with ethyl acetate. The combined organic extracts were washed further with water and brine, dried over Na$_2$SO$_4$, filtered and the filtrate concentrated in vacuo. Trituration of the crude product thus obtained in a mixture of ether and hexanes afforded the title compound as a white solid.

Step 2: N-Cyclopropyl-3,5-bis[(1E)-3-methoxyprop-1-en-1-yl]benzamide

To a solution of 3,5-dibromo-N-cyclopropylbenzamide (1 eq.) from the previous step and 4,4,5,5-tetramethyl-2-[(1E)-3-(methyloxy)-1-propen-1-yl]-1,3,2-dioxaborolane (2.3 eq.) in DMF (0.13 M) was added trans-bis(triphenylphosphine) palladium(II) bromide (0.1 eq.). The vessel was repeatedly evacuated and back-filled with nitrogen. Finally, 2 M aq. Na$_2$CO$_3$ (6 eq.) was added and the resulting mixture was heated at 90° C. for 16 h. The now black suspension was cooled to RT, diluted with water and extracted with ethyl acetate. The combined organic extracts were washed further with 1 N aq. NaOH, 10% aq. HCl, water and brine, dried over Na$_2$SO$_4$ and filtered. Concentration of the filtrate in vacuo afforded the crude title compound as a black oil.

Step 3: N-Cyclopropyl-3,5-bis(3-methoxypropyl)benzamide

An EtOAc (0.15 M) solution of N-cyclopropyl-3,5-bis[(1E)-3-methoxyprop-1-en-1-yl]benzamide (1 eq.) from the previous step was eluted through an H-Cube hydrogenation apparatus equipped with a 10% palladium over carbon cartridge at a rate of 1 mL/min with EtOAc as the eluent. The hydrogenation was carried out using full hydrogen setting at RT. Purification of the crude product thus obtained by way of flash chromatography (SiO$_2$, 9:1 (v/v) Hex:EtOAc→EtOAc) afforded the title compound as a colorless oil.

Step 4: 2-Bromo-N-cyclopropyl-3,5-bis(3-methoxypropyl)benzamide

To a THF (0.1 M) solution of N-cyclopropyl-3,5-bis(3-methoxypropyl)benzamide (1 eq.) from the previous step and freshly distilled TMEDA (1 eq.) was added at −78° C. t-butyl lithium (1.7 M in pentanes, 1 eq.) dropwise over 10 min. The resulting reaction mixture was then slowly warmed to 0° C. over 1 h and stirred at 0° C. for 1 h. With the now orange reaction solution re-cooled to −78° C., 1,2-dibromotetrafluoroethane was added neat, dropwise over 10 min. The cooling bath was removed and the reaction mixture was stirred at RT for 18 h. The reaction was then quenched with 1 N aq. NaOH and extracted with EtOAc. The combined organic extracts were washed further with 10% aq. HCl, water and brine, dried over Na$_2$SO$_4$, filtered, and the filtrate concentrated in vacuo. Purification of the crude product thus obtained by way of flash chromatography (SiO$_2$, 9:1 (v/v) Hex:EtOAc→EtOAc) afforded the title compound as a pale yellow oil.

Step 5: Amine 79

To a stirred solution of 2-bromo-N-cyclopropyl-3,5-bis(3-methoxypropyl)benzamide (1 eq.) from the previous step in THF (0.16 M) was added sequentially sodium borohydride (4 eq.) and BF$_3$-THF complex (4.5 eq.). The reaction solution thus obtained was heated at 40° C. for 5 h, cooled to 0° C. and then poured slowly into 6 N aq. HCl (4.5 eq.). The resulting mixture was re-heated at 50° C. for 1 h, cooled to RT, basified with 10 N aq. NaOH and finally extracted with ether. The combined organic extracts were then washed further with water and brine, dried over Na$_2$SO$_4$, filtered and the filtrate concentrated in vacuo. Purification of the crude product thus obtained by way of flash chromatography (SiO$_2$, 4:1 (v/v) Hex:EtOAc→EtOAc) afforded the title compound as a colorless oil.

Amine 80

N-[2-Chloro-3,5-bis(3-methoxypropyl)benzyl]cyclopropanamine

Step 1: 2-Chloro-N-cyclopropyl-3,5-bis(3-methoxypropyl)benzamide

To a DMF (0.13 M) solution of 2-bromo-N-cyclopropyl-3,5-bis(3-methoxypropyl)benzamide (1 eq., Amine 79, Step 4) was added copper(I) chloride (2 eq.). The suspension was sealed and heated in a microwave at 150° C. for 10 min. The reaction was then quenched with 10% aq. HCl and extracted with EtOAc. The combined organic extracts were washed further with 1 N aq. NaOH, water and brine, dried over Na$_2$SO$_4$, filtered, and the filtrate concentrated in vacuo. Purification of the crude product thus obtained by way of flash chromatography (SiO$_2$, 4:1 (v/v) Hex:EtOAc→EtOAc) afforded the title compound as a pale yellow oil.

Step 2: Amine 80

To a stirred solution of 2-chloro-N-cyclopropyl-3,5-bis(3-methoxypropyl)benzamide (1 eq.) from the previous step in THF (0.06 M) was added sequentially sodium borohydride (4.2 eq.) and BF$_3$-THF complex (4.5 eq.). The reaction solution thus obtained was heated at 40° C. for 5 h, cooled to 0° C. and then poured slowly into 6 N aq. HCl (4.5 eq.). The resulting mixture was re-heated at 50° C. for 1 h, cooled to RT, basified with 10 N aq. NaOH and finally extracted with ether. The combined organic extracts were then washed further with water and brine, dried over Na$_2$SO$_4$, filtered and the filtrate concentrated in vacuo. Purification of the crude product thus obtained by way of flash chromatography (SiO$_2$, 4:1 (v/v) Hex:EtOAc→EtOAc) afforded the title compound as a colorless oil.

Amine 81

N-[2-Methoxy-3,5-bis(3-methoxypropyl)benzyl]cyclopropanamine

Step 1: 2-Methoxy-3,5-bis[(1E)-3-methoxyprop-1-en-1-yl]benzaldehyde

To a solution of 3,5-dibromo-2-methoxybenzaldehyde (1 eq.) and 4,4,5,5-tetramethyl-2-[(1E)-3-(methyloxy)-1-propen-1-yl]-1,3,2-dioxaborolane (2.2 eq.) in DMF (0.1 M) was added trans-bis(triphenylphosphine) palladium(II) bromide (0.1 eq.). The vessel was repeatedly evacuated and back-filled with nitrogen. Finally, 2 M aq. Na$_2$CO$_3$ (6.5 eq.) was added and the resulting mixture was heated at 90° C. for 16 h. The now black suspension was cooled to RT, diluted with water and extracted with ether. The combined organic extracts were washed further with 1 N aq. NaOH, 10% aq. HCl, water and brine, dried over Na$_2$SO$_4$ and filtered. Concentration of the filtrate in vacuo afforded the crude title compound as a brown oil.

Step 2: 2-Methoxy-3,5-bis(3-methoxypropyl)benzaldehyde

2-Methoxy-3,5-bis[(1E)-3-methoxyprop-1-en-1-yl]benzaldehyde (1 eq.) from the previous step and 10% w/w palladium over charcoal (0.1 eq.) were suspended in EtOAc (0.1 M). The vessel was then evacuated and purged with H$_2$. Under a balloon-filled H$_2$ atmosphere, the reaction suspension was stirred at RT for 4 h. The reaction suspension was then quenched with dichloromethane and filtered through a bed of celite. Concentration of the filtrate in vacuo to afford the crude product as a yellow oil. Further purification by way of flash chromatography (SiO$_2$, Hex→EtOAc) afforded the title compound as a colorless oil.

Step 3: Amine 81

2-Methoxy-3,5-bis(3-methoxypropyl)benzaldehyde (1 eq.) from the previous step and cyclopropylamine (2 eq.) were combined in CH$_2$Cl$_2$ (0.1 M). To this was then added MgSO$_4$ (1.2 eq.) and the resulting suspension was allowed to stir at RT for 20 h. The insolubles were then removed via filtration through a pad of celite and the filtrate was concentrated in vacuo. The crude imine thus obtained was then re-taken up in MeOH (0.1 M). To this solution was added sodium borohydride (2 eq.) portionwise and the resulting mixture was stirred at RT for 2.5 h. The reaction was quenched with 1 N aq. HCl, neutralized with 1 N aq. NaOH and extracted with ether. The combined organic extracts were then washed further with water and brine, dried over MgSO$_4$ and filtered. Concentration of the filtrate in vacuo afforded the title compound as a pale yellow oil.

Amine 82

N-[3-(3-Methoxypropyl)-5-(trifluoromethyl)benzyl]cyclopropanamine

Step 1: 3-Bromo-5-(trifluoromethyl)benzaldehyde

To a stirred solution of n-butyl lithium (2.5 M in hexanes, 0.8 eq.) in toluene (0.2 M) at −15° C. was added dropwise n-butyl magnesium chloride (2.0 M in THF, 0.4 eq.). After 20 min, a solution of 1,3-dibromo-5-(trifluoromethyl)benzene (1 eq.) in toluene was added over 10 min. The reaction mixture thus obtained was stirred at −15° C. for 2 h before DMF (3 eq.) was added. The reaction was allowed to warm to 0° C. After 45 min, saturated aqueous ammonium chloride was added. The reaction mixture was extracted with ethyl acetate. The combined organic extracts were then washed with brine, dried over Na$_2$SO$_4$, filtered and the filtrate concentrated in vacuo. Purification of the crude product by way of flash chromatography (SiO$_2$, Hex→1:1 (v/v) Hex:EtOAc) afforded the title compound.

Step 2: 3-[(1E)-3-Methoxyprop-1-en-1-yl]-5-(trifluoromethyl)benzaldehyde

To a solution of 3-bromo-5-(trifluoromethyl)benzaldehyde (1 eq.) from the previous step and 4,4,5,5-tetramethyl-2-[(1E)-3-(methyloxy)-1-propen-1-yl]-1,3,2-dioxaborolane (1.5 eq.) in DMF (0.2 M) was added trans-bis(triphenylphosphine) palladium(II) bromide (0.05 eq.). The vessel was repeatedly evacuated and back-filled with nitrogen. Finally, 2 M aq. Na$_2$CO$_3$ (3 eq.) was added and the resulting mixture was stirred at 100° C. for 2 h. The now black suspension was cooled to RT, diluted with water and extracted with ethyl acetate. The combined organic extracts were washed with water and brine, dried over Na$_2$SO$_4$, filtered and the filtrate concentrated in vacuo. Purification of the crude product by

Step 3: N-[3-[(1E)-3-Methoxyprop-1-en-1-yl]-5-(trifluoromethyl)benzyl]cyclopropanamine 3-[(1E)-3-Methoxyprop-1-en-1-yl]-5-(trifluoromethyl)benzaldehyde (1 eq.) from the previous step and cyclopropylamine (2 eq.) were combined in $CH_2Cl_2$ (0.2 M). To this was then added $MgSO_4$ (1.5 eq.) and the resulting suspension was stirred at RT for 18 h. The insolubles were then removed via filtration through a pad of celite and the filtrate was concentrated in vacuo. The crude imine thus obtained was then re-taken up in a 2:1 (v/v) mixture of THF:MeOH (0.2 M). To this solution was added sodium borohydride (5 eq.) portionwise and the resulting mixture was stirred at RT for 18 h. The reaction was quenched with saturated aqueous sodium bicarbonate and extracted with ethyl acetate. The combined organic extracts were then washed with brine, dried over $Na_2SO_4$, filtered and the filtrate concentrated in vacuo. Purification of the crude product by way of flash chromatography ($SiO_2$, 9:1 (v/v) Hex:EtOAc→EtOAc) afforded the title compound.

Step 5: Amine 82

N-[3-[(1E)-3-Methoxyprop-1-en-1-yl]-5-(trifluoromethyl)benzyl]cyclopropanamine (1 eq.) from the previous step and 10% w/w palladium over charcoal (0.1 eq.) were suspended in EtOAc (0.03 M). The vessel was then evacuated and purged with $H_2$. Under a balloon-filled $H_2$ atmosphere, the reaction suspension was stirred at RT overnight. The reaction was then filtered through a bed of celite and the filtrate concentrated in vacuo. Purification of the crude product by way of flash chromatography ($SiO_2$, Hex→1:9 (v/v) Hex:EtOAc) afforded the title compound as a colorless oil.

Amine 83

3-[(Cyclopropylamino)methyl]-5-(3-methoxypropyl)phenol

Amine 83 was prepared according to the procedure described in published patent application WO 2007/009250 A1.

Amine 84

N-(3-Bromo-5-iodobenzyl)cyclopropanamine

Step 1: (3-Bromo-5-iodophenyl)methanol

To a solution of 3-bromo-5-iodobenzoic acid (1.0 eq.) in THF (0.2 M) at RT was added borane-methyl sulfide complex (1.5 eq). After 3 days of stirring at RT, the reaction mixture was quenched cautiously with 2 N aq. HCl and extracted with ether. The combined organic extracts were washed with 1 N aq. NaOH, water and brine, dried over $MgSO_4$ and filtered. Concentration of the filtrate in vacuo afforded the title compound as a colorless oil.

Step 2: 3-Bromo-5-iodobenzaldehyde

A mixture of (3-bromo-5-iodophenyl)methanol from the previous step (1.0 eq.) and Dess-Martin periodinane (1.18 eq.) was stirred at RT in dichloromethane (0.1 M) for 45 min. The reaction mixture was diluted with ether, filtered through a plug of $SiO_2$, and the silica washed with a 3:1 (v/v) mixture of hexanes:EtOAc. The filtrate was concentrated in vacuo and passed again through a plug of $SiO_2$, eluting with a 3:1 (v/v) mixture of hexanes:EtOAc to afford the title compound as a light yellow solid.

Step 3: Amine 84

3-Bromo-5-iodobenzaldehyde (1 eq.) from the previous step and cyclopropylamine (2 eq.) were combined in $CH_2Cl_2$ (0.1 M). To this was then added $MgSO_4$ (1 eq.) and the resulting suspension was stirred at RT for 20 h. The insolubles were then removed via filtration through a pad of celite and the filtrate was concentrated in vacuo. The crude imine thus obtained was then re-taken up in MeOH (0.5 M). To this solution was added sodium borohydride (1.5 eq.) portionwise and the resulting mixture was stirred at 0° C. for 30 min, then at RT for 2 h. The reaction was quenched by stirring with 2 N aq. HCl for 25 min, basified with 1 N aq. NaOH and concentrated in vacuo. The residue was extracted with ether from water, dried over $Na_2SO_4$, filtered and the filtrate concentrated in vacuo to afford the title compound as a light yellow oil.

Amine 85

N-Cyclopropyl-6-(3-methoxypropyl)indan-1-amine

Step 1: 6-[(1E)-3-Methoxyprop-1-en-1-yl]indan-1-one

To a solution of 6-bromoindan-1-one (1 eq.) and 4,4,5,5-tetramethyl-2-[(1E)-3-(methyloxy)-1-propen-1-yl]-1,3,2-dioxaborolane (1.3 eq.) in DMF (0.1 M) was added trans-bis(triphenylphosphine) palladium(II) bromide (0.05 eq.). The vessel was repeatedly evacuated and back-filled with nitrogen. Finally, 2 M aq. $Na_2CO_3$ (3 eq.) was added and the resulting mixture was stirred at 100° C. for 1 h. The now black suspension was cooled to RT, diluted with water and extracted with ethyl acetate. The combined organic extracts were washed with water and brine, dried over $Na_2SO_4$, filtered and the filtrate concentrated in vacuo. Purification of the crude product by way of flash chromatography ($SiO_2$, Hex→1:1 (v/v) Hex:EtOAc) afforded the title compound as a beige solid.

Step 2: N-cyclopropyl-6-[(1E)-3-methoxyprop-1-en-1-yl]indan-1-amine

To a solution of 6-[(1E)-3-methoxyprop-1-en-1-yl]indan-1-one (1 eq.) from the previous step in MeOH (2 M) was added cyclopropylamine (2 eq.) and titanium(IV) isopropoxide (1.3 eq.). The solution was stirred at RT for 1 h before sodium borohydride (1 eq.) was added at 0° C. After 30 min, water was added and the mixture was extracted with ethyl acetate. The combined organic extracts were then washed with water and brine, dried over $Na_2SO_4$, filtered and the filtrate concentrated in vacuo. Purification of the crude product by way of flash chromatography ($SiO_2$, Hex→1:9 (v/v) Hex:EtOAc) afforded the title compound.

Step 3: Amine 85

N-Cyclopropyl-6-[(1E)-3-methoxyprop-1-en-1-yl]indan-1-amine (1 eq.) from the previous step and 10% w/w palladium over charcoal (0.1 eq.) were suspended in EtOAc (0.2 M). The vessel was then evacuated and purged with $H_2$. Under a balloon-filled H₂ atmosphere, the reaction suspension was stirred at RT for 3 h. The reaction was then filtered through a bed of celite and the filtrate concentrated in vacuo to afford the title compound.

Amine 86

N-Cyclopropyl-7-(3-methoxypropyl)-1,2,3,4-tetrahydronaphthalen-1-amine

Amine 86 was prepared according to the procedure described in Amine 85 but using instead 7-bromo-3,4-dihydronaphthalen-1(2H)-one as the starting material.

Amine 87

3-{3-Bromo-5-[(cyclopropylamino)methyl]-2-methylphenyl}-1-propanol

To a chloroform (0.1 M) solution of Amine 76 (1 eq.) was added iodotrimethylsilane (6 eq.). The resulting red solution was stirred at RT in darkness for 18 h. The reaction was quenched with methanol before the volatiles were removed in vacuo. The resulting residue was then partitioned between ether and 10% aq. HCl. The aqueous layer was separated, carefully brought to a pH of ~8 with 1 N aq. NaOH and extracted with EtOAc. The combined EtOAc extracts were washed further with water and brine, dried over Na₂SO₄, filtered and the filtrate concentrated in vacuo. Purification of the crude product by way of flash chromatography (SiO₂, 97:3 (v/v) CH₂Cl₂:2.0 M NH₃ in MeOH→94:6 (v/v) CH₂Cl₂: 2.0 M NH₃ in MeOH) afforded the title compound as a colorless oil.

Amine 88

N-[3-Bromo-5-(3-ethoxypropyl)-4-methylbenzyl]cyclopropanamine

Step 1: Methyl 3-bromo-5-[(1E)-3-methoxy-1-propen-1-yl]-4-methylbenzoate

To a solution of methyl 3,5-dibromo-4-methylbenzoate (1 eq.) and 4,4,5,5-tetramethyl-2-[(1E)-3-(methyloxy)-1-propen-1-yl]-1,3,2-dioxaborolane (1.1 eq.) in DMF (0.1 M) was added trans-bis(triphenylphosphine) palladium(II) bromide (0.02 eq.). The vessel was repeatedly evacuated and back-filled with nitrogen. Finally, 2 M aq. Na₂CO₃ (3 eq.) was added and the resulting mixture was heated at 100° C. for 2 h. The now black suspension was cooled to RT, diluted with water and extracted with ether. The combined organic extracts were washed further with water and brine, dried over Na₂SO₄, filtered and the filtrate concentrated in vacuo. Purification of the crude product by way of flash chromatography (SiO₂, 9:1 (v/v) Hex:EtOAc→→1:1 (v/v) Hex:EtOAc) afforded the title compound as a colorless oil.

Step 2: Methyl 3-bromo-5-(3-methoxypropyl)-4-methylbenzoate

To a dichloromethane (0.2 M) solution of methyl 3-bromo-5-[(1E)-3-methoxy-1-propen-1-yl]-4-methylbenzoate (1 eq.) from the previous step was added Crabtree's catalyst (0.01 eq.). The resulting orange red solution was bubbled with hydrogen for 10 min to activate the catalyst and then stirred at RT under a static balloon atmosphere of hydrogen for 3 h. Finally, removal of the volatiles in vacuo afforded the crude title compound as a yellow oil.

Step 3: Methyl 3-bromo-5-(3-iodopropyl)-4-methylbenzoate

To a chloroform (0.1 M) solution of methyl 3-bromo-5-(3-methoxypropyl)-4-methylbenzoate (1 eq.) from the previous step was added iodotrimethylsilane (10 eq.). The resulting red solution was stirred at RT in darkness for 18 h. The reaction was quenched with methanol before the volatiles were removed in vacuo. The resulting residue was then taken up in ether, washed sequentially with 10% aq. HCl, 1 N aq. NaOH, water and brine, dried over Na₂SO₄, filtered and the filtrate concentrated in vacuo. Purification of the crude product by way of flash chromatography (SiO₂, Hex→3:7 (v/v) Hex: EtOAc) afforded the title compound as an orange oil.

Step 4: Ethyl 3-bromo-5-(3-ethoxypropyl)-4-methylbenzoate

To an ethanol (0.1 M) solution of methyl 3-bromo-5-(3-iodopropyl)-4-methylbenzoate (1 eq.) from the previous step was added freshly prepared sodium ethoxide (3 eq.). The resulting solution was heated at reflux for 18 h. After cooling to RT, the volatiles were removed in vacuo. The resulting residue was then taken up in ether and washed further with 10% aq. HCl, 1 N aq. NaOH, water and brine, dried over Na₂SO₄, filtered and the filtrate concentrated in vacuo. Purification of the crude product by way of flash chromatography (SiO₂, Hex→1:1 (v/v) Hex:EtOAc) afforded the title compound as a yellow oil.

Step 5: 3-Bromo-5-(3-ethoxypropyl)-4-methylbenzaldehyde

To a dichloromethane (0.07 M) solution of ethyl 3-bromo-5-(3-ethoxypropyl)-4-methylbenzoate (1 eq.) from the previous step was added DIBAL-H (1.5 M solution in toluene, 2.2 eq.). The resulting solution was stirred at RT for 1.5 h and then carefully quenched with 10% aq. HCl. The aqueous layer was separated and back-extracted with ether. The combined organic extracts were washed further with brine, dried over Na₂SO₄, filtered and the filtrate concentrated in vacuo. The crude alcohol thus obtained was taken up again in dichloromethane (0.07 M) and then added Dess-Martin periodinane (1.0 eq.) and sodium bicarbonate (1.2 eq.). After stirring at RT for 40 min, the reaction mixture was diluted with ether and washed sequentially with sat. aq. NaHSO₃, 1 N aq. NaOH, water and brine. The organic extract was dried over Na₂SO₄, filtered and the filtrate concentrated in vacuo. Purification of the crude product by way of flash chromatography (SiO₂, Hex→1:1 (v/v) Hex:EtOAc) afforded the title compound as a colorless oil.

Step 6: Amine 88

3-Bromo-5-(3-ethoxypropyl)-4-methylbenzaldehyde (1 eq.) from the previous step and cyclopropylamine (2 eq.) were combined in CH₂Cl₂ (0.1 M). To this was then added MgSO₄ (1 eq.) and the resulting suspension was stirred at RT for 20 h. The insolubles were then removed via filtration through a pad of celite and the filtrate was concentrated in vacuo. The crude imine thus obtained was then re-taken up in MeOH (0.5 M). To this solution was added sodium borohydride (1.5 eq.) portionwise and the resulting mixture was stirred at 0° C. for 30 min, then at RT for 2 h. The reaction was quenched by stirring with 2 N aq. HCl for 25 min, basified with 1 N aq. NaOH and concentrated in vacuo. The residue was extracted with ether from water, dried over $Na_2SO_4$, filtered and the filtrate concentrated in vacuo to afford the title compound as a colorless oil.

Amine 89

N-{3-Bromo-5-[3-(difluoromethoxy)propyl]-4-methylbenzyl}cyclopropanamine

Step 1: Methyl 3-bromo-5-(3-hydroxypropyl)-4-methylbenzoate

To a chloroform (0.1 M) solution of methyl 3-bromo-5-(3-methoxypropyl)-4-methylbenzoate (1 eq., Amine 88, Step 2) was added iodotrimethylsilane (3 eq.). The resulting red solution was stirred at RT in darkness for 18 h. The reaction was quenched with methanol before the volatiles were removed in vacuo. The resulting residue was then taken up in ether, washed sequentially with 10% aq. HCl, 1 N aq. NaOH, water and brine, dried over $Na_2SO_4$, filtered and the filtrate concentrated in vacuo. Purification of the crude product by way of flash chromatography ($SiO_2$, Hex→3:7 (v/v) Hex:EtOAc) afforded the title compound as a pale yellow oil.

Step 2: Methyl 3-bromo-5-[3-(difluoromethoxy)propyl]-4-methylbenzoate

To an acetonitrile (0.6 M) suspension of methyl 3-bromo-5-(3-hydroxypropyl)-4-methylbenzoate (1 eq.) from the previous step and sodium sulfate (0.2 eq.) was added dropwise at 50° C. difluoro(fluorosulfonyl)acetic acid (1 eq.) over a period of 10 min. After the completion of addition, the reaction suspension was heated at 50° C. for another 16 h. The reaction mixture was then cooled to RT, poured into water and extracted with ether. The combined organic extracts were washed further with water and brine, dried over $Na_2SO_4$, filtered and the filtrate concentrated in vacuo. Purification of the crude product by way of flash chromatography ($SiO_2$, Hex→1:1 (v/v) Hex:EtOAc) afforded the title compound as a colorless oil.

Step 3: 3-Bromo-5-[3-(difluoromethoxy)propyl]-4-methylbenzaldehyde

To a dichloromethane (0.07 M) solution of methyl 3-bromo-5-[3-(difluoromethoxy)propyl]-4-methylbenzoate (1 eq.) from the previous step was added DIBAL-H (1.5 M solution in toluene, 2.2 eq.). The resulting solution was stirred at RT for 1.5 h and then carefully quenched with 10% aq. HCl. The aqueous layer was separated and back-extracted with ether. The combined organic extracts were washed further with brine, dried over $Na_2SO_4$, filtered and the filtrate concentrated in vacuo. The crude alcohol thus obtained was taken up again in dichloromethane (0.07 M) and then added Dess-Martin periodinane (1.0 eq.) and sodium bicarbonate (1.2 eq.). After stirring at RT for 40 min, the reaction mixture was diluted with ether and washed sequentially with sat. aq. $NaHSO_3$, 1 N aq. NaOH, water and brine. The organic extract was dried over $Na_2SO_4$, filtered and the filtrate concentrated in vacuo. Purification of the crude product by way of flash chromatography ($SiO_2$, Hex→1:1 (v/v) Hex:EtOAc) afforded the title compound as a colorless oil.

Step 6: Amine 89

3-Bromo-5-[3-(difluoromethoxy)propyl]-4-methylbenzaldehyde (1 eq.) from the previous step and cyclopropylamine (2 eq.) were combined in $CH_2Cl_2$ (0.1 M). To this was then added $MgSO_4$ (1 eq.) and the resulting suspension was stirred at RT for 20 h. The insolubles were then removed via filtration through a pad of celite and the filtrate was concentrated in vacuo. The crude imine thus obtained was then re-taken up in MeOH (0.5 M). To this solution was added sodium borohydride (1.5 eq.) portionwise and the resulting mixture was stirred at 0° C. for 30 min, then at RT for 2 h. The reaction was quenched by stirring with 2 N aq. HCl for 25 min, basified with 1 N aq. NaOH and concentrated in vacuo. The residue was extracted with ether from water, dried over $Na_2SO_4$, filtered and the filtrate concentrated in vacuo to afford the title compound as a colorless oil.

Amine 90

N-(3-Benzyl-5-methylbenzyl)cyclopropanamine

Step 1: 3-Benzyl-5-methylbenzaldehyde

To a DME solution (0.1 M) of (3-formyl-5-methylphenyl)boronic acid (1 eq.) was added cesium fluoride (3 eq.), tetrakis(triphenylphosphine)palladium (0.1 eq.) and benzyl bromide (1.2 eq.). The mixture was refluxed for 3 h, cooled down to RT and quenched with saturated aqueous sodium bicarbonate. The mixture was extracted with ethyl acetate. The combined organic extracts were then washed with brine, dried over $Na_2SO_4$, filtered and the filtrate concentrated in vacuo. Purification of the crude product by way of flash chromatography ($SiO_2$, Hex→7:3 (v/v) Hex:EtOAc) afforded the title compound.

Step 2: Amine 90

3-Benzyl-5-methylbenzaldehyde (1 eq.) from the previous step and cyclopropylamine (2 eq.) were combined in $CH_2Cl_2$ (0.2 M). To this was then added $MgSO_4$ (1.5 eq.) and the resulting suspension was stirred at RT for 18 h. The insolubles were then removed via filtration through a pad of celite and the filtrate was concentrated in vacuo. The crude imine thus obtained was then re-taken up in a 2:1 (v/v) mixture of THF:MeOH (0.2 M). To this solution was added sodium borohydride (10 eq.) portionwise and the resulting mixture was stirred at RT for 18 h. The reaction was quenched with saturated aqueous sodium bicarbonate and extracted with ethyl acetate. The combined organic extracts were then washed with brine, dried over $Na_2SO_4$, filtered and the filtrate concentrated in vacuo. Purification of the crude product by way of flash chromatography ($SiO_2$, $CH_2Cl_2$→9:1 (v/v) $CH_2Cl_2$:EtOH) afforded the title compound.

Amine 91

N-[3-Bromo-5-(3-fluorobenzyl)-4-methylbenzyl]cyclopropanamine

Step 1: Methyl 3-bromo-5-formyl-4-methylbenzoate

To a dichloromethane (0.16 M) solution of methyl 3-bromo-5-[(1E)-3-methoxy-1-propen-1-yl]-4-methylbenzoate (1 eq., Amine 88, Step 1) was bubbled at −78° C. with freshly generated ozone until a persistent blue color was observed. The reaction vessel was then thoroughly purged with nitrogen before triphenylphosphine (1.1 eq.) was added. The resulting mixture was slowly warmed to RT over 6 h. The volatiles were then removed in vacuo and the resulting residue was suspended in a 1:1 (v/v) mixture of hexanes and ether. The insolubles were removed via filtration through a pad of silica gel. Concentration of the filtrate thus obtained in vacuo afforded a white solid. Further purification of the crude product by way of flash chromatography (SiO$_2$, Hex→1:1 (v/v) Hex:EtOAc) afforded the title compound as a white solid.

Step 2: Methyl 3-bromo-5-(hydroxymethyl)-4-methylbenzoate

To a methanol (0.1 M) solution of methyl 3-bromo-5-formyl-4-methylbenzoate (1 eq.) from the previous step was added sodium borohydride (4 eq.) portionwise. The resulting mixture was stirred at RT for 3 h. The reaction was subsequently quenched with cold 10% aq. HCl and extracted with ether. The combined organic extracts were then washed with water and brine, dried over Na$_2$SO$_4$ and filtered. Concentration of the filtrate in vacuo afforded the title compound as a white solid.

Step 3: Methyl 3-bromo-5-(iodomethyl)-4-methylbenzoate

To a dichloromethane (0.05 M) solution of triphenylphosphine (1.1 eq) was added iodine (1.1 eq.). The resulting orange-yellow suspension was stirred at RT for 30 min before imidazole (1.2 eq.) and finally methyl 3-bromo-5-(hydroxymethyl)-4-methylbenzoate (1 eq.) from the previous step were added. The now pale yellow solution was stirred at RT for another 30 min. The volatiles were removed in vacuo and the residue was triturated with a 1:1 (v/v) mixture of hexanes and ether. The insolubles were then removed via filtration through a pad of silica gel. Concentration of the filtrate in vacuo afforded the title compound as a white solid.

Step 4: Methyl 3-bromo-5-(3-fluorobenzyl)-4-methylbenzoate

To a THF (0.1 M) suspension of CuCN (2 eq.) was added at −78° C. 3-fluorophenyl magnesium bromide (0.5 M solution in THF, 4 eq.) over a period of 5 min. The resulting mixture was stirred at −78° C. for 20 min and then at 0° C. for another 20 min. The now yellow suspension was re-cooled to −78° C. before methyl 3-bromo-5-(iodomethyl)-4-methylbenzoate (1 eq.) from the previous step was added. The resulting mixture was stirred at −78° C. for 20 min, 0° C. for another 20 min and finally at RT for 16 h. The crude reaction mixture was quenched with a 3:1 (v/v) mixture of sat. aq. NH$_4$Cl:conc. NH$_4$OH and then extracted with ether. The combined organic extracts were washed further with water and brine, dried over Na$_2$SO$_4$, filtered and the filtrate concentrated in vacuo. Further purification of the crude product by way of flash chromatography (SiO$_2$, Hex→1:1 (v/v) Hex:EtOAc) afforded the title compound as a colorless oil.

Step 5: 3-Bromo-5-(3-fluorobenzyl)-4-methylbenzaldehyde

To a dichloromethane (0.1 M) solution of methyl 3-bromo-5-(3-fluorobenzyl)-4-methylbenzoate (1 eq.) from the previous step was added DIBAL-H (1.5 M solution in toluene, 2.2 eq.). The resulting solution was stirred at RT for 1.5 h and then carefully quenched with 10% aq. HCl. The aqueous layer was separated and back-extracted with ether. The combined organic extracts were washed further with brine, dried over Na$_2$SO$_4$, filtered and the filtrate concentrated in vacuo. The crude alcohol thus obtained was taken up again in dichloromethane (0.1M) and then added Dess-Martin periodinane (1.0 eq.) and sodium bicarbonate (1.2 eq.). After stirring at RT for 40 min, the reaction mixture was diluted with ether and washed sequentially with sat. aq. NaHSO$_3$, 1 N aq. NaOH, water and brine. The organic extract was dried over Na$_2$SO$_4$, filtered and the filtrate concentrated in vacuo. Purification of the crude product by way of flash chromatography (SiO$_2$, Hex→1:1 (v/v) Hex:EtOAc) afforded the title compound as a colorless oil.

Step 6: Amine 91

3-Bromo-5-(3-fluorobenzyl)-4-methylbenzaldehyde (1 eq.) from the previous step and cyclopropylamine (2 eq.) were combined in CH$_2$Cl$_2$ (0.1 M). To this was then added MgSO$_4$ (1 eq.) and the resulting suspension was stirred at RT for 20 h. The insolubles were then removed via filtration through a pad of celite and the filtrate was concentrated in vacuo. The crude imine thus obtained was then re-taken up in MeOH (0.1 M). To this solution was added sodium borohydride (1.5 eq.) portionwise and the resulting mixture was stirred at 0° C. for 30 min, then at RT for 2 h. The reaction was quenched by stirring with 2 N aq. HCl for 25 min, basified with 1 N aq. NaOH and concentrated in vacuo. The residue was extracted with ether from water, dried over Na$_2$SO$_4$, filtered and the filtrate concentrated in vacuo to afford the title compound as a colorless oil.

Amine 92

{3-Bromo-5-[(cyclopropylamino)methyl]-2-methylphenyl}(3-fluorobenzyl)methanone

Step 1: 3-Bromo-5-[(1E)-3-methoxy-1-propen-1-yl]-4-methylbenzaldehyde

To a dichloromethane (0.1 M) solution of methyl 3-bromo-5-[(1E)-3-methoxy-1-propen-1-yl]-4-methylbenzoate (1 eq., Amine 88, Step 1) was added DIBAL-H (1.5 M solution in toluene, 2.2 eq.). The resulting solution was stirred at RT for 1.5 h and then carefully quenched with 10% aq. HCl. The aqueous layer was separated and back-extracted with ether. The combined organic extracts were washed further with brine, dried over Na$_2$SO$_4$, filtered and the filtrate concentrated in vacuo. The crude alcohol thus obtained was taken up again in dichloromethane (0.1M) and then added Dess-Martin periodinane (1.0 eq.) and sodium bicarbonate (1.2 eq.). After stirring at RT for 40 min, the reaction mixture was diluted with ether and washed sequentially with sat. aq. NaHSO$_3$, 1 N aq. NaOH, water and brine. The organic extract was dried over Na$_2$SO$_4$, filtered and the filtrate concentrated in vacuo. Purification of the crude product by way of flash chromatography (SiO$_2$, Hex→1:1 (v/v) Hex:EtOAc) afforded the title compound as a colorless oil that solidified upon standing.

Step 2: N-{3-Bromo-5-[(1E)-3-methoxy-1-propen-1-yl]-4-methylbenzyl}cyclopropanamine 3-Bromo-5-[(1E)-3-methoxy-1-propen-1-yl]-4-methylbenzaldehyde (1 eq.) from the previous step and cyclopropylamine (2 eq.) were combined in CH$_2$Cl$_2$ (0.1 M). To this was then added MgSO$_4$ (1 eq.) and the resulting suspension was stirred at RT for 20 h. The insolubles were then removed via filtration through a pad of celite and the filtrate was concentrated in vacuo. The crude imine thus obtained was then re-taken up in MeOH (0.1 M). To this solution was added sodium borohydride (1.5 eq.) portionwise and the resulting mixture was stirred at 0° C. for 30 min, then at RT for 2 h. The reaction was quenched by stirring with 2 N aq. HCl for 25 min, basified with 1 N aq. NaOH and concentrated in vacuo. The residue was extracted with ether from water, dried over Na$_2$SO$_4$, filtered and the filtrate concentrated in vacuo to afford the title compound as a colorless oil.

Step 3: tert-Butyl{3-bromo-5-[(1E)-3-methoxy-1-propen-1-yl]-4-methylbenzyl}cyclopropylcarbamate N-{3-Bromo-5-[(1E)-3-methoxy-1-propen-1-yl]-4-methylbenzyl}-cyclopropanamine (1 eq.) from the previous step and di-tert-butyl dicarbonate (1.1 eq.) were taken up in dichloromethane (0.11 M). To this was then added Hunig's base (1.2 eq.) and the resulting mixture was stirred at RT for 3 h. The volatiles were removed in vacuo and the resulting residue was taken up in a 1:1 (v/v) mixture of hexanes and ether. This suspension was subsequently washed with 10% aq. HCl, water and brine, dried over Na$_2$SO$_4$, filtered and the filtrate concentrated in vacuo. Purification of the crude product thus obtained by way of column chromatography (SiO$_2$, Hex→1:1 (v/v) Hex:EtOAc) afforded the title compound as a colorless oil.

Step 4: tert-Butyl (3-bromo-5-formyl-4-methylbenzyl)cyclopropylcarbamate

To a dichloromethane (0.08 M) solution of tert-butyl{3-bromo-5-[(1E)-3-methoxy-1-propen-1-yl]-4-methylbenzyl}cyclopropylcarbamate (1 eq.) from the previous step was bubbled at −78° C. with freshly generated ozone until a persistent blue color was observed. The reaction vessel was then thoroughly purged with nitrogen before triphenylphosphine (1 eq.) was added. The resulting mixture was slowly warmed to RT over 16 h. The volatiles were then removed in vacuo and the resulting residue was suspended in a 1:1 (v/v) mixture of hexanes and ether. The insolubles were removed via filtration through a pad of silica gel. Concentration of the filtrate thus obtained in vacuo afforded a colorless oil. Further purification of the crude product by way of flash chromatography (SiO$_2$, Hex→1:1 (v/v) Hex:EtOAc) afforded the title compound as a colorless oil.

Step 5: tert-Butyl{3-bromo-5-[(3-fluorophenyl)(hydroxyl)methyl]-4-methylbenzyl}-cyclopropylcarbamate To a THF (0.13 M) solution of tert-butyl (3-bromo-5-formyl-4-methylbenzyl)cyclopropylcarbamate (1 eq.) from the previous step was added at 0° C. 3-fluorophenyl magnesium bromide (0.5 M in THF, 1.1 eq.). The resulting solution was warmed slowly to RT over 2 h before it was quenched with sat. aq. NH$_4$Cl. The aqueous layer was separated and back-extracted with ether. The combined organic extracts were washed further with water and brine, dried over Na$_2$SO$_4$, filtered and the filtrate concentrated in vacuo. Further purification of the crude product by way of flash chromatography (SiO$_2$, Hex→1:1 (v/v) Hex:EtOAc) afforded the title compound as a colorless oil.

Step 6: tert-Butyl[3-bromo-5-(3-fluorobenzoyl)-4-methylbenzyl]cyclopropylcarbamate To a dichloromethane (0.1 M) solution of tert-butyl{3-bromo-5-[(3-fluorophenyl)(hydroxyl)methyl]-4-methylbenzyl}cyclopropylcarbamate (1 eq.) from the previous step was added Dess-Martin periodinane (1.0 eq.) and sodium bicarbonate (1.2 eq.). After stirring at RT for 1 h, the reaction mixture was diluted with ether and washed sequentially with sat. aq. NaHSO$_3$, 1 N aq. NaOH, water and brine. The organic extract was dried over Na$_2$SO$_4$, filtered and the filtrate concentrated in vacuo to afford the title compound as a colorless oil.

Step 7: Amine 92 tert-Butyl[3-bromo-5-(3-fluorobenzoyl)-4-methylbenzyl]cyclopropylcarbamate (1 eq.) from the previous step in CH$_2$Cl$_2$ (0.1 M) was added HCl (4.0 M in dioxane, 20 eq.). The resulting solution was stirred at RT for 2 h. The reaction was then quenched with 1 N aq. NaOH and extracted with ether. The combined organic extracts were then washed further with water and brine, dried over Na$_2$SO$_4$ and filtered. Concentration of the filtrate in vacuo afforded the title compound as a colorless oil.

The arene building blocks in Table 2 were synthesized as follows.

TABLE 2

| Compound | Structure |
|---|---|
| Arene 1 | 4-bromo-2-methoxypyridine structure |
| Arene 2 | 4-bromo-2,3-dimethyl-6-(benzyloxy)pyridine structure |
| Arene 3 | 3-(methoxymethoxy)-4-iodopyridine structure |
| Arene 4 | 4-bromo-2-(benzyloxy)pyridine structure |

Arene 1

4-Bromo-2-(methyloxy)pyridine

Arene 1 was prepared according to the procedure described by Fraley, M. E. et al. *Biorganic & Medicinal Chemistry Letters* 2002, 12, 3537-3542.

Arene 2

4-Bromo-2,3-dimethyl-6-[(phenylmethyl)oxy]pyridine

4-Bromo-5,6-dimethyl-2(1H)-pyridinone (1 eq.), prepared according to the procedure described by McElroy, W. T.; DeShong, P. *Organic Letters* 2003, 5, 4779-4782, was suspended in benzene (0.13 M). To this was then added silver carbonate (0.6 eq.) and benzyl bromide (1.2 eq.) before the suspension was heated at 45° C. for 3 days in the dark. The reaction suspension was cooled to RT, diluted with benzene and filtered through a bed of celite. The filtrate was washed with sat. aq. NaHCO$_3$, dried over Na$_2$SO$_4$, filtered and the filtrate concentrated in vacuo. Purification by way of column chromatography (SiO$_2$, Hex→10:1 (v/v) Hex:EtOAc) afforded the title compound as a colorless oil.

Arene 3

4-Iodo-3-{[(methyloxy)methyl]oxy}pyridine

Step 1: 2-{[(Methyloxy)methyl]oxy}pyridine

3-Pyridinol (1 eq.) was taken up in a 2:1 (v/v) mixture of DMF:THF (0.9 M). To this was then added, at −15° C., potassium tert-butoxide (1.1 eq.) and the resulting suspension was stirred at −15° C. for 25 min before chloromethyl methyl ether (1.1 eq.) was added dropwise over 15 min. The mixture was then warmed to RT over 1 h and allowed to stir at RT for another 2 h. The reaction mixture was then concentrated in vacuo and the resulting residue partitioned between EtOAc and water. The aqueous layer was separated and back-extracted with EtOAc. The combined organic extracts were then washed with water and brine, dried over Na$_2$SO$_4$, filtered through a short plug of SiO$_2$ and the filtrate concentrated in vacuo to afford the title compound as a colorless oil.

Step 2: Arene 3

To a solution of 2-{[(methyloxy)methyl]oxy}pyridine from the previous step (1 eq.) in ether (0.16 M) was added, at −78° C., t-butyl lithium (1.7 M in pentane, 1.1 eq.) dropwise over a period of 30 min. This was stirred at −78° C. for 15 min before iodine (0.5 M in ether, 1.2 eq.) was added dropwise over a period of 30 min. The reaction mixture was then allowed to stir at −78° C. for 1 h before the reaction was quenched with water. The aqueous layer was separated and back-extracted with ether. The combined organic extracts were washed sequentially with 10% aq. NaHSO$_3$, water and brine, dried over Na$_2$SO$_4$ and filtered. Concentration of the filtrate in vacuo afforded a beige powder. Purification of the crude product thus obtained by way of column chromatography (SiO$_2$, 9:1 (v/v) Hex:EtOAc→EtOAc) afforded the title compound as a white solid.

Arene 4

2-(Benzyloxy)-4-bromopyridine

To a solution of 4-bromo-2-fluoropyridine (1 eq.), benzyl alcohol (1.2 eq.) and dibenzo-18-crown-6 (0.05 eq.) in toluene (0.4 M) was added potassium hydroxide (2 eq.). A Dean-Stark apparatus was then attached and the reaction suspension was heated at reflux for 3 h. After cooling to RT, the reaction mixture was diluted with hexanes and then filtered through a pad of celite. Concentration of the filtrate in vacuo afforded a yellow oil. Purification of the crude product thus obtained by way of column chromatography (SiO$_2$, 97:3 (v/v) Hex:Et$_2$O) afforded the title compound as a colorless oil.

Carboxylic Acid 1

The carboxylic acid building block (carboxylic acid 1; (3S,4S)-1'-Methyl-2'-oxo-3,4,5,6,1',2'-hexahydro-2H-[4,4'] bipyridinyl-1,3-dicarboxylic acid 1-tert-butyl ester) was synthesized as follows.

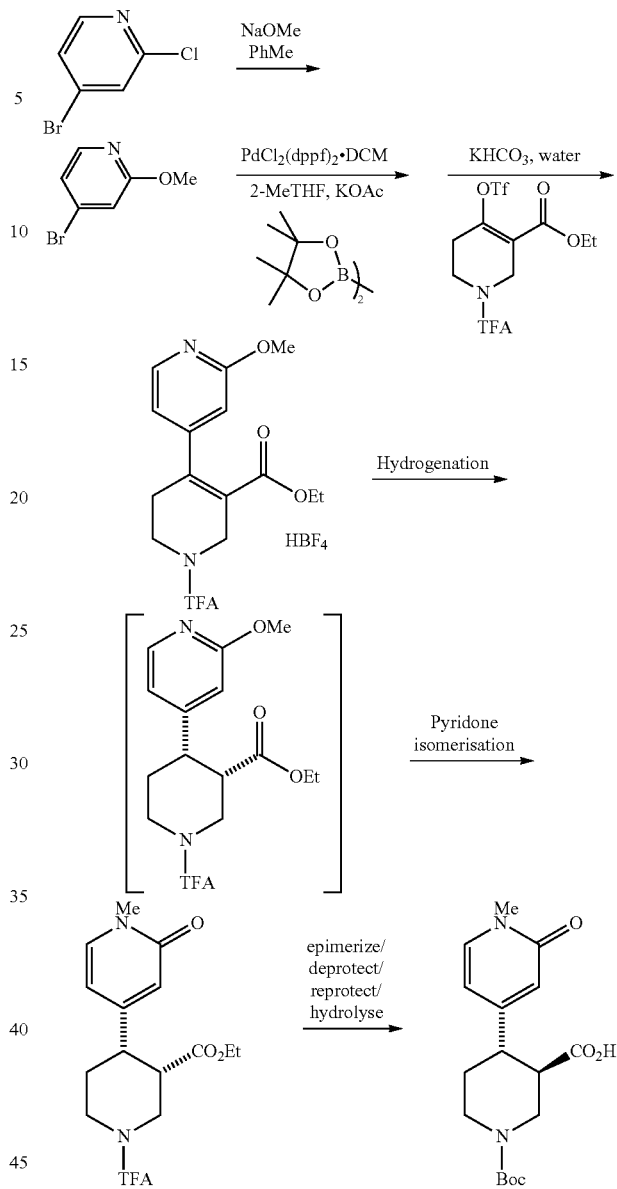

Step 1: 4-Bromo-2-methoxypyridine

4-Bromo-2-chloropyridine, sodium methoxide (1.6 equiv.) and toluene (6.1 volumes) were heated to 95° C. for 40 h. Toluene (6.1 volumes) and water (3 volumes) were added and the lower aqueous phase cut away. The organic was washed with water (1.5 volumes) and then the volatiles evaporated to give the title compound as an oil. HRMS (ES, M+H) Calcd 187.9711. Found 187.9711.

Step 2: 2'-Methoxy-5,6-dihydro-2-H[4,4']bipyridinyl-1,3-dicarboxylic acid 3-ethyl ester 1-trifluoromethyl ester Potassium acetate (2.0 equiv.), bis(pinacolato)diboron (1.05 equiv.) and Pd(Cl)$_2$dppf.dichloromethane complex commercially available (0.02 equiv.) were mixed in 2-methyl THF (6.5 volumes) and N,N-dimethylacetamide (1 volume). 4-Bromo-2-methoxypyridine in 2-methyl THF (3.4 volumes)

was added and the mixture heated to 85° C. for 4 h and then cooled to 25° C. Potassium hydrogen carbonate (3.0 equiv.) dissolved in water (4.9 volumes) was added and then 3-(ethoxycarbonyl)-1-(2,2,2-trifluoroacetyl)-1,2,5,6-tetrahydropyridin-4-yl trifluoromethanesulfonate (1.02 equiv.). 3-(ethoxycarbonyl)-1-(2,2,2-trifluoroacetyl)-1,2,5,6-tetrahydropyridin-4-yltrifluoromethanesulfonate can be obtained using known methods for obtaining the analagous compound where the trifluoracetacetamide group on the nitrogen is a Boc group by using commercially available betaketoester (1 below).

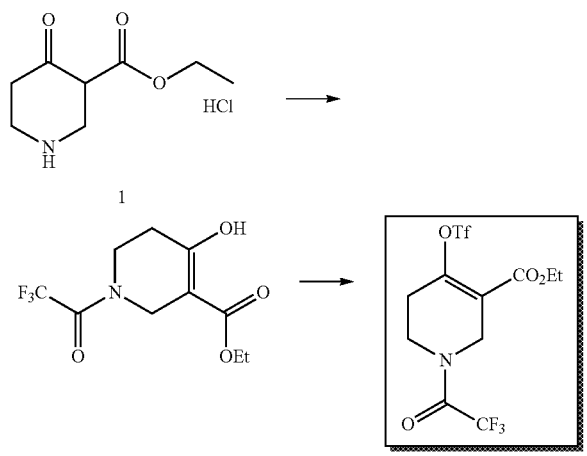

Additional Pd(Cl)$_2$dppf.dichloromethane complex (0.005 equiv.) was added and the batch heated to 85° C. for 2 h before cooling to 20° C. and allowing to settle. The lower aqueous phase was cut away and the organic was washed with water and then passed through a plug of silica gel. The organic solution was concentrated to ~11.6 volumes and then HBF$_4$.OEt$_2$ commercially available (1.1 equiv.) was added. The batch was cooled to 20° C., aged 18 h and then a further 4 volumes solvent were removed by distillation and the slurry was cooled to −1° C. The resultant slurry was filtered and the solids washed with isopropyl acetate to afford the title compound as an off-white solid. $^1$H NMR (400 MHz, dmso-d$_6$) δ 12.2 (br s, 1H), 8.17 (d, J=5.2 Hz, 1 H), 6.90 (d, J=4.8 Hz, 1 H), 6.81-6.79 (m, 1 H), 4.43-4.35 (m, 2 H), 3.97-3.83 (m, 5 H), 3.82-3.75 (m, 2 H), 2.62-2.55 (m, 2 H), 0.92-0.83 (m, 3H). HRMS (ES, M+H) Calcd 359.1219. Found 359.1237.

Step 3: (3R,4S)-2'-Methoxy-3,4,5,6-tetrahydro-2H-[4,4']bipyridinyl-1,3-dicarboxylic acid 3-ethyl ester 1-trifluoromethyl ester 2'-Methoxy-5,6-dihydro-2H-[4,4]bipyridinyl-1,3-dicarboxylic acid 3-ethyl ester 1-trifluoromethyl ester was slurried in 2-methyl THF (6.4 volumes) and dichloromethane (1.5 volumes) and HBF$_4$.OEt$_2$ (0.1 equiv.) added. A catalyst solution prepared by dissolving bis(2-methylallyl)(COD)Ru(II) (0.01 equiv.) commercially available and (R)-1-[(S)-Di-2-furylphosphino]ferrocenyl]ethyldi-tert-butylphosphine (0.0125 equiv.) commercially available in dichloromethane (0.12 volumes) and was added to the previous slurry. The slurry was then heated to 50° C. and pressurised to 8 bar with hydrogen. After aging for 2 h, the batch was cooled to 20° C. An aqueous solution of NaHCO$_3$ (1.5 equiv) was added and the layers allowed to settle. The lower aqueous phase was run off and discarded. The organic layer was washed a 10 wt % NaCl solution and the lower aqueous phase cut away and discarded. The solution was distilled in vacuo to ~2 volumes with respect to product then DMF (2 volumes) were added and the resultant solution used for the next step. HRMS (ES, M+H) Calcd 361.1375. Found 361.1367.

Step 4: (3R,4S)-1'-Methyl-2'-oxo-3,4,5,6,1',2'-hexahydro-2H-[4,4]bipyridinyl-1,3-dicarboxylic acid 3-ethyl ester 1-trifluoromethyl ester To a stirred solution of (3R,4S)-1'-methyl-2'-oxo-3,4,5,6,1',2'-hexahydro-2H-[4,4]bipyridinyl-1,3-dicarboxylic acid 3-ethyl ester 1-trifluoromethyl ester, as a solution in DMF/2-MeTHF, was added trimethylsulfoxonium iodide (1.5 equiv.), magnesium hydroxide (1.5 equiv.) and water (1.0 equiv.). The slurry was heated to 100° C. for 5 h then cooled to ambient. Dichloromethane (3 volumes) and isopropyl acetate (5 volumes) were added, followed by 4 M HCl (2.5 equiv.). The phases were then separated and lower aqueous was extracted with dichloromethane (1.89 volumes) and the organics combined. The organics were washed with 25 wt % LiCl solution. The organic layer was distilled in vacuo to ~5 volumes with respect to product and the product crystallised. Distillation was continued to ~2.5 volumes with respect to product then methyl-tert butyl ether (1 volume) was added and the slurry cooled to −3° C., aged 2 h then filtered. The solids were washed with methyl-tert butyl ether to give the product as a white solid. $^1$H NMR (400 MHz, dmso-d$_6$): δ 7.61-7.56 (m, 1 H), 6.18-6.13 (m, 2 H), 4.59-4.55 (m, 0.6 H), 4.47-4.40 (m, 0.4 H), 4.08-3.95 (m, 1 H), 3.92-3.82 (m, 2 H), 3.69-3.53 (m, 0.4 H), 3.45-3.25 (m, 4.6 H), 3.12-2.95 (m, 1 H), 2.34-2.18 (m, 1 H), 1.85-1.75 (m, 1 H), 1.03-0.96 (m, 3 H). HRMS (ES, M+H) Calcd 361.1375. Found 361.1392.

Step 5: (3S,4S)-1'-Methyl-2'-oxo-3,4,5,6,1',2'-hexahydro-2H-[4,4']bipyridinyl-1,3-dicarboxylic acid 1-tert-butyl ester To a stirred solution of (3R,4S)-1'-methyl-2'-oxo-3,4,5,6,1',2'-hexahydro-2H-[4,4]bipyridinyl-1,3-dicarboxylic acid 3-ethyl ester 1-trifluoromethyl ester in ethanol (4.1 volumes) was added sodium ethoxide (1.20 equiv.) The mixture was aged for 30 min and then water (1.20 equiv.) was added. After 1 h aging, Boc anhydride (1.20 equiv.) was added and the solution was aged for 1 h. Sodium hydroxide (2M, 5.00 equiv.) was added and the solution heated to 70° C. for 1 h. The mixture was cooled to 30° C., and the solution was concentrated to ~8 volumes, such that most of the ethanol was removed. The solution was washed with MTBE (2.5 volumes). The aqueous layer was separated and then acidified with c.HCl to afford a slurry. 2-Methyltetrahydrofuran (6 volumes) was then added and the mixture rapidly stirred after which the layers were allowed to separate. The aqueous layer was removed, and the organic collected. The aqueous layer was then re-charged to the extractor and back-extracted with MeTHF (2 volumes). The organic fractions were then both recharged to the extractor, washed with 50% sodium chloride solution. The organic layer was collected and concentrated in vacuo to afford a slushy pale-yellow solid. The solid was slurried in MTBE (6 volumes) and stirred at room temperature for 18 h. The slurry was filtered into and washed with MTBE to afford the title compound as an off-white solid. $^1$H NMR (500 MHz, CHCl$_3$): δ 7.30-7.26 (m, 1 H), 6.74 (s, 1 H), 6.25 (dd, J=6.96, 2.00 Hz, 1 H), 4.44 (s, 1 H), 4.30 (s, 1 H), 3.52 (s, 3 H), 3.09-2.73 (m, 3 H), 2.59 (s, 1 H), 1.77 (d, J=13.10 Hz, 1 H), 1.61 (d, J=12.58 Hz, 1 H), 1.48 (s, 9 H). HRMS (ES, M+H) Calcd 337.1763. Found 337.1768.

EXAMPLE 1 trans-N-Cyclopropyl-N-[(2,3-dichlorophenyl)methyl]-4-(1-methyl-2-oxo-1,2-dihydro-4-pyridinyl)-3-piperidinecarboxamide

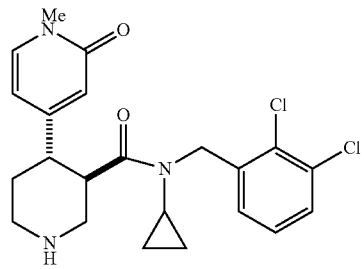

Step 1: 1-(1,1-Dimethylethyl) 3-ethyl 4-(4,4,5,5-tetramethyl-1,3,2-dioxaborolan-2-yl)-5,6-dihydro-1,3(2H)-pyridinedicarboxylate To a dioxane solution (0.17 M) of 1-(1,1-dimethylethyl) 3-ethyl 4-{[(trifluoromethyl)sulfonyl]oxy}-5,6-dihydro-1,3(2H)-pyridinedicarboxylate (1 eq.) and 4,4,4',4',5,5,5',5'-octamethyl-2,2'-bi-1,3,2-dioxaborolane (1.1 eq.) was added potassium acetate (3 eq.). The suspension was evacuated and back-filled with $N_2$. Finally, [1,1'-bis(diphenylphosphino)ferrocene]dichloropalladium(II) (0.03 eq.) was added in one rapid portion and the reaction suspension was heated at 80° C. for 14 h. The reaction was then quenched with the addition of diethyl ether and sat. aq. $NH_4Cl$. The aqueous layer was separated and back-extracted with ether. The combined organic extracts were washed further with water and brine, dried over $Na_2SO_4$, filtered and the filtrate concentrated in vacuo. Purification of the crude product thus obtained by way of column chromatography ($SiO_2$, 95:5→80:20 (v/v) toluene:EtOAc) afforded the title compound as a golden yellow oil.

Step 2: 1-(1,1-Dimethylethyl) 3-ethyl 2'-(methyloxy)-5,6-dihydro-4,4'-bipyridine-1,3(2H)-dicarboxylate To a n-PrOH solution (0.15 M) of 1-(1,1-dimethylethyl) 3-ethyl 4-(4,4,5,5-tetramethyl-1,3,2-dioxaborolan-2-yl)-5,6-dihydro-1,3(2H)-pyridinedicarboxylate (1 eq.) from the previous step and Arene 1 (1 eq.) was added sodium carbonate (2 M aq. solution, 3 eq.). The suspension was evacuated and back-filled with $N_2$. Finally, [1,1'-bis(diphenylphosphino)ferrocene]dichloropalladium(II) (0.03 eq.) was added in one rapid portion and the reaction suspension was heated at 80° C. for 14 h. The reaction was then quenched with the addition of diethyl ether and sat. aq. $NH_4Cl$. The aqueous layer was separated and back-extracted with ether. The combined organic extracts were washed further with water and brine, dried over $Na_2SO_4$, filtered and the filtrate concentrated in vacuo. Purification of the crude product thus obtained by way of column chromatography ($SiO_2$, 95:5 (v/v) Hex:EtOAc→EtOAc) afforded the title compound as a white solid.

Step 3: cis-1-(1,1-Dimethylethyl) 3-ethyl 4-[2-(methyloxy)-4-pyridinyl]-1,3-piperidinedicarboxylate To a MeOH solution (0.1 M) of 1-(1,1-dimethylethyl) 3-ethyl 2'-(methyloxy)-5,6-dihydro-4,4'-bipyridine-1,3(2H)-dicarboxylate (1 eq.) from the previous step was added magnesium turnings (3.3 eq.). The suspension was evacuated and back-filled with $N_2$. Finally, the reaction mixture was sonicated at RT for 3.5 h during which the magnesium turnings disappeared. The reaction was then quenched with the addition of diethyl ether and sat. aq. $NH_4Cl$. The aqueous layer was separated and back-extracted with ether. The combined organic extracts were washed further with water and brine, dried over $Na_2SO_4$, filtered and the filtrate concentrated in vacuo. Purification of the crude product thus obtained by way of column chromatography ($SiO_2$, 90:10 (v/v) Hex:EtOAc→EtOAc) afforded the title compound as a colorless oil.

Step 4: trans-1-(1,1-Dimethylethyl) 3-ethyl 4-[2-(methyloxy)-4-pyridinyl]-1,3-piperidinedicarboxylate To an ethanol solution (0.1 M) of cis-1-(1,1-dimethylethyl) 3-ethyl 4-[2-(methyloxy)-4-pyridinyl]-1,3-piperidinedicarboxylate (1 eq.) from the previous step was added freshly prepared sodium ethoxide (1.1 eq.). The resulting yellow-orange solution was heated at 55° C. for 12 h. The volatiles were then removed in vacuo and the residue was partitioned between diethyl ether and sat. aq. $NH_4Cl$. The aqueous layer was separated and back-extracted with ether. The combined organic extracts were washed further with water and brine, dried over $Na_2SO_4$, filtered and the filtrate concentrated in vacuo. Purification of the crude product thus obtained by way of column chromatography ($SiO_2$, 90:10 (v/v) Hex:EtOAc→EtOAc) afforded the title compound as a colorless oil.

Step 5: trans-1-(1,1-Dimethylethyl) 3-ethyl 4-(1-methyl-2-oxo-1,2-dihydro-4-pyridinyl)-1,3-piperidinedicarboxylate To an acetonitrile suspension (0.1 M) of trans-1-(1,1-dimethylethyl) 3-ethyl 4-[2-(methyloxy)-4-pyridinyl]-1,3-piperidinedicarboxylate (1 eq.) from the previous step and sodium iodide (1 eq.) was added neat iodomethane (3 eq.). The reaction vessel was then sealed and heated at 45° C. for 3 days. The volatiles were then removed in vacuo and the residue was partitioned between EtOAc and sat. aq. $NH_4Cl$. The aqueous layer was separated and back-extracted with EtOAc. The combined organic extracts were washed further with 1 N aq. NaOH, water and brine, dried over $Na_2SO_4$, filtered and the filtrate concentrated in vacuo. Purification of the crude product thus obtained by way of column chromatography ($SiO_2$, 80:20 (v/v) Hex:EtOAc→EtOAc→95:5 (v/v) $CH_2Cl_2$: 2.0 M $NH_3$ in MeOH) afforded the title compound as a colorless oil.

Step 6: trans-1-{[(1,1-Dimethylethyl)oxy]carbonyl}-4-(1-methyl-2-oxo-1,2-dihydro-4-pyridinyl)-3-piperidinecarboxylic acid To a 3:2 (v/v) THF:MeOH solution (0.07 M) of trans-1-(1,1-dimethylethyl) 3-ethyl 4-(1-methyl-2-oxo-1,2-dihydro-4-pyridinyl)-1,3-piperidinedicarboxylate (1 eq.) from the previous step was added lithium hydroxide (1 M aq. solution, 3.1 eq.). The resulting cloudy solution was stirred vigorously at RT for 18 h. The volatiles were then removed in vacuo and the residue was partitioned between EtOAc and 10% aq. HCl. The aqueous layer was separated and back-extracted with EtOAc. The combined organic extracts were washed further with water and brine, dried over $Na_2SO_4$ and filtered. Concentration of the filtrate in vacuo afforded the title compound as a white solid.

Step 7: trans-1,1-Dimethylethyl 3-({cyclopropyl[(2, 3-dichlorophenyl)methyl]amino}carbonyl)-4-(1-methyl-2-oxo-1,2-dihydro-4-pyridinyl)-1-piperidinecarboxylate To a DMF (0.1 M) solution of trans-1-{[(1,1-dimethylethyl)oxy]carbonyl}-4-(1-methyl-2-oxo-1,2-dihydro-4-pyridinyl)-3-piperidinecarboxylic acid (1 eq.) from the previous step, Hunig's base (3 eq.) and Amine 1 (1 eq.) was added portionwise O-(7-azabenzotriazol-1-yl)-N,N,N',N'-tetramethyluronium hexafluorophosphate (1.2 eq.). The resulting reaction solution was stirred at RT for 48 h. The now reddish solution was diluted with EtOAc and washed sequentially with 10% aq. HCl, 1 N aq. NaOH and brine. The organic extract was then dried over $Na_2SO_4$, filtered and the filtrate concentrated in vacuo to afford a yellow oil. Purification of the crude product thus obtained by way of flash chromatography ($SiO_2$, 7:3 (v/v) Hex:EtOAc →EtOAc→95:5 (v/v) $CH_2Cl_2$:2.0 M $NH_3$ in MeOH) afforded the title compound as a white froth.

Step 8: trans-N-Cyclopropyl-N-[(2,3-dichlorophenyl)methyl]-4-(1-methyl-2-oxo-1,2-dihydro-4-pyridinyl)-3-piperidinecarboxamide To a $CH_2Cl_2$ solution (0.05 M) of trans-1,1-dimethylethyl 3-({cyclopropyl[(2,3-dichlorophenyl)methyl]amino}carbonyl)-4-(1-methyl-2-oxo-1,2-dihydro-4-pyridinyl)-1-piperidinecarboxylate (1 eq.) from the previous step was added HCl (4.0 M dioxane solution, 30 eq.). The resulting solution was stirred at RT for 3 h. Following the removal of the volatiles in vacuo, the resulting residue was directly loaded onto a $SiO_2$ column packed with 94:6 (v/v) $CH_2Cl_2$: 2.0 M $NH_3$ in MeOH. Elution with the same solvent system furnished the title compound as a white froth. MS (ESI+, M+H): 434.

EXAMPLE 2 trans-N-[{5-Chloro-2-[3-(methyloxy)propyl]-4-pyridinyl}methyl]-N-cyclopropyl-4-(1-methyl-2-oxo-1,2-dihydro-4-pyridinyl)-3-piperidinecarboxamide

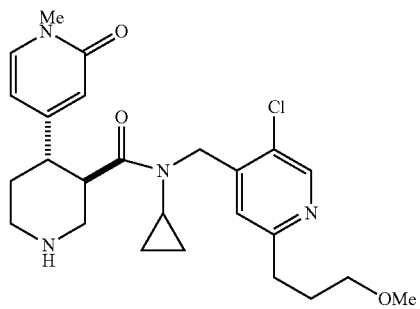

Prepared according to the procedure described in Example 1 but using instead Amine 2 as starting material. The title compound was obtained as a white froth. MS (ESI+, M+H): 473.

EXAMPLE 3 trans-N-({2-Chloro-5-[3-(methyloxy)propyl] phenyl}methyl)-N-cyclopropyl-4-(1-methyl-2-oxo-1, 2-dihydro-4-pyridinyl)-3-piperidinecarboxamide

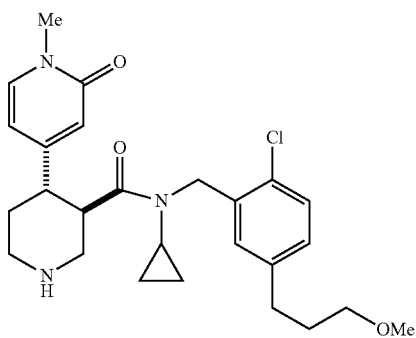

Prepared according to the procedure described in Example 1 but using instead Amine 3 as starting material. The title compound was obtained as a white froth. MS (ESI+, M+H): 472.

EXAMPLE 4 trans-N-({2-Chloro-5-[2-(methyloxy)ethyl] phenyl}methyl)-N-cyclopropyl-4-(1-methyl-2-oxo-1, 2-dihydro-4-pyridinyl)-3-piperidinecarboxamide

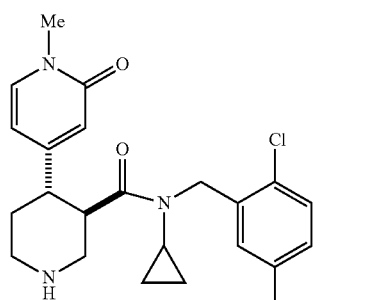

Prepared according to the procedure described in Example 1 but using instead Amine 4 as starting material. The title compound was obtained as a white froth. MS (ESI+, M+H): 458.

EXAMPLE 5 trans-N-Cyclopropyl-N-({2,3-dichloro-5-[3-(methyloxy)propyl]phenyl}methyl)-4-(1-methyl-2-oxo-1,2-dihydro-4-pyridinyl)-3-piperidinecarboxamide

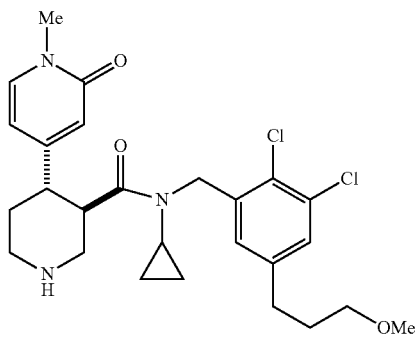

Prepared according to the procedure described in Example 1 but using instead Amine 5 as starting material. The title compound was obtained as a white froth. MS (ESI+, M+H): 508. 1H NMR (CDCl$_3$) δ (ppm): 0.65-0.68 (m, 2H), 0.89-0.94 (m, 2H), 1.60-1.90 (m, 6H), 2.49-2.63 (m, 3H), 2.76-2.90 (m, 2H), 2.95-3.04 (m, 1H), 3.19-3.24 (m, 1H), 3.27-3.38 (m, 6H), 3.48-3.55 (m, 4H), 4.49 (d, J=15.6 Hz, 1H), 4.56 (d, J=15.6 Hz, 1H), 6.05-6.09 (m, 1H), 6.46 (s, 1H), 6.70 (s, 1H), 7.13 (d, J=6.9 Hz, 1H), 7.19 (s, 1H). Human Renin IC$_{50}$ (buffer): 0.3 nM. Human Renin IC$_{50}$ (plasma): 1.3 nM.

EXAMPLE 6 trans-N-Cyclopropyl-N-({2,3-dichloro-5-[2-(methyloxy)ethyl]phenyl}methyl)-4-(1-methyl-2-oxo-1,2-dihydro-4-pyridinyl)-3-piperidinecarboxamide

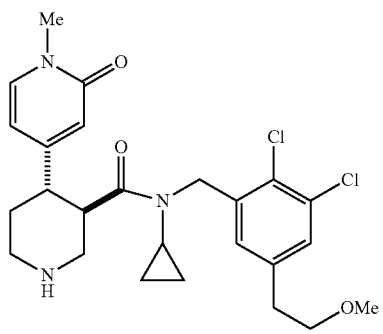

Prepared according to the procedure described in Example 1 but using instead Amine 6 as starting material. The title compound was obtained as a colorless oil. MS (ESI+, M+H): 492.

EXAMPLE 7 trans-N-Cyclopropyl-N-({2-methyl-5-[3-(methyloxy)propyl]phenyl}methyl)-4-(1-methyl-2-oxo-1,2-dihydro-4-pyridinyl)-3-piperidinecarboxamide

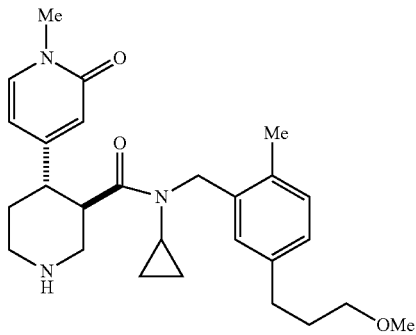

Prepared according to the procedure described in Example 1 but using instead Amine 7 as starting materials. The title compound was obtained as a white froth. MS (ESI+, M+H): 452.

EXAMPLE 8 trans-N-Cyclopropyl-N-({2-methyl-5-[2-(methyloxy)ethyl]phenyl}methyl)-4-(1-methyl-2-oxo-1,2-dihydro-4-pyridinyl)-3-piperidinecarboxamide

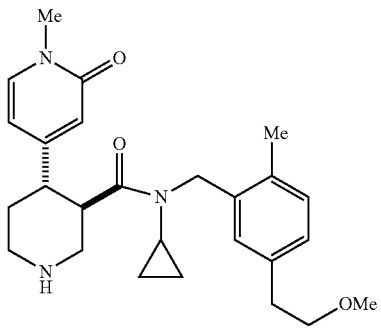

Prepared according to the procedure described in Example 1 but using instead Amine 8 as starting material. The title compound was obtained as a white froth. MS (ESI+, M+H): 438.

EXAMPLE 9 trans-N-Cyclopropyl-N-({2,3-difluoro-5-[3-(methyloxy)propyl]phenyl}methyl)-4-(1-methyl-2-oxo-1,2-dihydro-4-pyridinyl)-3-piperidinecarboxamide

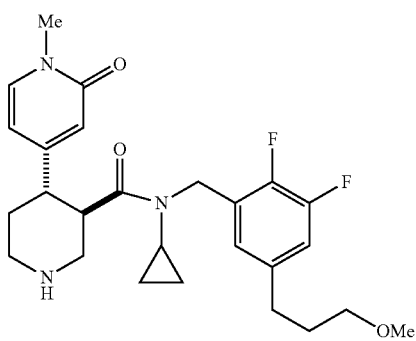

Prepared according to the procedure described in Example 1 but using instead Amine 9 as starting material. The title compound was obtained as a white froth. MS (ESI+, M+H): 474.

EXAMPLE 10 trans-N-Cyclopropyl-4-(1-methyl-2-oxo-1,2-dihydro-4-pyridinyl)-N-({3-(methyloxy)-5-[3-(methyloxy)propyl]phenyl}methyl)-3-piperidinecarboxamide

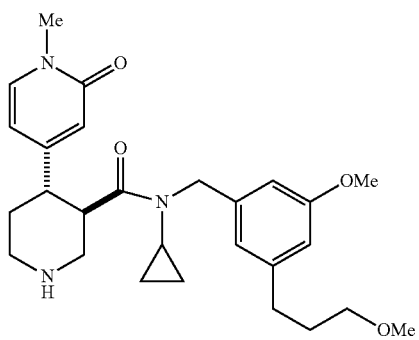

Prepared according to the procedure described in Example 1 but using instead Amine 10 as starting material. The title compound was obtained as a white froth. MS (ESI+, M+H): 468.

EXAMPLE 11 trans-N-Cyclopropyl-4-(1-methyl-2-oxo-1,2-dihydro-4-pyridinyl)-N-({3-{[2-(methyloxy)ethyl]oxy}-5-[3-(methyloxy)propyl]phenyl}methyl)-3-piperidinecarboxamide

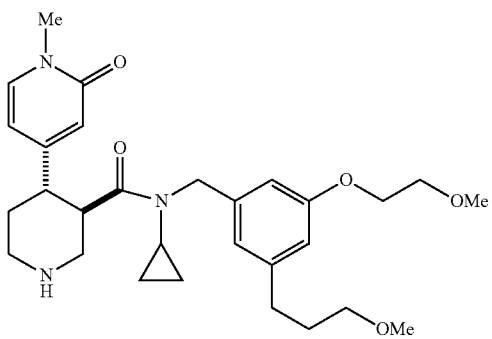

Prepared according to the procedure described in Example 1 but using instead Amine 11 as starting material. The title compound was obtained as a white froth. MS (ESI+, M+H): 512.

EXAMPLE 12 trans-N-Cyclopropyl-4-(1-ethyl-2-oxo-1,2-dihydro-4-pyridinyl)-N-({3-{[2-(methyloxy)ethyl]oxy}-5-[3-(methyloxy)propyl]phenyl}methyl)-3-piperidinecarboxamide

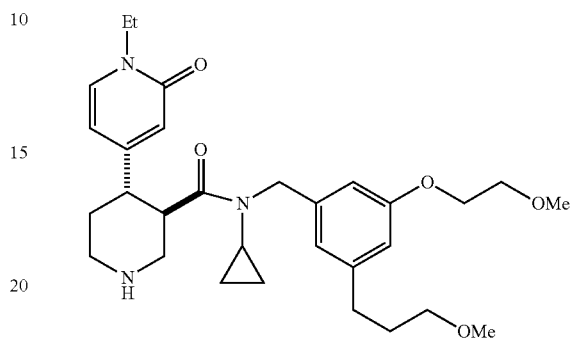

Step 1: 1-(1,1-Dimethylethyl) 3-ethyl 5,6-dihydro-4,4'-bipyridine-1,3(2H)-dicarboxylate To a 1:1 (v/v) ethanol:toluene solution (0.18 M) of 1-(1,1-dimethylethyl) 3-ethyl 4-{[(trifluoromethyl)sulfonyl]oxy}-5,6-dihydro-1,3(2H)-pyridinedicarboxylate (1 eq.) and 4-pyridinylboronic acid (1.1 eq.) was added sodium carbonate (2 M aq. solution, 2.6 eq.). The suspension was evacuated and back-filled with $N_2$. Finally, tetrakis(triphenylphosphine)palladium(0) (0.04 eq.) was added in one rapid portion and the reaction suspension was heated at 80° C. for 18 h. The reaction was then quenched with sat. aq. $NH_4Cl$ and extracted with EtOAc. The combined organic extracts were washed further with water and brine, dried over $Na_2SO_4$, filtered and the filtrate concentrated in vacuo. Purification of the crude product thus obtained by way of column chromatography ($SiO_2$, 80:20 (v/v) Hex:EtOAc→ EtOAc) afforded the title compound as a golden yellow oil.

Step 2: cis-1-(1,1-Dimethylethyl) 3-ethyl 4-(4-pyridinyl)-1,3-piperidinedicarboxylate To a MeOH solution (0.2 M) of 1-(1,1-dimethylethyl) 3-ethyl 5,6-dihydro-4,4'-bipyridine-1,3(2H)-dicarboxylate (1 eq.) from the previous step was added magnesium turnings (3 eq.). The suspension was evacuated and back-filled with $N_2$. Finally, the reaction mixture was sonicated at RT for 2 h during which the magnesium turnings disappeared. The reaction was then quenched with the addition of EtOAc and 1 N aq. NaOH. The aqueous layer was separated and back-extracted with EtOAc. The combined organic extracts were washed further with water and brine, dried over $Na_2SO_4$ and filtered. Concentration of the filtrate in vacuo afforded the title compound as a golden yellow oil.

Step 3: trans-1-(1,1-Dimethylethyl) 3-ethyl 4-(4-pyridinyl)-1,3-piperidinedicarboxylate To an ethanol solution (0.4 M) of cis-1-(1,1-dimethylethyl) 3-ethyl 4-(4-pyridinyl)-1,3-piperidinedicarboxylate (1 eq.) from the previous step was added freshly prepared sodium ethoxide (1.1 eq.). The resulting yellow-orange solution was heated at 60° C. for 12 h. The volatiles were then removed in vacuo and the residue was partitioned between EtOAc and sat. aq. NH₄Cl. The aqueous layer was separated and back-extracted with EtOAc. The combined organic extracts were washed further with water and brine, dried over Na₂SO₄, treated with activated charcoal, filtered and the filtrate concentrated in vacuo. Purification of the crude product thus obtained by way of column chromatography (SiO₂, 80:20 (v/v) Hex:EtOAc→EtOAc) afforded the title compound as a pale yellow oil.

Step 4: trans-1-(1,1-Dimethylethyl) 3-ethyl 4-(1-oxido-4-pyridinyl)-1,3-piperidinedicarboxylate To a dichloromethane solution (0.1 M) of trans-1-(1,1-dimethylethyl) 3-ethyl 4-(4-pyridinyl)-1,3-piperidinedicarboxylate (1 eq.) from the previous step was added 3-chloroperoxybenzoic acid (1 eq.). The resulting colorless solution was stirred at RT for 13 h. The reaction was then quenched with sat. aq. NaHSO₃ and 1 N aq. NaOH. The aqueous layer was separated and back-extracted with EtOAc. The combined organic extracts were washed further with water and brine, dried over Na₂SO₄ and filtered. Concentration of the filtrate in vacuo afforded the title compound as a white solid.

Step 5: trans-1-(1,1-Dimethylethyl) 3-ethyl 4-(1-ethyl-2-oxo-1,2-dihydro-4-pyridinyl)-1,3-piperidinedicarboxylate To a toluene solution (0.06 M) of trans-1-(1,1-dimethylethyl) 3-ethyl 4-(1-oxido-4-pyridinyl)-1,3-piperidinedicarboxylate (1 eq.) from the previous step was added triethylamine (3 eq.). With the reaction vessel immersed in an ice-water bath, trifluoroacetic anhydride (3 eq.) was added dropwise neat over a period of 5 min. The resulting yellow solution was warmed slowly to RT and then allowed to stir at RT for 18 h. The reaction was quenched with the addition of EtOAc and sat. aq. NH₄Cl. The aqueous layer was separated and back-extracted with EtOAc. The combined organic extracts were washed further with water and brine, dried over Na₂SO₄, filtered and the filtrate concentrated in vacuo. The gummy, orange oil thus obtained was immediately taken up in ethanol (0.1 M). To this was then added sodium hydroxide (2 M aq. solution, 3 eq.) and diethyl sulfate (4 eq.) at 0° C. The resulting orange solution was warmed slowly to RT and then allowed to stir at RT for 42 h. The volatiles were removed in vacuo and the residue was partitioned between EtOAc and water. The aqueous layer was separated and back-extracted with EtOAc. The combined organic extracts were washed further with water and brine, dried over Na₂SO₄, filtered and the filtrate concentrated in vacuo. Purification of the crude product thus obtained by way of column chromatography (SiO₂, 95:5 (v/v) CH₂Cl₂:2.0 M NH₃ in MeOH) afforded the title compound as a pale yellow froth.

Step 6: trans-1-{[(1,1-Dimethylethyl)oxy]carbonyl}-4-(1-ethyl-2-oxo-1,2-dihydro-4-pyridinyl)-3-piperidinecarboxylic acid To a 3:2 (v/v) THF:MeOH solution (0.07 M) of trans-1-(1,1-dimethylethyl) 3-ethyl 4-(1-ethyl-2-oxo-1,2-dihydro-4-pyridinyl)-1,3-piperidinedicarboxylate (1 eq.) from the previous step was added lithium hydroxide (1 M aq. solution, 3.1 eq.). The resulting cloudy solution was stirred vigorously at RT for 18 h. The volatiles were then removed in vacuo and the residue was partitioned between EtOAc and 10% aq. HCl. The aqueous layer was separated and back-extracted with EtOAc. The combined organic extracts were washed further with water and brine, dried over Na₂SO₄ and filtered. Concentration of the filtrate in vacuo afforded the title compound as a white solid.

Step 7: trans-1,1-Dimethylethyl 3-{[cyclopropyl({3-{[2-(methyloxy)ethyl]oxy}-5-[3-(methyloxy)propyl]phenyl}methyl)amino]carbonyl}-4-(1-ethyl-2-oxo-1,2-dihydro-4-pyridinyl)-1-piperidinecarboxylate To a DMF solution of trans-1-{[(1,1-dimethylethyl)oxy]carbonyl}-4-(1-ethyl-2-oxo-1,2-dihydro-4-pyridinyl)-3-piperidinecarboxylic acid (1 eq.) from the previous step, Hunig's base (3 eq.) and Amine 11 (1 eq.) was added portionwise O-(7-azabenzotriazol-1-yl)-N,N,N',N'-tetramethyluronium hexafluorophosphate (1.2 eq.). The resulting reaction solution was stirred at RT for 48 h. The now reddish solution was diluted with EtOAc and washed sequentially with 10% aq. HCl, 1 N aq. NaOH and brine. The organic extract was then dried over Na₂SO₄, filtered and the filtrate concentrated in vacuo to afford a yellow oil. Purification of the crude product thus obtained by way of flash chromatography (SiO₂, 7:3 (v/v) Hex:EtOAc→EtOAc 95:5 (v/v) CH₂Cl₂:2.0 M NH₃ in MeOH) afforded the title compound as a white froth.

Step 8: trans-N-Cyclopropyl-4-(1-ethyl-2-oxo-1,2-dihydro-4-pyridinyl)-N-({3-{[2-(methyloxy)ethyl]oxy}-5-[3-(methyloxy)propyl]phenyl}methyl)-3-piperidinecarboxamide To a CH₂Cl₂ solution (0.07 M) of trans-1,1-dimethylethyl 3-{[cyclopropyl({3-{[2-(methyloxy)ethyl]oxy}-5-[3-(methyloxy)propyl]phenyl}methyl)amino]carbonyl}-4-(1-ethyl-2-oxo-1,2-dihydro-4-pyridinyl)-1-piperidinecarboxylate (1 eq.) from the previous step was added HCl (4.0 M dioxane solution, 30 eq.). The resulting solution was stirred at RT for 3 h. Following the removal of the volatiles in vacuo, the resulting residue was directly loaded onto a SiO₂ column packed with 93:7 (v/v) CH₂Cl₂:2.0 M NH₃ in MeOH. Elution with the same solvent system furnished the title compound as a white froth. MS (ESI+, M+H): 526. Human Renin IC₅₀ (buffer): 200 nM. Human Renin IC₅₀ (plasma): 460 nM.

EXAMPLE 13 trans-N-Cyclopropyl-N-({3-{[2-(methyloxy)ethyl]oxy}-5-[3-(methyloxy)propyl]phenyl}methyl)-4-(1,5,6-trimethyl-2-oxo-1,2-dihydro-4-pyridinyl)-3-piperidinecarboxamide

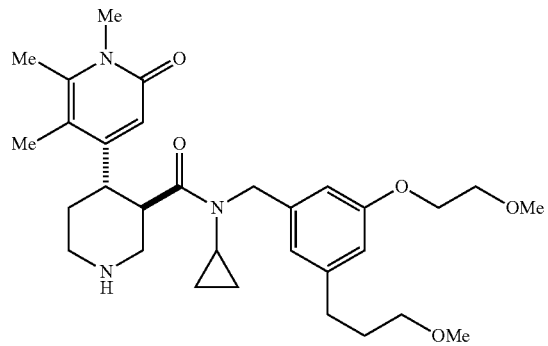

Step 1: 1-(1,1-Dimethylethyl) 3-ethyl 2',3'-dimethyl-6'-[(phenylmethyl)oxy]-5,6-dihydro-4,4'-bipyridine-1,3(2H)-dicarboxylate To a 3:1 (v/v) toluene:ethanol solution (0.085 M) of 1-(1,1-dimethylethyl) 3-ethyl 4-(4,4,5,5-tetramethyl-1,3,2-dioxaborolan-2-yl)-5,6-dihydro-1,3(2H)-pyridinedicarboxylate (1 eq., Example 1, Step 1) and Arene 2 (1 eq.) was added sodium carbonate (2 M aq. solution, 3 eq.). The suspension was evacuated and back-filled with $N_2$. Finally, [1,1'-bis(diphenylphosphino)ferrocene]dichloropalladium(II) (0.06 eq.) was added in one rapid portion and the reaction suspension was heated at 80° C. for 18 h. The reaction was then quenched with the addition of diethyl ether and sat. aq. $NH_4Cl$. The aqueous layer was separated and back-extracted with ether. The combined organic extracts were washed further with water and brine, dried over $Na_2SO_4$, filtered and the filtrate concentrated in vacuo. Purification of the crude product thus obtained by way of column chromatography ($SiO_2$, 95:5 (v/v) Hex:EtOAc→70:30 (v/v) EtOAc:Hex) afforded the title compound as a colorless oil.

Step 2: cis-1-(1,1-Dimethylethyl) 3-ethyl 4-{2,3-dimethyl-6-[(phenylmethyl)oxy]-4-pyridinyl}-1,3-piperidinedicarboxylate To a MeOH solution (0.09 M) of 1-(1,1-dimethylethyl) 3-ethyl 2',3'-dimethyl-6'-[(phenylmethyl)oxy]-5,6-dihydro-4,4'-bipyridine-1,3(2H)-dicarboxylate (1 eq.) from the previous step was added magnesium turnings (3.3 eq.). The suspension was evacuated and back-filled with $N_2$. Finally, the reaction mixture was sonicated at RT for 3 h during which the magnesium turnings disappeared. The reaction was then quenched with the addition of diethyl ether and sat. aq. $NH_4Cl$. The aqueous layer was separated and back-extracted with ether. The combined organic extracts were washed further with water and brine, dried over $Na_2SO_4$, filtered and the filtrate concentrated in vacuo. Purification of the crude product thus obtained by way of column chromatography ($SiO_2$, 95:5 (v/v) Hex:EtOAc→1:1 (v/v) Hex:EtOAc) afforded the title compound as a pale yellow oil.

Step 3: trans-1-(1,1-Dimethylethyl) 3-ethyl 4-{2,3-dimethyl-6-[(phenylmethyl)oxy]-4-pyridinyl}-1,3-piperidinedicarboxylate To an ethanol solution (0.1 M) of cis-1-(1,1-dimethylethyl) 3-ethyl 4-{2,3-dimethyl-6-[(phenylmethyl)oxy]-4-pyridinyl}-1,3-piperidinedicarboxylate (1 eq.) from the previous step was added freshly prepared sodium ethoxide (1.2 eq.). The resulting yellow-orange solution was heated at 55° C. for 16 h. The volatiles were then removed in vacuo and the residue was partitioned between EtOAc and sat. aq. $NH_4Cl$. The aqueous layer was separated and back-extracted with EtOAc. The combined organic extracts were washed further with water and brine, dried over $Na_2SO_4$, filtered and the filtrate concentrated in vacuo. Purification of the crude product thus obtained by way of column chromatography ($SiO_2$, 90:10 (v/v) Hex:EtOAc→1:1 (v/v) Hex:EtOAc) afforded the title compound as a pale yellow oil.

Step 4: trans-1-(1,1-Dimethylethyl) 3-ethyl 4-(6-hydroxy-2,3-dimethyl-4-pyridinyl)-1,3-piperidinedicarboxylate To an ethanol solution (0.07 M) of trans-1-(1,1-dimethylethyl) 3-ethyl 4-{2,3-dimethyl-6-[(phenylmethyl)oxy]-4-pyridinyl}-1,3-piperidinedicarboxylate (1 eq.) from the previous step was added palladium (10% w/w over carbon, 0.1 eq.). The resulting suspension was evacuated and purged with hydrogen. Under a balloon-filled hydrogen atmosphere, the reaction mixture was stirred at RT for 2 h. The reaction was then quenched with $CH_2Cl_2$, filtered through a bed of celite and the insolubles rinsed with EtOAc. Concentration of the filtrate in vacuo afforded the title compound as a white solid.

Step 5: trans-1-(1,1-Dimethylethyl) 3-ethyl 4-(1,5,6-trimethyl-2-oxo-1,2-dihydro-4-pyridinyl)-1,3-piperidinedicarboxylate To a DMF suspension (0.11 M) of trans-1-(1,1-dimethylethyl) 3-ethyl 4-(6-hydroxy-2,3-dimethyl-4-pyridinyl)-1,3-piperidinedicarboxylate (1 eq.) from the previous step and sodium hydride (60% dispersion in oil, 2 eq.) was added iodomethane (1.5 eq.). The resulting mixture was then stirred at RT for 18 h. The reaction was quenched with the addition EtOAc and sat. aq. $NH_4Cl$. The aqueous phase was separated and back-extracted with EtOAc. The combined organic extracts were washed sequentially with water and brine, dried over $Na_2SO_4$, filtered and the filtrate concentrated in vacuo. Purification of the crude product thus obtained by way of column chromatography ($SiO_2$, 95:5 (v/v) $CH_2Cl_2$:2.0 M $NH_3$ in MeOH) afforded the title compound as a pale yellow froth.

Step 6: trans-1-{[(1,1-Dimethylethyl)oxy]carbonyl}-4-(1,5,6-trimethyl-2-oxo-1,2-dihydro-4-pyridinyl)-3-piperidinecarboxylic acid To a 3:2 (v/v) THF:MeOH solution (0.07 M) of trans-1-(1,1-dimethylethyl) 3-ethyl 4-(1,5,6-trimethyl-2-oxo-1,2-dihydro-4-pyridinyl)-1,3-piperidinedicarboxylate (1 eq.) from the previous step was added lithium hydroxide (1 M aq. solution, 3.1 eq.). The resulting cloudy solution was stirred vigorously at RT for 18 h. The volatiles were then removed in vacuo and the residue was partitioned between EtOAc and 10% aq. HCl. The aqueous layer was separated and back-extracted with EtOAc. The combined organic extracts were washed further with water and brine, dried over $Na_2SO_4$ and filtered. Concentration of the filtrate in vacuo afforded the title compound as a white solid.

Step 7: trans-1,1-Dimethylethyl 3-{[cyclopropyl({3-{[2-(methyloxy)ethyl]oxy}-5-[3-(methyloxy)propyl]phenyl}methyl)amino]carbonyl}-4-(1,5,6-trimethyl-2-oxo-1,2-dihydro-4-pyridinyl)-1-piperidinecarboxylate To a DMF (0.1 M) solution of trans-1-{[(1,1-dimethylethyl)oxy]carbonyl}-4-(1,5,6-trimethyl-2-oxo-1,2-dihydro-4-pyridinyl)-3-piperidinecarboxylic acid (1 eq.) from the previous step, Hunig's base (3 eq.) and Amine 11 (1 eq.) was added portionwise O-(7-azabenzotriazol-1-yl)-N,N,N',N'-tetramethyluronium hexafluorophosphate (1.2 eq.). The resulting reaction solution was stirred at RT for 48 h. The now reddish solution was diluted with EtOAc and washed sequentially with 10% aq. HCl, 1 N aq. NaOH and brine. The organic extract was then dried over $Na_2SO_4$, filtered and the filtrate concentrated in vacuo to afford a yellow oil. Purification of the crude product thus obtained by way of flash chromatography ($SiO_2$, 7:3 (v/v) Hex:EtOAc→EtOAc→95:5 (v/v) $CH_2Cl_2$:2.0 M $NH_3$ in MeOH) afforded the title compound as a white solid.

Step 8: trans-N-Cyclopropyl-N-({3-{[2-(methyloxy)ethyl]oxy}-5-[3-(methyloxy)propyl]phenyl}methyl)-4-(1,5,6-trimethyl-2-oxo-1,2-dihydro-4-pyridinyl)-3-piperidinecarboxamide To a CH$_2$Cl$_2$ solution (0.06 M) of trans-1,1-dimethylethyl 3-{[cyclopropyl({3-{[2-(methyloxy)ethyl]oxy}-5-[3-(methyloxy)propyl]phenyl}methyl)amino]carbonyl}-4-(1,5,6-trimethyl-2-oxo-1,2-dihydro-4-pyridinyl)-1-piperidinecarboxylate (1 eq.) from the previous step was added HCl (4.0 M dioxane solution, 30 eq.). The resulting solution was stirred at RT for 4 h. Following the removal of the volatiles in vacuo, the resulting residue was directly loaded onto a SiO$_2$ column packed with 94:6 (v/v) CH$_2$Cl$_2$:2.0 M NH$_3$ in MeOH. Elution with the same solvent system furnished the title compound as a white froth. MS (ESI+, M+H): 540. Human Renin IC$_{50}$ (buffer): 25 nM. Human Renin IC$_{50}$ (plasma): 80 nM.

EXAMPLE 14 trans-N-Cyclopropyl-4-(1-methyl-5-{[(methyloxy)methyl]oxy}-2-oxo-1,2-dihydro-4-pyridinyl)-N-({3-{[2-(methyloxy)ethyl]oxy}-5-[3-(methyloxy)propyl]phenyl}methyl)-3-piperidinecarboxamide

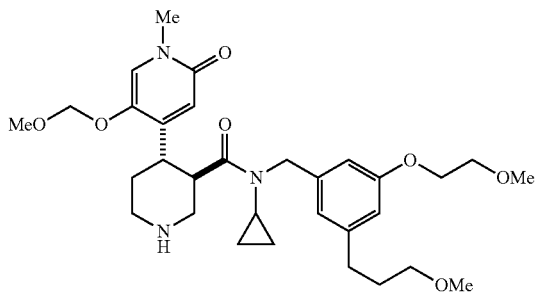

Step 1: 1-(1,1-Dimethylethyl) 3-ethyl 3'-{[(methyloxy)methyl]oxy}-5,6-dihydro-4,4'-bipyridine-1,3(2H)-dicarboxylate To a 3:1 (v/v) toluene:ethanol solution (0.1 M) of 1-(1,1-dimethylethyl) 3-ethyl 4-(4,4,5,5-tetramethyl-1,3,2-dioxaborolan-2-yl)-5,6-dihydro-1,3(2H)-pyridinedicarboxylate (1 eq., Example 1, Step 1) and Arene 3 (1 eq.) was added sodium carbonate (2 M aq. solution, 3 eq.). The suspension was evacuated and back-filled with N$_2$. Finally, [1,1'-bis(diphenylphosphino)ferrocene]dichloropalladium(II) (0.06 eq.) was added in one rapid portion and the reaction suspension was heated at 80° C. for 16 h. The reaction was then quenched with the addition of EtOAc and water. The aqueous layer was separated and back-extracted with EtOAc. The combined organic extracts were washed further with 1 N aq. NaOH, water and brine, dried over Na$_2$SO$_4$, filtered and the filtrate concentrated in vacuo. Purification of the crude product thus obtained by way of column chromatography (SiO$_2$, 90:10 (v/v) Hex:EtOAc 4 EtOAc) afforded the title compound as a pale yellow oil.

Step 2: cis-1-(1,1-Dimethylethyl) 3-ethyl 4-(3-{[(methyl oxy)methyl]oxy}-4-pyridinyl)-1,3-piperidinedicarboxylate To a MeOH solution (0.09 M) of 1-(1,1-dimethylethyl) 3-ethyl 3'-{[(methyloxy)methyl]oxy}-5,6-dihydro-4,4'-bipyridine-1,3(2H)-dicarboxylate (1 eq.) from the previous step was added magnesium turnings (3.3 eq.). The suspension was evacuated and back-filled with N$_2$. Finally, the reaction mixture was sonicated at RT for 1.5 h during which the magnesium turnings disappeared. The reaction was then quenched with the addition of EtOAc and 1 N aq. NaOH. The aqueous layer was separated and back-extracted with EtOAc. The combined organic extracts were washed further with water and brine, dried over Na$_2$SO$_4$ and filtered. Concentration of the filtrate in vacuo afforded the title compound as a pale yellow oil.

Step 3: trans-1-(1,1-Dimethylethyl) 3-ethyl 4-(3-{[(methyloxy)methyl]oxy}-4-pyridinyl)-1,3-piperidinedicarboxylate To an ethanol solution (0.1 M) of cis-1-(1,1-dimethylethyl) 3-ethyl 4-(3-{[(methyloxy)methyl]oxy}-4-pyridinyl)-1,3-piperidinedicarboxylate (1 eq.) from the previous step was added freshly prepared sodium ethoxide (1.2 eq.). The resulting yellow-orange solution was heated at 55° C. for 16 h. The volatiles were then removed in vacuo and the residue was partitioned between EtOAc and sat. aq. NH$_4$Cl. The aqueous layer was separated and back-extracted with EtOAc. The combined organic extracts were washed further with water and brine, dried over Na$_2$SO$_4$, filtered and the filtrate concentrated in vacuo. Purification of the crude product thus obtained by way of column chromatography (SiO$_2$, 95:5 (v/v) Hex:EtOAc→1:1 (v/v) Hex:EtOAc) afforded the title compound as a pale yellow oil.

Step 4: trans-1-(1,1-Dimethylethyl) 3-ethyl 4-(3-{[(methyloxy)methyl]oxy}-1-oxido-4-pyridinyl)-1,3-piperidinedicarboxylate To a dichloromethane solution (0.1 M) of trans-1-(1,1-dimethylethyl) 3-ethyl 4-(3-{[(methyloxy)methyl]oxy}-4-pyridinyl)-1,3-piperidinedicarboxylate (1 eq.) from the previous step was added 3-chloroperoxybenzoic acid (1 eq.). The resulting colorless solution was stirred at RT for 13 h. The reaction was then quenched with sat. aq. NaHSO$_3$ and 1 N aq. NaOH. The aqueous layer was separated and back-extracted with EtOAc. The combined organic extracts were washed further with water and brine, dried over Na$_2$SO$_4$ and filtered. Concentration of the filtrate in vacuo afforded the title compound as a white solid.

Step 5: trans-1-(1,1-Dimethylethyl) 3-ethyl 4-(1-methyl-5-{[(methyloxy)methyl]oxy}-2-oxo-1,2-dihydro-4-pyridinyl)-1,3-piperidinedicarboxylate To a toluene solution (0.06 M) of trans-1-(1,1-dimethylethyl) 3-ethyl 4-(3-{[(methyloxy)methyl]oxy}-1-oxido-4-pyridinyl)-1,3-piperidinedicarboxylate (1 eq.) from the previous step was added triethylamine (3 eq.). With the reaction vessel immersed in an ice-water bath, trifluoroacetic anhydride (3 eq.) was added dropwise neat over a period of 2 min. The resulting yellow solution was warmed slowly to RT and then allowed to stir at RT for 18 h. The reaction was quenched with the addition of EtOAc and sat. aq. NH$_4$Cl. The aqueous layer was separated and back-extracted with EtOAc. The combined organic extracts were washed further with water and brine, dried over Na$_2$SO$_4$, filtered and the filtrate concentrated in vacuo. The gummy, orange oil thus obtained was immediately taken up in methanol (0.06 M). To this was then added sodium hydroxide (2 M aq. solution, 3 eq.) and dimethyl sulfate (4 eq.) at 0° C. The resulting orange solution was warmed slowly to RT and then allowed to stir at RT for 18 h. The volatiles were removed in vacuo and the residue was partitioned between EtOAc and sat. aq. NH$_4$Cl. The aqueous layer was separated and back-extracted with EtOAc. The combined organic extracts were washed further with water and brine, dried over Na$_2$SO$_4$, filtered and the filtrate concentrated in vacuo. Purification of the crude product thus obtained by way of column chromatography (SiO$_2$, 95:5 (v/v) CH$_2$Cl$_2$:2.0 M NH$_3$ in MeOH) afforded the title compound as a pale purple froth.

Step 6: trans-1-{[(1,1-Dimethylethyl)oxy]carbonyl}-4-(1-methyl-5-{[(methyloxy)methyl]oxy}-2-oxo-1,2-dihydro-4-pyridinyl)-3-piperidinecarboxylic acid To a 3:2 (v/v) THF:MeOH solution (0.04 M) of trans-1-(1,1-dimethylethyl) 3-ethyl 4-(1-methyl-5-{[(methyloxy)methyl]oxy}-2-oxo-1,2-dihydro-4-pyridinyl)-1,3-piperidinedicarboxylate (1 eq.) from the previous step was added lithium hydroxide (1 M aq. solution, 3 eq.). The resulting cloudy solution was stirred vigorously at RT for 24 h. The volatiles were then removed in vacuo and the residue was partitioned between EtOAc and 10% aq. HCl. The aqueous layer was separated and back-extracted with EtOAc. The combined organic extracts were washed further with water and brine, dried over Na$_2$SO$_4$ and filtered. Concentration of the filtrate in vacuo afforded the title compound as a pink solid.

Step 7: trans-1,1-Dimethylethyl 3-{[cyclopropyl({3-{[2-(methyloxy)ethyl]oxy}-5-[3-(methyloxy)propyl]phenyl}methyl)amino]carbonyl}-4-(1-methyl-5-{[(methyloxy)methyl]oxy}-2-oxo-1,2-dihydro-4-pyridinyl)-1-piperidinecarboxylate To a DMF (0.1 M) solution of trans-1-{[(1,1-dimethylethyl)oxy]carbonyl}-4-(1-methyl-5-{[(methyloxy)methyl]oxy}-2-oxo-1,2-dihydro-4-pyridinyl)-3-piperidinecarboxylic acid (1 eq.) from the previous step, Hunig's base (3 eq.) and Amine 11 (1 eq.) was added portionwise O-(7-azabenzotriazol-1-yl)-N,N,N',N'-tetramethyluronium hexafluorophosphate (1.2 eq.). The resulting reaction solution was stirred at RT for 48 h. The now reddish solution was diluted with EtOAc and washed sequentially with 10% aq. HCl, 1 N aq. NaOH and brine. The organic extract was then dried over Na$_2$SO$_4$, filtered and the filtrate concentrated in vacuo to afford a purple oil. Purification of the crude product thus obtained by way of flash chromatography (SiO$_2$, 96:4 (v/v) CH$_2$Cl$_2$:2.0 M NH$_3$ in MeOH) afforded the title compound as a pinkish froth.

Step 8: trans-N-Cyclopropyl-4-(1-methyl-5-{[(methyloxy)methyl]oxy}-2-oxo-1,2-dihydro-4-pyridinyl)-N-({3-{[2-(methyloxy)ethyl]oxy}-5-[3-(methyloxy)propyl]phenyl}methyl)-3-piperidinecarboxamide To a CH$_2$Cl$_2$ solution (0.02 M) of trans-1,1-dimethylethyl 3-{[cyclopropyl({3-{[2-(methyloxy)ethyl]oxy}-5-[3-(methyloxy)propyl]phenyl}methyl)amino]carbonyl}-4-(1-methyl-5-{[(methyloxy)methyl]oxy}-2-oxo-1,2-dihydro-4-pyridinyl)-1-piperidinecarboxylate (1 eq.) from the previous step was added zinc(II) bromide (10 eq.). The resulting suspension was sonicated for 15 min and stirred at RT for 13 h. The reaction was quenched with the addition of EtOAc and 1 N aq. NaOH, and then sonicated for 15 min. The aqueous phase was separated and back-extracted with EtOAc. The combined organic extracts were washed further with water and brine, dried over Na$_2$SO$_4$, filtered and the filtrate concentrated in vacuo. Purification of the crude product thus obtained by way of flash chromatography (SiO$_2$, 90:10 (v/v) CH$_2$Cl$_2$:2.0 M NH$_3$ in MeOH) afforded the title compound as a colorless oil. MS (ESI+, M+H): 572.

EXAMPLE 15 trans-N-Cyclopropyl-N-{[2,3-dichloro-5-(3-cyanopropyl)phenyl]methyl}-4-(1-methyl-2-oxo-1,2-dihydro-4-pyridinyl)-3-piperidinecarboxamide

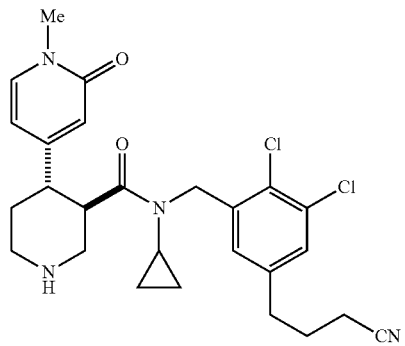

Prepared according to the procedure described in Example 1 but using instead Amine 12 as starting material and zinc(II) bromide-promoted BOC-deprotection as in Example 14, Step 8. The title compound was obtained as a pale green froth. MS (ESI+, M+H): 502.

EXAMPLE 16 trans-N-{[5-(3-Cyanopropyl)-2,3-difluorophenyl]methyl}-N-cyclopropyl-4-(1-methyl-2-oxo-1,2-dihydro-4-pyridinyl)-3-piperidinecarboxamide

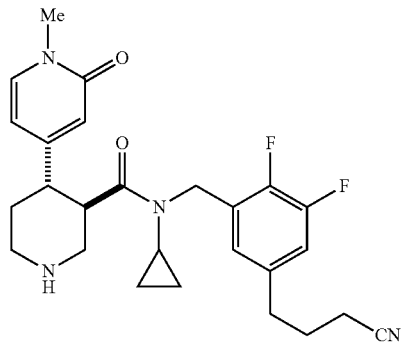

Prepared according to the procedure described in Example 1 but using instead Amine 13 as starting material and zinc(II) bromide-promoted BOC-deprotection as in Example 14, Step 8. The title compound was obtained as a pale green froth. MS (ESI+, M+H): 469.

EXAMPLE 17 trans-N-Cyclopropyl-N-{[2,3-dichloro-5-(4-hydroxybutyl)phenyl]methyl}-4-(1-methyl-2-oxo-1,2-dihydro-4-pyridinyl)-3-piperidinecarboxamide

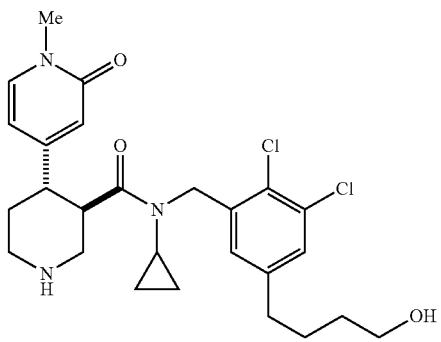

Step 1: trans-1,1-Dimethylethyl 3-{[cyclopropyl({2,3-dichloro-5-[4-(methyloxy)-4-oxobutyl]phenyl}methyl)amino]carbonyl}-4-(1-methyl-2-oxo-1,2-dihydro-4-pyridinyl)-1-piperidinecarboxylate To a DMF (0.1 M) solution of trans-1-{[(1,1-dimethylethyl)oxy]carbonyl}-4-(1-methyl-2-oxo-1,2-dihydro-4-pyridinyl)-3-piperidinecarboxylic acid (1 eq., Example 1, Step 6), Hunig's base (3 eq.) and Amine 14 (1 eq.) was added portionwise O-(7-azabenzotriazol-1-yl)-N,N,N',N'-tetramethyluronium hexafluorophosphate (1.2 eq.). The resulting reaction solution was stirred at RT for 48 h. The now yellow solution was diluted with EtOAc and washed sequentially with 10% aq. HCl, 1 N aq. NaOH and brine. The organic extract was then dried over Na$_2$SO$_4$, filtered and the filtrate concentrated in vacuo to afford a reddish-orange oil. Purification of the crude product thus obtained by way of flash chromatography (SiO$_2$, 7:3 (v/v) Hex:EtOAc→EtOAc→95:5 (v/v) CH$_2$Cl$_2$:2.0 M NH$_3$ in MeOH) afforded the title compound as a pale yellow froth.

Step 2: trans-1,1-Dimethylethyl 3-[(cyclopropyl{[2,3-dichloro-5-(4-hydroxybutyl)phenyl]methyl}amino]carbonyl}-4-(1-methyl-2-oxo-1,2-dihydro-4-pyridinyl)-1-piperidinecarboxylate To a THF solution (0.08 M) of trans-1,1-dimethylethyl 3-{[cyclopropyl({2,3-dichloro-5-[4-(methyloxy)-4-oxobutyl]phenyl}methyl)amino]carbonyl}-4-(1-methyl-2-oxo-1,2-dihydro-4-pyridinyl)-1-piperidinecarboxylate (1 eq.) from the previous step was added lithium borohydride (6 eq.) in one rapid portion. After 3 h, the reaction was quenched with the careful addition of 10% aq. HCl. The aqueous layer was separated and back-extracted with EtOAc. The combined organic extract were washed further with 1 N aq. NaOH, water and brine, dried over Na$_2$SO$_4$ and filtered. Concentration of the filtrate in vacuo afforded the title compound as a white froth.

Step 3: trans-N-Cyclopropyl-N-{[2,3-dichloro-5-(4-hydroxybutyl)phenyl]methyl}-4-(1-methyl-2-oxo-1,2-dihydro-4-pyridinyl)-3-piperidinecarboxamide To a CH$_2$Cl$_2$ solution (0.05 M) of trans-1,1-dimethylethyl 3-[(cyclopropyl{[2,3-dichloro-5-(4-hydroxybutyl)phenyl]methyl}amino]carbonyl}-4-(1-methyl-2-oxo-1,2-dihydro-4-pyridinyl)-1-piperidinecarboxylate (1 eq.) from the previous step was added HCl (4.0 M dioxane solution, 30 eq.). The resulting solution was stirred at RT for 3 h. Following the removal of the volatiles in vacuo, the resulting residue was directly loaded onto a SiO$_2$ column packed with 93:7 (v/v) CH$_2$Cl$_2$:2.0 M NH$_3$ in MeOH. Elution with the same solvent system furnished the title compound as a white froth. MS (ESI+, M+H): 508.

EXAMPLE 18 trans-N-Cyclopropyl-4-(1-methyl-2-oxo-1,2-dihydro-4-pyridinyl)-N-({3-[3-(methyloxy)propyl]-1-naphthalenyl}methyl)-3-piperidinecarboxamide

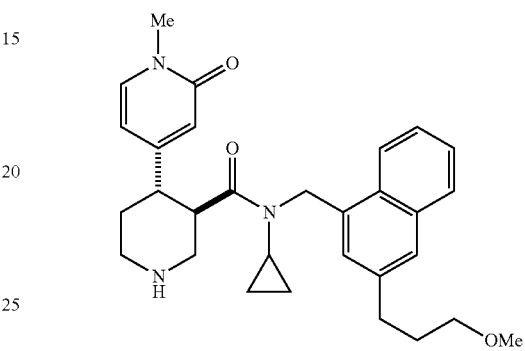

Prepared according to the procedure described in Example 1 but using instead Amine 15 as starting material. The title compound was obtained as a white froth. MS (ESI+, M+Na): 510. $^1$H NMR (CDCl$_3$) δ (ppm): 0.72-0.78 (br m, 1H), 0.82-0.96 (br m, 3H), 1.59-1.66 (m, 1H), 1.74-1.84 (br s, 2H), 1.91-1.97 (m, 2H), 2.22-2.28 (br m, 1H), 2.74-2.87 (m, 4H), 3.03 (dt, J=10.4, 5.2 Hz, 1H), 3.14-3.21 (m, 2H), 3.36 (s, 3H), 3.37 (s, 3H), 3.42 (t, J=7.4 Hz, 2H), 3.43-3.47 (m, 1H), 4.83 (d, J=14 Hz, 1H), 5.02 (d, J=14 Hz, 1H), 5.94, (d, J=6.9 Hz, 1H), 6.34 (s, 1H), 6.78 (d, J=6.9 Hz, 1H), 7.16 (s, 1H), 7.33-7.46 (m, 2H), 7.55 (s, 1H), 7.77 (d, J=7.2 Hz, 1H), 7.94 (d, J=7.2 Hz, 1H). Human Renin IC$_{50}$ (buffer): 0.4 nM. Human Renin IC$_{50}$ (plasma): 1.8 nM.

EXAMPLE 19 trans-Methyl (2-{3,4-dichloro-5-[(cyclopropyl{[4-(1-methyl-2-oxo-1,2-dihydro-4-pyridinyl)-3-piperidinyl]carbonyl}amino)methyl]phenyl}ethyl)carbamate

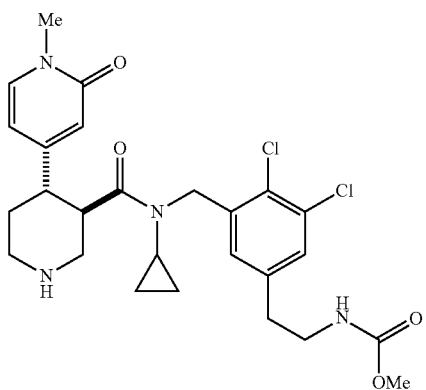

Prepared according to the procedure described in Example 1 but using instead Amine 16 as starting material. The title compound was obtained as a white froth. MS (ESI+, M+H): 535.

EXAMPLE 20 trans-N-Cyclopropyl-4-(1-methyl-2-oxo-1,2-dihydro-4-pyridinyl)-N-(8-quinolinylmethyl)-3-piperidinecarboxamide

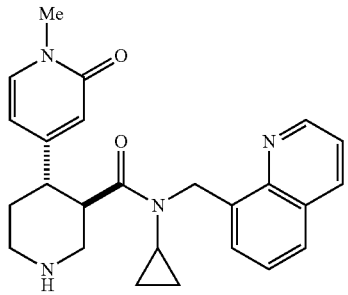

Prepared according to the procedure described in Example 1 but using instead Amine 17 as starting material. The title compound was obtained as a white froth. MS (ESI+, M+H): 417.

EXAMPLE 21 trans-N-Cyclopropyl-N-(8-isoquinolinylmethyl)-4-(1-methyl-2-oxo-1,2-dihydro-4-pyridinyl)-3-piperidinecarboxamide

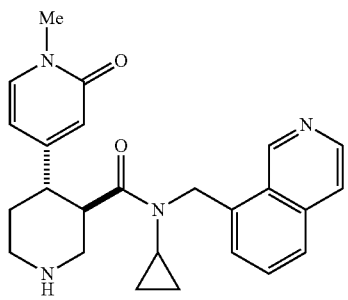

Prepared according to the procedure described in Example 1 but using instead Amine 18 as starting material. The title compound was obtained as a white froth. MS (ESI+, M+H): 417.

EXAMPLE 22 trans-N-Cyclopropyl-N-(5-isoquinolinylmethyl)-4-(1-methyl-2-oxo-1,2-dihydro-4-pyridinyl)-3-piperidinecarboxamide

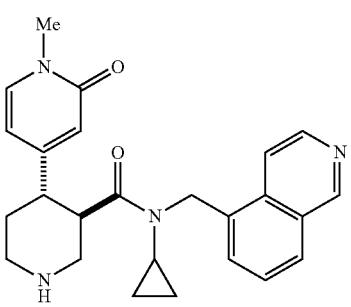

Prepared according to the procedure described in Example 1 but using instead Amine 19 as starting material. The title compound was obtained as a white froth. MS (ESI+, M+H): 417.

EXAMPLE 23 trans-N-Cyclopropyl-4-(1-methyl-2-oxo-1,2-dihydro-4-pyridinyl)-N-(5-quinolinylmethyl)-3-piperidinecarboxamide

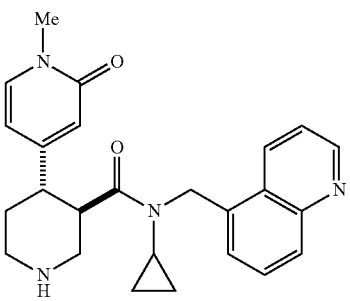

Prepared according to the procedure described in Example 1 but using instead Amine 20 as starting material. The title compound was obtained as a white froth. MS (ESI+, M+H): 417.

EXAMPLE 24 trans-N-Cyclopropyl-N-(1-isoquinolinylmethyl)-4-(1-methyl-2-oxo-1,2-dihydro-4-pyridinyl)-3-piperidinecarboxamide

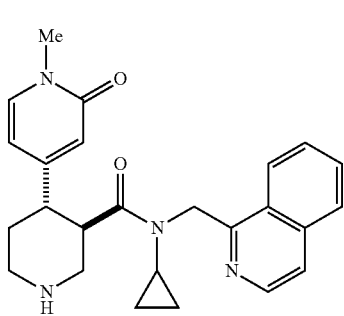

Prepared according to the procedure described in Example 1 but using instead Amine 21 as starting material. The title compound was obtained as a white froth. MS (ESI+, M+H): 417.

EXAMPLE 25 trans-N-Cyclopropyl-4-(1-methyl-2-oxo-1,2-dihydro-4-pyridinyl)-N-({2-[3-(methyloxy)propyl]-4-quinolinyl}methyl)-3-piperidinecarboxamide

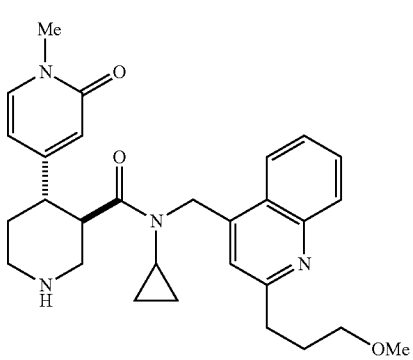

Prepared according to the procedure described in Example 1 but using instead Amine 22 as starting material. The title compound was obtained as a white froth. MS (ESI+, M+H): 489. $^1$H NMR (CD$_3$OD) δ (ppm): 0.83-0.88 (m, 1H), 0.89-0.97 (m, 1H), 1.00-1.08 (m, 2H), 1.69 (qd, J=12.8, 4.1 Hz, 1H), 1.82 (d, J=13.3 Hz, 1H), 2.02 (p, J=7.0 Hz, 2H), 2.67-2.71 (m, 1H), 2.72-2.81 (m, 2H), 2.93 (m, 2H), 3.04 (dt, J=12.8, 4.1 Hz, 1H), 3.18 (d, J=13.0 Hz, 1H), 3.32-3.38 (m, 3H), 3.40-3.47 (m, 5H), 3.72 (m, 2H), 4.78 (d, J=7.5 Hz, 1H), 5.18 (d, J=7.5 Hz, 1H), 6.27 (d, J=6.9 Hz, 1H), 6.42 (s, 1H), 6.99 (s, 1H), 7.39 (d, J=6.9 Hz, 1H), 7.51 (t, J=7.6 Hz, 1H), 7.74 (t, J=7.7 Hz, 1H), 7.99 (t, J=7.3 Hz, 2H). Human Renin IC$_{50}$ (buffer): 1.4 nM. Human Renin IC$_{50}$ (plasma): 3.0 nM.

EXAMPLE 26 trans-N-Cyclopropyl-4-(1-methyl-2-oxo-1,2-dihydro-4-pyridinyl)-N-({6-[3-(methyloxy)propyl]-8-quinolinyl}methyl)-3-piperidinecarboxamide

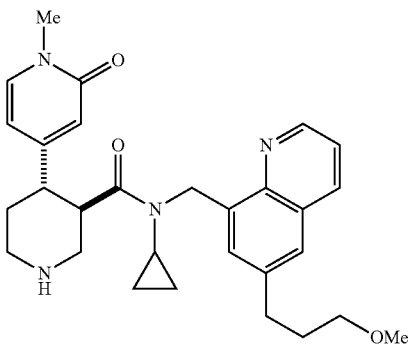

Prepared according to the procedure described in Example 1 but using instead Amine 23 as starting material. The title compound was obtained as a white froth. MS (ESI+, M+H): 489.

EXAMPLE 27 trans-N-[(5-Bromo-2,3-dichlorophenyl)methyl]-N-cyclopropyl-4-(1-methyl-2-oxo-1,2-dihydro-4-pyridinyl)-3-piperidinecarboxamide

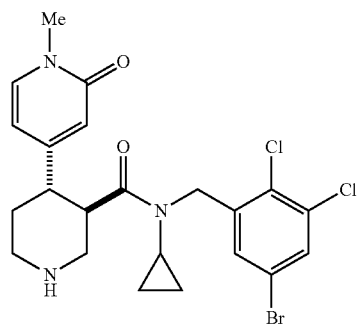

Prepared according to the procedure described in Example 1 but using instead N-[(5-bromo-2,3-dichlorophenyl)methyl]cyclopropanamine (Step 2, Amine 5) as the amine starting material. The title compound was obtained as a white froth. MS (ESI+, M+H): 512.

EXAMPLE 28 trans-N-({3-Chloro-5-[3-(methyloxy)propyl]phenyl}methyl)-N-cyclopropyl-4-(1-methyl-2-oxo-1,2-dihydro-4-pyridinyl)-3-piperidinecarboxamide

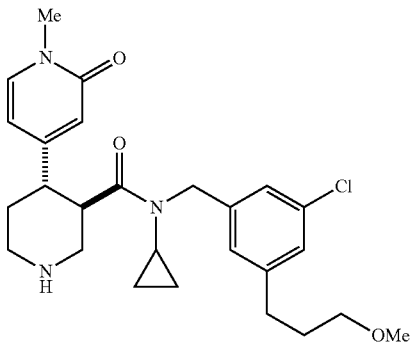

Prepared according to the procedure described in Example 1 but using instead Amine 24 starting material. The title compound was obtained as a pale yellow froth. MS (ESI+, M+H): 472.

EXAMPLE 29 trans-N-Cyclopropyl-4-(1-methyl-2-oxo-1,2-dihydro-4-pyridinyl)-N-({1-[3-(methyloxy)propyl]-1H-indol-3-yl}methyl)-3-piperidinecarboxamide

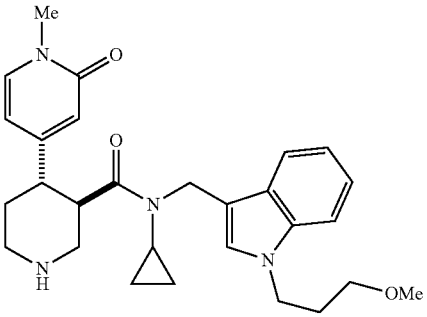

Prepared according to the procedure described in Example 1 but using instead Amine 25 as starting material and zinc(II) bromide-promoted BOC-deprotection as in Example 14, Step 8. The title compound was obtained as a white froth. MS (ESI+, M+H): 477.

EXAMPLE 30 trans-N-Cyclopropyl-N-{[2,3-dichloro-5-(2-cyanoethyl)phenyl]methyl}-4-(1-methyl-2-oxo-1,2-dihydro-4-pyridinyl)-3-piperidinecarboxamide

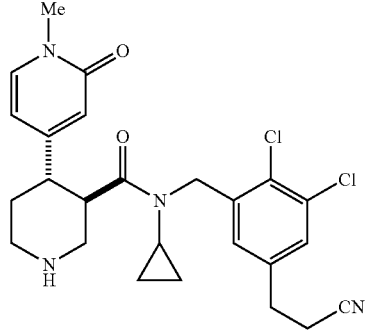

Prepared according to the procedure described in Example 1 but using instead Amine 26 as starting material and zinc(II)

bromide-promoted BOC-deprotection as in Example 14, Step 8. The title compound was obtained as a white froth. MS (ESI+, M+H): 487. Human Renin $IC_{50}$ (buffer): 8.4 nM. Human Renin $IC_{50}$ (plasma): 17 nM.

EXAMPLE 31 trans-Ethyl (2-{3,4-dichloro-5-[(cyclopropyl{[4-(1-methyl-2-oxo-1,2-dihydro-4-pyridinyl)-3-piperidinyl]carbonyl}amino)methyl]phenyl}ethyl)carbamate

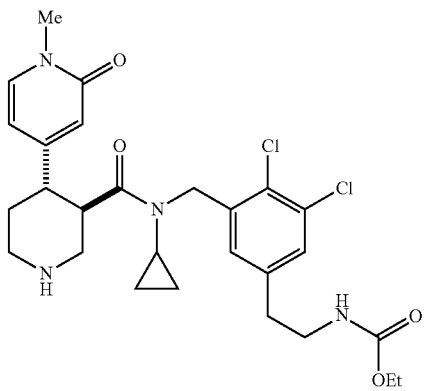

Prepared according to the procedure described in Example 1 but using instead Amine 27 as starting material. The title compound was obtained as a white solid. MS (ESI+, M+H): 549.

EXAMPLE 32 trans-N-({3-Bromo-5-[3-(methyloxy)propyl]phenyl}methyl)-N-cyclopropyl-4-(1-methyl-2-oxo-1,2-dihydro-4-pyridinyl)-3-piperidinecarboxamide

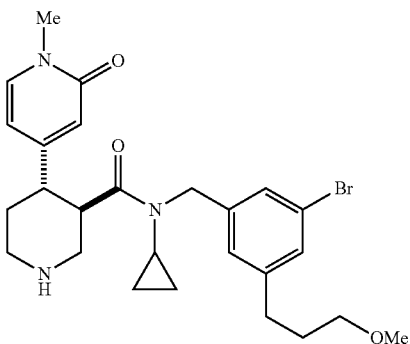

Step 1: trans-tert-Butyl 3-{[[3-bromo-5-(3-methoxypropyl)benzyl](cyclopropyl)amino]carbonyl}-4-(1-methyl-2-oxo-1,2-dihydropyridin-4-yl)-1-piperidinecarboxylate To a DMF (0.1 M) solution of trans-1-{[(1,1-Dimethylethyl)oxy]carbonyl}-4-(1-methyl-2-oxo-1,2-dihydro-4-pyridinyl)-3-piperidinecarboxylic acid (1 eq., Example 1, Step 6), Hunig's base (3 eq.) and Amine 28 (1 eq.) was added portionwise O-(7-azabenzotriazol-1-yl)-N,N,N',N'-tetramethyluronium hexafluorophosphate (1.2 eq.). The resulting reaction solution was stirred at RT for 48 h. The now yellow solution was diluted with EtOAc and washed sequentially with 10% aq. HCl, 1 N aq. NaOH and brine. The organic extract was then dried over $Na_2SO_4$, filtered and the filtrate concentrated in vacuo to afford a reddish-orange oil. Purification of the crude product thus obtained by way of flash chromatography ($SiO_2$, EtOAc→5:95 (v/v) 2.0 M $NH_3$ in MeOH:$CH_2Cl_2$) afforded the title compound as a yellow oil.

Step 2: trans-N-({3-Bromo-5-[3-(methyloxy)propyl]phenyl}methyl)-N-cyclopropyl-4-(1-methyl-2-oxo-1,2-dihydro-4-pyridinyl)-3-piperidinecarboxamide To a $CH_2Cl_2$ solution (0.05 M) of trans-tert-butyl 3-{[[3-bromo-5-(3-methoxypropyl)benzyl](cyclopropyl)amino]carbonyl}-4-(1-methyl-2-oxo-1,2-dihydropyridin-4-yl)-1-piperidinecarboxylate (1 eq.) from the previous step was added HCl (4.0 M dioxane solution, 30 eq.). The resulting solution was stirred at RT for 1.5 h. Following the removal of the volatiles in vacuo, the resulting residue was directly loaded onto a $SiO_2$ column packed with 93:7 (v/v) $CH_2Cl_2$: 2.0 M $NH_3$ in MeOH. Elution with the same solvent system furnished the title compound as a white froth. MS (ESI+, M+H): 516.

EXAMPLE 33 trans-N-Cyclopropyl-4-(1-methyl-2-oxo-1,2-dihydro-4-pyridinyl)-N-({5-[3-(methyloxy)propyl]-3-biphenylyl}methyl)-3-piperidinecarboxamide

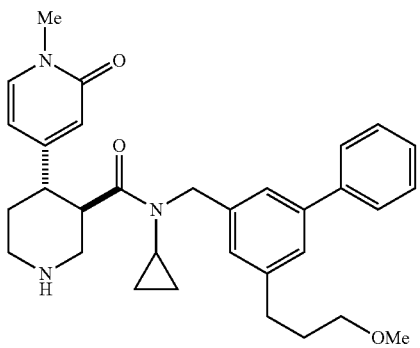

Step 1: trans-tert-Butyl 3-[(cyclopropyl{[5-(3-methoxypropyl)biphenyl-3-yl]methyl}amino)carbonyl]-4-(1-methyl-2-oxo-1,2-dihydropyridin-4-yl)piperidine-1-carboxylate A solution of trans-tert-butyl 3-{[[3-bromo-5-(3-methoxypropyl)benzyl](cyclopropyl)amino]carbonyl}-4-(1-methyl-2-oxo-1,2-dihydropyridin-4-yl)-1-piperidinecarboxylate (1.0 eq., Example 32, Step 1), phenylboronic acid (1.2 eq.) and sodium carbonate (4.0 eq.) in DMF (0.1 M) was repeatedly evacuated and back-filled with nitrogen. Pd(dppf)$Cl_2$ (0.13 eq.) was then added and the flask was evacuated and backfilled again with nitrogen. The reaction mixture was heated to 90° C. for 16 h, and at 100-110° C. for 30 min. The reaction mixture was cooled to RT and extracted with EtOAc from water. The combined organic extracts were dried over $Na_2SO_4$, filtered and the filtrate concentrated in vacuo. Purification of the crude product thus obtained by way of flash chromatography ($SiO_2$, EtOAc→5:95 (v/v) 2.0 M $NH_3$ in MeOH:$CH_2Cl_2$) afforded the title compound as a light brown oil Step 2: trans-N-Cyclopropyl-4-(1-methyl-2-oxo-1,2-dihydro-4-pyridinyl)-N-({5-[3-(methyloxy)propyl]-3-biphenylyl}methyl)-3-piperidinecarboxamide To a $CH_2Cl_2$ solution (0.05 M) of trans-tert-butyl 3-[(cyclopropyl{[5-(3-methoxypropyl)biphenyl-3-yl]

methyl}amino)carbonyl]-4-(1-methyl-2-oxo-1,2-dihydro-pyridin-4-yl)piperidine-1-carboxylate (1 eq.) from the previous step was added HCl (4.0 M dioxane solution, 30 eq.). The resulting solution was stirred at RT for 45 min. Following the removal of the volatiles in vacuo, the resulting residue was directly loaded onto a SiO$_2$ column packed with 93:7 (v/v) CH$_2$Cl$_2$:2.0 M NH$_3$ in MeOH. Elution with the same solvent system furnished the title compound as a white froth. MS (ESI+, M+H): 514. Human Renin IC$_{50}$ (buffer): 15 nM. Human Renin IC$_{50}$ (plasma): 81 nM.

EXAMPLE 34 trans-N-Cyclopropyl-4-(1-methyl-2-oxo-1,2-dihydro-4-pyridinyl)-N-{[[3-(methyloxy)propyl]-5-(3-pyridinyl)phenyl]methyl}-3-piperidinecarboxamide

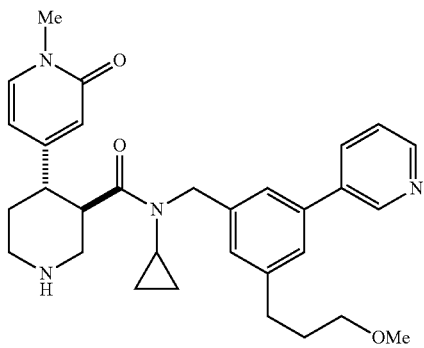

Prepared according to the procedure described in Example 33 but using instead pyridine-3-boronic acid as the starting material in step 1. The title compound was obtained as a white solid. MS (ESI+, M+H): 515.

EXAMPLE 35 trans-N-Cyclopropyl-N-[(2,3-dichloro-5-{[2-(methyloxy)ethyl]amino}phenyl)methyl]-4-(1-methyl-2-oxo-1,2-dihydro-4-pyridinyl)-3-piperidinecarboxamide

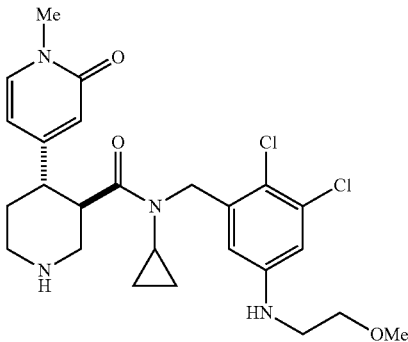

Step 1: trans-1,1-Dimethylethyl 3-({cyclopropyl[(2,3-dichloro-5-{[2-(methoxy)ethyl]amino}phenyl)methyl]amino}carbonyl)-4-(1-methyl-2-oxo-1,2-dihydro-4-pyridinyl)-1-piperidinecarboxylate Freshly purified cesium carbonate (1.4 eq.), palladium(II) acetate (0.02 eq.) and rac-BINAP (0.03 eq.) were combined in anhydrous toluene (0.08 M). The vessel was repeatedly evacuated and back-filled with nitrogen. Finally, trans-1,1-dimethylethyl 3-{[[(5-bromo-2,3-dichlorophenyl)methyl](cyclopropyl)amino]carbonyl}-4-(1-methyl-2-oxo-1,2-dihydro-4-pyridinyl)-1-piperidinecarboxylate (1.0 eq., Example 27) and 2-methoxyethylamine (1.2 eq.) were added and the resulting mixture was heated at 100° C. for 20 h. The now black suspension was cooled to RT, diluted with EtOAc and sat. aq. NH$_4$Cl. The organic layer was then separated, washed further with water and brine, dried over Na$_2$SO$_4$, filtered and the filtrate concentrated in vacuo. Purification of the crude product thus obtained by way of column chromatography (SiO$_2$, 96:4 CH$_2$Cl$_2$:2.0 M NH$_3$ in MeOH) afforded the title compound as a yellow oil.

Step 2: trans-N-Cyclopropyl-N-[(2,3-dichloro-5-{[2-(methyloxy)ethyl]amino}phenyl)methyl]-4-(1-methyl-2-oxo-1,2-dihydro-4-pyridinyl)-3-piperidinecarboxamide To a CH$_2$Cl$_2$ solution (0.09 M) of trans-1,1-dimethylethyl 3-({cyclopropyl[(2,3-dichloro-5-{[2-(methoxy)ethyl]amino}phenyl)methyl]amino}carbonyl)-4-(1-methyl-2-oxo-1,2-dihydro-4-pyridinyl)-1-piperidinecarboxylate (1 eq.) from the previous step was added HCl (4.0 M dioxane solution, 30 eq.). The resulting solution was stirred at RT for 4 h. Following the removal of the volatiles in vacuo, the resulting residue was directly loaded onto a SiO$_2$ column packed with 95:5 (v/v) CH$_2$Cl$_2$:2.0 M NH$_3$ in MeOH. Elution with the same solvent system furnished the desired compound but still contaminated with impurities. Further purification using preparatory HPLC-MS (C-18 reverse phase column, 15 mL/min, 95:5 (v/v) H$_2$O:CH$_3$CN→5:95 (v/v) H$_2$O:CH$_3$CN) afforded the title compound as a white solid. MS (ESI+, M+H): 508.

EXAMPLE 36 trans-N-Cyclopropyl-4-(1-methyl-2-oxo-1,2-dihydro-4-pyridinyl)-N-[(3-{[2-(methyloxy)ethyl]amino}-1-naphthalenyl)methyl]-3-piperidinecarboxamide

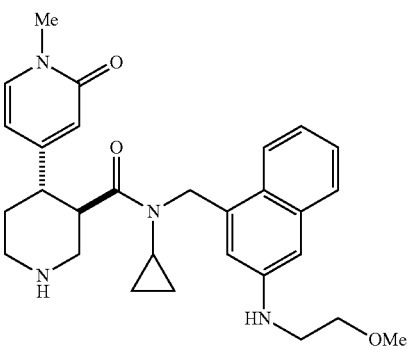

Prepared according to the procedure described in Example 1 but using instead Amine 29 as starting material. The title compound was obtained as a white solid. MS (ESI+, M+H): 489. Renin IC$_{50}$ (buffer): 5.3 nM. Human Renin IC$_{50}$ (plasma): 2.4 nM.

EXAMPLE 37
trans-N-[6-(2-cyanoethyl)-8-quinolinyl]methyl 1-N-cyclopropyl-4-(1-methyl-2-oxo-1,2-dihydro-4-pyridinyl)-3-piperidinecarboxamide

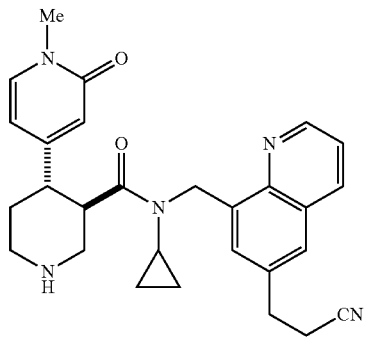

Prepared according to the procedure described in Example 1 but using instead Amine 30 as starting material and zinc(II) bromide-promoted BOC-deprotection as in Example 14, Step 8. The title compound was obtained as a white froth. MS (ESI+, M+H): 470.

EXAMPLE 38
trans-N-Cyclopropyl-4-(1-methyl-2-oxo-1,2-dihydro-4-pyridinyl)-N-({3-[2-(methyloxy)ethyl]-1-naphthalenyl}methyl)-3-piperidinecarboxamide

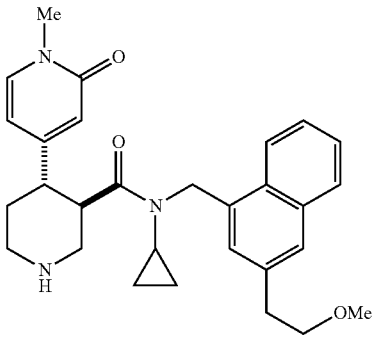

Prepared according to the procedure described in Example 1 but using instead Amine 31 as starting material. The title compound was obtained as a white solid. MS (ESI+, M+H): 474.

EXAMPLE 39
trans-N-({3-[2-(Acetylamino)ethyl]-1-naphthalenyl}methyl)-N-cyclopropyl-4-(1-methyl-2-oxo-1,2-dihydro-4-pyridinyl)-3-piperidinecarboxamide

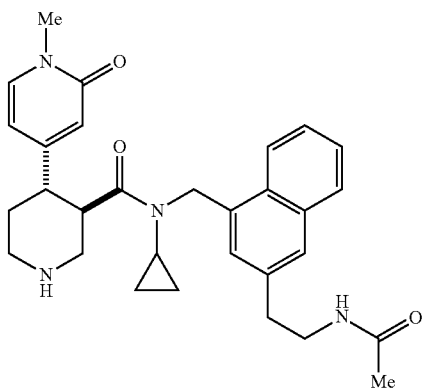

Prepared according to the procedure described in Example 1 but using instead Amine 32 as starting material. The title compound was obtained as a white solid. MS (ESI+, M+H): 501.

EXAMPLE 40
trans-N-[(2-Bromophenyl)methyl]-N-cyclopropyl-4-(1-methyl-2-oxo-1,2-dihydro-4-pyridinyl)-3-piperidinecarboxamide

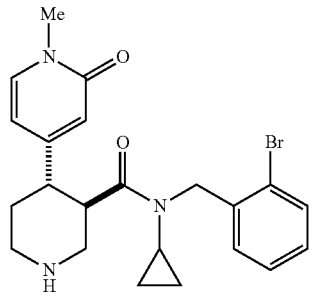

Prepared according to the procedure described in Example 1 but using instead Amine 33 as starting material. The title compound was obtained as a white solid. MS (ESI+, M+H): 444.

EXAMPLE 41
trans-N-Cyclopropyl-4-(1-methyl-2-oxo-1,2-dihydro-4-pyridinyl)-N-({1-[2-(methyloxy)ethyl]-1H-indol-3-yl}methyl)-3-piperidinecarboxamide

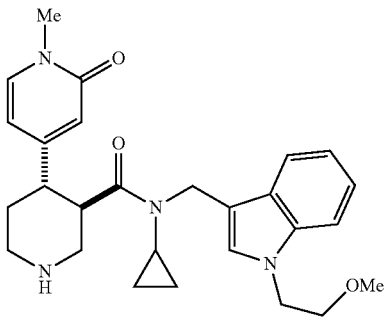

Prepared according to the procedure described in Example 1 but using instead Amine 34 as starting material and zinc(II) bromide-promoted BOC-deprotection as in Example 14, Step 8. The title compound was obtained as a white froth. MS (ESI+, M+Na): 485.

EXAMPLE 42
trans-N-Cyclopropyl-4-(1-methyl-2-oxo-1,2-dihydro-4-pyridinyl)-N-{[1-(2,2,2-trifluoroethyl)-1H-indol-3-yl]methyl}-3-piperidinecarboxamide

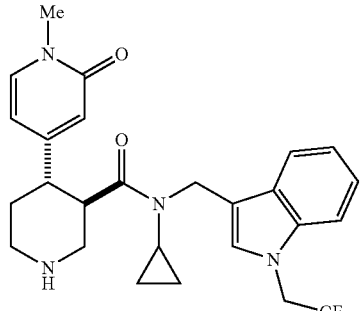

Prepared according to the procedure described in Example 1 but using instead Amine 35 as starting material and zinc(II)

bromide-promoted BOC-deprotection as in Example 14, Step 8. The title compound was obtained as a white froth. MS (ESI+, M+H): 487.

EXAMPLE 43 trans-N-Cyclopropyl-4-(1-methyl-2-oxo-1,2-dihydro-4-pyridinyl)-N-{[1-(4,4,4-trifluorobutyl)-1H-indol-3-yl]methyl}-3-piperidinecarboxamide

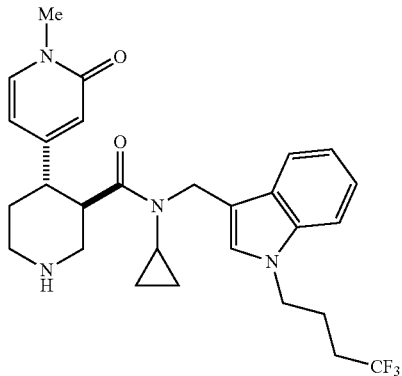

Prepared according to the procedure described in Example 1 but using instead Amine 36 as starting material and zinc(II) bromide-promoted BOC-deprotection as in Example 14, Step 8. The title compound was obtained as a white froth. MS (ESI+, M+H): 515.

EXAMPLE 44 trans-N-[(1-Butyl-1H-indol-3-yl)methyl]-N-cyclopropyl-4-(1-methyl-2-oxo-1,2-dihydro-4-pyridinyl)-3-piperidinecarboxamide

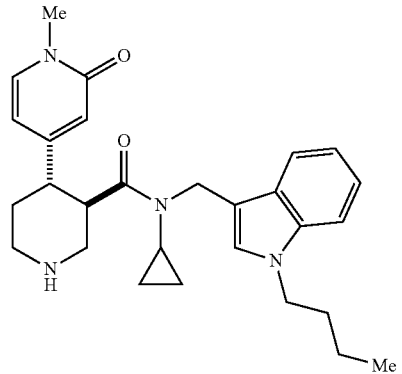

Prepared according to the procedure described in Example 1 but using instead Amine 37 as starting material and zinc(II) bromide-promoted BOC-deprotection as in Example 14, Step 8. The title compound was obtained as a white froth. MS (ESI+, M+H): 461.

EXAMPLE 45 trans-N-Cyclopropyl-N-({1-[3-(ethyloxy)propyl]-1H-indol-3-yl}methyl)-4-(1-methyl-2-oxo-1,2-dihydro-4-pyridinyl)-3-piperidinecarboxamide

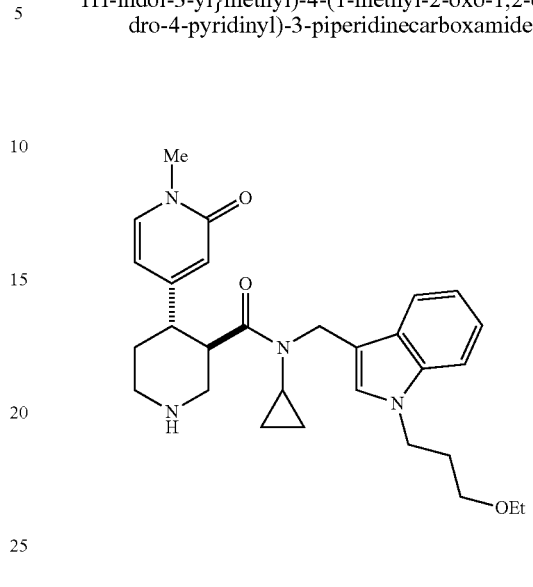

Prepared according to the procedure described in Example 1 but using instead Amine 38 as starting material and zinc(II) bromide-promoted BOC-deprotection as in Example 14, Step 8. The title compound was obtained as a white froth. MS (ESI+, M+H): 491.

EXAMPLE 46 trans-N-Cyclopropyl-4-(1-methyl-2-oxo-1,2-dihydro-4-pyridinyl)-N-({1-[3,3,3-trifluoro-2-(trifluoromethyl)propyl]-1H-indol-3-yl}methyl)-3-piperidinecarboxamide

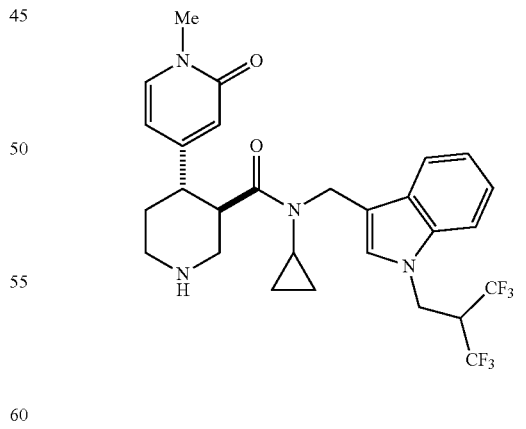

Prepared according to the procedure described in Example 1 but using instead Amine 39 as starting material and zinc(II) bromide-promoted BOC-deprotection as in Example 14, Step 8. The title compound was obtained as a white froth. MS (ESI+, M+H): 569.

EXAMPLE 47 trans-N-({1-[3-(Acetylamino)propyl]-1H-indol-3-yl}methyl)-N-cyclopropyl-4-(1-methyl-2-oxo-1,2-dihydro-4-pyridinyl)-3-piperidinecarboxamide

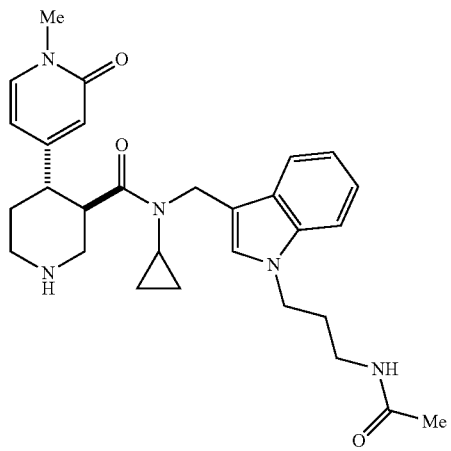

Prepared according to the procedure described in Example 1 but using instead Amine 40 as starting material and zinc(II) bromide-promoted BOC-deprotection as in Example 14, Step 8. The title compound was obtained as a white froth. MS (ESI+, M+H): 504.

EXAMPLE 48 trans-N-Cyclopropyl-4-(1-methyl-2-oxo-1,2-dihydro-4-pyridinyl)-N-({1-[3-(propanoylamino)propyl]-1H-indol-3-yl}methyl)-3-piperidinecarboxamide

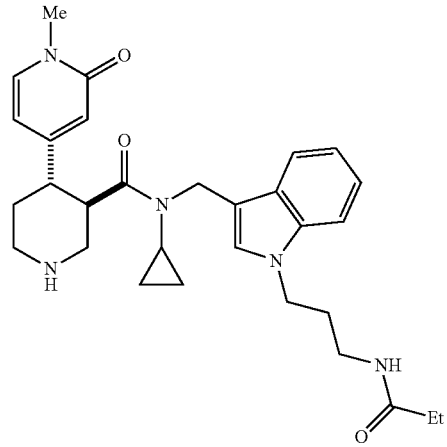

Prepared according to the procedure described in Example 1 but using instead Amine 41 as starting material and zinc(II) bromide-promoted BOC-deprotection as in Example 14, Step 8. The title compound was obtained as a white froth. MS (ESI+, M+H): 518.

EXAMPLE 49 trans-N-({1-[2-(Acetylamino)ethyl]-1H-indol-3-yl}methyl)-N-cyclopropyl-4-(1-methyl-2-oxo-1,2-dihydro-4-pyridinyl)-3-piperidinecarboxamide

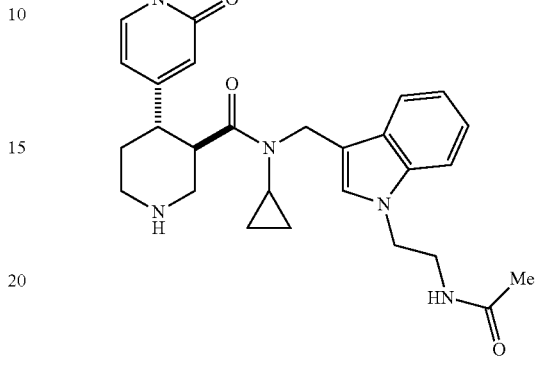

Prepared according to the procedure described in Example 1 but using instead Amine 42 as starting material and zinc(II) bromide-promoted BOC-deprotection as in Example 14, Step 8. The title compound was obtained as a white froth. MS (ESI+, M+H): 490.

EXAMPLE 50 trans-N-Cyclopropyl-4-(1-methyl-2-oxo-1,2-dihydro-4-pyridinyl)-N-({1-[2-(propanoylamino)ethyl]-1H-indol-3-yl}methyl)-3-piperidinecarboxamide

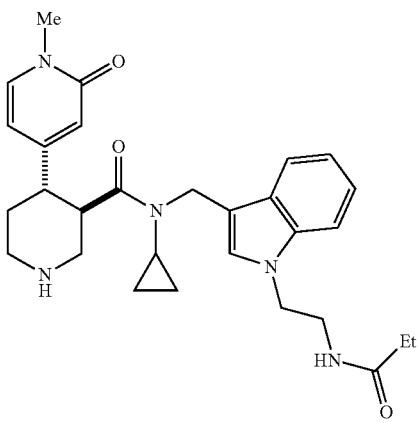

Prepared according to the procedure described in Example 1 but using instead Amine 43 as starting material and zinc(II) bromide-promoted BOC-deprotection as in Example 14, Step 8. The title compound was obtained as a white froth. MS (ESI+, M+H): 504.

EXAMPLE 51 trans-N-Cyclopropyl-4-(1-methyl-2-oxo-1,2-dihydro-4-pyridinyl)-N-{[1-(2-propen-1-yl)-1H-indol-3-yl]methyl}-3-piperidinecarboxamide

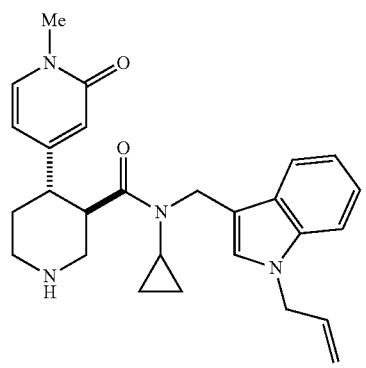

Prepared according to the procedure described in Example 1 but using instead Amine 44 as starting material and zinc(II) bromide-promoted BOC-deprotection as in Example 14, Step 8. The title compound was obtained as a white froth. MS (ESI+, M+H): 445.

EXAMPLE 52 trans-N-Cyclopropyl-4-(1-methyl-2-oxo-1,2-dihydro-4-pyridinyl)-N-{[1-(phenylmethyl)-1H-indol-3-yl]methyl}-3-piperidinecarboxamide

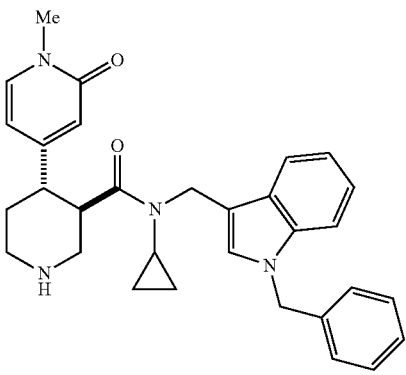

Prepared according to the procedure described in Example 1 but using instead Amine 45 as starting material and zinc(II) bromide-promoted BOC-deprotection as in Example 14, Step 8. The title compound was obtained as a white froth. MS (ESI+, M+H): 495.

EXAMPLE 53 trans-N-Cyclopropyl-4-(1-methyl-2-oxo-1,2-dihydro-4-pyridinyl)-N-{[1-(2-pyridinylmethyl)-1H-indol-3-yl]methyl}-3-piperidinecarboxamide

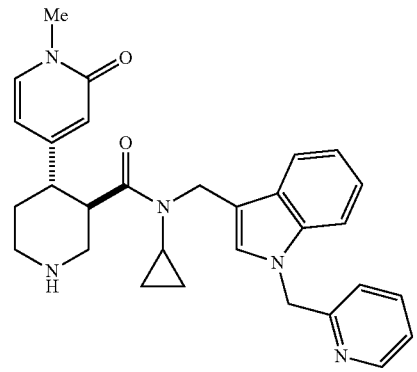

Prepared according to the procedure described in Example 1 but using instead Amine 46 as starting material and zinc(II) bromide-promoted BOC-deprotection as in Example 14, Step 8. The title compound was obtained as a white froth. MS (ESI+, M+H): 496.

EXAMPLE 54 trans-N-Cyclopropyl-4-(1-methyl-2-oxo-1,2-dihydro-4-pyridinyl)-N-{[1-(3-pyridinylmethyl)-1H-indol-3-yl]methyl}-3-piperidinecarboxamide

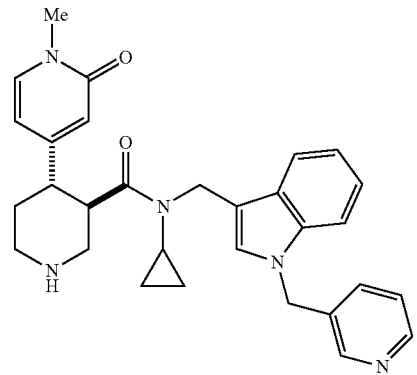

Prepared according to the procedure described in Example 1 but using instead Amine 47 as starting material and zinc(II) bromide-promoted BOC-deprotection as in Example 14, Step 8. The title compound was obtained as a white froth. MS (ESI+, M+H): 496.

EXAMPLE 55 trans-N-Cyclopropyl-4-(1-methyl-2-oxo-1,2-dihydro-4-pyridinyl)-N-{[1-(4-pyridinylmethyl)-1H-indol-3-yl]methyl}-3-piperidinecarboxamide

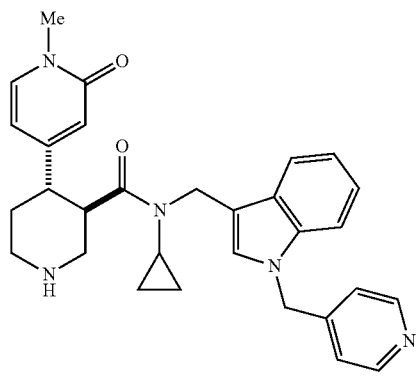

Prepared according to the procedure described in Example 1 but using instead Amine 48 as starting material and zinc(II) bromide-promoted BOC-deprotection as in Example 14, Step 8. The title compound was obtained as a white froth. MS (ESI+, M+H): 496.

EXAMPLE 56 trans-N-Cyclopropyl-N-({1-[(4-fluorophenyl)methyl]-1H-indol-3-yl}methyl)-4-(1-methyl-2-oxo-1,2-dihydro-4-pyridinyl)-3-piperidinecarboxamide

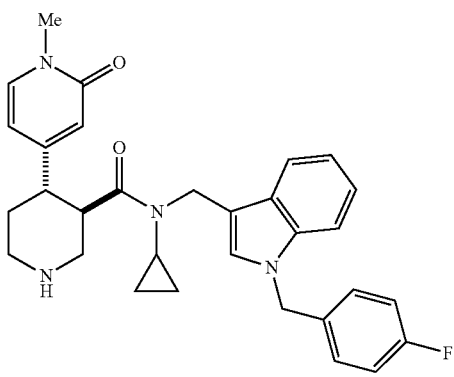

Prepared according to the procedure described in Example 1 but using instead Amine 49 as starting material and zinc(II) bromide-promoted BOC-deprotection as in Example 14, Step 8. The title compound was obtained as a white froth. MS (ESI+, M+H): 513.

EXAMPLE 57 trans-N-({1-[(4-Chlorophenyl)methyl]-1H-indol-3-yl}methyl)-N-cyclopropyl-4-(1-methyl-2-oxo-1,2-dihydro-4-pyridinyl)-3-piperidinecarboxamide

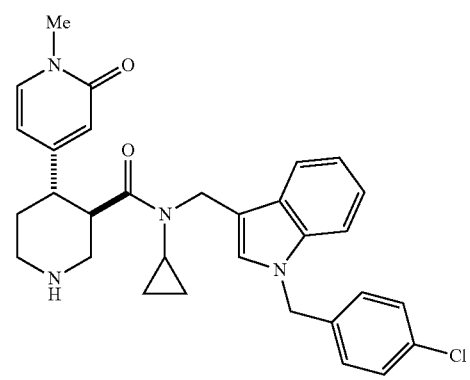

Prepared according to the procedure described in Example 1 but using instead Amine 50 as starting material and zinc(II) bromide-promoted BOC-deprotection as in Example 14, Step 8. The title compound was obtained as a white froth. MS (ESI+, M+H): 529.

EXAMPLE 58 trans-N-Cyclopropyl-N-({1-[(3-fluorophenyl)methyl]-1H-indol-3-yl}methyl)-4-(1-methyl-2-oxo-1,2-dihydro-4-pyridinyl)-3-piperidinecarboxamide

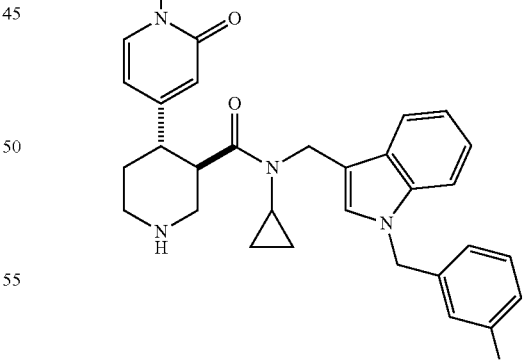

Prepared according to the procedure described in Example 1 but using instead Amine 51 as starting material and zinc(II) bromide-promoted BOC-deprotection as in Example 14, Step 8. The title compound was obtained as a white froth. MS (ESI+, M+H): 513.

EXAMPLE 59 trans-N-({1-[(3-Chlorophenyl)methyl]-1H-indol-3-yl}methyl)-N-cyclopropyl-4-(1-methyl-2-oxo-1,2-dihydro-4-pyridinyl)-3-piperidinecarboxamide

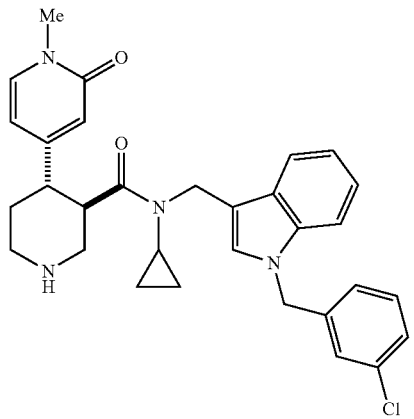

Prepared according to the procedure described in Example 1 but using instead Amine 52 as starting material and zinc(II) bromide-promoted BOC-deprotection as in Example 14, Step 8. The title compound was obtained as a white froth. MS (ESI+, M+H): 529.

EXAMPLE 60 trans-N-({1-[(3-Cyanophenyl)methyl]-1H-indol-3-yl}methyl)-N-cyclopropyl-4-(1-methyl-2-oxo-1,2-dihydro-4-pyridinyl)-3-piperidinecarboxamide

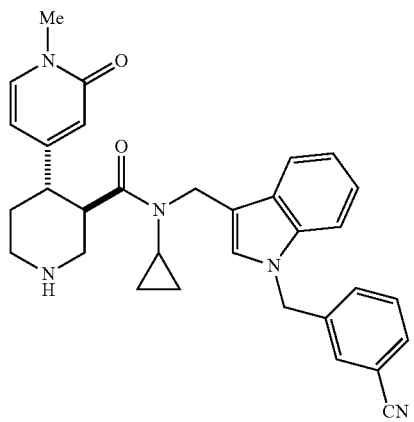

Prepared according to the procedure described in Example 1 but using instead Amine 53 as starting material and zinc(II) bromide-promoted BOC-deprotection as in Example 14, Step 8. The title compound was obtained as a white froth. MS (ESI+, M+H): 520.

EXAMPLE 61 trans-N-Cyclopropyl-4-(1-methyl-2-oxo-1,2-dihydro-4-pyridinyl)-N-({1-[(3-methylphenyl)methyl]-1H-indol-3-yl}methyl)-3-piperidinecarboxamide

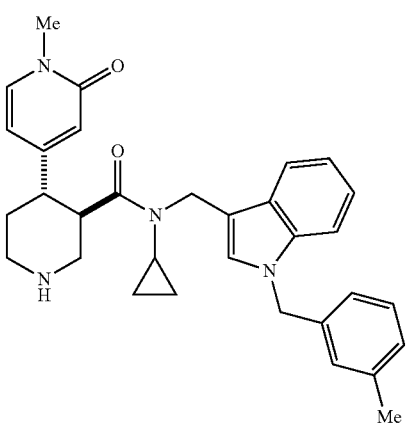

Prepared according to the procedure described in Example 1 but using instead Amine 54 as starting material and zinc(II) bromide-promoted BOC-deprotection as in Example 14, Step 8. The title compound was obtained as a white froth. MS (ESI+, M+H): 509.

EXAMPLE 62 trans-N-Cyclopropyl-N-({5-fluoro-1-[3-(methyloxy)propyl]-1H-indol-3-yl}methyl)-4-(1-methyl-2-oxo-1,2-dihydro-4-pyridinyl)-3-piperidinecarboxamide

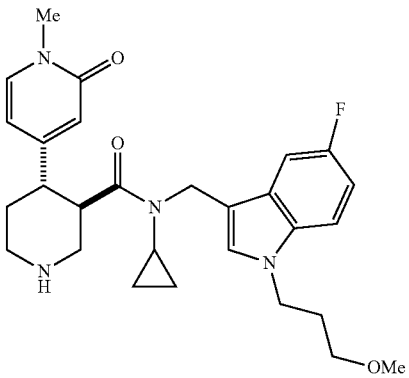

Prepared according to the procedure described in Example 1 but using instead Amine 55 as starting material and zinc(II) bromide-promoted BOC-deprotection as in Example 14, Step 8. The title compound was obtained as a white froth. MS (ESI+, M+H): 495.

EXAMPLE 63 trans-N-{[6-Bromo-1-(phenylmethyl)-1H-indol-3-yl]methyl}-N-cyclopropyl-4-(1-methyl-2-oxo-1,2-dihydro-4-pyridinyl)-3-piperidinecarboxamide

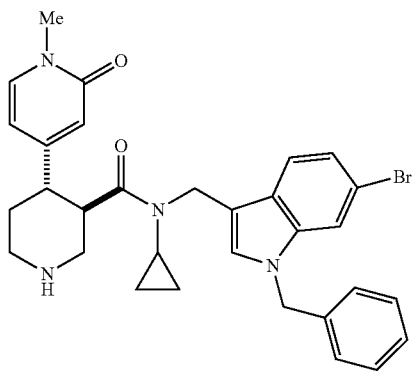

Prepared according to the procedure described in Example 1 but using instead Amine 56 as starting material and zinc(II) bromide-promoted BOC-deprotection as in Example 14, Step 8. The title compound was obtained as a white froth. MS (ESI+, M+H): 573.

EXAMPLE 64 trans-N-Cyclopropyl-N-{[1-[(3-fluorophenyl)methyl]-6-(methyloxy)-1H-indol-3-yl]methyl}-4-(1-methyl-2-oxo-1,2-dihydro-4-pyridinyl)-3-piperidinecarboxamide

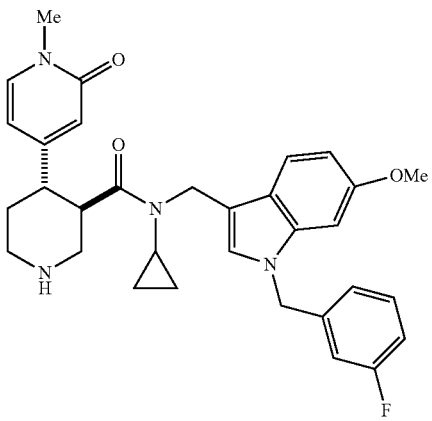

Prepared according to the procedure described in Example 1 but using instead Amine 57 as starting material and zinc(II) bromide-promoted BOC-deprotection as in Example 14, Step 8. The title compound was obtained as a white froth. MS (ESI+, M+H): 543.

EXAMPLE 65 trans-N-Cyclopropyl-4-(1-methyl-2-oxo-1,2-dihydro-4-pyridinyl)-N-{[4-methyl-1-(phenylmethyl)-1H-indol-3-yl]methyl}-3-piperidinecarboxamide

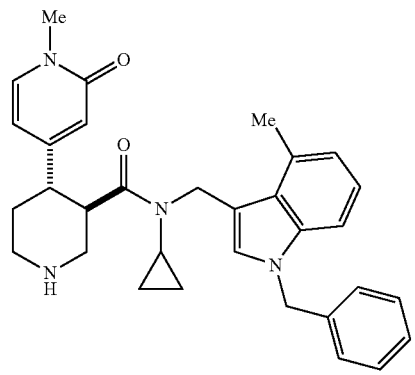

Prepared according to the procedure described in Example 1 but using instead Amine 58 as starting material and zinc(II) bromide-promoted BOC-deprotection as in Example 14, Step 8. The title compound was obtained as a white froth. MS (ESI+, M+H): 509.

EXAMPLE 66 trans-N-{[4-Cyano-1-(phenylmethyl)-1H-indol-3-yl]methyl}-N-cyclopropyl-4-(1-methyl-2-oxo-1,2-dihydro-4-pyridinyl)-3-piperidinecarboxamide

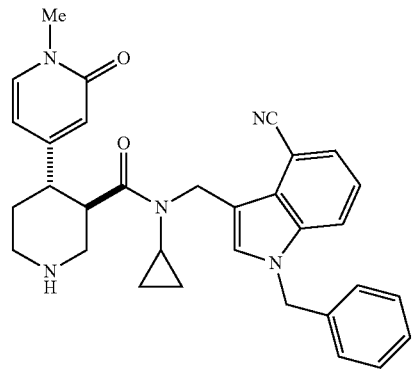

Prepared according to the procedure described in Example 1 but using instead Amine 59 as starting material and zinc(II) bromide-promoted BOC-deprotection as in Example 14, Step 8. The title compound was obtained as a white froth. MS (ESI+, M+H): 520.

EXAMPLE 67 trans-N-Cyclopropyl-N-[4-fluoro-1-(phenylmethyl)-1H-indol-3-yl]methyl)-4-(1-methyl-2-oxo-1,2-dihydro-4-pyridinyl)-3-piperidinecarboxamide

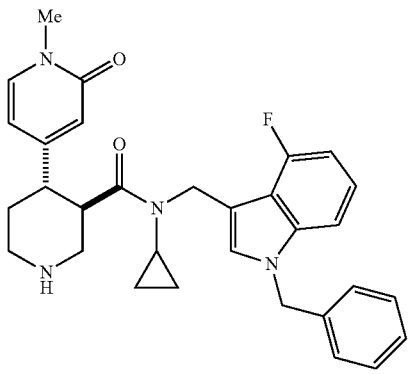

Prepared according to the procedure described in Example 1 but using instead Amine 60 as starting material and zinc(II) bromide-promoted BOC-deprotection as in Example 14, Step 8. The title compound was obtained as a white froth. MS (ESI+, M+H): 513.

EXAMPLE 68 trans-N-Cyclopropyl-N-({4-fluoro-1-[(3-fluorophenyl)methyl]-1H-indol-3-yl]methyl}-4-(1-methyl-2-oxo-1,2-dihydro-4-pyridinyl)-3-piperidinecarboxamide

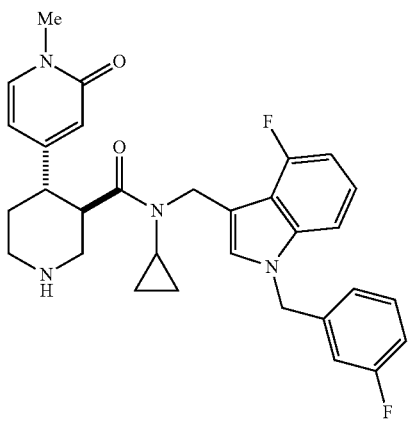

Prepared according to the procedure described in Example 1 but using instead Amine 61 as starting material and zinc(II) bromide-promoted BOC-deprotection as in Example 14, Step 8. The title compound was obtained as a white froth. MS (ESI+, M+H): 531. Human Renin IC$_{50}$ (buffer): 0.06 nM. Human Renin IC$_{50}$ (plasma): 0.6 nM.

EXAMPLE 69 trans-N-Cyclopropyl-N-({4-fluoro-1-[3-(methyloxy)propyl]-1H-indol-3-yl}methyl)-4-(1-methyl-2-oxo-1,2-dihydro-4-pyridinyl)-3-piperidinecarboxamide

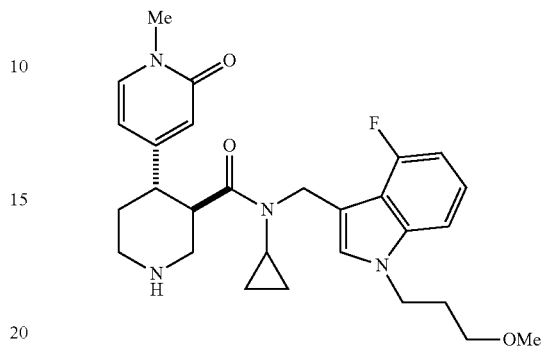

Prepared according to the procedure described in Example 1 but using instead Amine 62 as starting material and zinc(II) bromide-promoted BOC-deprotection as in Example 14, Step 8. The title compound was obtained as a white froth. MS (ESI+, M+H): 495. $^1$H NMR (CD$_3$OD) δ (ppm): 0.56-0.71 (m, 1H), 0.76-0.98 (m, 3H), 1.50-1.70 (m, 2H), 1.90 (m, 2H), 2.52 (m, 1H), 2.60-2.71 (m, 2H), 2.88 (td, J=11.6, 3.9 Hz, 1H), 3.05 (br d, J=7.0 Hz, 1H), 3.09-3.19 (m, 3H), 3.23, (s, 3H) 3.27 (s, 3H) 3.43-3.58 (m, 1H), 4.00-4.21 (m, 2H), 4.41 (d, J=14.8 Hz, 1 H), 4.7 (m, 2H), 6.11-6.22 (m, 1H), 6.30 (d, J=1.8 Hz, 1H), 6.54-6.67 (m, 1H), 6.74 (s, 1H), 6.93-7.04 (m, 1H), 7.10 (d, J=4.0 Hz, 1H), 7.16 (d, J=3.6 Hz, 1H). Human Renin IC$_{50}$ (buffer): 0.3 nM. Human Renin IC$_{50}$ (plasma): 0.9 nM.

EXAMPLE 70 trans-N-({4-Chloro-1-[3-(methyloxy)propyl]-1H-indol-3-yl}methyl)-N-cyclopropyl-4-(1-methyl-2-oxo-1,2-dihydro-4-pyridinyl)-3-piperidinecarboxamide

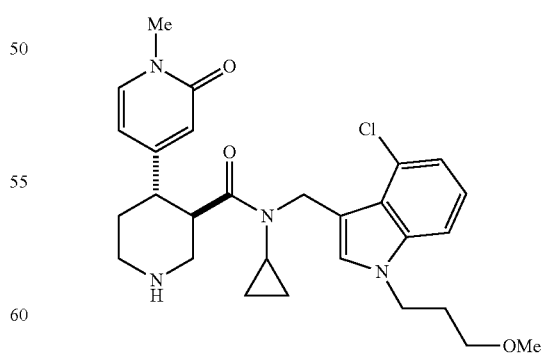

Prepared according to the procedure described in Example 1 but using instead Amine 63 as starting material and zinc(II) bromide-promoted BOC-deprotection as in Example 14, Step 8. The title compound was obtained as a white froth. MS (ESI+, M+H): 511.

EXAMPLE 71 trans-N-{[4-Chloro-1-(phenylmethyl)-1H-indol-3-yl]methyl}-N-cyclopropyl-4-(1-methyl-2-oxo-1,2-dihydro-4-pyridinyl)-3-piperidinecarboxamide

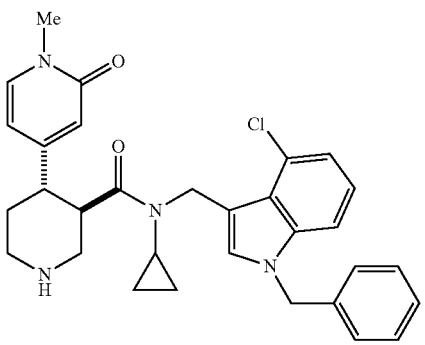

Prepared according to the procedure described in Example 1 but using instead Amine 64 as starting material and zinc(II) bromide-promoted BOC-deprotection as in Example 14, Step 8. The title compound was obtained as a white froth. MS (ESI+, M+H): 529.

EXAMPLE 72 trans-N-{[4-Bromo-1-(phenylmethyl)-1H-indol-3-yl]methyl}-N-cyclopropyl-4-(1-methyl-2-oxo-1,2-dihydro-4-pyridinyl)-3-piperidinecarboxamide

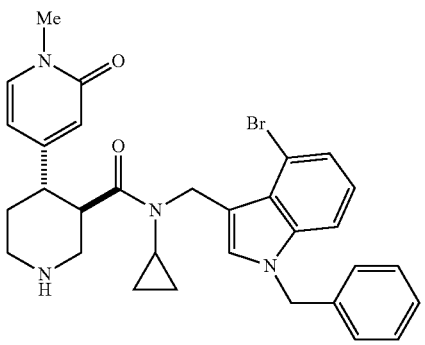

Prepared according to the procedure described in Example 1 but using instead Amine 65 as starting material and zinc(II) bromide-promoted BOC-deprotection as in Example 14, Step 8. The title compound was obtained as a white froth. MS (ESI+, M+H): 575.

EXAMPLE 73 trans-N-({4-Bromo-1-[(3-fluorophenyl)methyl]-1H-indol-3-yl}methyl)-N-cyclopropyl-4-(1-methyl-2-oxo-1,2-dihydro-4-pyridinyl)-3-piperidinecarboxamide

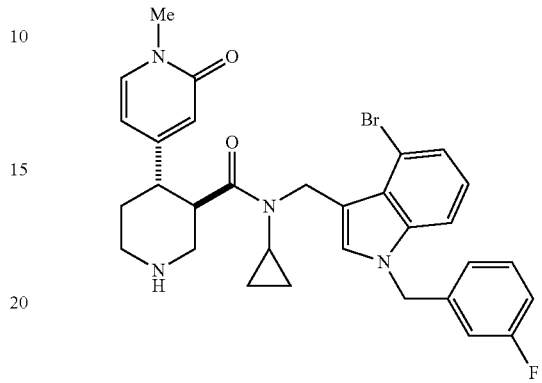

Prepared according to the procedure described in Example 1 but using instead Amine 66 as starting material and zinc(II) bromide-promoted BOC-deprotection as in Example 14, Step 8. The title compound was obtained as a white froth. MS (ESI+, M+H): 591.3. $^1$H NMR (DMSO-$d_6$): δ (ppm) 0.60-0.66 (m, 1H), 0.89-0.94 (m, 3H), 1.56 (dd, J=13.3, 10.6 Hz, 1H), 1.67 (d, J=12.6 Hz, 1H), 2.58 (dt, J=12.4, 2.2 Hz, 1H), 2.71 (s, 3H), 2.83-2.94 (m, 2H), 3.04 (br d, J=6.1 Hz, 1H), 3.23 (s, 3H), 3.3 (dd, J=6.7, 4.0 Hz, 1H), 3.04 (d, J=12.3 Hz, 1H), 4.87 (q, J=10.1 Hz, 2H), 5.35 (d, J=2.6 Hz, 2H), 6.16-6.23 (m, 1H), 6.79 (s, 1H), 6.88 (d, J=8.3 Hz, 2H), 6.99 (t, J=7.9 Hz, 1H), 7.05-7.12 (m, 1H), 7.20 (d, J=7.5 Hz, 1H), 7.29-7.40 (m, 2H), 7.54 (d, J=6.9 Hz, 1H). Human Renin IC$_{50}$ (buffer): <0.06 nM. Human Renin IC$_{50}$ (plasma): 0.5 nM.

EXAMPLE 74 trans-N-({Bromo-[3-(methyloxy)propyl]-1H-indol-3-yl}methyl)-N-cyclopropyl-4-(1-methyl-2-oxo-1,2-dihydro-4-pyridinyl)-3-piperidinecarboxamide

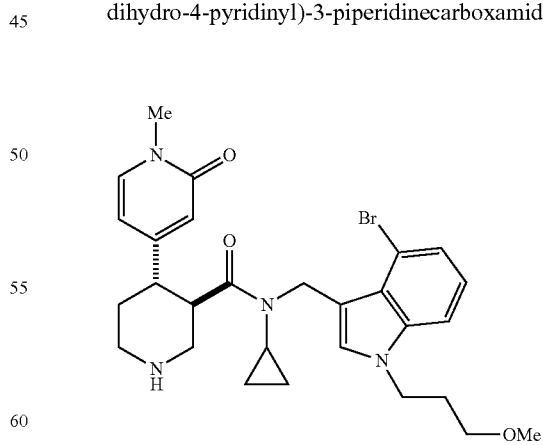

Prepared according to the procedure described in Example 1 but using instead Amine 67 as starting material and zinc(II) bromide-promoted BOC-deprotection as in Example 14, Step 8. The title compound was obtained as a white froth. MS (ESI+, M+H): 557.

EXAMPLE 75 trans-N-Cyclopropyl-N-[(4-fluoro-1H-indol-3-yl)methyl]-4-(1-methyl-2-oxo-1,2-dihydro-4-pyridinyl)-3-piperidinecarboxamide

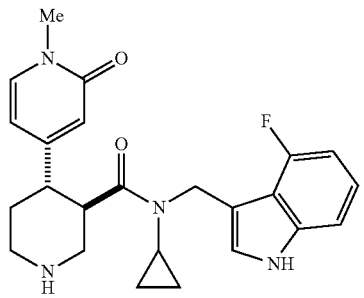

Step 1: trans-1,1-Dimethylethyl 3-({cyclopropyl[(4-fluoro-1H-indol-3-yl)methyl]amino}-carbonyl)-4-(1-methyl-2-oxo-1,2-dihydro-4-pyridinyl)-1-piperidinecarboxylate To a DMF (0.1 M) solution of trans-1-{[(1,1-dimethylethyl)oxy]carbonyl}-4-(1-methyl-2-oxo-1,2-dihydro-4-pyridinyl)-3-piperidinecarboxylic acid (1 eq., Example 1, Step 6), Hunig's base (3 eq.) and Amine 68 (1 eq.) was added portionwise O-(7-azabenzotriazol-1-yl)-N,N,N',N'-tetramethyluronium hexafluorophosphate (1.2 eq.). The resulting reaction solution was stirred at RT for 48 h. The now yellow solution was diluted with EtOAc and washed sequentially with 10% aq. HCl, water and brine. The organic extract was then dried over $Na_2SO_4$, filtered and the filtrate concentrated in vacuo to afford a black oil. Purification of the crude product thus obtained by way of flash chromatography ($SiO_2$, $CH_2Cl_2 \rightarrow 90:10$ (v/v) $CH_2Cl_2$:2.0 M $NH_3$ in MeOH) afforded the title compound as a white solid.

Step 2: trans-N-Cyclopropyl-N-[(4-fluoro-1H-indol-3-yl)methyl]-4-(1-methyl-2-oxo-1,2-dihydro-4-pyridinyl)-3-piperidinecarboxamide To a $CH_2Cl_2$ solution (0.05 M) of trans-1,1-dimethylethyl-3-({cyclopropyl[(4-fluoro-1H-indol-3-yl)methyl]amino}carbonyl)-4-(1-methyl-2-oxo-1,2-dihydro-4-pyridinyl)-1-piperidinecarboxylate (1 eq.) from the previous step was added zinc(II) bromide (10 eq.). The resulting suspension was sonicated for 15 min and stirred at RT for 13 h. The reaction was quenched with the addition of EtOAc and 1 N aq. NaOH, and then sonicated for 15 min. The aqueous phase was separated and back-extracted with EtOAc. The combined organic extracts were washed further with water and brine, dried over $Na_2SO_4$, filtered and the filtrate concentrated in vacuo. Purification of the crude product thus obtained by way of flash chromatography ($SiO_2$, 90:10 (v/v) $CH_2Cl_2$:2.0 M $NH_3$ in MeOH) afforded the title compound as a colorless oil. MS (ESI+, M+H): 423. $^1$H NMR ($CD_3OD$) δ (ppm): 0.79 (m, 1H), 0.87-0.99 (m, 2H), 0.99-1.11 (m, 1H), 1.65-1.75 (m, 1H), 1.78 (m, 1H), 2.53 (m, 1H), 2.72-2.82 (m, 2H), 2.89-3.00 (m, 1H), 3.14-3.26 (m, 2H), 3.34 (s, 3H), 3.51-3.67 (m, 1H), 4.43 (d, J=14.7 Hz, 1H), 4.96 (d, J=14.7 Hz, 1H), 6.18 (m, 1H), 6.39 (s, 1H), 6.66 (m, 1H), 6.88 (s, 1H), 6.99-7.06 (m, 1H), 7.14-7.18 (m, 2H). Human Renin $IC_{50}$ (buffer): 12.7 nM. Human Renin $IC_{50}$ (plasma): 8.4 nM.

EXAMPLE 76 trans-N-Cyclopropyl-N-{[4-fluoro-1-(3-pyridinylmethyl)-1H-indol-3-yl]methyl}-4-(1-methyl-2-oxo-1,2-dihydro-4-pyridinyl)-3-piperidinecarboxamide

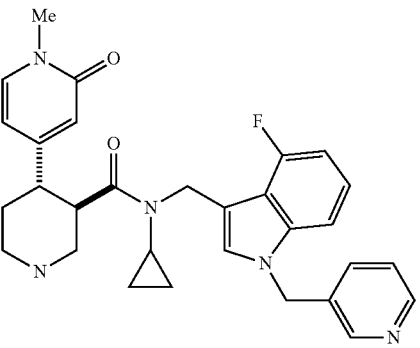

Step 1: trans-1,1-Dimethylethyl 3-[(cyclopropyl{[4-fluoro-1-(3-pyridinylmethyl)-1H-indol-3-yl]methyl}amino)carbonyl]-4-(1-methyl-2-oxo-1,2-dihydro-4-pyridinyl)-1-piperidinecarboxylate To a DMF (0.1 M) solution of trans-1,1-dimethylethyl 3-({cyclopropyl[(4-fluoro-1H-indol-3-yl)methyl]amino}carbonyl)-4-(1-methyl-2-oxo-1,2-dihydro-4-pyridinyl)-1-piperidinecarboxylate (1 eq., Example 75, Step 1) was added sequentially at 0° C. KHMDS (15% w/v solution in toluene, 1.1 eq.) and 3-picolyl chloride (1.3 eq.). The resulting solution was then allowed to warm slowly to RT over 16 h. The mixture was re-cooled to 0° C. before it was diluted with EtOAc and then carefully quenched with sat. aq. $NaHCO_3$. The aqueous layer was separated and back-extracted with EtOAc. The combined organic extracts were washed further with sat. aq, $NaHCO_3$ and brine, dried over $Na_2SO_4$, filtered and the filtrate concentrated in vacuo. Purification of the crude product thus obtained by way of flash chromatography ($SiO_2$, $CH_2Cl_2 \rightarrow 90:10$ (v/v) $CH_2Cl_2$:2.0 M $NH_3$ in MeOH) afforded the title compound as a white foam.

Step 2: trans-N-Cyclopropyl-N-{[4-fluoro-1-(3-pyridinylmethyl)-1H-indol-3-yl]methyl}-4-(1-methyl-2-oxo-1,2-dihydro-4-pyridinyl)-3-piperidinecarboxamide To a $CH_2Cl_2$ solution (0.05 M) of trans-1,1-dimethylethyl 3-[(cyclopropyl{[4-fluoro-1-(3-pyridinylmethyl)-1H-indol-3-yl]methyl}amino)carbonyl]-4-(1-methyl-2-oxo-1,2-dihydro-4-pyridinyl)-1-piperidinecarboxylate (1 eq.) from previous step was added zinc(II) bromide (10 eq.). The resulting suspension was sonicated for 15 min and stirred at RT for 13 h. The reaction was quenched with the addition of EtOAc and 1 N aq. NaOH, and then sonicated for 15 min. The aqueous phase was separated and back-extracted with EtOAc. The combined organic extracts were washed further with water and brine, dried over $Na_2SO_4$, filtered and the filtrate concentrated in vacuo. Purification of the crude product thus obtained by way of flash chromatography ($SiO_2$, 90:10 (v/v) $CH_2Cl_2$:2.0 M $NH_3$ in MeOH) afforded the title compound as a colorless oil. MS (ESI+, M+H): 514.

EXAMPLE 77 trans-N-Cyclopropyl-N-{[4-fluoro-1-(4-pyridinylmethyl)-1H-indol-3-yl]methyl}-4-(1-methyl-2-oxo-1,2-dihydro-4-pyridinyl)-3-piperidinecarboxamide

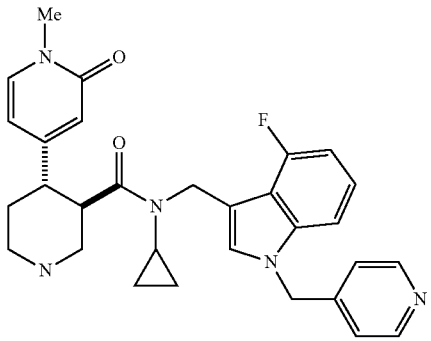

Prepared according to the procedure described in Example 76, but using instead 4-picolyl chloride as the alkylation reagent in Step 1. The title compound was obtained as a white froth. MS (ESI+, M+H): 514. Human Renin $IC_{50}$ (buffer): 0.2 nM. Human Renin $IC_{50}$ (plasma): 0.5 nM.

EXAMPLE 78 trans-N-({3-Acetyl-5-[3-(methyloxy)propyl]phenyl}methyl)-N-cyclopropyl-4-(1-methyl-2-oxo-1,2-dihydro-4-pyridinyl)-3-piperidinecarboxamide

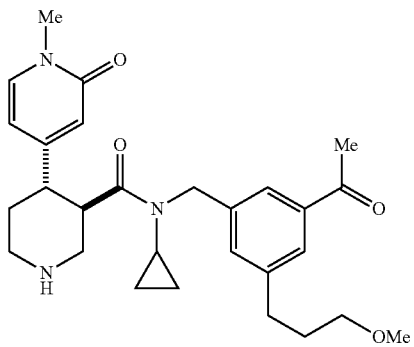

Prepared according to the procedure described in Example 1 but using instead Amine 69 as starting material. The title compound was obtained as a white froth. MS (ESI+, M+H): 480.

EXAMPLE 79 trans-N-({1,3-Bis[3-(methyloxy)propyl]-2,4-dioxo-1,2,3,4-tetrahydro-5-pyrimidinyl}methyl)-N-cyclopropyl-4-(1-methyl-2-oxo-1,2-dihydro-4-pyridinyl)-3-piperidinecarboxamide

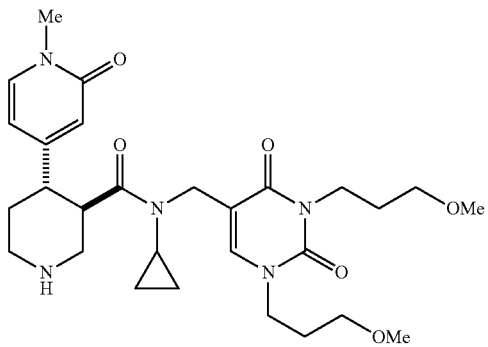

Prepared according to the procedure described in Example 1 but using instead Amine 70 as starting material. The title compound was obtained as a white froth. MS (ESI+, M+H): 544. Human Renin $IC_{50}$ (buffer): 58 nM. Human Renin $IC_{50}$ (plasma): 75 nM.

EXAMPLE 80 trans-N-Cyclopropyl-N-({2,3-dimethyl-5-[3-(methyloxy)propyl]phenyl}methyl)-4-(1-methyl-2-oxo-1,2-dihydro-4-pyridinyl)-3-piperidinecarboxamide

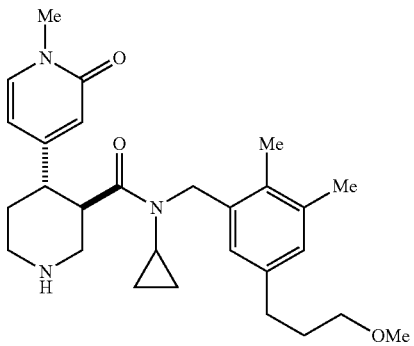

Prepared according to the procedure described in Example 1 but using instead Amine 71 as starting material. The title compound was obtained as a white froth. MS (ESI+, M+H): 466.

EXAMPLE 81 trans-N-[(2-Chloro-5-{[2-(methyloxy)ethyl]oxy}phenyl)methyl]-N-cyclopropyl-4-(1-methyl-2-oxo-1,2-dihydro-4-pyridinyl)-3-piperidinecarboxamide

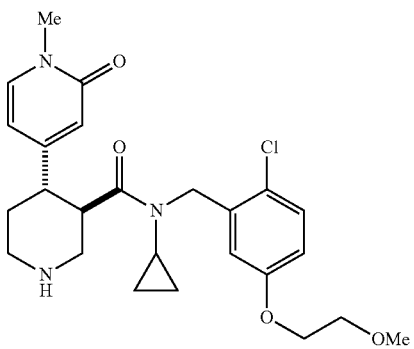

Prepared according to the procedure described in Example 1 but using instead Amine 72 as starting material. The title compound was obtained as a white froth. MS (ESI+, M+H): 474.

EXAMPLE 82 trans-N-Cyclopropyl-4-(1-methyl-2-oxo-1,2-dihydro-4-pyridinyl)-N-(2-naphthalenylmethyl)-3-piperidinecarboxamide

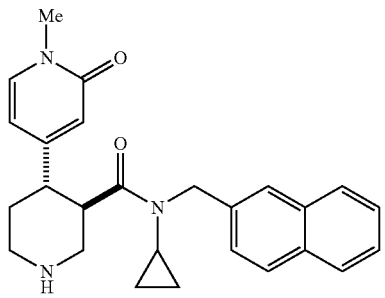

Prepared according to the procedure described in Example 1 but using instead Amine 73 as starting material. The title compound was obtained as a white froth. MS (ESI+, M+H): 416.

EXAMPLE 83 trans-N-Cyclopropyl-4-(1-methyl-2-oxo-1,2-dihydro-4-pyridinyl)-N-({3-[(trifluoromethyl)thio]phenyl}methyl)-3-piperidinecarboxamide

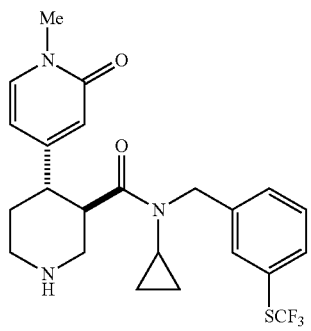

Prepared according to the procedure described in Example 1 but using instead Amine 74 as starting material. The title compound was obtained as a white froth. MS (ESI+, M+H): 466.

EXAMPLE 84 trans-N-Cyclopropyl-4-(1-methyl-2-oxo-1,2-dihydro-4-pyridinyl)-N-{[5-[3-(methyloxy)propyl]-2-(methylthio)phenyl]methyl}-3-piperidinecarboxamide

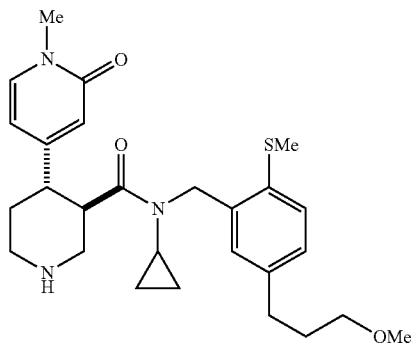 [SMILES: COCCCc1ccc(SC)c(CN(C(=O)[C@H]2CNCC[C@@H]2c2ccn(C)c(=O)c2)C2CC2)c1]

Prepared according to the procedure described in Example 1 but using instead Amine 75 as starting material. The title compound was obtained as a white froth. MS (ESI+, M+H): 484. Human Renin IC$_{50}$ (buffer): 4.7 nM. Human Renin IC$_{50}$ (plasma): 12.3 nM.

EXAMPLE 85 trans-N-({3-Bromo-4-methyl-5-[3-(methyloxy)propyl]phenyl}methyl)-N-cyclopropyl-4-(1-methyl-2-oxo-1,2-dihydro-4-pyridinyl)-3-piperidinecarboxamide

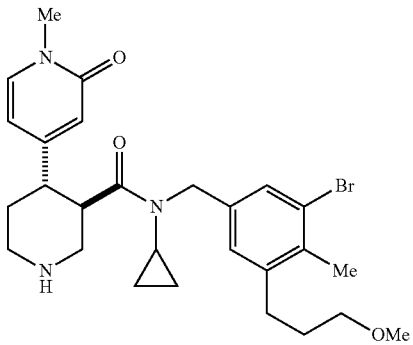 [SMILES: COCCCc1cc(CN(C(=O)[C@H]2CNCC[C@@H]2c2ccn(C)c(=O)c2)C2CC2)cc(Br)c1C]

Prepared according to the procedure described in Example 1 but using instead Amine 76 as starting material. The title compound was obtained as a white froth. MS (ESI+, M+H): 530. 1H NMR (CDCl$_3$) δ (ppm): 0.65-0.72 (m, 1H), 0.76-0.82 (m, 1H), 0.89-1.00 (m, 2H), 1.66-1.90 (m, 5H), 2.33 (s, 3H), 2.41-2.47 (s, 1H), 2.69 (t, 2H), 2.78-2.91 (m, 2H), 2.98-3.05 (m, 1H), 3.21-3.27 (m, 2H), 3.35-3.41 (m, 5H), 3.45-3.54 (m, 4H), 4.20 (d, J=14.5 Hz, 1H), 4.54 (d, J=14.5 Hz, 1H), 6.05-6.09 (m, 1H), 6.41 (s, 1H), 6.88 (s, 1H), 7.08 (s, 1H), 7.12 (d, J=6.9 Hz, 1H). Human Renin IC$_{50}$ (buffer): 0.9 nM. Human Renin IC$_{50}$ (plasma): 1.3 nM.

trans-N-({3-Bromo-4-methyl-5-[3-(methyloxy)propyl]phenyl}methyl)-N-cyclopropyl-4-(1-methyl-2-oxo-1,2-dihydro-4-pyridinyl)-3-piperidinecarboxamide hydrochloride To an acetonitrile solution (0.07 M) of compound above (1 eq.) was added dropwise HCl (4 M dioxane solution, 10 eq.). The mixture was allowed to stand at RT for 40 min during which crystals precipitated from the solution. This was then diluted with tert-butyl dimethyl ether until no further precipitation of the product could be discerned. The resulting suspension was then gently warmed and sonicated before it was allowed to age at RT for 18 h. The title compound thus obtained could be isolated via filtration as a white, crystalline solid.

Alternative Procedure:

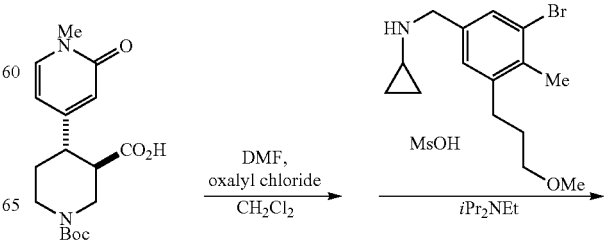

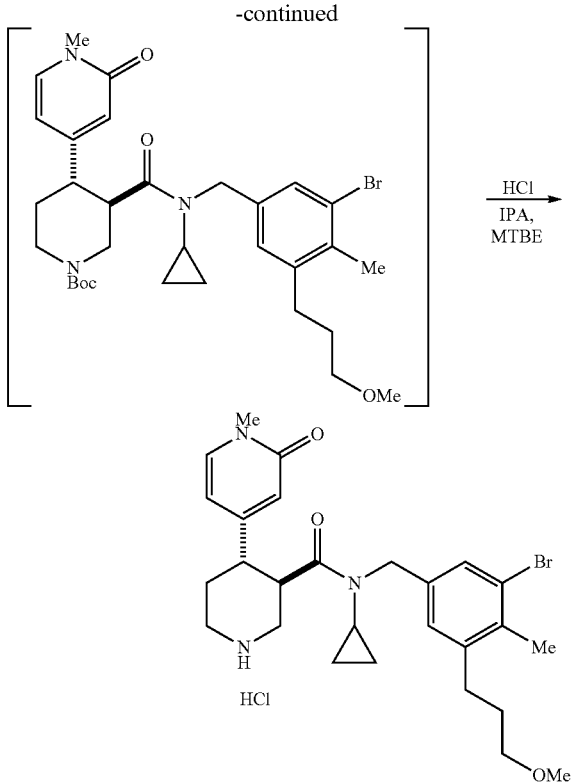

(3S,4S)-1'-Methyl-2'-oxo-3,4,5,6,1',2'-hexahydro-2H-[4,4']bipyridinyl-1,3-dicarboxylic acid 1-tert-butyl ester (carboxylic acid 1; 1.0 equiv.) was dissolved in dichloromethane (10 volumes). DMF (0.2 equiv.) was charged and the solution cooled to −15° C. Oxalyl chloride (0.95 equiv.) was added over 2.5 h. N-[3-Bromo-5-(3-methoxypropyl)-4-methylbenzyl]cyclopropanamine mesylate (amine 76 mesylate; 0.90 equiv.) dissolved in dichloromethane (2 volumes) and i-Pr$_2$NEt (3.3 equiv.) was then added over 1 h at ~−15° C. The reaction was quenched with water (10 volumes) and the layers were cut and the organic layer was washed with NaHCO$_3$ solution. The layers were cut and the organic layer was washed with HCl solution. The organic layer was concentrated to ~5.7 volumes. 2-Propanol (0.57 volumes) was added followed by conc. HCl (6.0 equiv.). The reaction mixture was aged for 75 min at 35° C. and then water (5.7 volumes) was added. The layers were cut and to the aqueous layer was added dichloromethane (11.4 volumes). Sodium hydroxide (6.7 equiv.) was added and the layers were cut. The organic layer was washed with water (5.7 volumes) and concentrated to ~5 volumes. 2-Propanol was added 8 volumes) and the remaining dichloromethane was removed by distillation. Conc. HCl (0.2 equiv., 37%) in IPA 0.11 volumes) was then added and the batch was aged for 30 min. Further c. HCl (0.9 equiv., 37%) in IPA (0.5 volumes) was added over 1 h. MTBE (5.4 volumes) was added and the batch was aged for 1 h. The resultant slurry was filtered and the solids washed with MTBE to give (3S,4R)-N-({3-Bromo-4-methyl-5-[3-(methyloxy)propyl]phenyl}methyl)-N-cyclopropyl-4-(1-methyl-2-oxo-1,2-dihydro-4-pyridinyl)-3-piperidinecarboxamide hydrochloride as a white solid. $^1$H NMR (500 MHz, dmso-d$_6$) δ 9.45 (br s, 2H), 7.57 (d, J=6.9 Hz, 1H), 6.96 (d, J=0.9 Hz, 1H), 6.79 (d, J=0.9 Hz, 1H), 6.13 (d, J=1.7 Hz, 1H), 6.04 (dd, J=6.9, 1.7, 1H). 4.58 (d, J=14.9 Hz, 1H), 4.12 (td, J=11.5, 3.5, 1H), 4.05 (d, J=14.9 Hz, 1H), 3.48 (dd, J=12.2, 3.5 Hz, 1H), 3.34 (s, 1H), 3.32 (m, 1H), 3.30 (t, J=6.2 Hz, 1H), 3.24 (s, 1H), 3.07-2.97 (om, 2H), 2.85 (m, 1H), 2.57 (m, 1H), 2.04 (qd, J=13.0, 3.8 Hz, 1H), 1.82 (m, 1H), 1.65 (m, 1H), 0.98 (m, 1H), 0.91-0.82 (om, 2H), 0.61 (m, 1H). HRMS (ES, M+H) Calcd 530.2018. Found 530.2008.

Figure 5:
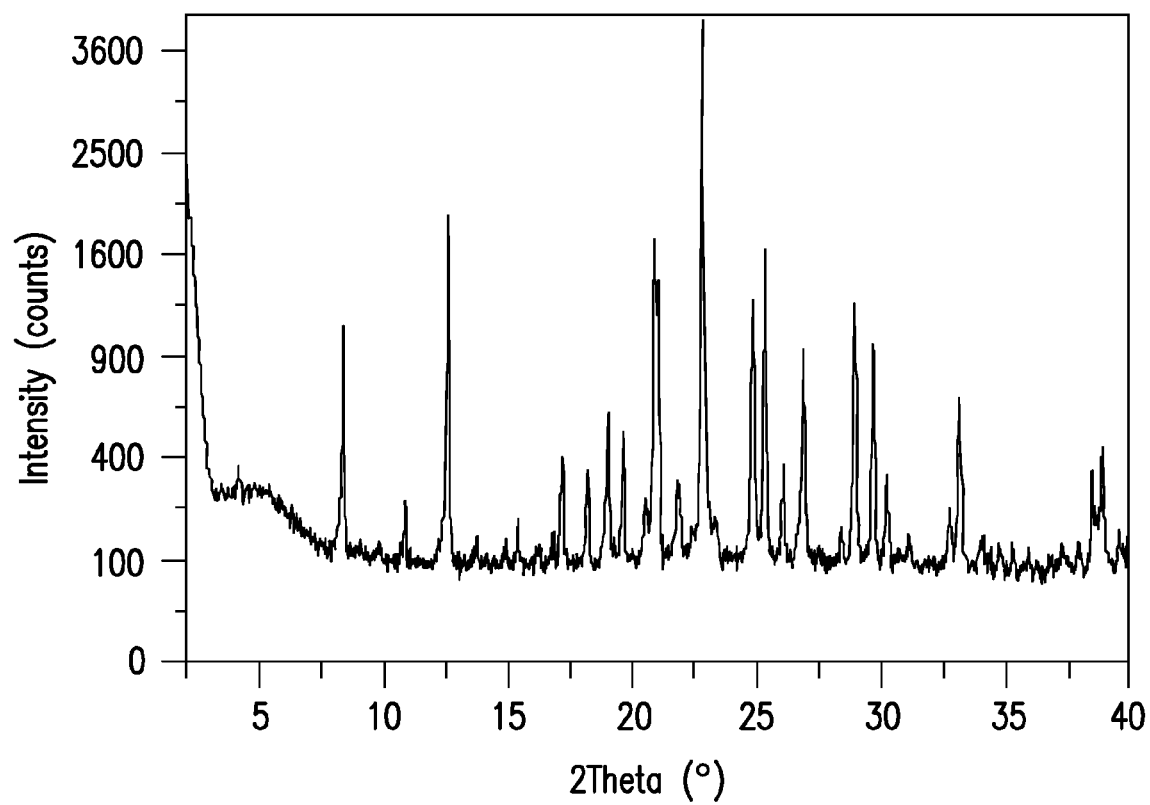
FIG. 5 illustrates an X-ray diffraction pattern of crystalline Form I.

X-Ray Powder Diffraction:

X-ray powder diffraction studies are widely used to characterize molecular structures, crystallinity, and polymorphism. The X-ray powder diffraction patterns were generated on a Philips Analytical X'Pert PRO X-ray Diffraction System with PW3040/60 console. A PW3373/00 ceramic Cu LEF X-ray tube K-Alpha radiation was used as the source. FIG. 5 illustrates a characteristic X-ray diffraction pattern of crystalline Form I, (3S,4R)-N-({3-Bromo-4-methyl-5-[3-(methyloxy)propyl]phenyl}methyl)-N-cyclopropyl-4-(1-methyl-2-oxo-1,2-dihydro-4-pyridinyl)-3-piperidinecarboxamide hydrochloride. Form I exhibits characteristic reflections corresponding to d-spacings listed in the following Table 9:

TABLE 9

| d-spacing [Å] | Height [cts] |
|---|---|
| 10.59 | 945.75 |
| 7.04 | 1736.99 |
| 4.24 | 1588.22 |
| 4.22 | 1312.59 |
| 3.88 | 3855.93 |
| 3.58 | 1166.01 |
| 3.51 | 1569.66 |
| 3.31 | 860.32 |
| 3.08 | 1148.31 |

Figure 2:
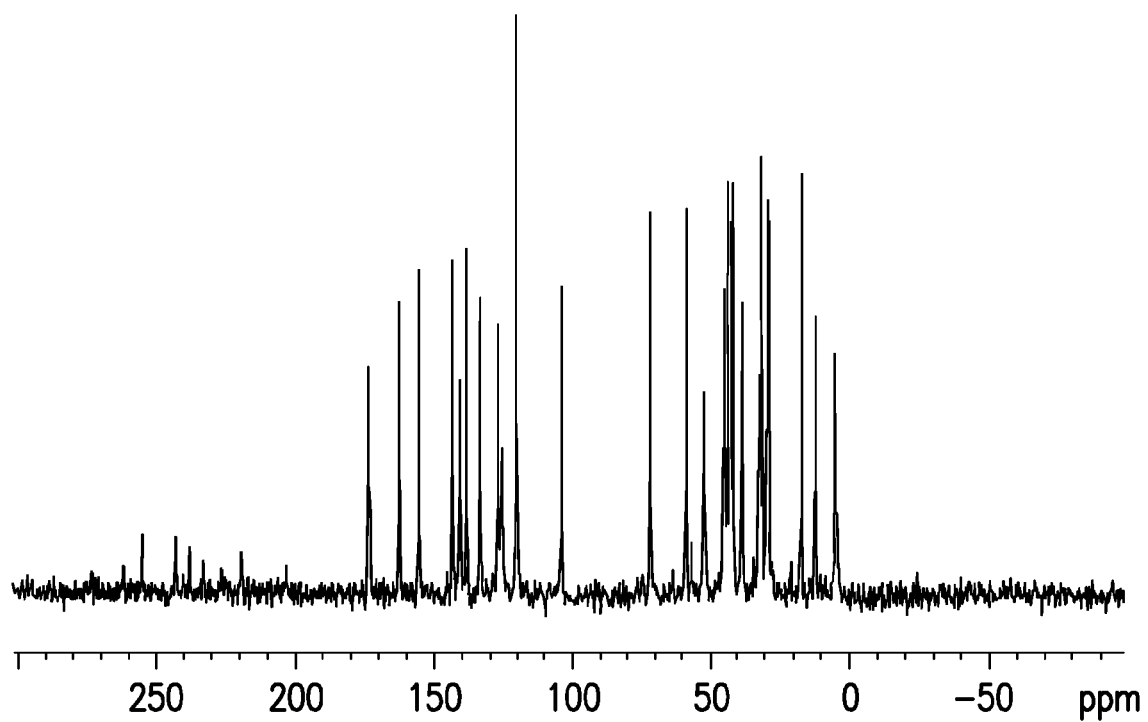
FIG. 2 illustrates a solid state C-13 CPMAS NMR spectrum for the crystalline Form I.

Solid State NMR:

In addition to the X-ray powder diffraction patterns described above, crystalline Form I was further characterized by its solid-state carbon-13 nuclear magnetic resonance (NMR) spectra. The carbon-13 spectrum was recorded using a Bruker 4 mm HX CPMAS probe. The carbon-13 spectra were collected utilizing proton/carbon-13 variable-amplitude cross-polarization (VACP) with a contact time of 5 ms, and a pulse delay of 10 s, while magic-angle spinning (MAS) the sample at 10 kHz. A line broadening of 10 Hz was applied to the carbon-13 spectra before Fourier Transformation. Chemical shifts are reported on the TMS scale using the carbonyl carbon of glycine (176.03 ppm) as a secondary reference. FIG. 2 illustrates a solid state carbon-13 CPMAS NMR spectrum for crystalline Form I. Form I exhibits characteristic peaks corresponding to the chemical shifts listed in the following Table 10:

TABLE 10

| Peak (ppm) | Relative Intensity |
|---|---|
| 120.1 | 100 |
| 31.2 | 76 |
| 17.1 | 73 |
| 43.5 | 71 |
| 41.6 | 71 |
| 29.4 | 68 |
| 58.5 | 67 |
| 71.4 | 66 |
| 28.7 | 64 |
| 42.5 | 64 |
| 138.3 | 60 |
| 143.6 | 58 |

Figure 4:
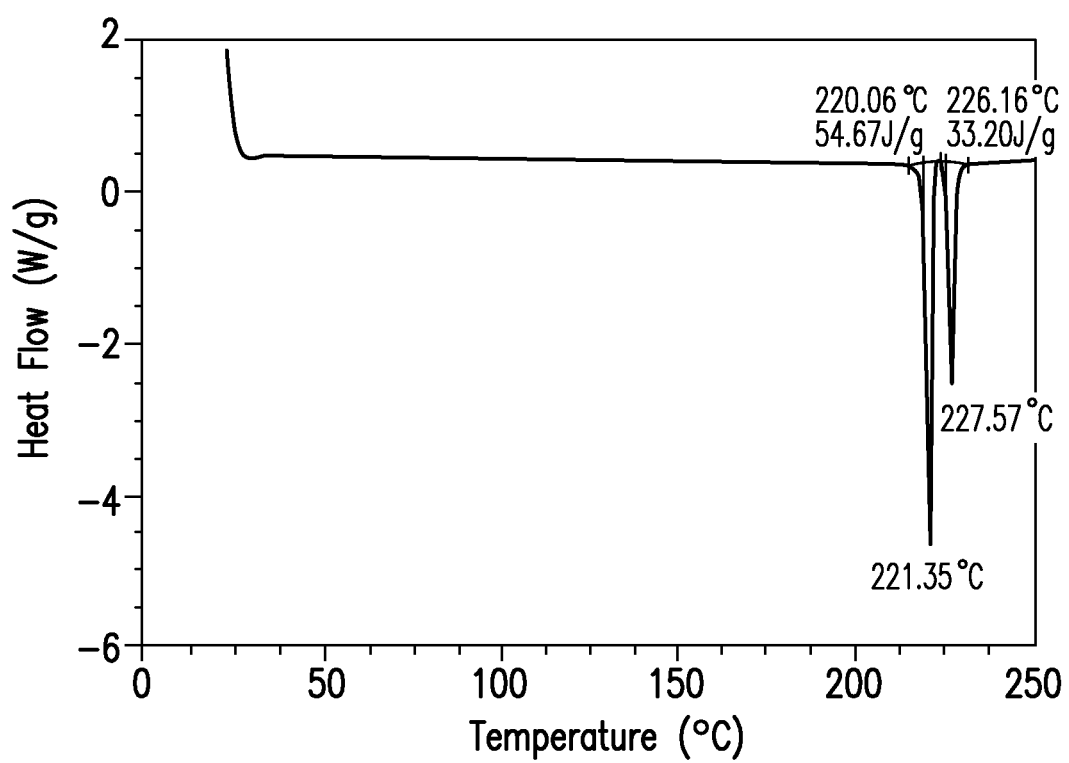
FIG. 4 illustrates a differential scanning calorimetry ("DSC") curve of crystalline Form I.

Differential Scanning Calorimetry:

DSC data are acquired using TA Instruments DSC 2910 or equivalent. Between 2 and 6 mg sample is weighed into a pan and covered. This pan is then crimped and placed at the sample position in the calorimeter cell. An empty pan is placed at the reference position. The calorimeter cell is closed and a flow of nitrogen is passed through the cell. The heating program is set to heat the sample at a heating rate of 10° C./min to a temperature of approximately 250° C. The heating program is started. When the run is completed, the data are analyzed using the DSC analysis program contained in the system software. The thermal events are integrated between baseline temperature points that are above and below the temperature range over which the thermal event is observed. The data reported are the onset temperature, peak temperature and enthalpy. FIG. 4 illustrates a differential scanning calorimetry curve for crystalline Form I.

Figure 3:
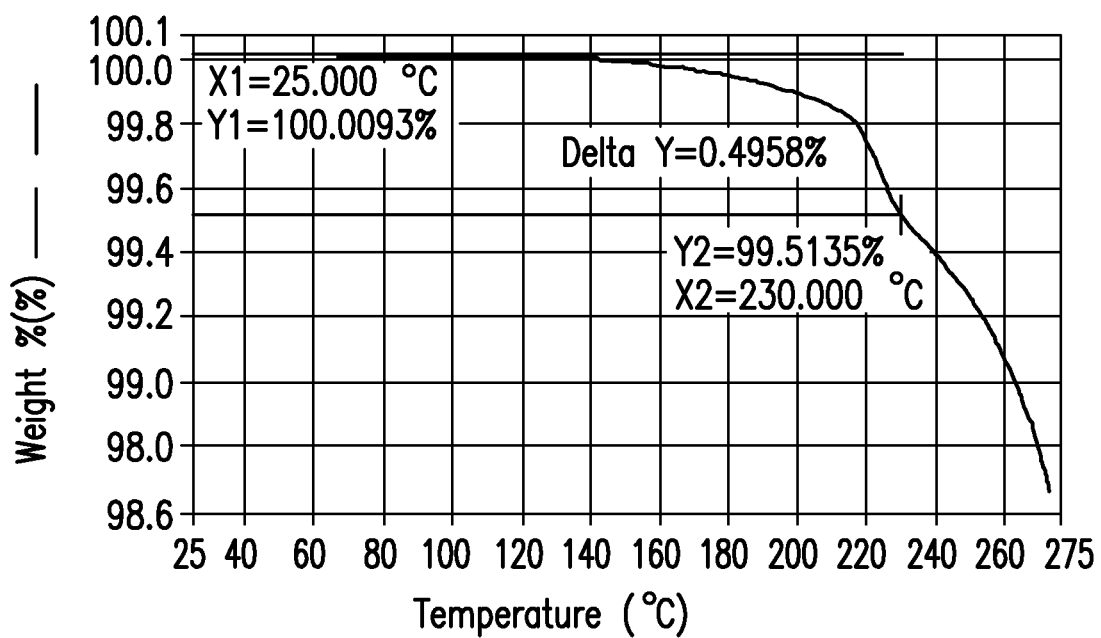
FIG. 3 illustrates a thermogravimetric analysis curve of crystalline Form I.

Thermogravimetric Analysis:

TG data are acquired using a Perkin Elmer model TGA 7. Experiments were performed under a flow of nitrogen and using a heating rate of 10° C./min to a maximum temperature of approximately 250° C. After automatically taring the balance, 5 to 20 mg of sample is added to the platinum pan, the furnace is raised, and the heating program started. Weight/temperature data are collected automatically by the instrument. Analysis of the results are carried out by selecting the Delta Y function within the instrument software and choosing the temperatures between which the weight loss is to be calculated. Weight losses are reported up to the onset of decomposition/evaporation. FIG. 3 illustrates a thermogravimetric analysis curve for crystalline Form I.

Purity: Purity can be upgraded, where desired, by slurrying in isopropanol.

| Materials | MW | Equiv. | Moles | Quantity |
|---|---|---|---|---|
| HCl salt | 566.96 | 1.0 | 16.74 | 9.491 kg |
| IPA (d = 0.786) | | | | 178 kg |

HCl salt (9.491 kg) was slurried in isopropanol (149 kg, 190 L). The slurry was warmed to 68° C. for 2 hours then cooled to 20° C. over 1 hour, then filtered, washing with isopropanol (38 L, 29 kg). The solid was dried under vacuum at 40° C. with $N_2$ sweep to give the product (8.203 kg) in 86% yield.

EXAMPLE 86 trans-N-[3,5-Bis(3-methoxypropyl)benzyl]-N-cyclopropyl-4-(1-methyl-2-oxo-1,2-dihydro-4-pyridinyl)-3-piperidinecarboxamide

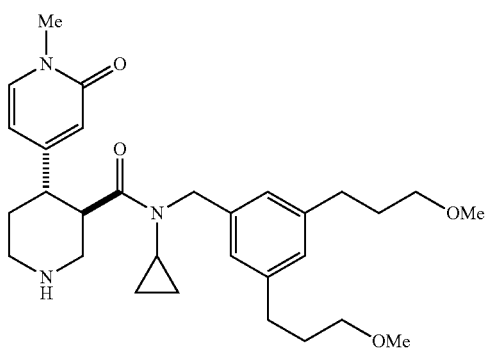 [SMILES: COCCCc1cc(CCCOC)cc(CN(C(=O)[C@H]2CNCC[C@@H]2c2ccn(C)c(=O)c2)C2CC2)c1]

Prepared according to the procedure described in Example 1 but using instead Amine 77 as starting material. The title compound was obtained as a white froth. MS (ESI+, M+H): 510.

EXAMPLE 87 trans-N-Cyclopropyl-N-[3-(3-methoxypropyl)-5-methylbenzyl]-4-(1-methyl-2-oxo-1,2-dihydro-4-pyridinyl)-3-piperidinecarboxamide

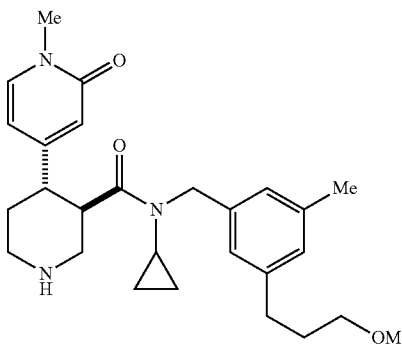

Prepared according to the procedure described in Example 1 but using instead Amine 78 as starting material. The title compound was obtained as a white froth. MS (ESI+, M+H): 452.

EXAMPLE 88 trans-N-[2-Bromo-3,5-bis(3-methoxypropyl)benzyl]-N-cyclopropyl-4-(1-methyl-2-oxo-1,2-dihydro-4-pyridinyl)-3-piperidinecarboxamide

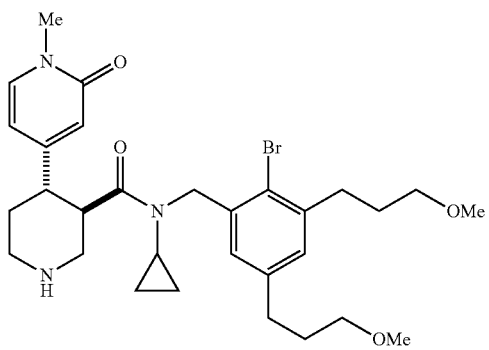

Prepared according to the procedure described in Example 1 but using instead Amine 79 as starting material. The title compound was obtained as a white froth. MS (ESI+, M+H): 589.

EXAMPLE 89 trans-N-[2-Chloro-3,5-bis(3-methoxypropyl)benzyl]-N-cyclopropyl-4-(1-methyl-2-oxo-1,2-dihydro-4-pyridinyl)-3-piperidinecarboxamide

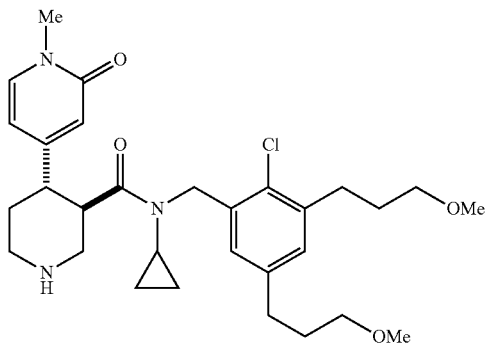 [SMILES: COCCCc1cc(CCCOC)c(Cl)c(CN(C(=O)[C@H]2CNCC[C@@H]2c2ccn(C)c(=O)c2)C2CC2)c1]

Prepared according to the procedure described in Example 1 but using instead Amine 80 as starting material. The title compound was obtained as a white froth. MS (ESI+, M+H):

544. ¹H NMR (CDCl₃) δ (ppm): 0.62-0.68 (m, 1H), 0.74-0.79 (m, 1H), 0.82-0.90 (m, 2H), 1.63-1.93 (m, 8H), 2.46-2.55 (m, 2H), 2.55-2.61 (br m, 1H), 2.72-2.89 (m, 4H), 3.05 (dt, J=10.1, 5.5 Hz, 1H), 3.22 (br m, 1H), 3.32-3.37 (m, 9H), 3.38 (t, d=7.2 Hz, 1H), 3.50-3.58 (m, 4H), 4.23 (d, J=13.5 Hz, 1H), 4.70 (d, J=13.5 Hz, 1H), 6.12 (d, J=7.0 Hz, 1H), 6.47 (s, 1H), 6.52 (s, 1H), 6.92 (s, 1H), 7.18 (d, J=7.0 Hz, 1H). Human Renin IC$_{50}$ (buffer): 0.2 nM. Human Renin IC$_{50}$ (plasma): 0.5 nM.

EXAMPLE 90 trans-N-Cyclopropyl-N-[2-methoxy-3,5-bis(3-methoxypropyl)benzyl]-4-(1-methyl-2-oxo-1,2-dihydro-4-pyridinyl)-3-piperidinecarboxamide

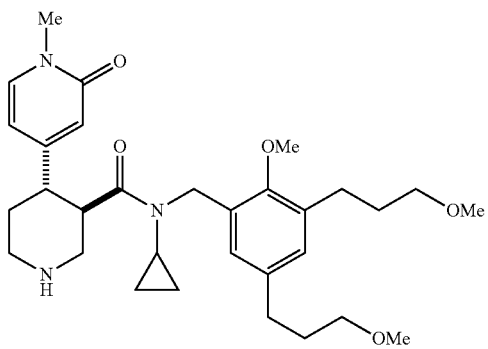 [SMILES: COCCCc1cc(CCCOC)c(OC)c(CN(C(=O)[C@H]2CNCC[C@@H]2c2ccn(C)c(=O)c2)C2CC2)c1]

Prepared according to the procedure described in Example 1 but using instead Amine 81 as starting material. The title compound was obtained as a white froth. MS (ESI+, M+H): 540.

EXAMPLE 91 trans-N-Cyclopropyl-N-[3-(3-methoxypropyl)-5-(trifluoromethyl)benzyl]-4-(1-methyl-2-oxo-1,2-dihydro-4-pyridinyl)-3-piperidinecarboxamide

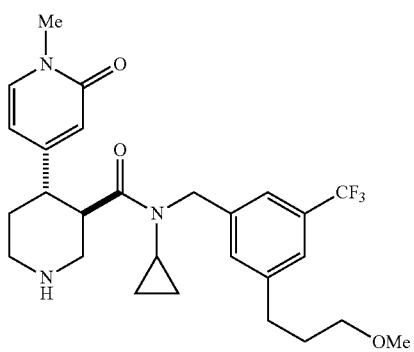

Prepared according to the procedure described in Example 1 but using instead Amine 82 as starting material. The title compound was obtained as a white froth. MS (ESI+, M+H): 506.

EXAMPLE 92 trans-N-Cyclopropyl-N-[3-hydroxy-5-(3-methoxypropyl)benzyl]-4-(1-methyl-2-oxo-1,2-dihydro-4-pyridinyl)-3-piperidinecarboxamide

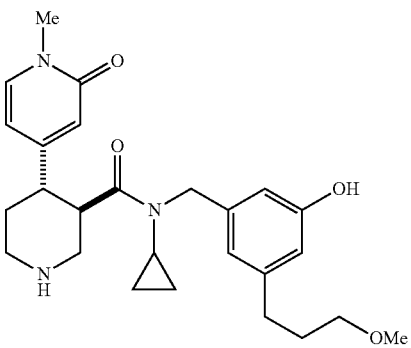 [SMILES: COCCCc1cc(O)cc(CN(C(=O)[C@H]2CNCC[C@@H]2c2ccn(C)c(=O)c2)C2CC2)c1]

Prepared according to the procedure described in Example 1 but using instead Amine 83 as starting material. The title compound was obtained as a white froth. MS (ESI+, M+H): 454.

EXAMPLE 93 trans-N-(3-Benzoyl-5-bromobenzyl)-N-cyclopropyl-4-(1-methyl-2-oxo-1,2-dihydro-4-pyridinyl)-3-piperidinecarboxamide

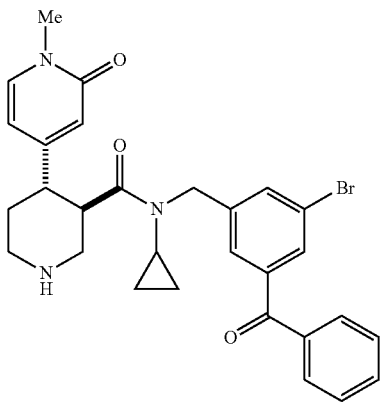

Step 1: trans-tert-Butyl 3-{[(3-bromo-5-iodobenzyl)(cyclopropyl)amino]carbonyl}-4-(1-methyl-2-oxo-1,2-dihydropyridin-4-yl)-1-piperidinecarboxylate To a DMF (0.1 M) solution of trans-1-{[(1,1-dimethylethyl)oxy]carbonyl}-4-(1-methyl-2-oxo-1,2-dihydro-4-pyridinyl)-3-piperidinecarboxylic acid (1 eq., Example 1, Step 6), Hunig's base (3 eq.) and Amine 84 (1 eq.) was added portionwise O-(7-azabenzotriazol-1-yl)-N,N,N',N'-tetramethyluronium hexafluorophosphate (1.2 eq.). The resulting reaction solution was stirred at RT for 48 h. The now yellow solution was diluted with EtOAc and washed sequentially with 10% aq. HCl, 1 N aq. NaOH and brine. The organic extract was then dried over Na₂SO₄, filtered and the filtrate concentrated in vacuo to afford a reddish-orange oil. Purification of the crude product thus obtained by way of flash chromatography (SiO₂, 97:3 (v/v) CH₂Cl₂:2.0 M NH₃ in MeOH) afforded the title compound as a yellow oil.

Step 2: trans-tert-Butyl 3-{[(3-benzoyl-5-bromobenzyl)(cyclopropyl)amino]carbonyl}-4-(1-methyl-2-oxo-1,2-dihydropyridin-4-yl)piperidine-1-carboxylate To a solution of 1,5-bis(bromomagnesium)pentane (1.0 eq.) in THF (0.05 M) at −78° C. was added a solution of CuCN-2LiCl prepared from CuCN (1.0 eq.) and LiCl (2.0 eq.) in THF (0.9 M with respect to CuCN). The resulting mixture was stirred at −78° C. for 30 min. A solution of trans-tert-butyl 3-{[(3-bromo-5-iodobenzyl)(cyclopropyl)amino]carbonyl}-4-(1-methyl-2-oxo-1,2-dihydropyridin-4-yl)-1-piperidinecarboxylate (1.0 eq.) from the previous step in THF (0.2 M) was then added and the reaction mixture was warmed to RT over 1 h. Finally, benzoyl chloride (1.5 eq.) was added and the reaction mixture was stirred for another hour. The reaction mixture was quenched with the addition of water and subsequently extracted with EtOAc. The combined organic extracts were dried over $Na_2SO_4$, filtered and the filtrate concentrated in vacuo. Purification of the crude product thus obtained by way of flash chromatography ($SiO_2$, 2:98 (v/v)→15:85 (v/v) MeOH:$CH_2Cl_2$) afforded the title compound as a brown oil.

Step 3: trans-N-(3-Benzoyl-5-bromobenzyl)-N-cyclopropyl-4-(1-methyl-2-oxo-1,2-dihydro-4-pyridinyl)-3-piperidinecarboxamide To a $CH_2Cl_2$ solution (0.1 M) of trans-tert-butyl 3-{[(3-benzoyl-5-bromobenzyl)(cyclopropyl)amino]carbonyl}-4-(1-methyl-2-oxo-1,2-dihydropyridin-4-yl)piperidine-1-carboxylate (1 eq.) from the previous step was added HCl (4.0 M dioxane solution, 30 eq.). The resulting solution was stirred at RT for 45 min. Following the removal of the volatiles in vacuo, the resulting residue was directly loaded onto a $SiO_2$ column packed with 93:7 (v/v) $CH_2Cl_2$:2.0 M $NH_3$ in MeOH. Elution with the same solvent system furnished the title compound. MS (ESI+, M+H): 548.

EXAMPLE 94 trans-N-{3-Bromo-5-[(1E)-3-methoxy-1-propen-1yl]benzyl}-N-cyclopropyl-4-(1-methyl-2-oxo-1,2-dihydro-4-pyridinyl)-3-piperidinecarboxamide

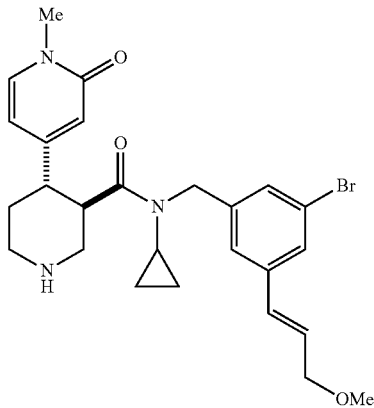

Step 1: trans-tert-Butyl 3-{[{3-bromo-5-[(1E)-3-methoxyprop-1-en-1-yl]benzyl}(cyclopropyl)amino]carbonyl}-4-(1-methyl-2-oxo-1,2-dihydropyridin-4-yl)piperidine-1-carboxylate A mixture of trans-tert-butyl 3-{[(3-bromo-5-iodobenzyl)(cyclopropyl)amino]carbonyl}-4-(1-methyl-2-oxo-1,2-dihydropyridin-4-yl)-1-piperidinecarboxylate (1.0 eq., Example 93, Step 1), 2-[(1E)-3-methoxyprop-1-en-1-yl]-4,4,5,5-tetramethyl-1,3,2-dioxaborolane (1.2 eq.), sodium carbonate (4.5 eq.) and Pd(dppf)Cl2 (0.1 eq.) in dioxane (0.1 M) was repeatedly evacuated and back-filled with nitrogen. The mixture was stirred at RT in the dark for 2 h. The now black suspension was diluted with brine and extracted with EtOAc. The combined organic extracts were dried over $Na_2SO_4$, filtered and the filtrate concentrated in vacuo. Purification of the crude product thus obtained by way of flash chromatography ($SiO_2$, EtOAc→4:96 (v/v) 2 M $NH_3$ in MeOH:EtOAc) afforded the title compound as a light orange oil.

Step 2: trans-N-{3-Bromo-5-[(1E)-3-methoxy-1-propen-1yl]benzyl}-N-cyclopropyl-4-(1-methyl-2-oxo-1,2-dihydro-4-pyridinyl)-3-piperidinecarboxamide To a $CH_2Cl_2$ solution (0.1 M) of trans-tert-butyl 3-{[{3-bromo-5-[(1E)-3-methoxyprop-1-en-1-yl]benzyl}(cyclopropyl)amino]carbonyl}-4-(1-methyl-2-oxo-1,2-dihydropyridin-4-yl)piperidine-1-carboxylate (1 eq.) from the previous step was added HCl (4.0 M dioxane solution, 30 eq.). The resulting solution was stirred at RT for 45 min. Following the removal of the volatiles in vacuo, the resulting residue was directly loaded onto a $SiO_2$ column packed with 93:7 (v/v) $CH_2Cl_2$:2.0 M $NH_3$ in MeOH. Elution with the same solvent system furnished the title compound. MS (ESI+, M+H): 516.

EXAMPLE 95 trans-N-{3-Bromo-5-[(2-hydroxyethyl)thio]benzyl}-N-cyclopropyl-4-(1-methyl-2-oxo-1,2-dihydro-4-pyridinyl)-3-piperidinecarboxamide

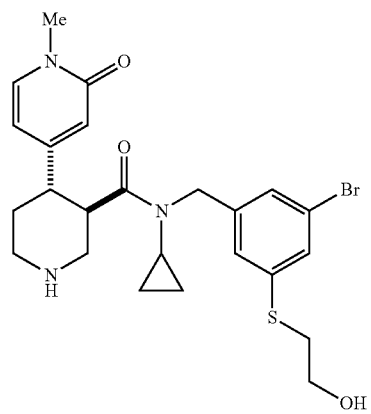

Step 1: trans-tert-Butyl 3-{[{3-bromo-5-[(2-hydroxyethyl)thio]benzyl}(cyclopropyl)-amino]carbonyl}-4-(1-methyl-2-oxo-1,2-dihydropyridin-4-yl)piperidine-1-carboxylate To a solution of trans-tert-butyl 3-{[(3-bromo-5-iodobenzyl)(cyclopropyl)-amino]carbonyl}-4-(1-methyl-2-oxo-1,2-dihydropyridin-4-yl)-1-piperidinecarboxylate (1.0 eq., Example 93, Step 1) in DMF (0.3 M) was added copper bronze (1.1 eq.) and 2,2'-dithiodiethanol (0.6 eq.). The reaction mixture was heated to 110° C. for 24 h, cooled and diluted with EtOAc. The resultant suspension was stirred at RT for 20 min, filtered through celite and the insolubles were rinsed further with EtOAc. The filtrate thus obtained was washed sequentially with a 3:1 (v/v) mixture of conc. $NH_4OH$:sat. aq. $NH_4Cl$, water and brine, dried over $MgSO_4$, filtered and the filtrate concentrated in vacuo. Purification of the crude product thus obtained by way of flash chromatography (SiO$_2$, EtOAc→4:96 (v/v) 2 M NH$_3$ in MeOH:EtOAc) afforded the title compound as a colorless oil.

Step 2: trans-N-{3-Bromo-5-[(2-hydroxyethyl)thio]benzyl}-N-cyclopropyl-4-(1-methyl-2-oxo-1,2-dihydro-4-pyridinyl)-3-piperidinecarboxamide To a CH$_2$Cl$_2$ solution (0.1 M) of trans-tert-butyl 3-{[{3-bromo-5-[(2-hydroxyethyl)thio]benzyl}(cyclopropyl)amino]carbonyl}-4-(1-methyl-2-oxo-1,2-dihydropyridin-4-yl)piperidine-1-carboxylate (1 eq.) from the previous step was added HCl (4.0 M dioxane solution, 30 eq.). The resulting solution was stirred at RT for 45 min. Following the removal of the volatiles in vacuo, the resulting residue was directly loaded onto a SiO$_2$ column packed with 90:10 (v/v) CH$_2$Cl$_2$:2.0 M NH$_3$ in MeOH. Elution with the same solvent system furnished the title compound. MS (ESI+, M+H): 520.

EXAMPLE 96 trans-N-Cyclopropyl-N-[3-[2-(cyclopropyloxy)ethoxy]-5-(3-methoxypropyl)benzyl]-4-(1-methyl-2-oxo-1,2-dihydro-4-pyridinyl)-3-piperidinecarboxamide

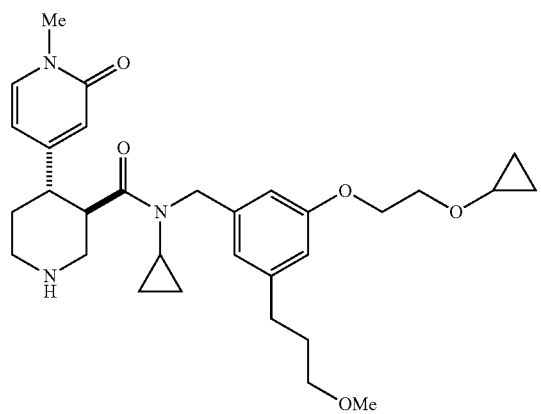

Step 1: trans-tert-Butyl 3-({cyclopropyl[3-[2-(cyclopropyloxy)ethoxy]-5-(3-methoxypropyl)benzyl]amino}carbonyl)-4-(1-methyl-2-oxo-1,2-dihydro-4-pyridinyl)-1-piperidinecarboxylate To a solution of trans-tert-butyl 3-({cyclopropyl[3-hydroxy-5-(3-methoxypropyl)benzyl]amino}carbonyl)-4-(1-methyl-2-oxo-1,2-dihydro-4-pyridinyl)-1-piperidinecarboxylate (1.0 eq., Example 92) in DMF (0.1 M) was added cesium carbonate (2 eq.), sodium iodide (0.05 eq.) and (2-chloroethoxy)cyclopropane (3 eq.). The reaction mixture was heated at 100° C. for 22 h. After cooling to RT, the reaction was quenched with sat. aq. ammonium chloride and extracted with EtOAc. The combined organic extracts were washed further with water and brine, dried over MgSO$_4$, filtered and the filtrate concentrated in vacuo. Purification of the crude product thus obtained by way of flash chromatography (SiO$_2$, 95:5 (v/v) CH$_2$Cl$_2$:MeOH) afforded the title compound as a colorless oil.

Step 2: trans-N-Cyclopropyl-N-[3-[2-(cyclopropyloxy)ethoxy]-5-(3-methoxypropyl)benzyl]-4-(1-methyl-2-oxo-1,2-dihydro-4-pyridinyl)-3-piperidinecarboxamide To a CH$_2$Cl$_2$ solution (0.1 M) of trans-tert-butyl 3-({cyclopropyl[3-[2-(cyclopropyloxy)ethoxy]-5-(3-methoxypropyl)benzyl]amino}carbonyl)-4-(1-methyl-2-oxo-1,2-dihydro-4-pyridinyl)-1-piperidinecarboxylate (1 eq.) from the previous step was added HCl (4.0 M dioxane solution, 30 eq.). The resulting solution was stirred at RT for 4 h. Following the removal of the volatiles in vacuo, the resulting residue was directly loaded onto a SiO$_2$ column packed with 93:7 (v/v) CH$_2$Cl$_2$:2.0 M NH$_3$ in MeOH. Elution with the same solvent system furnished the title compound. MS (ESI+, M+H): 538.

EXAMPLE 97 trans-N-Cyclopropyl-N-{3-(3-methoxypropyl)-5-[2-(4-morpholinyl)ethoxy]benzyl}-4-(1-methyl-2-oxo-1,2-dihydro-4-pyridinyl)-3-piperidinecarboxamide

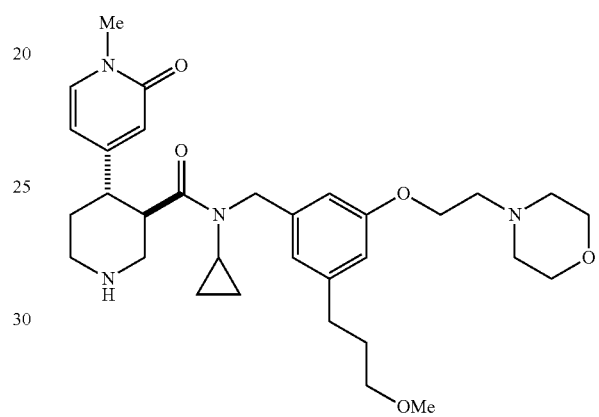

Prepared according to the procedure described in Example 96, but using instead 4-(2-chloroethyl)morpholine as the alkylation reagent in Step 1. MS (ESI+, M+H): 567.

EXAMPLE 98

Trans-3-[(Cyclopropyl{[4-(1-methyl-2-oxo-1,2-dihydro-4-pyridinyl)-3-piperidinyl]carbonyl}amino)methyl]-5-(3-methoxypropyl)phenyl 4-morpholinecarboxylate

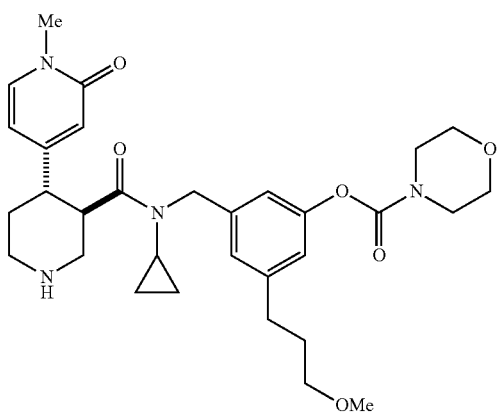

Prepared according to the procedure described in Example 96, but using instead morpholine-4-carbonyl chloride as the alkylation reagent, triethylamine as the base, and DMAP as the catalyst in Step 1. MS (ESI+, M+H): 567.

EXAMPLE 99 trans-N-Cyclopropyl-N-[6-(3-methoxypropyl)-2,3-dihydro-1H-inden-1-yl]-4-(1-methyl-2-oxo-1,2-dihydro-4-pyridinyl)-3-piperidinecarboxamide

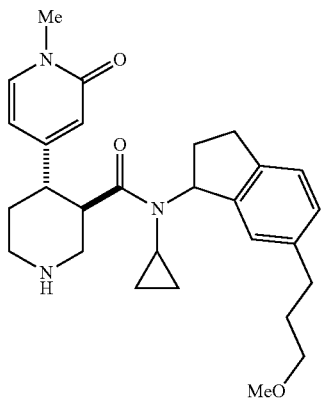

Prepared as a mixture of diastereomers according to the procedure described in Example 1 but using instead Amine 85 as starting material. MS (ESI+, M+H): 464. Furthermore, the two diastereomers can be separated on a preparatory reverse-phase HPLC prior to removal of the BOC-protecting group.

EXAMPLE 100 trans-N-Cyclopropyl-N-[7-(3-methoxypropyl)-1,2,3,4-tetrahydro-1-naphthalenyl]-4-(1-methyl-2-oxo-1,2-dihydro-4-pyridinyl)-3-piperidinecarboxamide

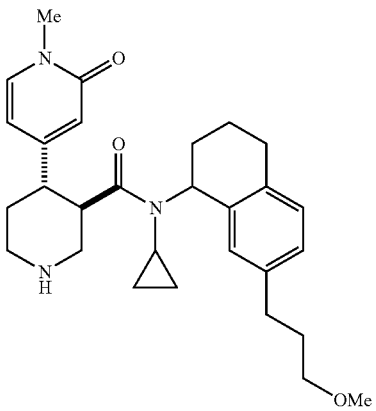

Prepared as a mixture of diastereomers according to the procedure described in Example 1 but using instead Amine 86 as starting material. Furthermore, the two diastereomers can be separated on a preparatory reverse-phase HPLC prior to removal of the BOC-protecting group. Diastereomer A: MS (ESI+, M+H): 478. Human Renin $IC_{50}$ (buffer): 0.3 nM. Human Renin $IC_{50}$ (plasma): 1.2 nM. Diastereomer B: MS (ESI+, M+H): 478. Human Renin $IC_{50}$ (buffer): 3.6 nM. Human Renin $IC_{50}$ (plasma): 16.2 nM.

EXAMPLE 101 trans-N-[3-Bromo-5-(3-hydroxypropyl)-4-methylbenzyl]-N-cyclopropyl-4-(1-methyl-2-oxo-1,2-dihydro-4-pyridinyl)-3-piperidinecarboxamide

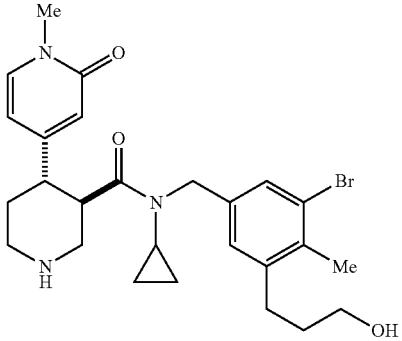

Prepared according to the procedure described in Example 1 but using instead Amine 87 as starting material. The title compound was obtained as a white froth. MS (ESI+, M+Na): 538.

EXAMPLE 102 trans-N-[3-Bromo-5-(3-ethoxypropyl)-4-methylbenzyl]-N-cyclopropyl-4-(1-methyl-2-oxo-1,2-dihydro-4-pyridinyl)-3-piperidinecarboxamide

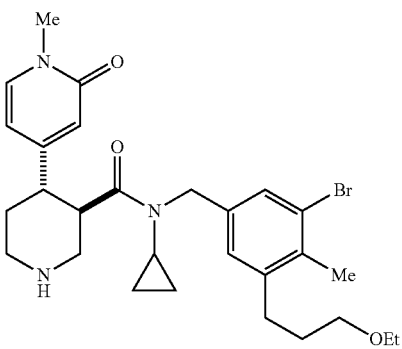

Prepared according to the procedure described in Example 1 but using instead Amine 88 as starting material. The title compound was obtained as a white froth. MS (ESI+, M+H): 544.

EXAMPLE 103 trans-N-{3-Bromo-5-[3-(difluoromethoxy)propyl]-4-methylbenzyl}-N-cyclopropyl-4-(1-methyl-2-oxo-1,2-dihydro-4-pyridinyl)-3-piperidinecarboxamide

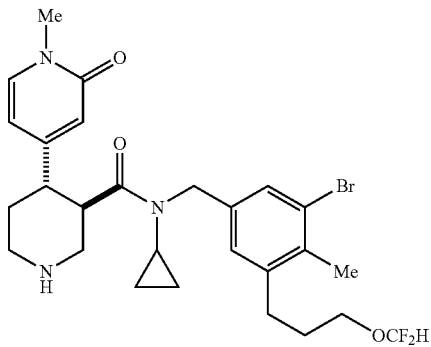

Prepared according to the procedure described in Example 1 but using instead Amine 89 as starting material and zinc(II)

bromide-promoted BOC-deprotection as in Example 14, Step 8. The title compound was obtained as a white froth The title compound was obtained as a white froth. MS (ESI+, M+H): 566. Human Renin IC$_{50}$ (buffer): 0.3 nM. Human Renin IC$_{50}$ (plasma): 1.4 nM.

EXAMPLE 104 trans-N-(3-Benzyl-5-methylbenzyl)-N-cyclopropyl-4-(1-methyl-2-oxo-1,2-dihydro-4-pyridinyl)-3-piperidinecarboxamide

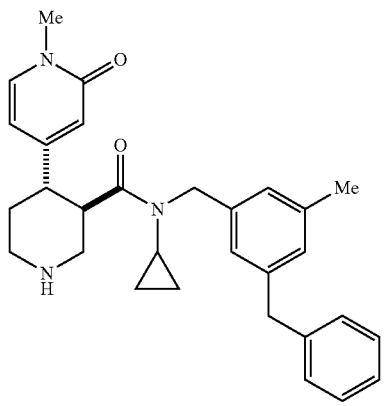

Prepared according to the procedure described in Example 1 but using instead Amine 90 as starting material. The title compound was obtained as a white froth. MS (ESI+, M+H): 470. Human Renin IC$_{50}$ (buffer): 7.5 nM. Human Renin IC$_{50}$ (plasma): 21 nM.

EXAMPLE 105 trans-N-[3-Bromo-5-(3-fluorobenzyl)-4-methylbenzyl]-N-cyclopropyl-4-(1-methyl-2-oxo-1,2-dihydro-4-pyridinyl)-3-piperidinecarboxamide

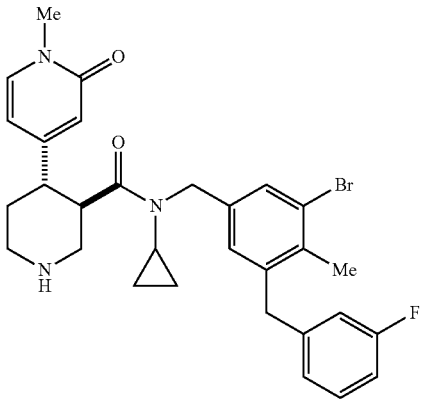

Prepared according to the procedure described in Example 1 but using instead Amine 91 as starting material. The title compound was obtained as a white froth. MS (ESI+, M+H): 566.

EXAMPLE 106 trans-N-[3-Bromo-5-(3-fluorobenzoyl)-4-methylbenzyl]-N-cyclopropyl-4-(1-methyl-2-oxo-1,2-dihydro-4-pyridinyl)-3-piperidinecarboxamide

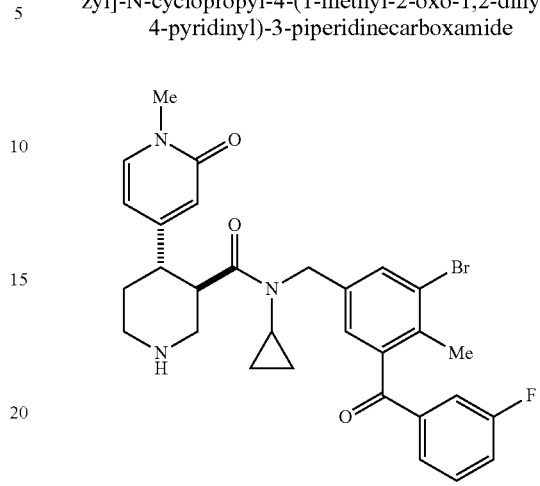

Prepared according to the procedure described in Example 1 but using instead Amine 92 as starting material. The title compound was obtained as a white froth. MS (ESI+, M+H): 582.

EXAMPLE 107 trans-N-{3-Bromo-5-[(3-fluorophenyl)(hydroxyl)methyl]-4-methylbenzyl}-N-cyclopropyl-4-(1-methyl-2-oxo-1,2-dihydro-4-pyridinyl)-3-piperidinecarboxamide

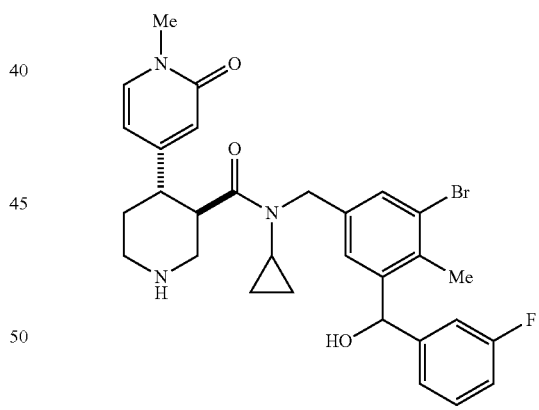

To a MeOH (0.09 M) solution of trans-N-[3-bromo-5-(3-fluorobenzoyl)-4-methylbenzyl]-N-cyclopropyl-4-(1-methyl-2-oxo-1,2-dihydro-4-pyridinyl)-3-piperidine-carboxamide (1 eq., Example 106) was added sodium borohydride (1.4 eq.). The resulting solution was stirred at RT for 15 h before the volatiles were removed in vacuo. The resulting residue carefully added 10% aq. HCl, followed by 1 N aq. NaOH so that the pH of the final solution is ~10. After extraction with EtOAc, the combined organic extracts were washed further with brine, dried over Na$_2$SO$_4$, filtered and the filtrate concentrated in vacuo. Further purification by way of column chromatography (SiO$_2$, 93:7 (v/v) CH$_2$Cl$_2$:2.0 M NH$_3$ in MeOH) afforded the title compound as a mixture of diastereomers. MS (ESI+, M+H): 584.

EXAMPLE 108 trans-N-[2-Chloro-5-(2-methoxyethyl)benzyl]-N-cyclopropyl-4-hydroxy-4-(1-methyl-2-oxo-1,2-dihydro-4-pyridinyl)-3-piperidinecarboxamide

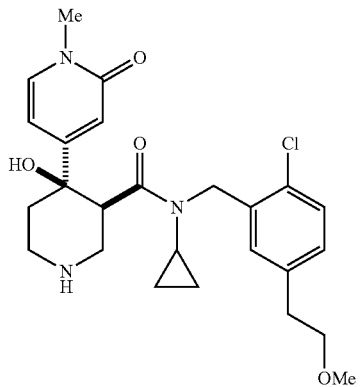

Step 1: tert-Butyl 3-{[[2-chloro-5-(2-methoxyethyl)benzyl](cyclopropyl)amino]carbonyl}-4-oxo-1-piperidinecarboxylate 1-tert-Butyl 3-ethyl 4-oxo-1,3-piperidinedicarboxylate (1 eq.), Amine 4 (1 eq.) and DMAP (0.2 eq.) were heated at 140° C. for 5 h. Purification of the crude product thus obtained by way of column chromatography (SiO$_2$, 95:5→3:7 (v/v) Hex: EtOAc) followed by swishing in 9:1 (v/v) Hex:Et$_2$O afforded the title compound as a white solid.

Step 2: tert-Butyl trans-4-[2-(benzyloxy)-4-pyridinyl]-3-{[[2-chloro-5-(2-methoxyethyl)benzyl](cyclopropyl)amino]carbonyl}-4-hydroxy-1-piperidinecarboxylate To a THF solution (0.05 M) of Arene 4 was added at −78° C. n-butyl lithium (2.5 M solution in hexanes, 2.1 eq.). After stirring at −78° C. for 30 min, solid magnesium bromide (2.5 eq.) was added in one rapid portion and the resulting mixture was stirred at −78° C. for 20 min. The reaction mixture was then slowly warmed to 0° C. over 30 min and tert-butyl 3-{[[2-chloro-5-(2-methoxyethyl)benzyl](cyclopropyl)amino]carbonyl}-4-oxo-1-piperidinecarboxylate (1 eq.) from the previous step was added as a THF solution. The reaction mixture was then stirred at 0° C. for 1 h and at RT for 30 min. The reaction was then quenched with the addition of sat. aq. NH$_4$Cl and ether. The aqueous layer was separated and back-extracted with ether. The combined organic extracts were washed further with brine, dried over MgSO$_4$, filtered and the filtrate concentrated in vacuo. Purification of the crude product thus obtained by way of column chromatography (SiO$_2$, 96:4→93:7 (v/v) acetone:toluene) afforded the title compound.

Step 3: tert-Butyl trans-3-{[[2-chloro-5-(2-methoxyethyl)benzyl](cyclopropyl)amino]carbonyl}-4-hydroxy-4-(2-oxo-1,2-dihydro-4-pyridinyl)-1-piperidinecarboxylate To a solution of tert-butyl trans-4-[2-(benzyloxy)-4-pyridinyl]-3-{[[2-chloro-5-(2-methoxyethyl)benzyl](cyclopropyl)amino]carbonyl}-4-hydroxy-1-piperidinecarboxylate (1 eq.) from the previous step in EtOAc (0.08 M) was added palladium (10% w/w on carbon, 0.5 eq.) and acetic acid (1.1 eq.). The resulting suspension was stirred under a balloon atmosphere of hydrogen for 4 h. The reaction was quenched with dichloromethane and the insolubles were removed via filtration through a pad of celite. Concentration of the filtrate thus obtained afforded the title compound.

Step 4: tert-Butyl trans-3-{[[2-chloro-5-(2-methoxyethyl)benzyl](cyclopropyl)amino]carbonyl}-4-hydroxy-4-(1-methyl-2-oxo-1,2-dihydro-4-pyridinyl)-1-piperidinecarboxylate To a methanol solution (0.1 M) of tert-butyl trans-3-{[[2-chloro-5-(2-methoxyethyl)benzyl](cyclopropyl)amino]carbonyl}-4-hydroxy-4-(2-oxo-1,2-dihydro-4-pyridinyl)-1-piperidinecarboxylate (1 eq.) from the previous step was added at 0 NaOH (2 N aq. solution, 3 eq.) and dimethyl sulfate (3 eq.). The resulting mixture was then stirred at RT for 12 h. The volatiles were then removed in vacuo and the residue was partitioned between water and dichloromethane. The aqueous layer was separated and back-extracted with dichloromethane. The combined organic extracts were washed further with brine, dried over MgSO$_4$, filtered and the filtrate concentrated in vacuo. Purification of the crude product thus obtained by way of column chromatography (SiO$_2$, 96:3 (v/v) CH$_2$Cl$_2$:MeOH) afforded the title compound.

Step 5: trans-N-[2-Chloro-5-(2-methoxyethyl)benzyl]-N-cyclopropyl-4-hydroxy-4-(1-methyl-2-oxo-1,2-dihydro-4-pyridinyl)-3-piperidinecarboxamide To a CH$_2$Cl$_2$ solution (0.05 M) of tert-butyl trans-3-{[[2-chloro-5-(2-methoxyethyl)benzyl](cyclopropyl)amino]carbonyl}-4-hydroxy-4-(1-methyl-2-oxo-1,2-dihydro-4-pyridinyl)-1-piperidinecarboxylate (1 eq.) from the previous step was added HCl (4.0 M dioxane solution, 30 eq.). The resulting solution was stirred at RT for 3 h. Following the removal of the volatiles in vacuo, the resulting residue was directly loaded onto a SiO$_2$ column packed with 94:6 (v/v) CH$_2$Cl$_2$: 2.0 M NH$_3$ in MeOH. Elution with the same solvent system furnished the title compound. MS (ESI+, M+H): 474.

EXAMPLE 109 trans-N-[2-Chloro-5-(2-methoxyethyl)benzyl]-N-cyclopropyl-4-methoxy-4-(1-methyl-2-oxo-1,2-dihydro-4-pyridinyl)-3-piperidinecarboxamide

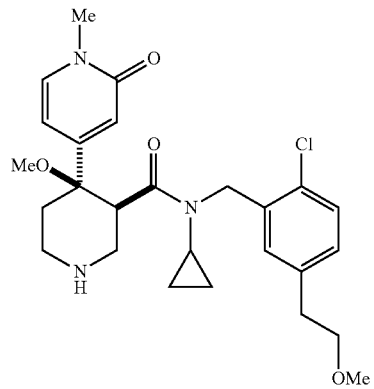

Step 1: tert-Butyl trans-4-[2-(benzyloxy-4-pyridinyl)-3-{[[2-chloro-5-(2-methyoxyethyl)benzyl](cyclopropyl)amino]carbonyl}-4-methoxy-1-piperidinecarboxylate To a DMF solution (0.18 M) of tert-butyl trans-4-[2-(benzyloxy)-4-pyridinyl]-3-{[[2-chloro-5-(2-methoxyethyl)benzyl](cyclopropyl)amino]carbonyl}-4-hydroxy-1-piperidinecarboxylate (1 eq., Example 108, Step 2) was added sodium hydride (1.2 eq.) and iodomethane (1.2 eq.). The reaction mixture was stirred at RT for 30 min before it was diluted with ether and water. The organic layer was separated and washed further with water and brine, dried over $MgSO_4$, filtered and the filtrate concentrated in vacuo. Purification of the crude product thus obtained by way of column chromatography ($SiO_2$, 3:2 (v/v) Hex:EtOAc→EtOAc) afforded the title compound.

Step 2: tert-Butyl trans-3-{[[2-chloro-5-(2-methoxyethyl)benzyl](cyclopropyl)amino]carbonyl}-4-methoxy-4-(2-oxo-1,2-dihydro-4-pyridinyl)-1-piperidinecarboxylate To a solution of tert-butyl trans-4-[2-(benzyloxy-4-pyridinyl)-3-{[[2-chloro-5-(2-methyoxyethyl)benzyl](cyclopropyl)amino]carbonyl}-4-methoxy-1-piperidinecarboxylate (1 eq.) from the previous step in EtOAc (0.1 M) was added palladium (10% w/w on carbon, 0.5 eq.) and acetic acid (1.1 eq.). The resulting suspension was stirred under a balloon atmosphere of hydrogen for 4 h. The reaction was quenched with dichloromethane and the insolubles were removed via filtration through a pad of celite. Concentration of the filtrate thus obtained afforded the title compound.

Step 3: tert-Butyl trans-3-{[[2-chloro-5-(2-methoxyethyl)benzyl](cyclopropyl)amino]carbonyl}-4-methoxy-4-(1-methyl-2-oxo-1,2-dihydro-4-pyridinyl)-1-piperidinecarboxylate To a methanol solution (0.07 M) of tert-butyl trans-3-{[[2-chloro-5-(2-methoxyethyl)benzyl](cyclopropyl)amino]carbonyl}-4-methoxy-4-(2-oxo-1,2-dihydro-4-pyridinyl)-1-piperidinecarboxylate (1 eq.) from the previous step was added at 0 NaOH (2 N aq. solution, 3 eq.) and dimethyl sulfate (4 eq.). The resulting mixture was then stirred at RT for 12 h. The volatiles were then removed in vacuo and the residue was partitioned between water and dichloromethane. The aqueous layer was separated and back-extracted with dichloromethane. The combined organic extracts were washed further with brine, dried over $MgSO_4$, filtered and the filtrate concentrated in vacuo. Purification of the crude product thus obtained by way of column chromatography ($SiO_2$, 96:3 (v/v) $CH_2Cl_2$:MeOH) afforded the title compound.

Step 5: trans-N-[2-Chloro-5-(2-methoxyethyl)benzyl]-N-cyclopropyl-4-methoxy-4-(1-methyl-2-oxo-1,2-dihydro-4-pyridinyl)-3-piperidinecarboxamide To a $CH_2Cl_2$ solution (0.05 M) of tert-butyl trans-3-{[[2-chloro-5-(2-methoxyethyl)benzyl](cyclopropyl)amino]carbonyl}-4-methoxy-4-(1-methyl-2-oxo-1,2-dihydro-4-pyridinyl)-1-piperidinecarboxylate (1 eq.) from the previous step was added HCl (4.0 M dioxane solution, 30 eq.). The resulting solution was stirred at RT for 3 h. Following the removal of the volatiles in vacuo, the resulting residue was directly loaded onto a $SiO_2$ column packed with 94:6 (v/v) $CH_2Cl_2$:2.0 M $NH_3$ in MeOH. Elution with the same solvent system furnished the title compound. MS (ESI+, M+H): 488. $^1$H NMR (acetone-$d_6$): δ (ppm) 0.77-1.03 (m, 4H), 2.22-2.36 (m, 2H), 2.52-2.59 (br m, 1H), 2.74-2.85 (br m, 2H), 3.03 (s, 3H), 3.12-3.17 (br m, 2H), 3.28 (s, 3H), 3.32-3.37 (m, 4H), 3.49 (s, 3H), 3.53 (t, d=7.0 Hz, 1H), 3.91 (br s, 1H), 4.53 (d, J=13.2 Hz, 1H), 4.75 (d, J=13.2 Hz, 1H), 6.41 (m, 1H), 6.52 (s, 1H), 7.11-7.15 (m, 2H), 7.31 (d, J=7.0 Hz, 1H), 7.58 (d, J=7.0 Hz, 1H). Human Renin $IC_{50}$ (buffer): 1.3 nM. Human Renin $IC_{50}$ (plasma): 3.2 nM.

EXAMPLE 110 trans-N-Cyclopropyl-4-hydroxy-N-[3-(2-methoxyethoxy)-5-(3-methoxypropyl)benzyl]-4-(1-methyl-2-oxo-1,2-dihydro-4-pyridinyl)-3-piperidinecarboxamide

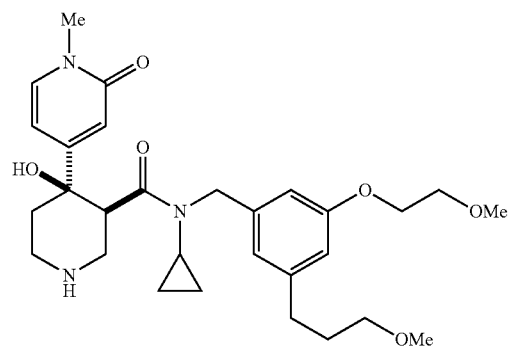

Prepared according to the procedure described in Example 108 but using instead Amine 11 as starting material. MS (ESI+, M+H): 514.

EXAMPLE 111 trans-N-Cyclopropyl-4-methoxy-N-[3-(2-methoxyethoxy)-5-(3-methoxypropyl)benzyl]-4-(1-methyl-2-oxo-1,2-dihydro-4-pyridinyl)-3-piperidinecarboxamide

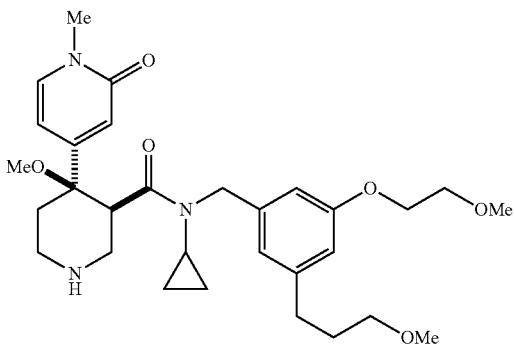

Prepared according to the procedure described in Example 109 but using instead Amine 11 as starting material. MS (ESI+, M+H): 528.

EXAMPLE 112

Assays Demonstrating Biological Activity

Inhibition of Human Recombinant Renin

Human recombinant renin (Proteos) in 50 mM MOPS pH 7.4, 100 mM NaCl, 0.002% Tween 20 at a final concentration of 100 pM is incubated with inhibitors from a 50 fold concentrated DMSO solution and 6 μM of an internally-quench fluorescent peptide: DNP-Lys-His-Pro-Phe-His-Leu-Val-Ile-His-D,L-Amp (SEQ ID NO: 1); Paschalidou K. et al., *Biochem J.*, 2004, 382, 1031). The reactions take place in a Costar 384 well black plate (#3573) at 37° C. for 3 hours. Fluorescence is measured at times 0 and 3 hours with a SpectraMax Gemini EM reader set at an excitation wavelength of 328 nm and at an emission wavelength of 388 nm. Background fluorescence at t=0 is subtracted from the measurement at t=3 hours. Inhibitory activity of the compounds is expressed as $IC_{50}$.

Inhibition of Renin in Human Plasma

Human EDTA-collected plasma is rapidly thawed in warm water and centrifuged at 2900 g for 15 minutes at 4° C. The supernatant is collected and recombinant renin (Proteos) is added at a final concentration of 1 nM. The plasma is transferred to a Costar black 384 well plate (#3573). Renin inhibitors are added from a 17.5 fold concentrated DMSO solution and pre-incubated at 37° C. for 10 minutes. The internally-quench fluorescent peptide QXL520™-Lys-His-Pro-Phe-His-Leu-Val-Ile-His-Lys (5-FAM) (Anaspec) is diluted in 3M Tris pH 7.2, 200 mM EDTA and added to the plasma. The final concentrations are: 6 µM substrate, 342 mM Tris, 23 mM EDTA. The plate is incubated at 37° C. for 1 hour. The plate is read in a SpectraMax Gemini EM reader set at an excitation wavelength of 490 nm and an emission wavelength of 520 nM at times 0 and 1 hour. Background fluorescence at t=0 is subtracted from the measurement at t=1 hour. Inhibitory activity of the compounds is expressed as $IC_{50}$.

In vivo Animal Model

Female double transgenic rats were purchased from RCC Ltd, Fullingsdorf, Switzerland. All animals were maintained under identical conditions and had free access to normal pelleted rat chow and water. Rats were initially treated with enalapril (1 mg/kg/day) during 2 months. After approximately two weeks following cessation of enalapril treatment the double transgenic rats become hypertensive and reach mean arterial blood pressures in the range of 160-170 mmHg.

Transmitter implantation—The rats were anaesthetised with a mixture of 90 mg/kg Ketamin-HCl (Ketavet, Parke-Davis, Berlin FRG) and 10 mg/kg xylazin (Rompun, Bayer, Leverkusen, FRG) i.p. The pressure transmitter was implanted under aseptic conditions into the peritoneal cavity with the sensing catheter placed in the descending aorta below the renal arteries pointing upstream. The transmitter was sutured to the abdominal musculature and the skin closed.

Telemetry-System—Telemetry units were obtained from Data Sciences (St. Paul, Minn.). The implanted sensor consisted of a fluid-filled catheter (0.7 mm diameter, 8 cm long; model TA11PA-C40) connected to a highly stable low-conductance strain-gauge pressure transducer, which measured the absolute arterial pressure relative to a vacuum, and a radio-frequency transmitter. The tip of the catheter was filled with a viscous gel that prevents blood reflux and was coated with an antithrombogenic film to inhibit thrombus formation. The implants (length=2.5 cm, diameter=1.2 cm) weighted 9 g and have a typical battery life of 6 months. A receiver platform (RPC-1, Data Sciences) connected the radio signal to digitized input that was sent to a dedicated personal computer (Compaq, deskpro). Arterial pressures were calibrated by using an input from an ambient-pressure reference (APR-1, Data Sciences). Systolic, mean and diastolic blood pressure was expressed in millimeter of mercury (mmHg).

Hemodynamic measurements—Double transgenic rats with implanted pressure transmitters were dosed by oral gavage with vehicle or 10 mg/kg of the test substance (n=6 per group) and the mean arterial blood pressure was continuously monitored. The effect of the test substance is expressed as maximal decrease of mean arterial pressure (MAP) in the treated group versus the control group.

Results

Compounds in accordance herewith were active, exhibiting an IC50<1 µM in both renin buffer and plasma assays. Data with respect to certain compounds is provided throughout the examples above.

EXAMPLE 113

Animal Studies Comparing Oral and Transdermal Administration of the Test Compound, trans-N-({3-Bromo-4-methyl-5-[3-(methyloxy)propyl]phenyl}methyl)-N-cyclopropyl-4-(1-methyl-2-oxo-1,2-dihydro-4-pyridinyl)-3-piperidinecarboxamide, in Telemetrized, Female Double Transgenic Rats Female double transgenic rats (rats transgenic for human renin and angiotensin (see, e.g., Bohlender et al., J Am Soc Nephrol 11:2056 (2000)) were developed. All animals were maintained under identical conditions and had free access to normal pelleted rat chow and water. Rats were initially treated with enalapril (1 mg/kg/day), starting 3 weeks after birth and during 9 weeks. Telemetry transmitters are implanted within 2 to 4 weeks after cessation of enalapril treatment. After approximately two weeks following cessation of enalapril treatment, the double transgenic rats are hypertensive with mean arterial blood pressures in the range of 160-170 mmHg.

Transmitter implantation—The rats were anesthetized using isoflurane (via inhalation, 2-3%) The pressure transmitter was implanted under aseptic conditions into the peritoneal cavity with the sensing catheter placed in the descending aorta below the renal arteries pointing upstream. The transmitter was sutured to the abdominal musculature, the skin closed, and the rats were individually housed in a cage, placed on a telemetry receiver pad to enable collection of the blood pressure data during recovery from anesthesia and thereafter. The rats were single-caged for the duration of the recording of telemetry data.

Telemetry System—Telemetry units were obtained from Data Sciences International (DSI, St. Paul, Minn.). The implanted sensor consisted of a fluid-filled catheter (0.7 mm diameter, 8 cm long; model TA11PA-C40) connected to a highly stable low-conductance strain-gauge pressure transducer, which measured the absolute arterial pressure relative to a vacuum, and a radio-frequency transmitter. The tip of the catheter was filled with a viscous gel that prevents blood reflux. The implants (length=2.5 cm, diameter=1.2 cm) weighed 9 g and have a typical battery life of 6 months. A receiver platform (RPC-1, DSI) connected the radio signal to digitized input that was sent to a dedicated personal computer. Arterial pressures were calibrated by using an input from an ambient-pressure reference (APR-1, DSI). Systolic, mean and diastolic blood pressure was expressed in millimeter of mercury (mmHg).

Telemetry data analysis—Signals received by the receivers were digitized for 10 seconds every 5 minutes, at 500 Hz. From this signal, mean arterial pressure (MAP), systolic and diastolic blood pressure (SBP and DPB), pulse pressure (PP), heart rate (HR) and activity (ACT) were derived. A one-hour moving average of the data was then performed by the DSI analysis software. Data were then exported to an Excel template for the calculation of group statistics, areas between curves (ABC), maximal effect and duration of MAP reduction.

Drug administration—For oral delivery, double transgenic rats with implanted pressure transmitters were dosed by oral gavage with a single bolus of vehicle (0.5% methocel; 5 ml/kg) or of the test substance (30 mg/5 ml/kg) (n=5 per group). After dosing, the rat was returned to his cage. Blood pressure data were collected up to 5 days after oral dosing.

For transdermal delivery, double transgenic rats with implanted pressure transmitters were dosed with a single application on the shaved skin of the rat of vehicle (250 µl of 100% DMSO; n=4) or of the test compound (10 mg in 250 µl of 100% DMSO, i.e. 33 mg/kg; n=5). The rat was lightly sedated under 2.5% isoflurane anesthesia, and its back was shaved over a 4 cm² area. The animal was returned to his cage to recover from anesthesia. Twenty-four hours later, the rat was lightly sedated under 2.5% isoflurane anesthesia, and the shaved area disinfected with 3 passes of ethanol.

After evaporation of the ethanol, a volume of 250 µl of 100% DMSO only, or of the compound dissolved in a 100% DMSO solution was applied over the shaved area using a micropipette. After complete evaporation of the DMSO solution (within 5 min after application), an occlusive transparent, waterproof film (OpSite) was taped to the back of the animal over the shaved area, and a jacket was fitted on the animal. Isoflurane inhalation was stopped, and the animal individually caged for telemetry data collection. Blood pressure data were collected up to 5 days after application of the compound/DMSO solution.

Figure 1B:
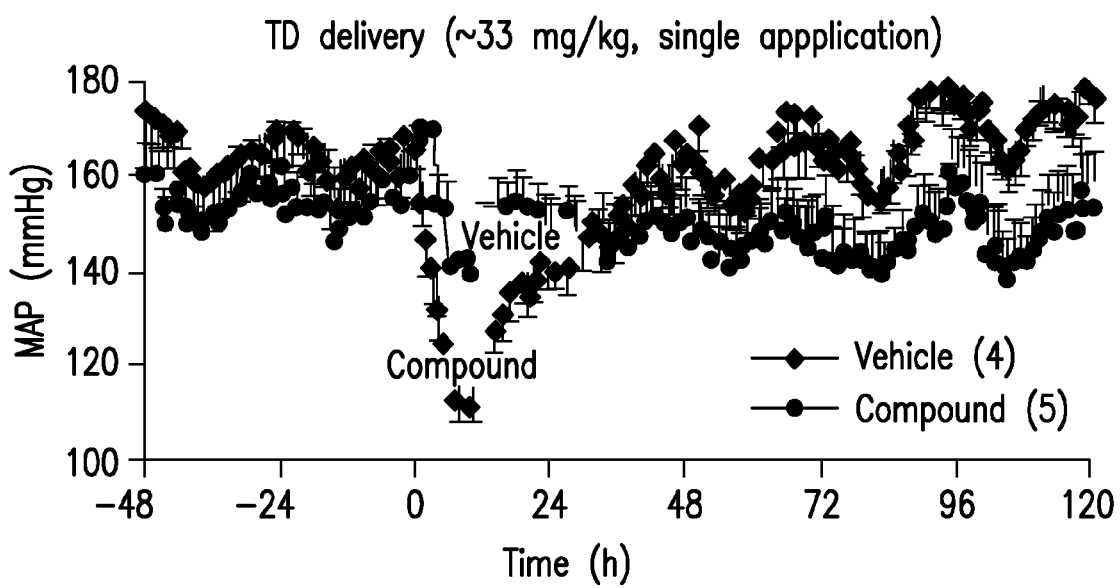

Exemplary results of the effect of the test substance on MAP after PO and TD delivery are shown in FIG. 1 and Table 7 below.

TABLE 7

Commparison of TD vs PO delivery of the test substance on ABC, max MAP decrease and duration of MAP reduction.

| Route | $ABC_{36h}$ (mmHg * h) | max MAP decrease (mmHg) | duration (days) |
|---|---|---|---|
| PO | 1143 | 57 | 2 |
| TD | 514 | 30 | 1 |

Pharmacokinetics, pharmacodynamics and biomarkers—A blood sample (0.3 ml) was taken by tail bleed or jugular iv in the telemetrized dTGs, at $T_0$, $T_{6h}$ and $T_{24h}$ after PO delivery to determine test substance levels and bioavailability (estimated as area under the curve, or AUC) of the active substance in systemic circulation.

A blood sample (0.3 ml) was taken by tail bleed or jugular iv in the telemetrized dTGs, at $T_{0h}$, $T_{4h}$ and $T_{24h}$ after TD delivery to determine test substance levels and bioavailability (estimated as area under the curve, or AUC) of the active substance in systemic circulation. Plasma renin activity (PRA) was also measured at $T_{0h}$ and $T_{4h}$. The effect of the test substance on PRA is expressed as the percentage of inhibition of PRA at $T_{4h}$ vs $T_{0h}$. Exemplary results are shown in Table 8 below.

TABLE 8

Comparison of the bioavailability of TD vs PO delivery of the test substance after PO vs TD delivery

| Route | $AUC_{24h}$ (µM * hr) | PRA inhibition at 4 h (%) |
|---|---|---|
| PO | 1.8 | n.a. |
| TD | 2.9 | 98 | n.a. not available

What is claimed is:

1. A compound of formula I, or a pharmaceutically acceptable salt thereof, having formula (I)

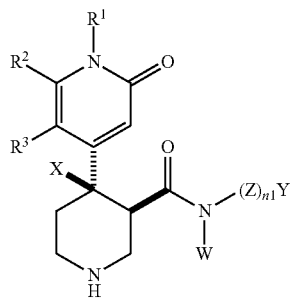

wherein:
$R^1$ is selected from the group consisting of: $C_1$-$C_6$-alkyl, $C_3$-$C_6$ cycloalkyl, $C_2$-$C_6$ alkenyl, $C_3$-$C_6$ cycloalkenyl and $C_2$-$C_6$ alkynyl, wherein each of the foregoing is optionally substituted with 1-3 halogens and/or $C_1$-$C_5$ alkoxy;

$R^2$ and $R^3$ are independently selected from the group consisting of: hydrogen, halogen, $C_1$-$C_5$ alkyl, $C_3$-$C_8$ cycloalkyl, $C_2$-$C_5$ alkenyl, $C_3$-$C_8$ cycloalkenyl, $C_2$-$C_5$ alkynyl, cyano, $C_1$-$C_5$ alkoxy, aryl and hetetoaryl,
wherein said heteroaryl contains from 1 to 3 heteroatoms, independently selected from the group consisting of: N, O and S, wherein each N is optionally in the form of an oxide and each S is optionally in the form of an oxide selected from the group consisting of S(=O) and S(=O)$_2$,
wherein said aryl and heteroaryl are optionally substituted with 1-4 halogens,
wherein said alkyl, cycloalkyl, alkenyl, cycloalkenyl, alkynyl and alkoxy are optionally substituted with 1-3 substituents, each of which is independently selected from the group consisting of: halogen, $C_1$-$C_5$ alkyl, $C_2$-$C_5$ alkenyl, cyano and $C_1$-$C_5$ alkoxy, wherein each of the foregoing alkyl, alkenyl and alkoxy substituents is optionally substituted with 1-3 halogens;

W is cyclopropyl, unsubstituted or mono-, di-, tri-, tetra- or penta-substituted with fluorine, X is H;

Z is $C_1$-$C_2$ alkylene optionally substituted with 1-2 substituents, independently selected from the group consisting of: halogen, $C_1$-$C_3$ alkyl and $C_3$ cycloalkyl, wherein the foregoing alkyl and cycloalkyl substituents are optionally substituted with 1-3 halogens;

n1 is 0 or 1;

Y is phenyl, which is optionally mono-, di-, tri-, tetra-, or penta-substituted, each substituent of which is independently selected from the group consisting of:
(1) halogen,
(2) —OH,
(3) —NH($R^6$),
(4) oxo,
(5) —C(=O)—$R^6$,
(6) —OC(=O)—$R^6$,
(7) $C_1$-$C_5$ alkyl optionally substituted with 1-3 halogens,
(8) $C_3$-$C_8$ cycloalkyl optionally substituted with 1-3 halogens,
(9) $C_2$-$C_5$ alkenyl optionally substituted with 1-3 halogens,
(10) $C_3$-$C_8$ cycloalkenyl optionally substituted with 1-3 halogens,
(11) $C_2$-$C_5$ alkynyl optionally substituted with 1-3 halogens,
(12) $C_1$-$C_5$ alkoxy optionally substituted with 1-3 halogens,
(13) cyano
(14) $C_1$-$C_5$-cyano optionally substituted with 1-3 halogens,
(15) —OCF$_3$,
(16) —C($R^7$)$_3$,
(17) —($C_1$-$C_5$ alkylene)-OR$^8$ optionally substituted with 1-3 halogens,
(18) —N($R^6$)—($C_1$-$C_5$ alkylene)-OR$^8$ optionally substituted with 1-3 halogens,
19) —O—($C_1$-$C_5$ alkylene)-OR$^8$ optionally substituted with 1-3 halogens,
(20) —S—($C_1$-$C_5$ alkylene)-OR$^8$ optionally substituted with 1-3 halogens,
(21) —S(=O)—($C_1$-$C_5$ alkylene)-OR$^8$ optionally substituted with 1-3 halogens,

(22) —S(=O)₂—(C₁-C₅ alkylene)-OR⁸ optionally substituted with 1-3 halogens,
(23) —(C₁-C₅ alkylene)-N(R⁶)—C(=O)—(C₁-C₅ alkylene)-R⁸ optionally substituted with 1-3 halogens,
(24) —(C₁-C₅ alkylene)-N(R⁶)—C(=O)—OR⁸ optionally substituted with 1-3 halogens,
(25) —(C₁-C₅ alkylene)-N(R⁶)(R⁸) optionally substituted with 1-3 halogens,
(26) —O—(C₁-C₅ alkylene)-C(R⁶)₂—C(=O)OR⁸ optionally substituted with 1-3 halogens,
(27) —(C₁-C₅ alkylene)-C(R⁶)₂—C(=O)OR⁸ optionally substituted with 1-3 halogens,
(28) —O—(C₁-C₅ alkylene)-morpholine optionally substituted with 1-3 halogens,
(29) —OC(=O)-morpholine,
(30) —SR⁸,
(31) —S(=O)—R⁸,
(32) —S(=O)₂—R⁸
(33) —N(R⁶)(R⁸),
(34) —(C₁-C₅ alkylene)-C(R⁶)₂—(R⁸) optionally substituted with 1-3 halogens,
(35) —(R⁹)₀₋₁R¹⁰,
(36) C₂-C₅ alkenyl-OR⁸ optionally substituted with 1-3 halogens,
(37) C₂-C₅ alkynyl-OR⁸ optionally-substituted with 1-3 halogens,
(38) —(C₁-C₅ alkylene)-C(=O)—(C₁-C₅ alkylene)-R⁸ optionally substituted with 1-3 halogens,
(39) —(C₁-C₅ alkylene)-O—C(=O)—(C₁-C₅ alkylene)-R⁸ optionally substituted with 1-3 halogens,
(40) —(C₁-C₅ alkylene)-C(=O)—N(R⁶)(R⁸) optionally substituted with 1-3 halogens,
(41) —(C₁-C₅ alkylene)-O—C(=O)—N(R⁶)(R⁸) optionally substituted with 1-3 halogens,
(42) —(C₁-C₅ alkylene)-SR⁸ optionally substituted with 1-3 halogens,
(43) —(C₁-C₅ alkylene)-S(=O)—R⁸ optionally substituted with 1-3 halogens, and
(44) —(C₁-C₅ alkylene)-S(=O)₂—R⁸ optionally substituted with 1-3 halogens,
wherein R⁶ is selected from the group consisting of: hydrogen, C₁-C₆ alkyl, C₃-C₈ cycloalkyl, C₂-C₆ alkenyl, C₃-C₈ cycloakenyl and C₂-C₆ alkynyl, wherein each of the foregoing alkyl, cycloalkyl, alkenyl, cycloalkenyl and alkynyl substituents is optionally substituted with 1-3 halogens,
wherein R⁷ is halogen,
wherein R⁸ is selected from the group consisting of: hydrogen, C₁-C₆ alkyl, C₃-C₈ cycloalkyl, C₂-C₆ alkenyl, C₃-C₈ cycloalkenyl and C₂-C₆ alkynyl, wherein each of the foregoing alkyl, cycloalkyl, alkenyl, cycloalkenyl and alkynyl substituents is optionally substituted with 1-3 halogens,
wherein R⁹ is selected from the group consisting of: —C(H)(OH)—, —C(=O)—, —OC(=O)—, —C(=O)O—, —O—, —OC(=O)O—, C₁-C₅ alkylene, C₁-C₅ alkenylene, —N(R⁶)—, —S—, —S(=O)—, —S(=O)₂—, —N(R⁶)—C(=O)—, —C(=O)—N(R⁶)—, —OC(=O)—N(R⁶)—, —N(R⁶)—C(=O)O—, —N(R⁶)—S(=O)₂—, —S(=O)₂—N(R⁶)—, wherein each of the foregoing alkylene and alkenylene substituents is optionally substituted with 1-3 halogens, and wherein R⁶ is defined above, and
wherein R¹⁰ is a five- or six-membered saturated or unsaturated heterocyclic or carbocyclic ring which is optionally mono-, di-, tri-, tetra- or penta-substituted, wherein each substituent is independently selected from the group consisting of: halogen, —OH, —SR⁶, —N(R⁶)(R⁸), C₁-C₅ alkyl, C₃-C₈ cycloalkyl, C₂-C₅ alkenyl, C₃-C₆ cycloalkenyl, C₂-C₅ alkynyl, C₁-C₅ alkoxy, cyano and C₁-C₅-cyano, wherein said heterocyclic ring contains from 1 to 3 heteroatoms, independently selected from N, O and S, wherein, each N is optionally in the form of an oxide and each S is optionally is in the form of an oxide selected from the group consisting of: S(=O) or S(=O)₂, and wherein R6 and R8 are defined above.

2. The compound of claim 1 wherein R¹ is —CH₃ or —CH₂CH₃.

3. The compound of claim 1 wherein R² and R³ are independently selected from the group consisting of: H, —OCH₂OCH₃ and —CH₃.

4. The compound of claim 1 wherein (Z)ₙ₁ is —CH₂— or a bond.

5. The compound of claim 1 wherein:
R¹ is C₁-C₂ alkyl optionally substituted with 1-3 halogens,
R² and R³ are independently selected from the group consisting of: hydrogen, halogen, C₁-C₅ alkyl and C₁-C₅ alkoxy wherein the alkyl and alkoxy are optionally substituted with 1-3 substituents independently selected from the group consisting of: halogen, C₁-C₅ alkyl optionally substituted with 1-3 halogens and C₁-C₅ alkoxy optionally substituted with 1-3 halogens,
X is hydrogen, and
Z is C₁-C₂ alkylene.

6. The compound of claim 5 having formula (II)

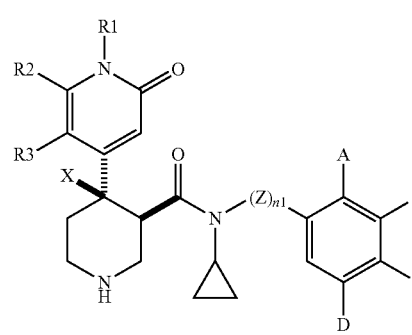

II wherein:
A is selected from the group consisting of:
(1) hydrogen,
(2) halogen,
(3) C₁-C₅ alkyl,
(4) C₁-C₅ alkoxy, and
(5) —S—(CH₂)₀₋₃—CH₃,
wherein (3) and (4) are optionally substituted with 1-3 halogens,
B is selected from the group consisting of:
(1) hydrogen,
(2) halogen,
(3) C₁-C₅ alkyl,
(4) C₁-C₅ alkoxy,
(5) —OH,
(6) —CF₃,
(7) —C(=O)—CH₃,
(8) —O—(C₁-C₅ alkylene)-O-cyclopropyl,
(9) —O—(C₁-C₅ alkylene)-O—(CH₂)₀₋₂—CH₃,
(10) —(C₁-C₅ alkylene)-O—(CH₂)₀₋₂—CH₃,
(11) —OC(=O)-morpholine,
(12) —O—(C₁-C₅ alkylene)-morpholine,
(13) —O—(C₁-C₅ alkylene)-C(CH₃)₂—C(=O)OH.
(14) —O—(C₁-C₅ alkylene)-C(CH₃)₂—C(=O)OCH₃,
(15)

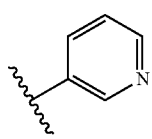 [SMILES: *c1cccnc1]

and
(16)

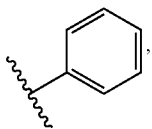 [SMILES: *c1ccccc1]

wherein (3), (4), (8), (9), (10), (12), (13), (14), (15) and (16) are optionally substituted with 1-3 halogens, C is selected from the group consisting of:
(1) hydrogen,
(2) $C_1$-$C_5$ alkyl optionally substituted with 1-3 halogens, and
(3) $C_1$-$C_5$ alkoxy optionally substituted with 1-3 halogens, and D is selected from the group consisting of:
(1) hydrogen,
(2) halogen,
(3) $C_1$-$C_5$ alkyl,
(4) $C_1$-$C_5$ alkoxy,
(5) $C_1$-$C_5$-cyano,
(6) $C_2$-$C_5$ alkenylene-O—$(C_{1-12})_{0-2}$—$CH_3$,
(7) —($C_1$-$C_5$ alkylene)-N(H)—C(=O)—O—$(CH_2)_{0-2}$—$CH_3$,
(8) —($C_1$-$C_5$ alkylene)-N(H)—C(=O)—$(CH_2)_{0-2}$—$CH_3$,
(9) —($C_1$-$C_5$ alkylene)-O—$CHF_2$,
(10) —($C_1$-$C_5$ alkylene)-O—$(CH_2)_{0-2}$—$CH_3$,
(11) —O—($C_1$-$C_5$ alkylene)-O—$(CH_2)_{0-2}$—$CH_3$,
(12) —($C_1$-$C_5$ alkylene)-OH,
(13) —S—($C_1$-$C_5$ alkylene)-OH,
(14) —$SCF_3$,
15) —N(H)—($C_1$-$C_5$ alkylene)-O—$(CH_2)_{0-2}$—$CH_3$, and
(16)

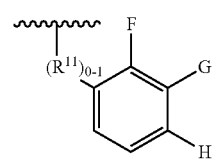

wherein F, G and H are independently selected from the group consisting of: hydrogen, halogen and $C_1$-$C_3$ alkyl, and wherein $R^{11}$ is selected from the group consisting of: —$CH_2$—, —C(H)(OH)— and —C(=O)—, and wherein (3), (4), (5), (6), (7), (8), (9), (10), (11), (12), (13) and (15) are optionally substituted with 1-3 halogens, or a pharmaceutically acceptable salt thereof.

7. A compound of claim 1 wherein the compound is selected from the following:

TABLE

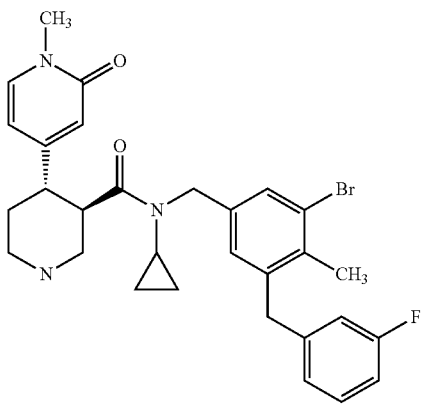 [SMILES: Cc1c(Br)cc(CN(C(=O)[C@H]2CNCC[C@@H]2c2ccn(C)c(=O)c2)C2CC2)cc1Cc1cccc(F)c1]

Ex. 105

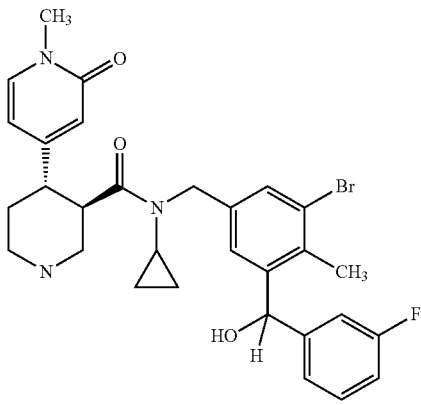 [SMILES: Cc1c(Br)cc(CN(C(=O)[C@H]2CNCC[C@@H]2c2ccn(C)c(=O)c2)C2CC2)cc1C(O)c1cccc(F)c1]

Ex. 107

TABLE-continued
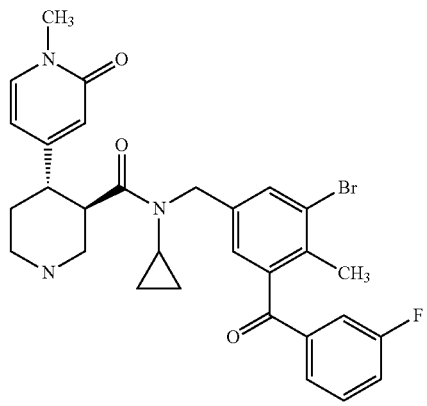 [SMILES: Cc1c(Br)cc(CN(C(=O)[C@H]2CNCC[C@@H]2c2ccn(C)c(=O)c2)C2CC2)cc1C(=O)c1cccc(F)c1]
Ex. 106
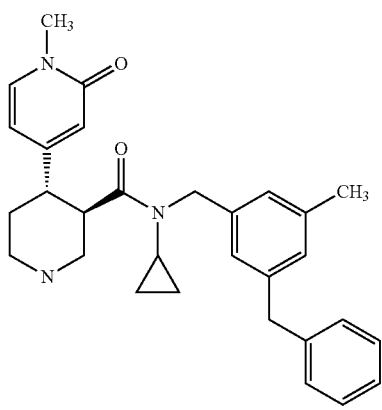 [SMILES: Cc1cc(Cc2ccccc2)cc(CN(C(=O)[C@H]2CNCC[C@@H]2c2ccn(C)c(=O)c2)C2CC2)c1]
Ex. 104
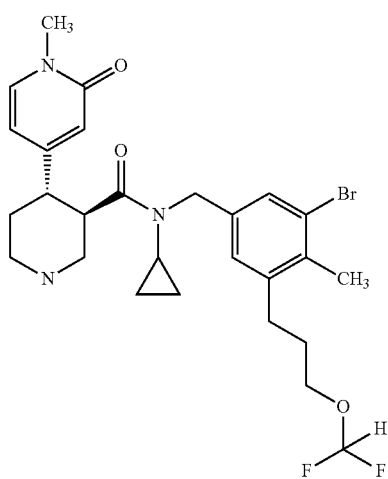 [SMILES: Cc1c(Br)cc(CN(C(=O)[C@H]2CNCC[C@@H]2c2ccn(C)c(=O)c2)C2CC2)cc1CCCOC(F)F]
Ex. 103

TABLE-continued
Ex. 102
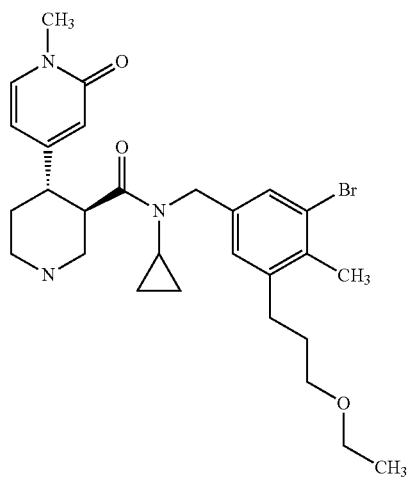 [SMILES: CCOCCCc1cc(CN(C(=O)[C@H]2CNCC[C@@H]2c2ccn(C)c(=O)c2)C2CC2)cc(Br)c1C]
Ex. 4
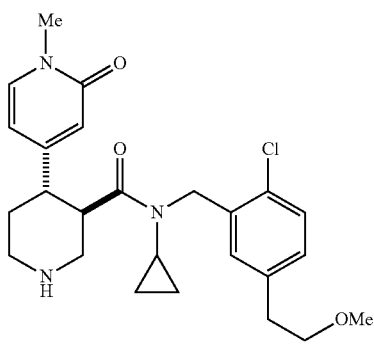 [SMILES: COCCc1ccc(Cl)c(CN(C(=O)[C@H]2CNCC[C@@H]2c2ccn(C)c(=O)c2)C2CC2)c1]
Ex. 101
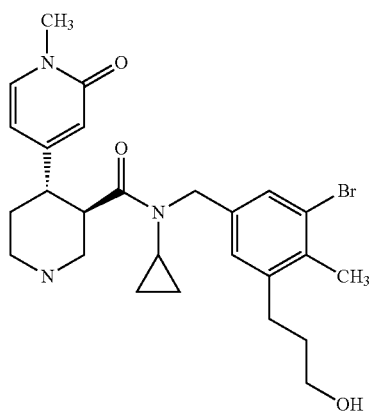 [SMILES: Cc1c(Br)cc(CN(C(=O)[C@H]2CNCC[C@@H]2c2ccn(C)c(=O)c2)C2CC2)cc1CCCO]
Ex. 96
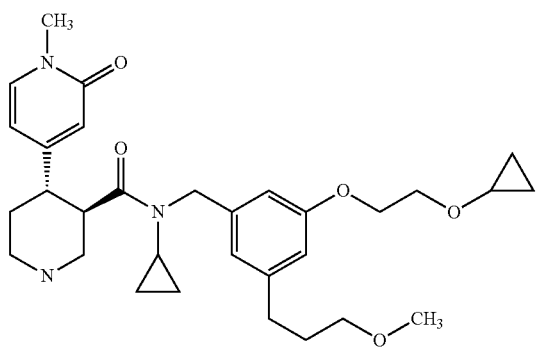 [SMILES: COCCCc1cc(CN(C(=O)[C@H]2CNCC[C@@H]2c2ccn(C)c(=O)c2)C2CC2)cc(OCCOC2CC2)c1]

TABLE-continued
Ex. 93
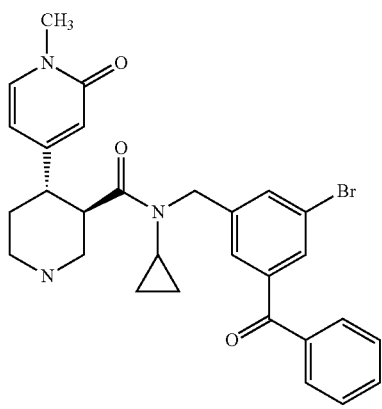 [SMILES: Cn1ccc([C@H]2CCNC[C@@H]2C(=O)N(Cc2cc(Br)cc(C(=O)c3ccccc3)c2)C2CC2)cc1=O]
Ex. 90
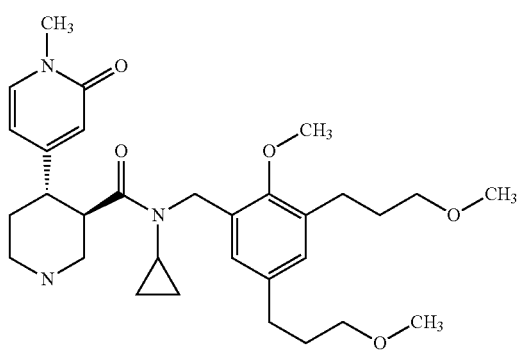
Ex. 92
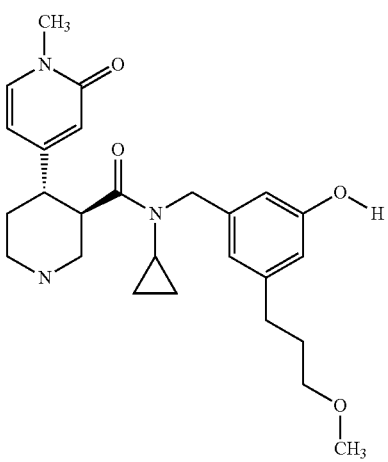 [SMILES: COCCCc1cc(O)cc(CN(C(=O)[C@H]2CNCC[C@@H]2c2ccn(C)c(=O)c2)C2CC2)c1]

TABLE-continued
Ex. 94
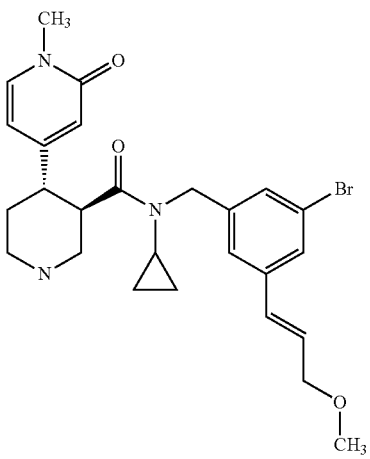 [SMILES: COC/C=C/c1cc(Br)cc(CN(C(=O)[C@H]2CNCC[C@@H]2c2ccn(C)c(=O)c2)C2CC2)c1]
Ex. 89
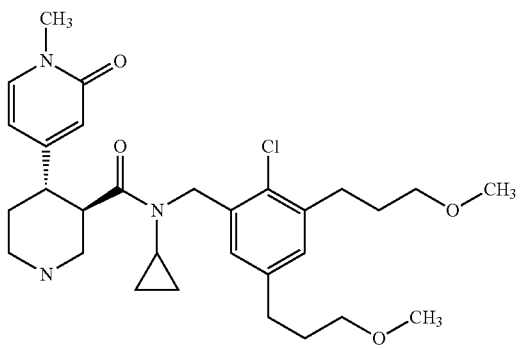
Ex. 88
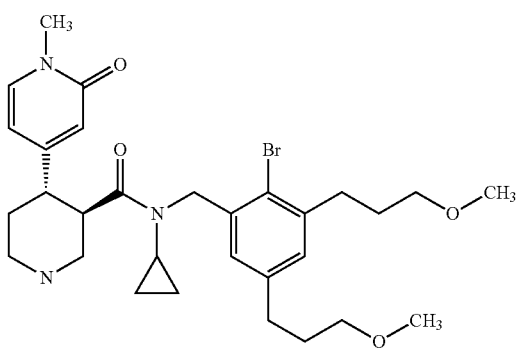 [SMILES: COCCCc1cc(CCCOC)c(Br)c(CN(C(=O)[C@H]2CNCC[C@@H]2c2ccn(C)c(=O)c2)C2CC2)c1]
Ex. 9
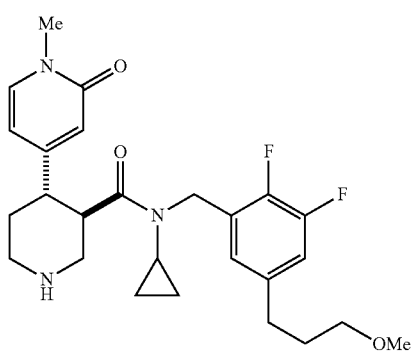 [SMILES: COCCCc1cc(F)c(F)c(CN(C(=O)[C@H]2CNCC[C@@H]2c2ccn(C)c(=O)c2)C2CC2)c1]

TABLE-continued
Ex. 16
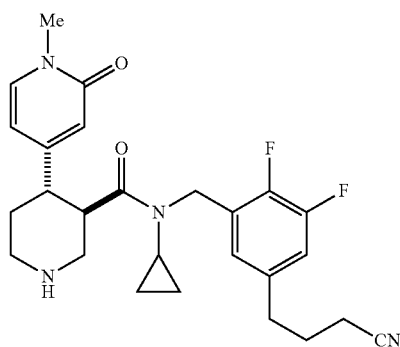 [SMILES: Cn1ccc([C@H]2CCNC[C@@H]2C(=O)N(Cc2cc(CCCC#N)cc(F)c2F)C2CC2)cc1=O]
Ex. 95
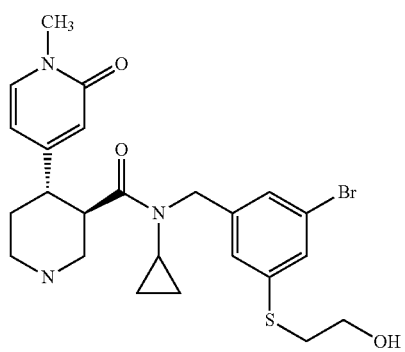 [SMILES: Cn1ccc([C@H]2CCNC[C@@H]2C(=O)N(Cc2cc(Br)cc(SCCO)c2)C2CC2)cc1=O]
Ex. 91
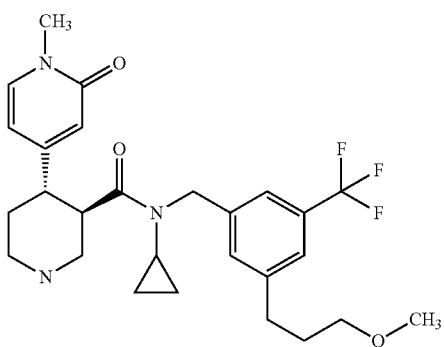 [SMILES: COCCCc1cc(CN(C(=O)[C@H]2CNCC[C@@H]2c2ccn(C)c(=O)c2)C2CC2)cc(C(F)(F)F)c1]
Ex. 87
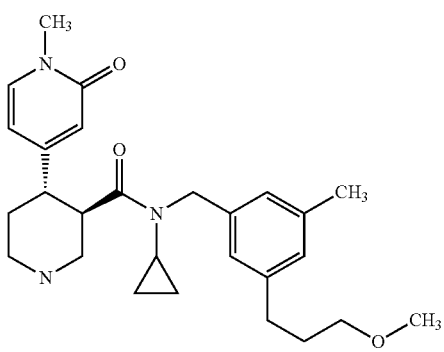 [SMILES: COCCCc1cc(C)cc(CN(C(=O)[C@H]2CNCC[C@@H]2c2ccn(C)c(=O)c2)C2CC2)c1]

TABLE-continued
Ex. 86
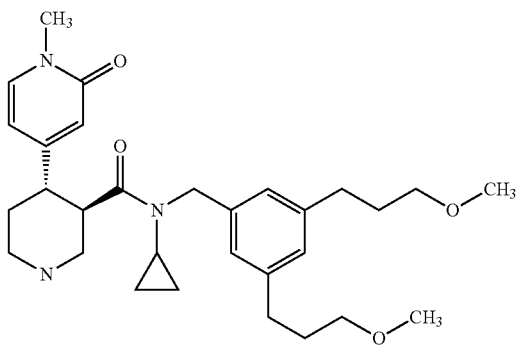 [SMILES: COCCCc1cc(CCCOC)cc(CN(C(=O)[C@H]2CNCC[C@@H]2c2ccn(C)c(=O)c2)C2CC2)c1]
Ex. 84
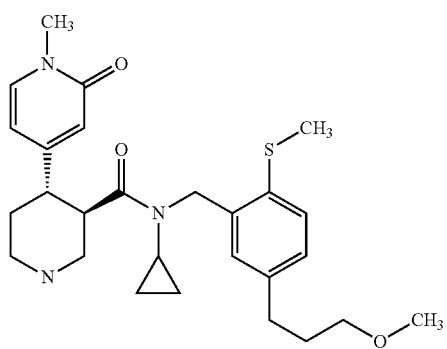 [SMILES: COCCCc1ccc(SC)c(CN(C(=O)[C@H]2CNCC[C@@H]2c2ccn(C)c(=O)c2)C2CC2)c1]
Ex. 85
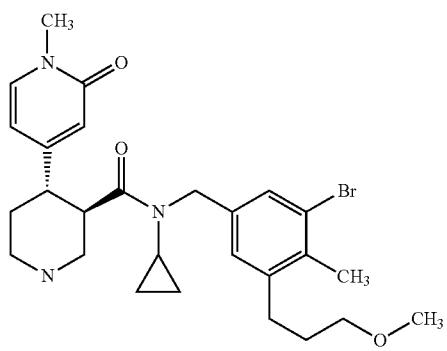
Ex. 83
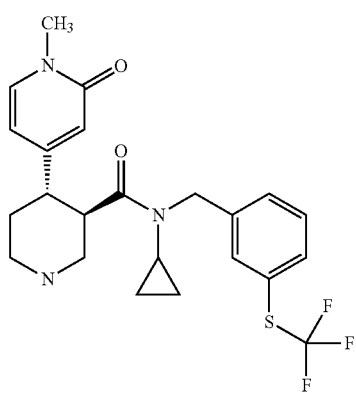 [SMILES: Cn1ccc([C@H]2CCNC[C@@H]2C(=O)N(Cc2cccc(SC(F)(F)F)c2)C2CC2)cc1=O]

TABLE-continued
Ex. 11
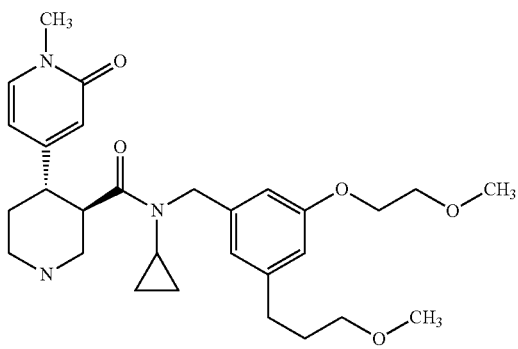 [SMILES: COCCCc1cc(CN(C(=O)[C@H]2CNCC[C@@H]2c2ccn(C)c(=O)c2)C2CC2)cc(OCCOC)c1]
Ex. 40
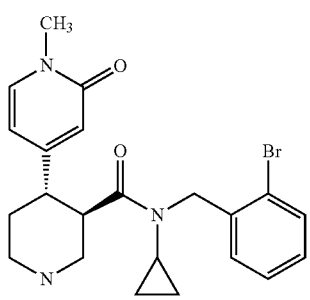 [SMILES: Cn1ccc([C@H]2CCNC[C@@H]2C(=O)N(Cc2ccccc2Br)C2CC2)cc1=O]
Ex. 81
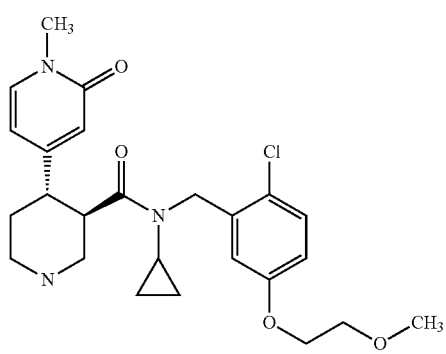 [SMILES: COCCOc1ccc(Cl)c(CN(C(=O)[C@H]2CNCC[C@@H]2c2ccn(C)c(=O)c2)C2CC2)c1]
Ex. 80
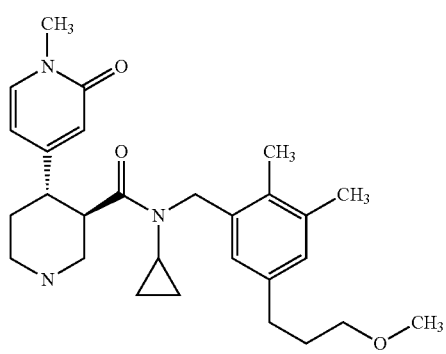 [SMILES: COCCCc1cc(C)c(C)c(CN(C(=O)[C@H]2CNCC[C@@H]2c2ccn(C)c(=O)c2)C2CC2)c1]

TABLE-continued
Ex. 98
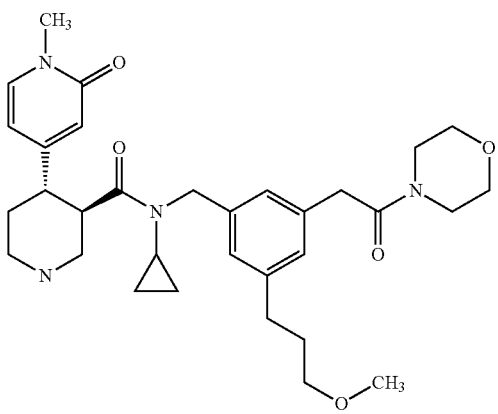 [SMILES: COCCCc1cc(CC(=O)N2CCOCC2)cc(CN(C(=O)[C@H]2CNCC[C@@H]2c2ccn(C)c(=O)c2)C2CC2)c1]
Ex. 97
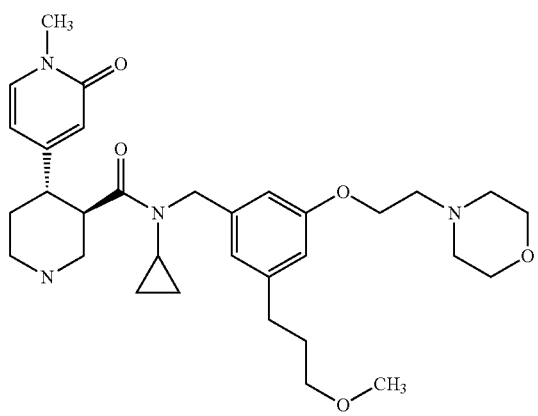 [SMILES: COCCCc1cc(CN(C(=O)[C@H]2CNCC[C@@H]2c2ccn(C)c(=O)c2)C2CC2)cc(OCCN2CCOCC2)c1]
Ex. 34
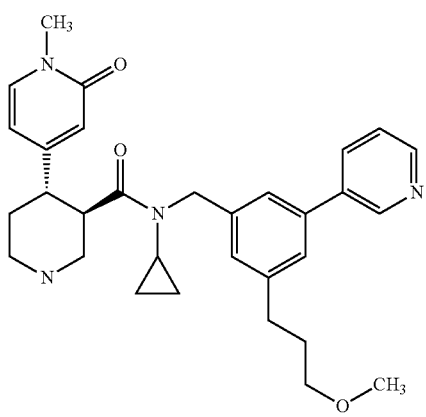 [SMILES: COCCCc1cc(CN(C(=O)[C@H]2CNCC[C@@H]2c2ccn(C)c(=O)c2)C2CC2)cc(-c2cccnc2)c1]

TABLE-continued
Ex. 33
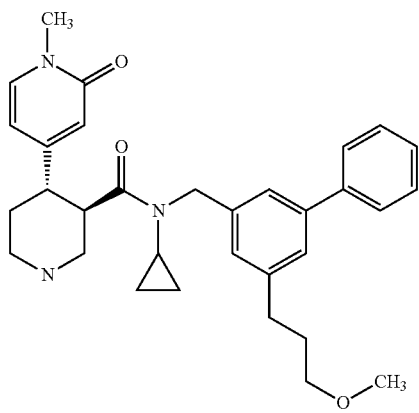 [SMILES: COCCCc1cc(CN(C(=O)[C@H]2CNCC[C@@H]2c2ccn(C)c(=O)c2)C2CC2)cc(-c2ccccc2)c1]
Ex. 35
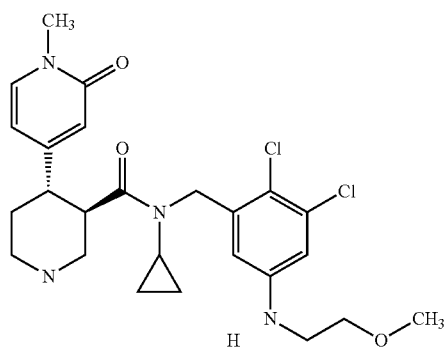
Ex. 31
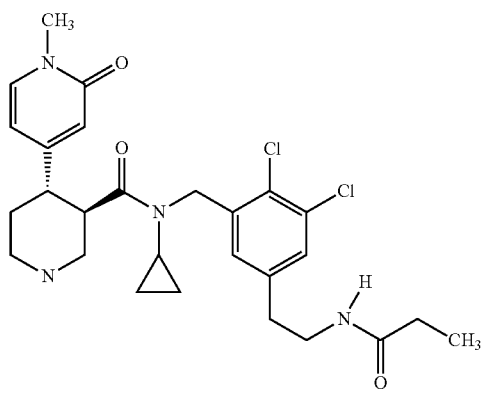 [SMILES: CCC(=O)NCCc1cc(Cl)c(Cl)c(CN(C(=O)[C@H]2CNCC[C@@H]2c2ccn(C)c(=O)c2)C2CC2)c1]
Ex. 30
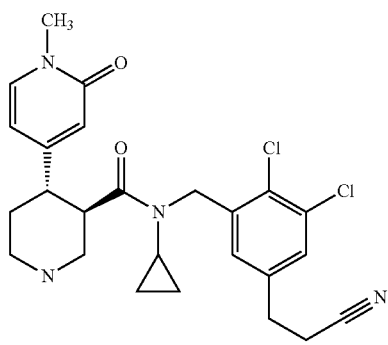 [SMILES: Cn1ccc([C@H]2CCNC[C@@H]2C(=O)N(Cc2cc(CCC#N)cc(Cl)c2Cl)C2CC2)cc1=O]

TABLE-continued
Ex. 78
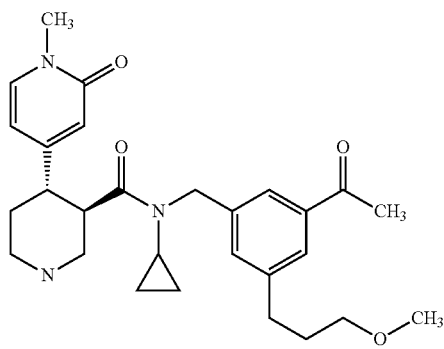 [SMILES: COCCCc1cc(CN(C(=O)[C@H]2CNCC[C@@H]2c2ccn(C)c(=O)c2)C2CC2)cc(C(C)=O)c1]
Ex. 28
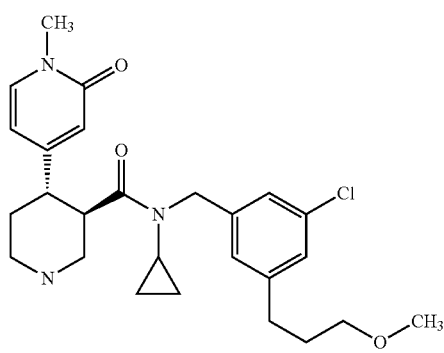 [SMILES: COCCCc1cc(Cl)cc(CN(C(=O)[C@H]2CNCC[C@@H]2c2ccn(C)c(=O)c2)C2CC2)c1]
Ex. 27
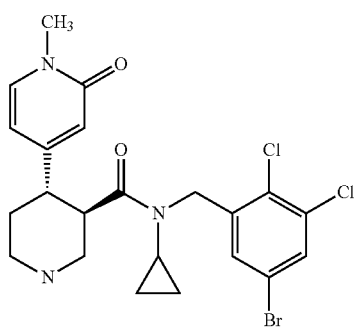 [SMILES: Cn1ccc([C@H]2CCNC[C@@H]2C(=O)N(Cc2cc(Br)cc(Cl)c2Cl)C2CC2)cc1=O]
Ex. 19
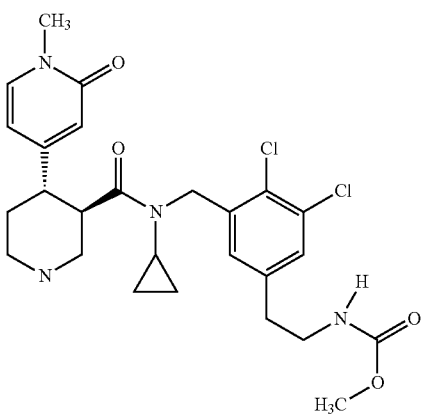 [SMILES: COC(=O)NCCc1cc(Cl)c(Cl)c(CN(C(=O)[C@H]2CNCC[C@@H]2c2ccn(C)c(=O)c2)C2CC2)c1]

TABLE-continued
Ex. 17
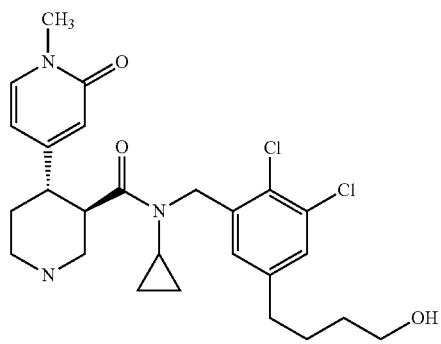 [SMILES: Cn1ccc([C@H]2CCNC[C@@H]2C(=O)N(Cc2cc(CCCCO)cc(Cl)c2Cl)C2CC2)cc1=O]
Ex. 15
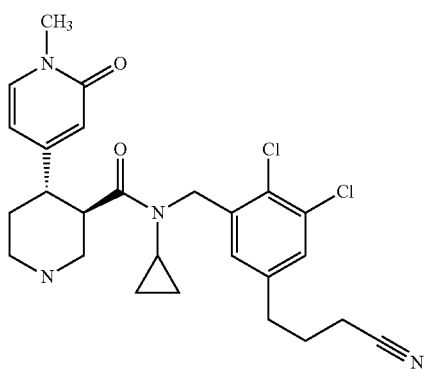 [SMILES: Cn1ccc([C@H]2CCNC[C@@H]2C(=O)N(Cc2cc(CCCC#N)cc(Cl)c2Cl)C2CC2)cc1=O]
Ex. 8
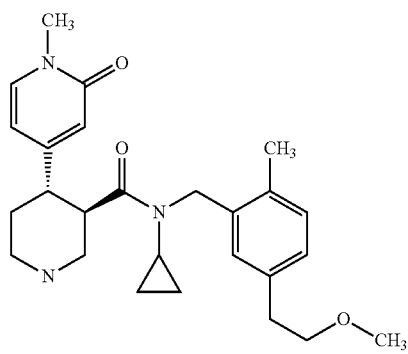 [SMILES: COCCc1ccc(C)c(CN(C(=O)[C@H]2CNCC[C@@H]2c2ccn(C)c(=O)c2)C2CC2)c1]
Ex. 7
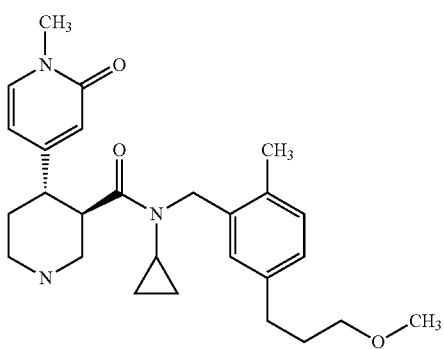

TABLE-continued
Ex. 10
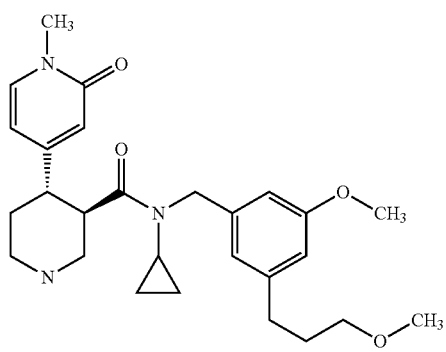 [SMILES: COCCCc1cc(CN(C(=O)[C@H]2CNCC[C@@H]2c2ccn(C)c(=O)c2)C2CC2)cc(OC)c1]
Ex. 6
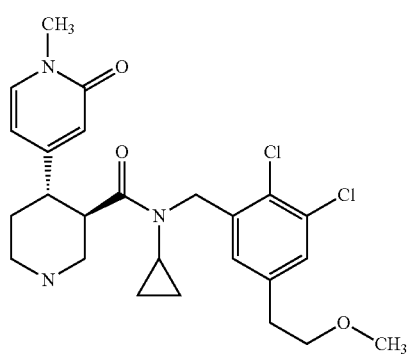 [SMILES: COCCc1cc(Cl)c(Cl)c(CN(C(=O)[C@H]2CNCC[C@@H]2c2ccn(C)c(=O)c2)C2CC2)c1]
Ex. 5
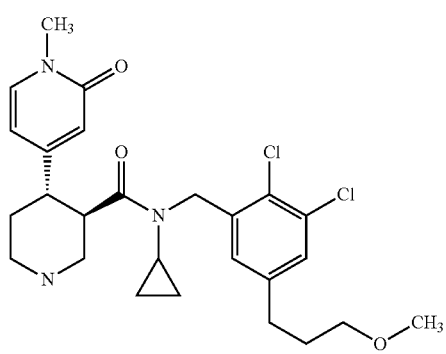 [SMILES: COCCCc1cc(Cl)c(Cl)c(CN(C(=O)[C@H]2CNCC[C@@H]2c2ccn(C)c(=O)c2)C2CC2)c1]
Ex. 32
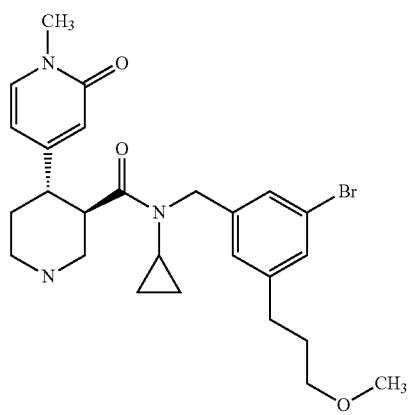 [SMILES: COCCCc1cc(Br)cc(CN(C(=O)[C@H]2CNCC[C@@H]2c2ccn(C)c(=O)c2)C2CC2)c1]

TABLE-continued
Ex. 1
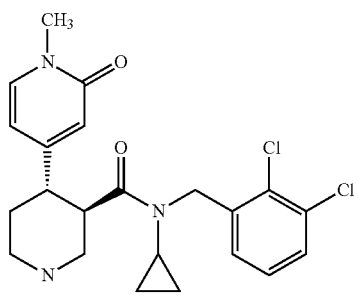 [SMILES: Cn1ccc([C@H]2CCNC[C@@H]2C(=O)N(Cc2cccc(Cl)c2Cl)C2CC2)cc1=O]
Ex. 3
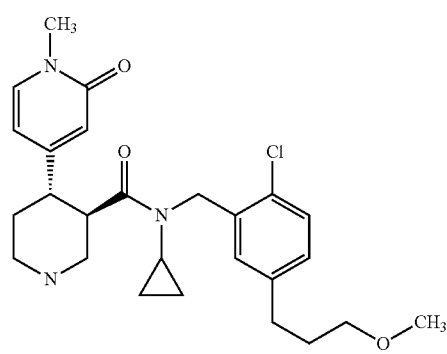 [SMILES: COCCCc1ccc(Cl)c(CN(C(=O)[C@H]2CNCC[C@@H]2c2ccn(C)c(=O)c2)C2CC2)c1]
Ex. 12
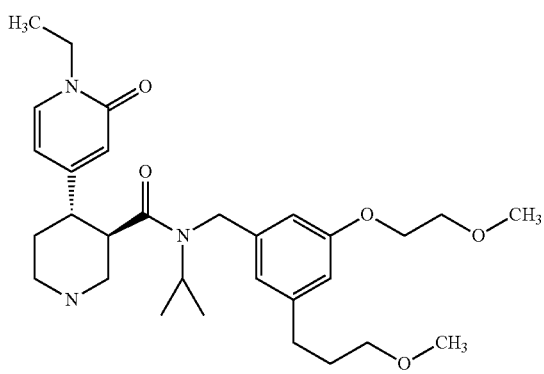 [SMILES: CCn1ccc([C@H]2CCNC[C@@H]2C(=O)N(Cc2cc(CCCOC)cc(OCCOC)c2)C(C)C)cc1=O]
Ex. 14
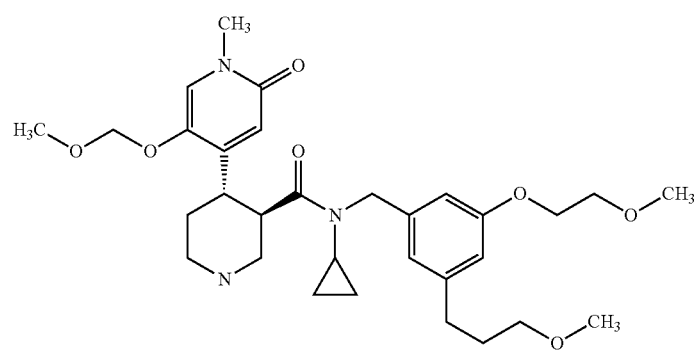
and

| TABLE-continued |
|---|
| 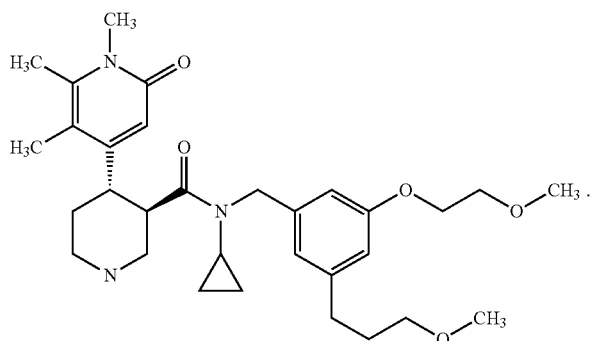 Ex. 13 |
8. The compound of claim 7 which is
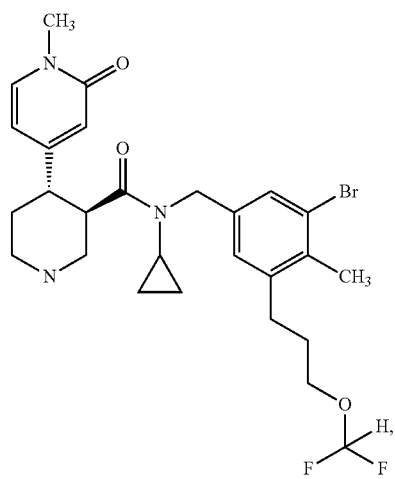
Ex. 103
or a pharmaceutically acceptable salt thereof.
9. A compound which is
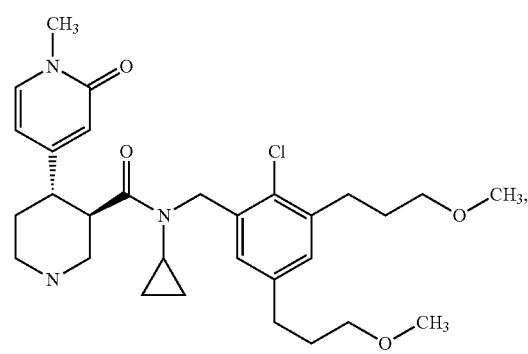
Ex. 89
or a pharmaceutically acceptable salt thereof.
10. The compound of claim 7 which is
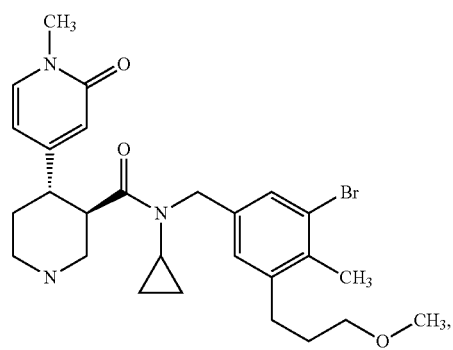
Ex. 85
or a pharmaceutically acceptable salt thereof.
11. The compound of claim 7 which is
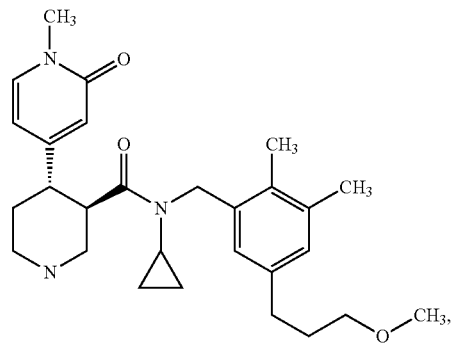
Ex. 80
or a pharmaceutically acceptable salt thereof.

12. The compound of claim 7 which is

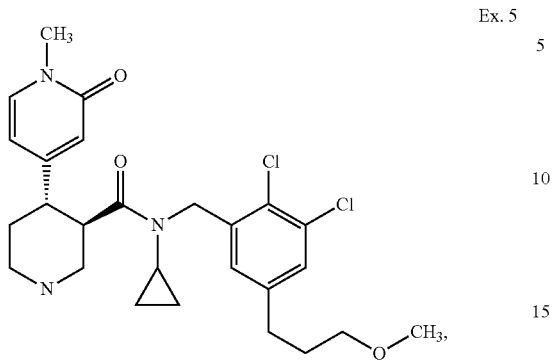

Ex. 5 or a pharmaceutically acceptable salt thereof.

13. A pharmaceutical composition comprising an effective amount of a compound according to claim 1, or a pharmaceutically acceptable salt thereof, and a pharmaceutically acceptable carrier.

14. A pharmaceutical composition comprising an effective amount of a compound according to claim 9, or a pharmaceutically acceptable salt thereof, and a pharmaceutically acceptable carrier.

15. A method for the treatment of hypertension or pulmonary hypertension, comprising the administration to a patient a pharmaceutically active amount of a compound according to claim 1.

* * * * *